US012391942B2

(12) United States Patent
Zhang et al.

(10) Patent No.: US 12,391,942 B2
(45) Date of Patent: Aug. 19, 2025

(54) OLIGONUCLEOTIDE COMPOSITIONS AND METHODS OF USE THEREOF

(71) Applicant: WAVE LIFE SCIENCES LTD., Singapore (SG)

(72) Inventors: Jason Jingxin Zhang, Walpole, MA (US); Chandra Vargeese, Schwenksville, PA (US); Naoki Iwamoto, Boston, MA (US); Chikdu Shakti Shivalila, Woburn, MA (US); Nayantara Kothari, Newton, MA (US); Ann Fiegen Durbin, Arlington, MA (US); Selvi Ramasamy, Wayland, MA (US); Pachamuthu Kandasamy, Belmont, MA (US); Jayakanthan Kumarasamy, Belmont, MA (US); Gopal Reddy Bommineni, Belmont, MA (US); Subramanian Marappan, Acton, MA (US); Sethumadhavan Divakaramenon, Lexington, MA (US); David Charles Donnell Butler, Medford, MA (US); Genliang Lu, Winchester, MA (US); Hailin Yang, Brighton, MA (US); Mamoru Shimizu, Arlington, MA (US); Prashant Monian, Arlington, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 996 days.

(21) Appl. No.: 17/054,452

(22) PCT Filed: May 10, 2019

(86) PCT No.: PCT/US2019/031672
§ 371 (c)(1),
(2) Date: Nov. 10, 2020

(87) PCT Pub. No.: WO2019/217784
PCT Pub. Date: Nov. 14, 2019

(65) Prior Publication Data
US 2021/0254062 A1    Aug. 19, 2021

Related U.S. Application Data

(60) Provisional application No. 62/776,432, filed on Dec. 6, 2018, provisional application No. 62/723,375, filed on Aug. 27, 2018, provisional application No. 62/715,684, filed on Aug. 7, 2018, provisional application No. 62/670,709, filed on May 11, 2018.

(30) Foreign Application Priority Data

Apr. 11, 2019    (WO) ............... PCT/US2019/027109

(51) Int. Cl.
C12N 15/113        (2010.01)

(52) U.S. Cl.
CPC ...... *C12N 15/113* (2013.01); *C12N 2310/315* (2013.01); *C12N 2310/321* (2013.01); *C12N 2310/322* (2013.01); *C12N 2320/33* (2013.01); *C12N 2330/30* (2013.01)

(58) Field of Classification Search
CPC ............ C12N 15/113; C12N 2310/315; C12N 2310/321; C12N 2310/322; C12N 2320/33; C12N 2330/30
See application file for complete search history.

(56) References Cited

U.S. PATENT DOCUMENTS

| 5,268,464 A | 12/1993 | Brill |
| 5,270,468 A | 12/1993 | Khanna et al. |
| 5,512,668 A | 4/1996 | Stec et al. |

(Continued)

FOREIGN PATENT DOCUMENTS

| EP | 3118311 A1 | 1/2017 |
| JP | 2003-238586 A | 8/2003 |

(Continued)

OTHER PUBLICATIONS

Scharner and Aznarez, Clinical applications of single-stranded oligonucleotides: current landscape of approved and in-development therapeutics, 2021, Molecular Therapy, p. 540-554 (Year: 2021).*
Oxford Dictionary on Google—Definition of enrich, accessed Dec. 5, 2023 (Year: 2023).*
Wu et al. Targeted Skipping of Human Dystrophin Exons in Transgenic Mouse Model Systemically for Antisense Drug Development , 2011, PloS One, e19906, p. 1-11 (Year: 2011).*
Harding et al., The Influence of Antisense Oligonucleotide Length on Dystrophin Exon Skipping, 2007, Molecular Therapy, 15, 157-166. (Year: 2007).*

(Continued)

*Primary Examiner* — Soren Harward
*Assistant Examiner* — Keyur A Vyas
(74) *Attorney, Agent, or Firm* — Choate, Hall & Stewart LLP; Xiaodong Li

(57) ABSTRACT

Among other things, the present disclosure provides designed DMD oligonucleotides, compositions, and methods of use thereof. In some embodiments, the present disclosure provides technologies useful for repairing mutant DMD transcripts by skipping exon 51 or exon 53, so that the transcript can be translated into an internally truncated but at least partially functional Dystrophin protein variant. In some embodiments, the present disclosure provides technologies useful for modulating DMD transcript splicing. In some embodiments, provided technologies can alter splicing of a dystrophin (DMD) DMD transcript. In some embodiments, the present disclosure provides methods for treating diseases, such as muscular dystrophy, including but not limited to Duchenne muscular dystrophy, Becker's muscular dystrophy, etc.

32 Claims, No Drawings
Specification includes a Sequence Listing.

(56) References Cited

U.S. PATENT DOCUMENTS

| | | |
|---|---|---|
| 5,750,669 A | 5/1998 | Rosch et al. |
| 5,852,188 A | 12/1998 | Cook |
| 7,598,227 B2 | 10/2009 | Crooke et al. |
| 7,750,141 B2 | 7/2010 | Crooke et al. |
| 8,470,987 B2 | 6/2013 | Wada et al. |
| 8,530,439 B2 | 9/2013 | Crooke et al. |
| 8,729,036 B2 | 5/2014 | Zamore et al. |
| 8,822,671 B2 | 9/2014 | Shimizu et al. |
| 8,859,755 B2 | 10/2014 | Wada et al. |
| 8,883,752 B2 | 11/2014 | Swayze et al. |
| 8,927,513 B2 | 1/2015 | Manoharan et al. |
| 9,157,082 B2 | 10/2015 | Mullick et al. |
| 9,163,239 B2 | 10/2015 | Prakash et al. |
| 9,365,848 B2 | 6/2016 | Crooke et al. |
| 9,394,333 B2 | 7/2016 | Wada et al. |
| 9,476,044 B2 | 10/2016 | Tuschl et al. |
| 9,593,333 B2 | 3/2017 | Alexander et al. |
| 9,598,458 B2 | 3/2017 | Shimizu et al. |
| 9,605,019 B2 | 3/2017 | Verdine et al. |
| 9,617,547 B2 | 4/2017 | Gemba |
| 9,624,496 B2 | 4/2017 | Crooke et al. |
| 9,695,211 B2 | 7/2017 | Wada et al. |
| 9,708,361 B2 | 7/2017 | Watanabe et al. |
| 9,744,183 B2 | 8/2017 | Verdine et al. |
| 9,982,257 B2 | 5/2018 | Butler et al. |
| 10,144,933 B2 | 12/2018 | Gemba et al. |
| 10,149,905 B2 | 12/2018 | Gemba et al. |
| 10,160,969 B2 | 12/2018 | Meena et al. |
| 10,167,309 B2 | 1/2019 | Shimizu et al. |
| 10,280,192 B2 | 5/2019 | Verdine et al. |
| 10,307,434 B2 | 6/2019 | Verdine et al. |
| 10,322,173 B2 | 6/2019 | Gemba et al. |
| 10,329,318 B2 | 6/2019 | Wada et al. |
| 10,428,019 B2 | 10/2019 | Wada et al. |
| 10,450,568 B2 | 10/2019 | Butler et al. |
| 10,479,995 B2 | 11/2019 | Vargeese et al. |
| 10,590,413 B2 | 3/2020 | Butler et al. |
| 10,696,711 B2 | 6/2020 | Shimizu et al. |
| 10,724,035 B2 | 7/2020 | Vargeese et al. |
| 10,815,482 B2 | 10/2020 | Meena et al. |
| 11,013,757 B2 | 5/2021 | Zhang et al. |
| 11,034,958 B2 | 6/2021 | Fitzgerald et al. |
| 11,136,346 B2 | 10/2021 | Shimizu et al. |
| 11,208,430 B2 | 12/2021 | Stetsenko et al. |
| 11,407,775 B2 | 8/2022 | Butler et al. |
| 11,596,646 B2 | 3/2023 | Zhang et al. |
| 11,597,927 B2 | 3/2023 | Vargeese et al. |
| 11,603,532 B2 | 3/2023 | Vargeese et al. |
| 11,608,355 B2 | 3/2023 | Bowman et al. |
| 11,634,710 B2 | 4/2023 | Frank-Kamenetsky et al. |
| 11,643,657 B2 | 5/2023 | Butler et al. |
| 11,718,638 B2 | 8/2023 | Butler et al. |
| 11,739,325 B2 | 8/2023 | Vargeese et al. |
| 11,873,316 B2 | 1/2024 | Butler et al. |
| 2004/0208856 A1 | 10/2004 | Crooke et al. |
| 2005/0059619 A1 | 3/2005 | Krieg et al. |
| 2006/0264395 A1 | 11/2006 | Crooke et al. |
| 2007/0155854 A1 | 7/2007 | Brunner et al. |
| 2007/0292875 A1 | 12/2007 | Crooke et al. |
| 2008/0200409 A1 | 8/2008 | Wilson et al. |
| 2009/0005550 A1 | 1/2009 | Heindl et al. |
| 2009/0023675 A1 | 1/2009 | McSwiggen et al. |
| 2009/0286851 A1 | 11/2009 | Akinc et al. |
| 2011/0130441 A1 | 6/2011 | Seth et al. |
| 2011/0263682 A1 | 10/2011 | De Kimpe et al. |
| 2012/0184595 A1 | 7/2012 | MacDonald et al. |
| 2013/0156845 A1 | 6/2013 | Manoharan et al. |
| 2013/0211062 A1 | 8/2013 | Watanabe et al. |
| 2014/0113957 A1 | 4/2014 | Bettencourt et al. |
| 2014/0323709 A1 | 10/2014 | Obika et al. |
| 2016/0060625 A1 | 3/2016 | Mullick et al. |
| 2016/0355808 A1 | 12/2016 | Khvorova et al. |
| 2017/0268004 A1 | 9/2017 | Mullick et al. |
| 2017/0312367 A1 | 11/2017 | Khvorova et al. |
| 2017/0320903 A1 | 11/2017 | Watanabe et al. |
| 2017/0340661 A1 | 11/2017 | Fitzgerald et al. |
| 2017/0362270 A1 | 12/2017 | Stetsenko et al. |
| 2018/0028554 A1* | 2/2018 | Van Deutekom ....... A61P 43/00 |
| 2019/0077817 A1 | 3/2019 | Butler et al. |
| 2019/0127733 A1 | 5/2019 | Butler et al. |
| 2019/0209604 A1 | 7/2019 | Zhang et al. |
| 2019/0249173 A1 | 8/2019 | Vargeese et al. |
| 2019/0264267 A1 | 8/2019 | Yang et al. |
| 2019/0375774 A1 | 12/2019 | Butler et al. |
| 2019/0390197 A1 | 12/2019 | Butler et al. |
| 2020/0080083 A1 | 3/2020 | Vargeese et al. |
| 2020/0157545 A1 | 5/2020 | Vargeese et al. |
| 2020/0190515 A1 | 6/2020 | Vargeese et al. |
| 2020/0231620 A1 | 7/2020 | Bowman et al. |
| 2020/0299692 A1 | 9/2020 | Frank-Kamenetsky et al. |
| 2020/0362337 A1 | 11/2020 | Dodart et al. |
| 2020/0385420 A1 | 12/2020 | Shimizu et al. |
| 2021/0032620 A1 | 2/2021 | Vargeese et al. |
| 2021/0115444 A1 | 4/2021 | Meena et al. |
| 2021/0130821 A1 | 5/2021 | Butler et al. |
| 2021/0198305 A1 | 7/2021 | Vargeese et al. |
| 2021/0228615 A1 | 7/2021 | Zhang et al. |
| 2022/0098585 A1 | 3/2022 | Brown et al. |
| 2022/0127301 A1 | 4/2022 | Shimizu et al. |
| 2022/0145300 A1 | 5/2022 | Liu et al. |
| 2022/0186217 A1 | 6/2022 | Zhang et al. |
| 2022/0195429 A1 | 6/2022 | Vargeese et al. |
| 2022/0306573 A1 | 9/2022 | Zhang et al. |
| 2022/0307019 A1 | 9/2022 | Yokota et al. |
| 2022/0401467 A1 | 12/2022 | Zhang et al. |
| 2023/0089442 A1 | 3/2023 | Kandasamy et al. |
| 2023/0136645 A1 | 5/2023 | Butler et al. |
| 2023/0145795 A1 | 5/2023 | Byrne et al. |
| 2023/0203087 A1 | 6/2023 | Kandasamy et al. |
| 2023/0220384 A1 | 7/2023 | Monian et al. |
| 2023/0295617 A1 | 9/2023 | Vargeese et al. |
| 2023/0295619 A1 | 9/2023 | Maguire et al. |
| 2023/0329201 A1 | 10/2023 | Yang et al. |
| 2023/0348524 A1 | 11/2023 | Bowman et al. |
| 2023/0392137 A1 | 12/2023 | Monian et al. |
| 2024/0026358 A1 | 1/2024 | Monian et al. |
| 2024/0109931 A1 | 4/2024 | Vargeese et al. |
| 2024/0117347 A1 | 4/2024 | Butler et al. |
| 2024/0132894 A1 | 4/2024 | Vargeese et al. |
| 2024/0150756 A1 | 5/2024 | Frank-Kamenetsky et al. |
| 2024/0174710 A1 | 5/2024 | Butler et al. |
| 2024/0175016 A1 | 5/2024 | Liu et al. |
| 2024/0175018 A1 | 5/2024 | Vargeese et al. |
| 2024/0229026 A1 | 7/2024 | Butler et al. |
| 2024/0368207 A1 | 11/2024 | Butler et al. |
| 2025/0051778 A1 | 2/2025 | Byrne et al. |
| 2025/0066775 A1 | 2/2025 | Vargeese et al. |

FOREIGN PATENT DOCUMENTS

| | | |
|---|---|---|
| JP | 2011-184318 A | 9/2011 |
| WO | WO-2000/004034 A2 | 1/2000 |
| WO | WO-2003/002587 A2 | 1/2003 |
| WO | WO-2003/025139 A2 | 3/2003 |
| WO | WO-2004/007718 A2 | 1/2004 |
| WO | WO-2004/093783 A2 | 11/2004 |
| WO | WO-2005/014609 A2 | 2/2005 |
| WO | WO-2005/023828 A1 | 3/2005 |
| WO | WO-2005/028494 A1 | 3/2005 |
| WO | WO-2005/070859 A1 | 8/2005 |
| WO | WO-2005/085272 A1 | 9/2005 |
| WO | WO-2005/092909 A1 | 10/2005 |
| WO | WO-2006/023880 A2 | 3/2006 |
| WO | WO-2007/059816 A1 | 5/2007 |
| WO | WO-2008/128686 A1 | 10/2008 |
| WO | WO-2009/054725 A2 | 4/2009 |
| WO | WO-2009/127060 A1 | 10/2009 |
| WO | WO-2010/048549 A2 | 4/2010 |
| WO | WO-2010/048585 A2 | 4/2010 |
| WO | WO-2010/050802 A2 | 5/2010 |
| WO | WO-2010/064146 A2 | 6/2010 |
| WO | WO-2011/005761 A1 | 1/2011 |
| WO | WO-2011/034072 A1 | 3/2011 |
| WO | WO-2011/108682 A1 | 9/2011 |

(56) References Cited

FOREIGN PATENT DOCUMENTS

| | | |
|---|---|---|
| WO | WO-2011/109427 A2 | 9/2011 |
| WO | WO-2011/139911 A2 | 11/2011 |
| WO | WO-2012/037254 A1 | 3/2012 |
| WO | WO-2012/039448 A1 | 3/2012 |
| WO | WO-2012/073857 A1 | 6/2012 |
| WO | WO-2012/149495 A1 | 11/2012 |
| WO | WO-2013/009735 A1 | 1/2013 |
| WO | WO-2013/012758 A1 | 1/2013 |
| WO | WO-2013/112053 A1 | 8/2013 |
| WO | WO-2014/007620 A2 | 1/2014 |
| WO | WO-2014/010250 A1 | 1/2014 |
| WO | WO-2014/010718 A1 | 1/2014 |
| WO | WO-2014/012081 A2 | 1/2014 |
| WO | WO-2014/076195 A1 | 5/2014 |
| WO | WO-2014/179626 A2 | 11/2014 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2015/168589 A2 | 11/2015 |
| WO | WO-2016/028187 A1 | 2/2016 |
| WO | WO-2016/081444 A1 | 5/2016 |
| WO | WO-2016/130806 A2 | 8/2016 |
| WO | WO-2017/015555 A1 | 1/2017 |
| WO | WO-2017/015575 A1 | 1/2017 |
| WO | WO-2017/048620 A1 | 3/2017 |
| WO | WO-2017/062835 A2 | 4/2017 |
| WO | WO-2017/062862 A2 | 4/2017 |
| WO | WO-2017/160741 A1 | 9/2017 |
| WO | WO-2017/192664 A1 | 11/2017 |
| WO | WO-2017/192679 A1 | 11/2017 |
| WO | WO-2017/205880 A1 | 11/2017 |
| WO | WO-2017/210647 A1 | 12/2017 |
| WO | WO-2018/014042 A1 | 1/2018 |
| WO | WO-2018/022473 A1 | 2/2018 |
| WO | WO-2018/056871 A1 | 3/2018 |
| WO | WO-2018/067973 A1 | 4/2018 |
| WO | WO-2018/098264 A1 | 5/2018 |
| WO | WO-2018/156056 A1 | 8/2018 |
| WO | WO-2018/223056 A1 | 12/2018 |
| WO | WO-2018/223073 A1 | 12/2018 |
| WO | WO-2018/223081 A1 | 12/2018 |
| WO | WO-2018/237194 A1 | 12/2018 |
| WO | WO-2019/002237 A1 | 1/2019 |
| WO | WO-2019/032607 A1 | 2/2019 |
| WO | WO-2019/032612 A1 | 2/2019 |
| WO | WO-2019/055951 A1 | 3/2019 |
| WO | WO-2019/071028 A1 | 4/2019 |
| WO | WO-2019/075357 A1 | 4/2019 |
| WO | WO-2019/118638 A2 | 6/2019 |
| WO | WO-2019/200185 A1 | 10/2019 |
| WO | WO-2019/217784 A1 | 11/2019 |
| WO | WO-2020/061200 A1 | 3/2020 |
| WO | WO-2020/118246 A1 | 6/2020 |
| WO | WO-2020/160336 A1 | 8/2020 |
| WO | WO-2020/191252 A1 | 9/2020 |
| WO | WO-2020/196662 A1 | 10/2020 |
| WO | WO-2020/219981 A2 | 10/2020 |
| WO | WO-2020/219983 A2 | 10/2020 |
| WO | WO-2020/227691 A2 | 11/2020 |
| WO | WO-2021/071788 A2 | 4/2021 |
| WO | WO-2021/071858 A1 | 4/2021 |
| WO | WO-2021/126734 A1 | 6/2021 |
| WO | WO-2021/178237 A2 | 9/2021 |
| WO | WO-2021/195467 A2 | 9/2021 |
| WO | WO-2021/234459 A2 | 11/2021 |
| WO | WO-2021/237223 A1 | 11/2021 |
| WO | WO-2022/046667 A1 | 3/2022 |
| WO | WO-2022/046723 A1 | 3/2022 |
| WO | WO-2022/072244 A1 | 4/2022 |
| WO | WO-2022/099159 A1 | 5/2022 |
| WO | WO-2023/049475 A1 | 3/2023 |
| WO | WO-2023/049477 A2 | 3/2023 |
| WO | WO-2023/075766 A1 | 5/2023 |
| WO | WO-2023/076352 A2 | 5/2023 |
| WO | WO-2023/154528 A1 | 8/2023 |
| WO | WO-2023/168014 A2 | 9/2023 |
| WO | WO-2023/201095 A2 | 10/2023 |
| WO | WO-2023/220440 A1 | 11/2023 |
| WO | WO-2024/035946 A1 | 2/2024 |
| WO | WO-2025/030155 A1 | 2/2025 |

OTHER PUBLICATIONS

U.S. Appl. No. 17/605,998, filed Oct. 22, 2021, Byrne et al.
U.S. Appl. No. 17/766,680, filed Apr. 5, 2022, Liu et al.
U.S. Appl. No. 17/907,895, filed Aug. 29, 2022, Maguire et al.
U.S. Appl. No. 17/953,292, filed Sep. 26, 2022, Monian et al.
U.S. Appl. No. 17/956,741, filed Sep. 29, 2022, Vargeese et al.
U.S. Appl. No. 17/960,090, filed Oct. 4, 2022, Vargeese et al.
U.S. Appl. No. 18/022,509, filed Feb. 21, 2023, Yang et al.
U.S. Appl. No. 18/062,422, filed Dec. 6, 2022, Butler et al.
U.S. Appl. No. 18/072,296, filed Nov. 30, 2022, Vargeese et al.
U.S. Appl. No. 18/178,470, filed Mar. 3, 2023, Vargeese et al.
U.S. Appl. No. 18/185,901, filed Mar. 17, 2023, Bowman et al.
U.S. Appl. No. 18/204,895, filed Jun. 1, 2023, Vargeese et al.
U.S. Appl. No. 18/252,029, filed May 5, 2023, Monian et al.
U.S. Appl. No. 18/305,195, filed Apr. 21, 2023, Frank-Kamenetsky et al.
U.S. Appl. No. 18/316,932, filed May 12, 2023, Butler et al.
Anderson, B. A. et al., Towards next generation antisense oligonucleotides: mesylphosphoramidate modification improves therapeutic index and duration of effect of gapmer antisense oligonucleotides, Nucl. Acids. Res., 49(16):9026-9041 (2021).
Kandasamy, P. et al., Control of backbone chemistry and chirality boost oligonucleotide splice switching activity, Nucleic Acids Research, 50(10):5443-5466 (2022).
Kandasamy, P. et al., Impact of guanidine-containing backbone linkages on stereopure antisense oligonucleotides in the CNS, Nucleic Acids Res., 50(10):5401-5423 (2022).
Kozarski, M. et al., 7-Methylguanosine monophosphate analogues with 5'-(1,2,3-triazoyl) moiety: Synthesis and evaluation as the inhibitors of cNIIIB nucleotidase, Bioorg. Med. Chem., 26(1):191-199 (2018).
Kupryushkin, M.S. et al., Antisense oligonucleotide gapmers containing phosphoryl guanidinegroups reverseMDR1-mediated multiple drug resistance of tumor cells, Mol. Ther. Nucleic Acids, 27:211-226, (2021).
Oka, N. et al., Solid-phase synthesis of stereoregular oligodeoxyribonucleoside phosphorothioates using bicyclic oxazaphospholidine derivatives as monomer units, J. Am. Chem. Soc., 130(47):16031-16037 (2008).
Pavlova, A. S. et al., SDS-PAGE procedure: Application for characterization of new entirely uncharged nucleic acids analogs, Electrophor., 39:670-674 (2018).
PubChem SID: 226629328, 9 pages, date available: Feb. 2, 2015.
PubChem SID: 316086382, 8 pages, date available: Aug. 2, 2016, date modified: Jun. 20, 2019.
PubChem SID: 355354479, 7 pages, date available: Apr. 8, 2018.
PubChem SID: 368967557, 7 pages, date available: May 25, 2018.
Vergeese, C., Exploring new oligonucleotide backbone chemistries and their deployment to improve the properties of stereopure oligonucleotides, Wave Life Sciences, presented at Tides USA on Sep. 22, 2021.
Wave Life Sciences, Second Quarter 2022 Earnings Presentation, 27 pages, (2022).
Wave Life Sciences, Third Quarter 2022 Earnings Presentation, 24 pages, (2022).
Wave Life Sciences, Wave Life Sciences Corporate Presentation, 32 pages, Aug. 3, 2023.
Wave Life Sciences, Wave Life Sciences Corporate Presentation, 63 pages, May 12, 2022.
Zhang, L. et al., The Combination of Mesyl-Phosphoramidate Inter-Nucleotide Linkages and 2'-O-Methyl in Selected Positions in the Antisense Oligonucleotide Enhances the Performance of RNaseH1 Active PS-ASOs, Nucleic Acid Ther., 32(5):401-411 (2022).
U.S. Appl. No. 16/618,003, filed Nov. 27, 2019, Vargeese et al.
U.S. Appl. No. 16/624,896, filed Dec. 19, 2019, Butler et al.
U.S. Appl. No. 16/869,126, filed May 7, 2020, Vargeese et al.

(56) References Cited

OTHER PUBLICATIONS

U.S. Appl. No. 17/046,752, filed Oct. 9, 2020, Zhang et al.
U.S. Appl. No. 17/054,452, filed Nov. 10, 2020, Zhang et al.
U.S. Appl. No. 17/177,111, filed Feb. 16, 2021, Zhang et al.
U.S. Appl. No. 17/311,285, filed Jun. 4, 2021, Zhang et al.
U.S. Appl. No. 17/375,658, filed Jul. 14, 2021, Vargeese et al.
U.S. Appl. No. 17/426,511, filed Jul. 28, 2021, Brown et al.
Belikova, A. M., et al., Synthesis of Ribonucleosides and Diribonucleoside phosphates containing 2-chloro-ethylamine and Nitrogen Mustard Residues, Terahedron Letters, 37:3557-3562 (1967).
Fokina, A. et al., Analysis of new charge-neutral DNA/RNA analogues phosphoryl guanidine oligonucleotides (PGO) by gel electrophoresis, Analytical Biochemistry, 555: 9-11 (2018).
International Search Report for PCT/US2018/035687, 4 pages (mailed Oct. 4, 2018).
International Search Report for PCT/US2018/035712, 5 pages (mailed Oct. 19, 2018).
International Search Report for PCT/US2018/035721, 5 pages (mailed Oct. 18, 2018).
International Search Report for PCT/US2019/027109, 7 pages (mailed Sep. 24, 2019).
International Search Report for PCT/US2019/031672, 5 pages (mailed Oct. 10, 2019).
International Search Report for PCT/US2019/065058, 6 pages (mailed May 4, 2020).
Jäger, A. et al., Oligonucleotide N-alkylphosphoramidates: synthesis and binding to polynucleotides, Biochemistry, 27(19):7237-46 (1988).
Koch, T., LNA Therapeutics—update, Navigate the phosphorothioate diastereoisomer space, Roche pRED RNA Therapeutics Research, EuroTIDES, PostillionConventionCenter, Amsterdam, Netherlands (Nov. 6-9, 2018).
Kupryushkin, M et al., 'Dodecyl-modified oligodeoxyribonucleotides as platform for oligonucleotide delivery into eukaryotic cells,' 13th Annual Meeting of the Oligonucleotide Therapeutics Society, (2017), abstract 057.
Kupryushkin, M. S. Phosphoryl Guanidines: A New Type of Nucleic Acid Analogues, Acta Naturae, 6(4): 116-118 (2014).
Kurata, C. et al., Characterization of high molecular weight impurities in synthetic phosphorothioate oligonucleotides, Bioorg. Med. Chem. Lett., 16:607-614 (2006).
Lebedeva, N. et al., Design of a New Fluorescent Oligonucleotide-Based Assay for a Highly Specific Real-Time Detection of Apurinic/Apyrimidinic Site Cleavage by Tyrosyl-DNA Phosphodiesterase 1, Bioconjugate Chem., 26(10):2046-2053 (2015).
Lee, M. Y. et al., Synthesis and SAR of sulfonyl- and phosphoryl amidine compounds as anti-resorptive agents, Bioorg. Med. Chem. Lett., 20:541-545 (2010).
Levina, A.S. et al., Impact of delivery method on antiviral activity of phosphodiester, phosphorothioate, and phosphoryl guanidine oligonucleotides in MDCK cells infected with H5N1 bird flu virus, Molecular Biology, 51(4): 633-638 (2017).
Ohkubo, A. et al., A new strategy for the synthesis of oligodeoxynucleotides directed towards perfect O-selective internucleotidic bond formation without base protection, Tetrahedron Letters, 45:363-366 (2004).
Ohkubo, A. et al., O-Selectivity and Utility of Phosphorylation Mediated by Phosphite Triester Intermediates in the N-Unprotected Phosphoramidite Method, J. Am. Chem., 126:10884-10896 (2004).
Prakash, T. P. et al., Identification of metabolically stable 5'-phosphate analogs that support single-stranded siRNA activity, Nucleic Acids Research, 43(6):2993-3011 (2015).
Rigo, F. et al., Synthetic oligonucleotides recruit ILF2/3 to RNA transcripts to modulate splicing, Nat. Chem. Bio., 8:555-562 (2012).
Sekine, M. et al., Proton-Block Strategy for the Synthesis of Oligodeoxynucleotides without Base Protection, Capping Reaction, and P—N Bond Cleavage Reaction, J. Org. Chem., 68:5478-5492 (2003).
Shen, W. et al., Acute hepatotoxicity of 2' fluoro-modified 5-10-5 gapmer phosphorothioate oligonucleotides in mice correlates with intracellular protein binding and the loss of DBHS proteins, Nucl. Acids Res., 46(5):2204-2217 (2018).
Skaric, V. and Raza, Z., The Homologation of 1-(2,3-Dihydroxypropyl)- into 1-(2,4-Dihydroxybutyl)-thymine, Croatica Chemica Acta, 52(1):51-59 (1979).
Skaric, V. et al., Aliphatic Thymidine and Deoxyuridine Analogs, Croatica Chemica Acta, 52(3):281-292 (1979).
Skvortsova, Y. V., et al., A new Antisense Phosphoryl Guanidine Oligo-2'-O-Methylribonucleotide Penetrates Into Intracellular Mycobacteria and Suppresses Target Gene Expression, 10:1-9 (2019).
Stetsenko, D. A., Phosphoryl Guanidines: New Chemical Analogues of Nucleic Acids, 4 pages (Aug. 2015), <https://scfh.ru/en/papers/phosphoryl-guanidines-new-chemical-analogues-of-nucleic-acids-/>. Retrieved Sep. 15, 2020.
Stetsenko, D.A. and Pyshnyi, D.V., Ex Siberia Semper Novi: Siberia Always Brings Us Something New, Phosphoryl Guanidines: New Chemical Analogues of Nucleic Acids, Science First Hand, N2(41): 2 pages (Aug. 30, 2015). URL: https://scfh.ru/en/papers/phosphoryl-guanidines-new-chemical-analogues-of-nucleic-acids-/.
Wave Life Sciences Press Release, Wave Life Sciences Announces Discontinuation of Suvodirsen Development for Duchenne Muscular Dystrophy, 2 pages (Dec. 16, 2019).
Wave Life Sciences, Analyst & Investor Research Webcast (Aug. 2020), 64 pages.
Written Opinion for PCT/US2018/035687, 10 pages (mailed Oct. 4, 2018).
Written Opinion for PCT/US2018/035712, 6 pages (mailed Oct. 19, 2018).
Written Opinion for PCT/US2018/035721, 10 pages (mailed Oct. 18, 2018).
Written Opinion for PCT/US2019/027109, 10 pages (mailed Sep. 24, 2019).
Written Opinion for PCT/US2019/031672, 11 pages (mailed Oct. 10, 2019).
Written Opinion for PCT/US2019/065058, 11 pages (mailed May 4, 2020).
U.S. Appl. No. 18/522,146, filed Nov. 28, 2023, Butler et al.
U.S. Appl. No. 18/613,034, filed Mar. 21, 2024, Vargeese et al.
U.S. Appl. No. 18/695,346, filed Mar. 25, 2024, Monian et al.
U.S. Appl. No. 18/695,348, filed Mar. 25, 2024, Acker et al.
Wave Life Sciences, R&D Day Presentation, 81 pages (Sep. 28, 2023).
U.S. Appl. No. 18/704,629, filed Apr. 25, 2024, Byrne et al.
U.S. Appl. No. 18/836,993, filed Aug. 8, 2024, Kandasamy et al.
U.S. Appl. No. 18/843,171, filed Aug. 30, 2024, Hu et al.
U.S. Appl. No. 18/856,553, filed Oct. 11, 2024, Lu et al.
U.S. Appl. No. 18/864,860, filed Nov. 11, 2024, Shivalila et al.
U.S. Appl. No. 18/864,863, filed Nov. 11, 2024, Liu et al.
U.S. Appl. No. 18/942,334, filed Nov. 8, 2024, Yang et al.
U.S. Appl. No. 18/953,020, filed Nov. 19, 2024, Meena et al.
U.S. Appl. No. 19/008,522, filed Jan. 2, 2025, Vargeese et al.
U.S. Appl. No. 19/102,669, filed Feb. 10, 2025, Lake et al.
Chen, S. et al., Systematic evaluation of 2'-Fluoro modified chimeric antisense oligonucleotide-mediated exon skipping in vitro, Sci. Repo., 9(6078):1-10 (2019).
Del Fresno, M. et al., Substituted Guanidines: Introducing Diversity in Combinatorial Chemistry, Org. Lett., 2(23):3539-3542 (2000).
Flanigan, K. M. et al., Rapid Direct Sequence Analysis of the Dystrophin Gene, Am. J. Hum. Genet., 72:931-939 (2003).
Inagawa, T. et al., Inhibition of human immunodeficiency virus type 1 replication by P-stereodefined oligo(nucleoside phosphorothioate)s in a long-term infection model, FEBS Letters, 528:48-52 (2002).
Jirka, S.M.G et al., Evaluation of 2'-Deoxy-2'-fluoro Antisense Oligonucleotides for Exon Skipping in Duchenne Muscular Dystrophy, Citation: Molecular Therapy-Nucleic Acids 4, e265 1-8 (2015).
Pannecouque, C. et al., Synthesis, enzymatic stability and physicochemical properties of oligonucleotides containing a N-cyanoguanidine linkage, Tetrahedron, 50(24):7231-7246 (1994).

(56) References Cited

OTHER PUBLICATIONS

Vandendriessche, F. et al., Synthesis, enzymatic stability and base-pairing properties of oligothymidylates containing thymidine dimers with different N-substituted guanidine linkages, J. Chem. Soc. Perk. Trans. 1, 14:1567-1575 (1993).

Wave Life Sciences, Fourth Quarter 2025 Financial Report, 5 pages, (2025).

Wave Life Sciences, Wave Life Sciences Corporate Presentation, 36 pages, Mar. 4, 2025.

* cited by examiner

OLIGONUCLEOTIDE COMPOSITIONS AND METHODS OF USE THEREOF

CROSS-REFERENCE TO RELATED APPLICATIONS

This application claims priority to U.S. Provisional Application Nos. 62/670,709, filed May 11, 2018, 62/715,684, filed Aug. 7, 2018, 62/723,375, filed Aug. 27, 2018, 62/776,432, filed Dec. 6, 2018, and PCT Application No. PCT/US19/27109, filed Apr. 11, 2019, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Jun. 2, 2019, is named SL.txt and is 24,484 bytes in size.

BACKGROUND

Oligonucleotides are useful in therapeutic, diagnostic, research and nanomaterials applications. The use of naturally occurring nucleic acids (e.g., unmodified DNA or RNA) for therapeutics can be limited, for example, because of their instability against extra- and intracellular nucleases and/or their poor cell penetration and distribution. There is a need for new and improved DMD oligonucleotides and DMD oligonucleotide compositions, such as, e.g., new DMD oligonucleotides and DMD oligonucleotide compositions capable of modulating skipping of Dystrophin exon 51 or exon 53 for treatment of muscular dystrophy.

SUMMARY

Among other things, the present disclosure encompasses the recognition that structural elements of DMD oligonucleotides, such as base sequence, chemical modifications (e.g., modifications of sugar, base, and/or internucleotidic linkages, and patterns thereof), and/or stereochemistry (e.g., stereochemistry of backbone chiral centers (chiral internucleotidic linkages), and/or patterns thereof), can have a significant impact on DMD oligonucleotide properties, e.g., skipping of exon 51 or 53, toxicities, stability, protein binding characteristics, etc.

In some embodiments, the present disclosure provides a DMD oligonucleotide or a DMD oligonucleotide composition capable of mediating skipping of DMD exon 51 or exon 53. In some embodiments, a DMD oligonucleotide or a DMD oligonucleotide composition is useful for treatment of muscular dystrophy. In some embodiments, a DMD oligonucleotide or DMD oligonucleotide composition is a DMD oligonucleotide or DMD oligonucleotide composition disclosed herein (including but not limited to, in Table A1).

In some embodiments, as demonstrated by example data described herein, provided technologies are particularly useful for reducing levels of a mutant mRNA (e.g., a DMD transcript comprising a deleterious mutation) and/or proteins encoded thereby, and increasing levels of repaired mRNA (e.g., a DMD transcript in which exon 51 or exon 53 is skipped to delete, correct or compensate for a deleterious mutation) and/or proteins encoded thereby.

In some embodiments, provided technologies are particularly useful for modulating splicing of DMD transcripts, e.g., to increase levels of desired splicing products and/or to reduce levels of undesired splicing products. In some embodiments, provided technologies are particularly useful for reducing levels of DMD transcripts, e.g., pre-mRNA, RNA, etc., and in many instances, reducing levels of products arising from or encoded by such DMD transcripts such as mRNA, proteins, etc. In some embodiments, a pre-mRNA or mRNA or RNA is transported from one cellular compartment (e.g., nucleus, cytoplasm, etc.) to another, and/or has been modified by one or more enzyme.

For example, in some embodiments, a Dystrophin gene can comprise an exon comprising one or more mutations associated with muscular dystrophy (including but not limited to Duchenne (Duchenne's) muscular dystrophy (DMD) and Becker (Becker's) muscular dystrophy (BMD)). In some embodiments, a disease-associated exon comprises a mutation (e.g., a missense mutation, a frameshift mutation, a nonsense mutation, a premature stop codon, etc.) in an exon. In some embodiments, the present disclosure provides compositions and methods for effectively skipping a disease-associated Dystrophin exon, while maintaining or restoring the reading frame so that a shorter (e.g., internally truncated) but partially functional dystrophin (e.g., a variant) can be produced.

Among other things, the present disclosure demonstrates that chemical modifications and/or stereochemistry can be used to modulate DMD transcript splicing by DMD oligonucleotide compositions. In some embodiments, the present disclosure provides combinations of chemical modifications and stereochemistry to improve properties of DMD oligonucleotides, e.g., their capabilities to alter splicing of DMD transcripts. In some embodiments, the present disclosure provides chirally controlled DMD oligonucleotide compositions that, when compared to a reference condition (e.g., absence of the composition, presence of a reference composition (e.g., a stereorandom composition of DMD oligonucleotides having the same constitution (as understood by those skilled in the art, unless otherwise indicated constitution generally refers to the description of the identity and connectivity (and corresponding bond multiplicities) of the atoms in a molecular entity but omitting any distinction arising from their spatial arrangement), a different chirally controlled DMD oligonucleotide composition, etc.), combinations thereof, etc.), provide increased skipping of DMD exon 51 or DMD exon 53 to produce a modified (e.g., repaired) mRNA, which can be translated to produce an internally truncated but at least partially functional Dystrophin protein variant.

In some embodiments, compared to a reference condition, provided chirally controlled DMD oligonucleotide compositions are surprisingly effective. In some embodiments, splicing of DMD exon 51 or 53 can be enhanced by more than 5, 10, 15, 20, 25, 30, 40, 50, or 100 fold.

The present disclosure recognizes challenges of providing low toxicity DMD oligonucleotide compositions and methods of use thereof. In some embodiments, the present disclosure provides DMD oligonucleotide compositions and methods with reduced toxicity. In some embodiments, the present disclosure provides DMD oligonucleotide compositions and methods with reduced induction of immune responses.

In some embodiments, the present disclosure provides DMD oligonucleotides with enhanced antagonism of hTLR9 activity. In some embodiments, muscular dystrophy is associated with inflammation in, e.g., muscle tissues. In some embodiments, provided technologies (e.g., DMD oligonucleotides, compositions, methods, etc.) provides both enhanced activities (e.g., exon-skipping activities) and hTLR9 antagonist activities which can be beneficial to one or more conditions and/or diseases associated with inflammation. In some embodiments, provided DMD oligonucleotides and/or compositions thereof provides both exon-skipping capabilities and decreased levels of toxicity and/or inflammation.

In some embodiments, a DMD oligonucleotide comprises multiple internucleotidic linkages, each independently selected from various types. Various types of internucleotidic linkages differ in properties. Without wishing to be bound by any theory, the present disclosure notes that a natural phosphate linkage (phosphodiester internucleotidic linkage) is anionic and may be unstable when used by itself without other chemical modifications in vivo; a phosphorothioate internucleotidic linkage is anionic, generally more stable in vivo than a natural phosphate linkage, and generally more hydrophobic; a neutral internucleotidic linkage such as one exemplified in the present disclosure comprising a cyclic guanidine moiety is neutral at physiological pH, can be more stable in vivo than a natural phosphate linkage, and more hydrophobic.

In some embodiments, a DMD oligonucleotide comprises a modified internucleotidic linkage which is a non-negatively charged (neutral or cationic) internucleotidic linkage in that at a pH [e.g., human physiological pH (~ 7.4), pH of a delivery site (e.g., an organelle, cell, tissue, organ, organism, etc.), etc.]. Without wishing to be bound by any particular theory, in at least some cases, a neutral internucleotidic linkage in a DMD oligonucleotide can provide improved properties and/or skipping of exon 51 or 53, e.g., improved delivery, improved resistance to exonucleases and endonucleases, improved cellular uptake, improved endosomal escape and/or improved nuclear uptake, etc., compared to a comparable nucleic acid which does not comprises a neutral internucleotidic linkage.

In some embodiments, a non-negatively charged internucleotidic linkage comprises a cyclic guanidine moiety. In some embodiments, non-negatively charged internucleotidic linkage has the structure of:

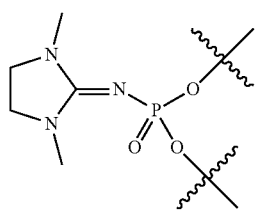 [SMILES: *OP(=O)(N=C1N(C)CCN1C)O*]

(n001) or a stereoisomer thereof (e.g., n001R or n001S). In some embodiments, a neutral internucleotidic linkage comprising a cyclic guanidine moiety is chirally controlled. In some embodiments, the present disclosure pertains to a composition comprising a DMD oligonucleotide comprising at least one neutral internucleotidic linkage and at least one phosphorothioate internucleotidic linkage.

Among other things, the present disclosure encompasses the recognition that stereorandom DMD oligonucleotide preparations contain a plurality of distinct chemical entities that differ from one another, e.g., in the stereochemical structure of individual backbone chiral centers within the DMD oligonucleotide chain. Without control of stereochemistry of backbone chiral centers, stereorandom DMD oligonucleotide preparations provide uncontrolled (or stereorandom) compositions comprising undetermined levels of DMD oligonucleotide stereoisomers. Even though these stereoisomers may have the same base sequence and/or chemical modifications, they are different chemical entities at least due to their different backbone stereochemistry, and they can have, as demonstrated herein, different properties, e.g., skipping of exon 51 or 53, toxicities, distribution etc. Among other things, the present disclosure provides chirally controlled compositions that are or contain particular stereoisomers of DMD oligonucleotides of interest; in contrast to chirally uncontrolled compositions, chirally controlled compositions comprise controlled levels of particular stereoisomers of DMD oligonucleotides. In some embodiments, a particular stereoisomer may be defined, for example, by its base sequence, its pattern of backbone linkages, its pattern of backbone chiral centers, and pattern of backbone phosphorus modifications, etc. As is understood in the art, in some embodiments, base sequence may refer solely to the sequence of bases and/or to the identity and/or modification status of nucleoside residues (e.g., of sugar and/or base components, relative to standard naturally occurring nucleotides such as adenine, cytosine, guanosine, thymine, and uracil) in a DMD oligonucleotide and/or to the hybridization character (i.e., the ability to hybridize with particular complementary residues) of such residues. In some embodiments, the present disclosure demonstrates that property improvements (e.g., improved skipping of exon 51 or 53, lower toxicities, etc.) achieved through inclusion and/or location of particular chiral structures within a DMD oligonucleotide can be comparable to, or even better than those achieved through use of chemical modifications, e.g., particular backbone linkages, residue modifications, etc. (e.g., through use of certain types of modified phosphates [e.g., phosphorothioate, substituted phosphorothioate, etc.], sugar modifications [e.g., 2'-modifications, etc.], and/or base modifications [e.g., methylation, etc.]). In some embodiments, the present disclosure demonstrates that chirally controlled DMD oligonucleotide compositions of DMD oligonucleotides comprising certain chemical modifications (e.g., 2'—F, 2'-OMe, phosphorothioate internucleotidic linkages, etc.) demonstrate unexpectedly high exon-skipping efficiency.

In some embodiments, the present disclosure provides a DMD oligonucleotide composition comprising a plurality of DMD oligonucleotides which:
1) have a common base sequence complementary to a target sequence in a DMD transcript; and
2) comprise one or more modified sugar moieties and modified internucleotidic linkages, wherein the DMD oligonucleotide is a DMD oligonucleotide described herein (e.g., in Table A1).

In some embodiments, a provided DMD oligonucleotide composition is characterized in that, when it is contacted with a DMD transcript in a DMD transcript splicing system, splicing of the DMD transcript is altered (e.g., skipping of exon 51 or 53 is increased) relative to that observed under a reference condition selected from the group consisting of absence of the composition, presence of a reference composition, and combinations thereof.

In some embodiments, a reference condition is absence of the composition. In some embodiments, a reference condition is presence of a reference composition. Example reference compositions comprising a reference plurality of DMD oligonucleotides are extensively described in this disclosure. In some embodiments, DMD oligonucleotides of the reference plurality have a different structural elements (chemical modifications, stereochemistry, etc.) compared with DMD oligonucleotides of the plurality in a provided composition. In some embodiments, a reference composition is a stereorandom preparation of DMD oligonucleotides having the same chemical modifications. In some embodiments, a reference composition is a mixture of stereoisomers while a provided composition is a chirally controlled DMD oligonucleotide composition of one stereoisomer. In some embodiments, DMD oligonucleotides of the reference plurality have the same base sequence, same sugar modifications, same base modifications, same internucleotidic linkage modifications, and/or same stereochemistry as DMD oligonucleotide of the plurality in a provided composition but different chemical modifications, e.g., base modification, sugar modification, internucleotidic linkage modifications, etc.

Example splicing systems are widely known in the art. In some embodiments, a splicing system is an in vivo or in vitro system including components sufficient to achieve splicing of a relevant target DMD transcript. In some embodiments, a splicing system is or comprises a spliceosome (e.g., protein and/or RNA components thereof). In some embodiments, a splicing system is or comprises an organellar membrane (e.g., a nuclear membrane) and/or an organelle (e.g., a nucleus). In some embodiments, a splicing system is or comprises a cell or population thereof. In some embodiments, a splicing system is or comprises a tissue. In some embodiments, a splicing system is or comprises an organism, e.g., an animal, e.g., a mammal such as a mouse, rat, monkey, dog, human, etc.

In some embodiments, the present disclosure provides a DMD oligonucleotide composition comprising a plurality of DMD oligonucleotides of a particular DMD oligonucleotide type defined by:
1) base sequence;
2) pattern of backbone linkages;
3) pattern of backbone chiral centers; and
4) pattern of backbone phosphorus modifications, wherein the DMD oligonucleotide is a DMD oligonucleotide described herein (e.g., in Table A1).

In some embodiments, the present disclosure provides a DMD oligonucleotide composition comprising a plurality of DMD oligonucleotides of a particular DMD oligonucleotide type defined by:
1) base sequence;
2) pattern of backbone linkages;
3) pattern of backbone chiral centers; and
4) pattern of backbone phosphorus modifications, which composition is chirally controlled and it is enriched, relative to a substantially racemic preparation of DMD oligonucleotides having the same base sequence, for DMD oligonucleotides of the particular DMD oligonucleotide type,
the DMD oligonucleotide composition being characterized in that, when it is contacted with the DMD transcript in a DMD transcript splicing system, splicing of the DMD transcript is altered (e.g., skipping of exon 51 or 53 is increased) relative to that observed under reference conditions selected from the group consisting of absence of the composition, presence of a reference composition, and combinations thereof, wherein the DMD oligonucleotide is a DMD oligonucleotide described herein (e.g., in Table A1).

In some embodiments, the present disclosure provides a chirally controlled oligonucleotide composition of an oligonucleotide in Table A1, wherein the oligonucleotide comprises one or more (e.g., 1, 2, 3, 4, 5, 6, 7, 8, 9, 10, 11, 12, 13, 14, 15, 16, 17, 18, 19, or 20 or more) chirally controlled internucleotidic linkages (e.g., those of S, R, nS, or nR), and wherein the oligonucleotide is optionally in a pharmaceutically acceptable salt form. In some embodiments, the oligonucleotide is provided as a sodium salt.

In some embodiments, as described herein a plurality of oligonucleotides share the same constitution. In some embodiments, for a chirally controlled internucleotidic linkage of a plurality of oligonucleotides in a composition, at least 85%, 90%, 91%, 92%, 93%, 94%, 95%, 96%, 97%, 98%, or 99%, preferably at least 90%, 91%, 92%, 93%, 94%, 95%, 96%, 97%, 98%, or 99%, of all oligonucleotides in the composition that share the same constitution of the plurality of the oligonucleotides share the same linkage phosphorus configuration at the chirally controlled internucleotidic linkage.

In some embodiments, a DMD transcript is of a Dystrophin gene or a variant thereof.

In some embodiments, the present disclosure provides a composition comprising any DMD oligonucleotide disclosed herein. In some embodiments, the present disclosure provides a composition comprising any chirally controlled DMD oligonucleotide disclosed herein. In some embodiments, the present disclosure provides a composition comprising any chirally controlled DMD oligonucleotide disclosed herein, wherein the DMD oligonucleotide is capable of mediating skipping of DMD exon 51 or DMD exon 53.

In some embodiments, the present disclosure pertains to any individual DMD oligonucleotide described herein (e.g., in Table A1).

In some embodiments, a provided DMD oligonucleotide and/or composition is capable of mediating skipping of exon 51. In some embodiments, non-limiting examples of such DMD oligonucleotides and compositions include those of: WV-12494, WV-12130, WV-12131, WV-12132, WV-12133, WV-12134, WV-12135, WV-12136, WV-12496, WV-12495, WV-12123, WV-12124, WV-12125, WV-12126, WV-12127, WV-12128, WV-12129, WV-12553, WV-12554, WV-12555, WV-12556, WV-12557, WV-12558, WV-12559, WV-12872, WV-12873, WV-12876, WV-12877, WV-12878, WV-12879, WV-12880, WV-12881, WV-12882, and WV-12883, and other DMD oligonucleotides having a base sequence which comprises at least 15 contiguous bases of any of these DMD oligonucleotides.

In some embodiments, a DMD oligonucleotide, e.g., a DMD oligonucleotide, is capable of mediating skipping of exon 53. Non-limiting examples of such DMD oligonucleotides include: WV-12880, WV-13826, WV-13827, WV-14791, WV-9517, WV-13835, WV-13864, WV-14344, and other DMD oligonucleotides having a base sequence which comprises at least 15 contiguous bases of any of these DMD oligonucleotides.

In some embodiments, the present disclosure pertains to a method of manufacturing any DMD oligonucleotide disclosed herein (e.g., in Table A1).

In some embodiments, the present disclosure pertains to a medicament comprising any DMD oligonucleotide disclosed herein (e.g., in Table A1).

In some embodiments, the present disclosure provides a chirally controlled DMD oligonucleotide composition of a DMD oligonucleotide selected from any of the Tables.

In some embodiments, a DMD oligonucleotide comprises an internucleotidic linkage which is a natural phosphate linkage or a phosphorothioate internucleotidic linkage. In some embodiments, a phosphorothioate internucleotidic linkage is not chirally controlled. In some embodiments, a phosphorothioate internucleotidic linkage is a chirally controlled internucleotidic linkage (e.g., Sp or Rp).

In some embodiments, a DMD oligonucleotide comprises a non-negatively charged internucleotidic linkage. In some embodiments, a DMD oligonucleotide comprises a neutral internucleotidic linkage. In some embodiments, a neutral internucleotidic linkage is or comprises a cyclic guanidine moiety.

In some embodiments, an internucleotidic linkage comprises a guanidine moiety. In some embodiments, an internucleotidic linkage comprises a cyclic guanidine moiety. In some embodiments, an internucleotidic linkage comprising a cyclic guanidine moiety has the structure of: n001. In some embodiments, a neutral internucleotidic linkage or internucleotidic linkage comprising a cyclic guanidine moiety is stereochemically controlled.

In general, properties of DMD oligonucleotide compositions as described herein can be assessed using any appropriate assay. Relative toxicity and/or protein binding properties for different compositions (e.g., stereocontrolled vs non-stereocontrolled, and/or different stereocontrolled compositions) are typically desirably determined in the same assay, in some embodiments substantially simultaneously and in some embodiments with reference to historical results.

Those of skill in the art will be aware of and/or will readily be able to develop appropriate assays for particular DMD oligonucleotide compositions. The present disclosure provides descriptions of certain particular assays, for example that may be useful in assessing one or more features of DMD oligonucleotide composition behavior e.g., complement activation, injection site inflammation, protein biding, etc.

For example, certain assays that may be useful in the assessment of toxicity and/or protein binding properties of DMD oligonucleotide compositions may include any assay described and/or exemplified herein.

In some embodiments, the present disclosure provides a DMD oligonucleotide composition comprising a plurality of DMD oligonucleotides which share the same base sequence, wherein oligonucleotides of the plurality comprise at least 1, 2, 3, 4, 5, 6, 7, 8, 9, 10, 11, 12, 13, 14, 15, 16, 17, 18, 19, or 20 chirally controlled internucleotidic linkages. In some embodiments, the present disclosure provides a DMD oligonucleotide composition comprising a plurality of DMD oligonucleotides which share the same constitution, wherein oligonucleotides of the plurality comprise at least 1, 2, 3, 4, 5, 6, 7, 8, 9, 10, 11, 12, 13, 14, 15, 16, 17, 18, 19, or 20 chirally controlled internucleotidic linkages. In some embodiments, when an oligonucleotide compositions is contacted with a DMD transcript in a DMD transcript splicing system, splicing of the DMD transcript is altered (e.g., skipping of exon 51 or 53 is increased) relative to that observed under a reference condition selected from the group consisting of absence of the composition, presence of a reference composition, and combinations thereof. In some embodiments, splicing products with one exon skipped (e.g., in some embodiments, exon 51; in some embodiments, exon 53) and/or proteins encoded thereby are provided at an increased level (e.g., 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500 or more fold) compared to a reference condition.

In some embodiments, the present disclosure provides a DMD oligonucleotide composition, comprising a plurality of DMD oligonucleotides of a particular DMD oligonucleotide type defined by:
1) base sequence;
2) pattern of backbone linkages;
3) pattern of backbone chiral centers; and
4) pattern of backbone phosphorus modifications,
wherein:
oligonucleotides of the plurality comprise at least 1, 2, 3, 4, 5, 6, 7, 8, 9, 10, 11, 12, 13, 14, 15, 16, 17, 18, 19, or 20 chirally controlled internucleotidic linkages; and
the DMD oligonucleotide composition being characterized in that, when it is contacted with a DMD transcript in a DMD transcript splicing system, splicing of the DMD transcript is altered (e.g., skipping of exon 51 or 53 is increased) relative to that observed under a reference condition selected from the group consisting of absence of the composition, presence of a reference composition, and combinations thereof.

In some embodiments, the present disclosure provides a method for treating or preventing muscular dystrophy, comprising administering to a subject a DMD oligonucleotide composition described herein.

In some embodiments, the present disclosure provides a method for treating or preventing muscular dystrophy, comprising administering to a subject a DMD oligonucleotide composition comprising a plurality of DMD oligonucleotides, which:
1) have a common base sequence complementary to a target sequence in a DMD transcript; and
2) comprise one or more modified sugar moieties and modified internucleotidic linkages,
the DMD oligonucleotide composition being characterized in that, when it is contacted with the DMD transcript in a DMD transcript splicing system, splicing of the DMD transcript is altered (e.g., skipping of exon 51 or 53 is increased) relative to that observed under reference conditions selected from the group consisting of absence of the composition, presence of a reference composition, and combinations thereof, wherein the DMD oligonucleotide is a DMD oligonucleotide described herein (e.g., in Table A1).

In some embodiments, the present disclosure provides a method for treating or preventing muscular dystrophy, comprising administering to a subject a chirally controlled DMD oligonucleotide composition comprising a plurality of DMD oligonucleotides of a particular DMD oligonucleotide type defined by:
1) base sequence;
2) pattern of backbone linkages;
3) pattern of backbone chiral centers; and
4) pattern of backbone phosphorus modifications, which composition is chirally controlled and it is enriched, relative to a substantially racemic preparation of DMD oligonucleotides having the same base sequence, for DMD oligonucleotides of the particular DMD oligonucleotide type, wherein:
the DMD oligonucleotide composition being characterized in that, when it is contacted with the DMD transcript in a DMD transcript splicing system, splicing of the DMD transcript is altered (e.g., skipping of exon 51 or 53 is increased) relative to that observed under reference conditions selected from the group consisting of absence of the composition, presence of a reference composition, and combinations thereof, wherein the DMD oligonucleotide is a DMD oligonucleotide described herein (e.g., in Table A1).

In some embodiments, provided oligonucleotides comprise at least one, e.g., 1, 2, 3, 4, 5, 6, 7, 8, 9, 10, 11, 12, 13, 14, 15, 16, 17, 18, 19, 20 non-negatively charged internucleotidic linkages, which are optionally and independently chirally controlled. In some embodiments, a provided oligonucleotide comprises a chirally controlled non-negatively charged internucleotidic linkage. In some embodiments, a non-negatively charged internucleotidic linkage is n001.

In some embodiments, the present disclosure provides a DMD oligonucleotide composition, comprising a plurality of DMD oligonucleotides of a particular DMD oligonucleotide type defined by:
1) base sequence;
2) pattern of backbone linkages;
3) pattern of backbone chiral centers; and
4) pattern of backbone phosphorus modifications,
wherein:
oligonucleotides of the plurality comprise at least 1, 2, 3, 4, 5, 6, 7, 8, 9, 10, 11, 12, 13, 14, 15, 16, 17, 18, 19, or 20 chirally controlled internucleotidic linkages; and
oligonucleotides of the plurality comprise at least 1, 2, 3, 4, 5, 6, 7, 8, 9, 10, 11, 12, 13, 14, 15, 16, 17, 18, 19, or 20 non-negatively charged internucleotidic linkages.

In some embodiments, in a muscular dystrophy, after skipping DMD exon 51 or DMD exon 53, functions of dystrophin can be restored, or at least partially restored, through an internally truncated but at least partially functional Dystrophin protein variant.

In some embodiments, a muscular dystrophy includes but is not limited to Duchenne (Duchenne's) muscular dystrophy (DMD) and Becker (Becker's) muscular dystrophy (BMD).

In some embodiments, the present disclosure provides a pharmaceutical composition comprising a DMD oligonucleotide or a DMD oligonucleotide composition of the present disclosure and a pharmaceutically acceptable carrier.

In some embodiments, the present disclosure provides a method for treating muscular dystrophy, Duchenne (Duchenne's) muscular dystrophy (DMD), or Becker (Becker's) muscular dystrophy (BMD), comprising administering to a subject susceptible thereto or suffering therefrom a composition described in the present disclosure.

In some embodiments, the present disclosure provides a method for treating muscular dystrophy, Duchenne (Duchenne's) muscular dystrophy (DMD), or Becker (Becker's) muscular dystrophy (BMD), comprising administering to a subject susceptible thereto or suffering therefrom a composition comprising any DMD oligonucleotide disclosed herein. In some embodiments, a composition is a pharmaceutical composition comprising an effective amount of an oligonucleotide and is chirally controlled. In some embodiments, an oligonucleotide is provided as a salt form, e.g., a sodium salt.

In some embodiments, the present disclosure provides a method for treating muscular dystrophy, Duchenne (Duchenne's) muscular dystrophy (DMD), or Becker (Becker's) muscular dystrophy (BMD), comprising (a) administering to a subject susceptible thereto or suffering therefrom a composition comprising any DMD oligonucleotide disclosed herein, and (b) administering to the subject an additional treatment which is capable of preventing, treating, ameliorating or slowing the progress of at least one symptom of muscular dystrophy, Duchenne (Duchenne's) muscular dystrophy (DMD), or Becker (Becker's) muscular dystrophy (BMD).

Definitions

As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means ±5 mg/kg/day.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Dosing regimen: As used herein, a "dosing regimen" or "therapeutic regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

Heteroatom: The term "heteroatom" means an atom that is not carbon or hydrogen. In some embodiments, a heteroatom is oxygen, sulfur, nitrogen, phosphorus, boron or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl); etc.). In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur.

In vitro: As used herein, the term "in vitro" refers to events that occur in an artificial environment, e.g., in a test tube or reaction vessel, in cell culture, etc., rather than within an organism (e.g., animal, plant, and/or microbe).

In vivo: As used herein, the term "in vivo" refers to events that occur within an organism (e.g., animal, plant, and/or microbe).

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a controlled therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66:1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate. In some embodiments, a provided compound, e.g., an oligonucleotide, comprises one or more acidic groups (e.g., natural phosphate linkage groups, phosphorothioate linkage groups, etc.) and a pharmaceutically acceptable salt is an alkali, alkaline earth metal, or ammonium (e.g., an ammonium salt of $N(R)_3$, wherein each R is independently as defined and described in the present disclosure) salt. Representative alkali or alkaline earth metal salts include salts of sodium, lithium, potassium, calcium, magnesium, and the like. In some embodiments, a pharmaceutically acceptable salt is a sodium salt. In some embodiments, a pharmaceutically acceptable salt is a potassium salt. In some embodiments, a pharmaceutically acceptable salt is a calcium salt. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate. In some embodiments, a provided compound comprises more than one acid groups, for example, an oligonucleotide may comprise two or more acidic groups (e.g., in natural phosphate linkages and/or modified internucleotidic linkages). In some embodiments, a pharmaceutically acceptable salt, or generally a salt, of such a compound comprises two or more cations, which can be the same or different. In some embodiments, in a pharmaceutically acceptable salt (or generally, a salt), each acidic group having sufficient acidity independently exists as its salt form (e.g., in an oligonucleotide comprising natural phosphate linkages and phosphorothioate internucleotidic linkages, each of the natural phosphate linkages and phosphorothioate internucleotidic linkages independently exists as its salt form). In some embodiments, a pharmaceutically acceptable salt of an oligonucleotide, e.g., a provided DMD oligonucleotide, is a sodium salt of a provided DMD oligonucleotide. In some embodiments, a pharmaceutically acceptable salt of an oligonucleotide, e.g., a DMD oligonucleotide, is a sodium salt of such an oligonucleotide, wherein each acidic linkage, e.g., each natural phosphate linkage and phosphorothioate internucleotidic linkage, exists as a sodium salt form (all sodium salt).

Protecting group: The term "protecting group," as used herein, is well known in the art and includes those described in detail in *Protecting Groups in Organic Synthesis*, T. W. Greene and P. G. M. Wuts, 3$^{rd}$ edition, John Wiley & Sons, 1999, the entirety of which is incorporated herein by reference. Also included are those protecting groups specially adapted for nucleoside and nucleotide chemistry, e.g., those described in *Current Protocols in Nucleic Acid Chemistry*, edited by Serge L. Beaucage et al. 06/2012, the entirety of Chapter 2 is incorporated herein by reference. Suitable amino-protecting groups include methyl carbamate, ethyl carbamante, 9-fluorenylmethyl carbamate (Fmoc), 9-(2-sulfo) fluorenylmethyl carbamate, 9-(2,7-dibromo) fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl) ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl) methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido) benzyl carbamate, 1,1-dimethyl-3-(N,N-dimethylcarboxamido) propyl carbamate, 1,1-dimethylpropynyl carbamate, di (2-pyridyl) methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl) ethyl carbamate, 1-methyl-1-(p-phenylazophenyl) ethyl carbamate, 1-methyl-1-phenylethyl carbamate, 1-methyl-1-(4-pyridyl) ethyl carbamate, phenyl carbamate, p-(phenylazo) benzyl carbamate, 2,4,6-tri-t-butylphenyl carbamate, 4-(trimethylammonium) benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino) acetamide, 3-(p-hydroxyphenyl) propanamide, 3-(o-nitrophenyl) propanamide, 2-methyl-2-(0-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl) ethoxy]methylamine (SEM), N-3-acetoxypropylamine, N-(1-isopropyl-4-nitro-2-oxo-3-pyroolin-3-yl) amine, quaternary ammonium salts, N-benzylamine, N-di (4-methoxyphenyl)methylamine, N-5-dibenzosuberylamine, N-triphenylmethylamine (Tr), N-[(4-methoxyphenyl]diphenylmethylJamine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl) mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl (pentacarbonylchromium-or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, 0-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4- methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), B-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy) methyl (p-AOM), guaiacolmethyl t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S, S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, a-naphthyldiphenylmethyl, p-methoxyphenyldiphenylmethyl, di (p-methoxyphenyl)phenylmethyl, tri (p-methoxyphenyl)methyl, 4-(4'-bromophenacyloxyphenyl) diphenylmethyl, 4,4',4"-tris (4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl) bis(4',4"-dimethoxyphenyl)methyl, 1,1-bis(4-methoxyphenyl)-1'-pyrenylmethyl, 9-anthryl, 9-(9-phenyl) xanthenyl, 9-(9-phenyl-10-oxo) anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio) pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, a-methoxybenzylidene ortho ester, 1-(N,N-dimethylamino)ethylidene derivative, a-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In some embodiments, a hydroxyl protecting group is acetyl, t-butyl, tbutoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, trityl, monomethoxytrityl (MMTr), 4,4'-dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris(benzoyloxy)trityl, diphenylcarbamoyl, levulinyl, 2-(dibromomethyl)benzoyl (Dbmb), 2-(isopropylthiomethyl)benzoyl (Ptmt), 9-phenylxanthen-9-yl (pixyl) or 9-(p-methoxyphenyl)xanthine-9-yl (MOX). In some embodiments, each of the hydroxyl protecting groups is, independently selected from acetyl, benzyl, t-butyldimethylsilyl, t-butyldiphenylsilyl and 4,4'-dimethoxytrityl. In some embodiments, the hydroxyl protecting group is selected from the group consisting of trityl, monomethoxytrityl and 4,4'-dimethoxytrityl group.

In some embodiments, a phosphorous protecting group is a group attached to the internucleotide phosphorous linkage throughout oligonucleotide synthesis. In some embodiments, the phosphorous protecting group is attached to the sulfur atom of the internucleotide phosphorothioate linkage. In some embodiments, the phosphorous protecting group is attached to the oxygen atom of the internucleotide phosphorothioate linkage. In some embodiments, the phosphorous protecting group is attached to the oxygen atom of the internucleotide phosphate linkage. In some embodiments the phosphorous protecting group is 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl) aminoethyl, 4-[N-methyl-N-(2,2,2-trifluoroacetyl)amino] butyl.

Protein: As used herein, the term "protein" refers to a polypeptide (i.e., a string of at least two amino acids linked to one another by peptide bonds). In some embodiments, proteins include only naturally-occurring amino acids. In some embodiments, proteins include one or more non-naturally-occurring amino acids (e.g., moieties that form one or more peptide bonds with adjacent amino acids). In some embodiments, one or more residues in a protein chain contain a non-amino-acid moiety (e.g., a glycan, etc). In some embodiments, a protein includes more than one polypeptide chain, for example linked by one or more disulfide bonds or associated by other means. In some embodiments, proteins contain L-amino acids, D-amino acids, or both; in some embodiments, proteins contain one or more amino acid modifications or analogs known in the art. Useful modifications include, e.g., terminal acetylation, amidation, methylation, etc. The term "peptide" is generally used to refer to a polypeptide having a length of less than about 100 amino acids, less than about 50 amino acids, less than 20 amino acids, or less than 10 amino acids.

Subject: As used herein, the term "subject" or "test subject" refers to any organism to which a provided compound or composition is administered in accordance with the present disclosure e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition, e.g., muscular dystrophy.

Substantially: As used herein, the term "substantially" refers to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder, and/or condition, e.g., muscular dystrophy has been diagnosed with and/or displays one or more symptoms of the disease, disorder, and/or condition, e.g., muscular dystrophy.

Susceptible to: An individual who is "susceptible to" a disease, disorder, and/or condition, e.g., muscular dystrophy is one who has a higher risk of developing the disease, disorder, and/or condition than does a member of the general public. In some embodiments, an individual who is susceptible to a disease, disorder, and/or condition, e.g. muscular dystrophy may not have been diagnosed with the disease, disorder, and/or condition. In some embodiments, an individual who is susceptible to a disease, disorder, and/or condition, e.g., muscular dystrophy may exhibit symptoms of the disease, disorder, and/or condition. In some embodiments, an individual who is susceptible to a disease, disorder, and/or condition, e.g., muscular dystrophy may not exhibit symptoms of the disease, disorder, and/or condition. In some embodiments, an individual who is susceptible to a disease, disorder, and/or condition, e.g., muscular dystrophy will develop the disease, disorder, and/or condition. In some embodiments, an individual who is susceptible to a disease, disorder, and/or condition, e.g., muscular dystrophy will not develop the disease, disorder, and/or condition.

Systemic: The phrases "systemic administration," "administered systemically," "peripheral administration," and "administered peripherally" as used herein have their art-understood meaning referring to administration of a compound or composition such that it enters the recipient's system.

Tautomeric forms: The phrase "tautomeric forms," as used herein and generally understood in the art, is used to describe different isomeric forms of organic compounds that are capable of facile interconversion. Tautomers may be characterized by the formal migration of a hydrogen atom or proton, accompanied by a switch of a single bond and adjacent double bond. In some embodiments, tautomers may result from prototropic tautomerism (i.e., the relocation of a proton). In some embodiments, tautomers may result from valence tautomerism (i.e., the rapid reorganization of bonding electrons). All such tautomeric forms are intended to be included within the scope of the present disclosure. In some embodiments, tautomeric forms of a compound exist in mobile equilibrium with each other, so that attempts to prepare the separate substances results in the formation of a mixture. In some embodiments, tautomeric forms of a compound are separable and isolatable compounds. In some embodiments of the disclosure, chemical compositions may be provided that are or include pure preparations of a single tautomeric form of a compound. In some embodiments of the disclosure, chemical compositions may be provided as mixtures of two or more tautomeric forms of a compound. In certain embodiments, such mixtures contain equal amounts of different tautomeric forms; in certain embodiments, such mixtures contain different amounts of at least two different tautomeric forms of a compound. In some embodiments of the disclosure, chemical compositions may contain all tautomeric forms of a compound. In some embodiments of the disclosure, chemical compositions may contain less than all tautomeric forms of a compound. In some embodiments of the disclosure, chemical compositions may contain one or more tautomeric forms of a compound in amounts that vary over time as a result of interconversion. In some embodiments of the disclosure, the tautomerism is keto-enol tautomerism. One of skill in the chemical arts would recognize that a keto-enol tautomer can be "trapped" (i.e., chemically modified such that it remains in the "enol" form) using any suitable reagent known in the chemical arts in to provide an enol derivative that may subsequently be isolated using one or more suitable techniques known in the art. Unless otherwise indicated, the present disclosure encompasses all tautomeric forms of relevant compounds, whether in pure form or in admixture with one another.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition, e.g., muscular dystrophy.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, e.g., muscular dystrophy, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition, e.g., muscular dystrophy is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are utilized to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition, e.g., muscular dystrophy. Treatment may be administered to a subject who does not exhibit signs of a disease, disorder, and/or condition, e.g., muscular dystrophy. In some embodiments, treatment may be administered to a subject who exhibits only early signs of the disease, disorder, and/or condition, for example for the purpose of decreasing the risk of developing pathology associated with the disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Unsaturated: The term "unsaturated," as used herein, means that a moiety has one or more units of unsaturation.

Wild-type: As used herein, the term "wild-type" has its art-understood meaning that refers to an entity having a structure and/or activity as found in nature in a "normal" (as contrasted with mutant, diseased, altered, etc) state or context. Those of ordinary skill in the art will appreciate that wild type genes and polypeptides often exist in multiple different forms (e.g., alleles).

Nucleic acid: The term "nucleic acid" includes any nucleotides, analogs thereof, and polymers thereof. The term "polynucleotide" as used herein refer to a polymeric form of nucleotides of any length, either ribonucleotides (RNA) or deoxyribonucleotides (DNA) or analogs thereof. These terms refer to the primary structure of the molecules and include double- and single-stranded DNA, and double- and single-stranded RNA. These terms include, as equivalents, analogs of either RNA or DNA made from nucleotide analogs and modified polynucleotides such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorus-atom bridges (also referred to herein as "internucleotidic linkages"). The term encompasses nucleic acids containing any combinations of nucleobases, modified nucleobases, sugars, modified sugars, natural natural phosphate internucleotidic linkages or non-natural internucleotidic linkages. Examples include, and are not limited to, nucleic acids containing ribose moieties, nucleic acids containing deoxy-ribose moieties, nucleic acids containing both ribose and deoxyribose moieties, nucleic acids containing ribose and modified ribose moieties. Unless otherwise specified, the prefix poly- refers to a nucleic acid containing 2 to about 10,000 nucleotide monomer units and wherein the prefix oligo- refers to a nucleic acid containing 2 to about 200 nucleotide monomer units.

Nucleotide: The term "nucleotide" as used herein refers to a monomeric unit of a polynucleotide that consists of a heterocyclic base, a sugar, and one or more phosphate groups or phosphorus-containing internucleotidic linkages. Naturally occurring bases, (guanine, (G), adenine, (A), cytosine, (C), thymine, (T), and uracil (U)) are derivatives of purine or pyrimidine, though it should be understood that naturally and non-naturally occurring base analogs are also included. Naturally occurring sugars include the pentose (five-carbon sugar) deoxyribose (which is found in natural DNA) or ribose (which is found in natural RNA), though it should be understood that naturally and non-naturally occurring sugar analogs are also included, such as sugars with 2'-modifications, sugars in locked nucleic acid (LNA) and phosphorodiamidate morpholino oligomer (PMO). Nucleotides are linked via internucleotidic linkages to form nucleic acids, or polynucleotides. Many internucleotidic linkages are known in the art (such as, though not limited to, natural phosphate linkage, phosphorothioate linkages, boranophosphate linkages and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, etc. In some embodiments, a nucleotide is a natural nucleotide comprising a naturally occurring nucleobase, a natural occurring sugar and the natural phosphate linkage. In some embodiments, a nucleotide is a modified nucleotide or a nucleotide analog, which is a structural analog that can be used in lieu of a natural nucleotide.

Modified nucleotide: The term "modified nucleotide" includes any chemical moiety which differs structurally from a natural nucleotide but is capable of performing at least one function of a natural nucleotide. In some embodiments, a modified nucleotide comprises a modification at a sugar, base and/or internucleotidic linkage. In some embodiments, a modified nucleotide comprises a modified sugar, modified nucleobase and/or modified internucleotidic linkage. In some embodiments, a modified nucleotide is capable of at least one function of a nucleotide, e.g., forming a subunit in a polymer capable of base-pairing to a nucleic acid comprising an at least complementary sequence of bases.

Analog: The term "analog" includes any chemical moiety which differs structurally from a reference chemical moiety or class of moieties, but which is capable of performing at least one function of such a reference chemical moiety or class of moieties. As non-limiting examples, a nucleotide analog differs structurally from a nucleotide but performs at least one function of a nucleotide; a nucleobase analog differs structurally from a nucleobase but performs at least one function of a nucleobase; a sugar analog differs structurally from a nucleobase but performs at least one function of a sugar, etc.

Nucleoside: The term "nucleoside" refers to a moiety wherein a nucleobase or a modified nucleobase is covalently bound to a sugar or modified sugar.

Modified nucleoside: The term "modified nucleoside" refers to a chemical moiety which is chemically distinct from a natural nucleoside, but which is capable of performing at least one function of a nucleoside. In some embodiments, a modified nucleoside is derived from or chemically similar to a natural nucleoside, but which comprises a chemical modification which differentiates it from a natural nucleoside. Non-limiting examples of modified nucleosides include those which comprise a modification at the base and/or the sugar. Non-limiting examples of modified nucleosides include those with a 2'-modification at a sugar. Non-limiting examples of modified nucleosides also include abasic nucleosides (which lack a nucleobase). In some embodiments, a modified nucleoside is capable of at least one function of a nucleoside, e.g., forming a moiety in a polymer capable of base-pairing to a nucleic acid comprising an at least complementary sequence of bases.

Nucleoside analog: The term "nucleoside analog" refers to a chemical moiety which is chemically distinct from a natural nucleoside, but which is capable of performing at least one function of a nucleoside. In some embodiments, a nucleoside analog comprises an analog of a sugar and/or an analog of a nucleobase. In some embodiments, a modified nucleoside is capable of at least one function of a nucleoside, e.g., forming a moiety in a polymer capable of base-pairing to a nucleic acid comprising a complementary sequence of bases.

Sugar: The term "sugar" refers to a monosaccharide or polysaccharide in closed and/or open form. In some embodiments, sugars are monosaccharides. In some embodiments, sugars are polysaccharides. Sugars include, but are not limited to, ribose, deoxyribose, pentofuranose, pentopyranose, and hexopyranose moieties. As used herein, the term "sugar" also encompasses structural analogs used in lieu of conventional sugar molecules, such as glycol, polymer of which forms the backbone of the nucleic acid analog, glycol nucleic acid ("GNA"), etc. As used herein, the term "sugar" also encompasses structural analogs used in lieu of natural or naturally-occurring nucleotides, such as modified sugars and nucleotide sugars. In some embodiments, a sugar is D-2-deoxyribose. In some embodiments, a sugar is beta-D-deoxyribofuranose. In some embodiments, a sugar moiety is a beta-D-deoxyribofuranose moiety. In some embodiments, a sugar is D-ribose. In some embodiments, a sugar is beta-D-ribofuranose. In some embodiments, a sugar moiety is a beta-D-ribofuranose moiety. In some embodiments, a sugar is optionally substituted beta-D-deoxyribofuranose or beta-D-ribofuranose. In some embodiments, a sugar moiety is an optionally substituted beta-D-deoxyribofuranose or beta-D-ribofuranose moiety. In some embodiments, a sugar moiety/unit in an oligonucleotide, e.g., a DMD oligonucleotide, nucleic acid, etc. is a sugar which comprises one or more carbon atoms each independently connected to an internucleotidic linkage, e.g., optionally substituted beta-D-deoxyribofuranose or beta-D-ribofuranose whose 5'-C and/or 3'-C are each independently connected to an internucleotidic linkage (e.g., a natural phosphate linkage, a modified internucleotidic linkage, a chirally controlled internucleotidic linkage, etc.).

Modified sugar: The term "modified sugar" refers to a moiety that can replace a sugar. A modified sugar mimics the spatial arrangement, electronic properties, or some other physicochemical property of a sugar. In some embodiments, a modified sugar is substituted beta-D-deoxyribofuranose or beta-D-ribofuranose. In some embodiments, a modified sugar comprises a 2'-modification. In some embodiments, a modified sugar comprises a linker (e.g., optionally substituted bivalent heteroaliphatic) connecting two sugar carbon atoms (e.g., C2 and C4), e.g., as found in LNA. In some embodiments, a linker is —O—CH(R)—, wherein R is as described in the present disclosure. In some embodiments, a linker is —O—CH(R)—, wherein O is connected to C2, and —CH(R)— is connected to C4 of a sugar, and R is as described in the present disclosure. In some embodiments, R is methyl. In some embodiments, R is —H. In some embodiments, —CH(R)— is of S configuration. In some embodiments, —CH(R)— is of R configuration.

Nucleobase: The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, a modified nucleobase is a substituted nucleobase which nucleobase is selected from A, T, C, G, U, and tautomers thereof. In some embodiments, the naturally-occurring nucleobases are modified adenine, guanine, uracil, cytosine, or thymine. In some embodiments, the naturally-occurring nucleobases are methylated adenine, guanine, uracil, cytosine, or thymine. In some embodiments, a nucleobase is a "modified nucleobase," e.g., a nucleobase other than adenine (A), guanine (G), uracil (U), cytosine (C), and thymine (T). In some embodiments, the modified nucleobases are methylated adenine, guanine, uracil, cytosine, or thymine. In some embodiments, the modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex. As used herein, the term "nucleobase" also encompasses structural analogs used in lieu of natural or naturally-occurring nucleotides, such as modified nucleobases and nucleobase analogs. In some embodiments, a nucleobase is an optionally substituted A, T, C, G, or U, or a substituted nucleobase which nucleobase is selected from A, T, C, G, U, and tautomers thereof.

Modified nucleobase: The terms "modified nucleobase", "modified base" and the like refer to a chemical moiety which is chemically distinct from a nucleobase, but which is capable of performing at least one function of a nucleobase. In some embodiments, a modified nucleobase is a nucleobase which comprises a modification. In some embodiments, a modified nucleobase is capable of at least one function of a nucleobase, e.g., forming a moiety in a polymer capable of base-pairing to a nucleic acid comprising an at least complementary sequence of bases. In some embodiments, a modified nucleobase is a substituted nucleobase which nucleobase is selected from A, T, C, G, U, and tautomers thereof.

Chiral ligand: The term "chiral ligand" or "chiral auxiliary" refers to a moiety that is chiral and can be incorporated into a reaction so that the reaction can be carried out with certain stereoselectivity. In some embodiments, the term may also refer to a compound that comprises such a moiety.

Blocking group: The term "blocking group" refers to a group that masks the reactivity of a functional group. The functional group can be subsequently unmasked by removal of the blocking group. In some embodiments, a blocking group is a protecting group.

Moiety: The term "moiety" refers to a specific segment or functional group of a molecule. Chemical moieties are often recognized chemical entities embedded in or appended to a molecule. In some embodiments, a moiety of a compound is a monovalent, bivalent, or polyvalent group formed from the compound by removing one or more —H and/or equivalents thereof from a compound. In some embodiments, depending on its context, "moiety" may also refer to a compound or entity from which the moiety is derived from.

Solid support: The term "solid support" when used in the context of preparation of nucleic acids, oligonucleotides, or other compounds refers to any support which enables synthesis of nucleic acids, oligonucleotides or other compounds. In some embodiments, the term refers to a glass or a polymer, that is insoluble in the media employed in the reaction steps performed to synthesize nucleic acids, and is derivatized to comprise reactive groups. In some embodiments, the solid support is Highly Cross-linked Polystyrene (HCP) or Controlled Pore Glass (CPG). In some embodiments, the solid support is Controlled Pore Glass (CPG). In some embodiments, the solid support is hybrid support of Controlled Pore Glass (CPG) and Highly Cross-linked Polystyrene (HCP).

Reading frame: The term "reading frame" refers to one of the six possible reading frames, three in each direction, of a double stranded DNA molecule. The reading frame that is used determines which codons are used to encode amino acids within the coding sequence of a DNA molecule.

Antisense: As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can associate via hydrogen bonds to a sense nucleic acid molecule. In some embodiments, transcripts, e.g., DMD transcripts, may be generated from both strands. In some embodiments, transcripts may or may not encode protein products. In some embodiments, when directed or targeted to a particular nucleic acid sequence, a "antisense" sequence may refer to a sequence that is complementary to the particular nucleic acid sequence.

Oligonucleotide: the term "oligonucleotide" refers to a polymer or oligomer of nucleotide monomers, containing any combination of nucleobases, modified nucleobases, sugars, modified sugars, natural phosphate linkages, or non-natural internucleotidic linkages.

Oligonucleosides of the present disclosure can be of various lengths. In particular embodiments, oligonucleosides can range from about 20 to about 200 nucleosides in length. In various related embodiments, oligonucleosides, single-stranded, double-stranded, and triple-stranded, can range in length from about 4 to about 10 nucleosides, from about 10 to about 50 nucleosides, from about 20 to about 50 nucleosides, from about 15 to about 30 nucleosides, from about 20 to about 30 nucleosides in length. In some embodiments, the oligonucleoside is from about 9 to about 39 nucleosides in length. In some embodiments, the oligonucleoside is at least 15 nucleosides in length. In some embodiments, the oligonucleoside is at least 20 nucleosides in length. In some embodiments, the oligonucleoside is at least 25 nucleosides in length. In some embodiments, the oligonucleoside is at least 30 nucleosides in length. In some embodiments, the oligonucleoside is a duplex of complementary strands of at least 18 nucleosides in length. In some embodiments, the oligonucleoside is a duplex of complementary strands of at least 21 nucleosides in length. In some embodiments, for the purpose of oligonucleotide lengths, each nucleoside counted independently comprises an optionally substituted nucleobase selected from A, T, C, G, U and their tautomers.

Internucleotidic linkage: As used herein, the phrase "internucleotidic linkage" refers generally to a linkage, typically a phosphorus-containing linkage, between nucleotide units of a nucleic acid or an oligonucleotide, and is interchangeable with "inter-sugar linkage", "internucleosidic linkage," and "phosphorus atom bridge," as used above and herein. As appreciated by those skilled in the art, natural DNA and RNA contain natural phosphate linkages. In some embodiments, an internucleotidic linkage is a natural phosphate linkage (—OP(O)(OH)O—, typically existing as its anionic form —OP(O)(O—)O— at pH e.g., ~7.4), as found in naturally occurring DNA and RNA molecules. In some embodiments, an internucleotidic linkage is a modified internucleotidic linkage (or non-natural internucleotidic linkage), which is structurally different from a natural phosphate linkage but may be utilized in place of a natural phosphate linkage, e.g., phosphorothioate internucleotidic linkage, PMO linkages, etc. In some embodiments, an internucleotidic linkage is a modified internucleotidic linkage wherein one or more oxygen atoms of a natural phosphodiester linkage are independently replaced by one or more organic or inorganic moieties. In some embodiments, such an organic or inorganic moiety is selected from but not limited to =S, =Se, =NR', —SR', —SeR', —N(R')$_2$, B(R')$_3$, —S—, —Se—, and —N(R')—, wherein each R' is independently as defined and described below. In some embodiments, an internucleotidic linkage is a phosphotriester linkage. In some embodiments, an internucleotidic linkage is a phosphorothioate diester linkage (phosphorothioate internucleotidic linkage,

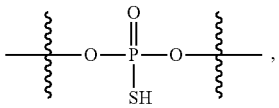 [SMILES: *OP(=O)(S)O*]

typically existing as its anionic form —OP(O)(S$^-$)O— at pH e.g., ~7.4). It is understood by a person of ordinary skill in the art that an internucleotidic linkage may exist as an anion or cation at a given pH due to the existence of acid or base moieties in the linkage.

Unless otherwise specified, the Rp/Sp designations preceding an oligonucleotide sequence describe the configurations of linkage phosphorus in chirally controlled internucleotidic linkages sequentially from 5' to 3' of the oligonucleotide sequence.

Oligonucleotide type: As used herein, the phrase "oligonucleotide type" is used to define oligonucleotides that have a particular base sequence, pattern of backbone linkages (i.e., pattern of internucleotidic linkage types, for example, natural phosphate linkages, phosphorothioate internucleotidic linkages, negatively charged internucleotidic linkages, neutral internucleotidic linkages etc), pattern of backbone chiral centers (i.e. pattern of linkage phosphorus stereochemistry (Rp/Sp)), and pattern of backbone phosphorus modifications. In some embodiments, oligonucleotides of a common designated "type" are structurally identical to one another.

One of skill in the art will appreciate that synthetic methods of the present disclosure provide for a degree of control during the synthesis of an oligonucleotide (e.g., a DMD oligonucleotide) strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, an oligonucleotide strand is designed and/or selected in advance to have a particular combination of stereocenters at the linkage phosphorus. In some embodiments, an oligonucleotide strand is designed and/or determined to have a particular combination of modifications at the linkage phosphorus. In some embodiments, an oligonucleotide strand is designed and/or selected to have a particular combination of bases. In some embodiments, an oligonucleotide strand is designed and/or selected to have a particular combination of one or more of the above structural characteristics. The present disclosure provides compositions comprising or consisting of a plurality of oligonucleotide molecules (e.g., chirally controlled oligonucleotide compositions). In some embodiments, all such molecules are of the same type. In some embodiments, all such molecules are structurally identical to one another. In some embodiments, provided compositions comprise a plurality of oligonucleotides of different types, typically in predetermined (non-random) relative amounts. In some embodiments, an oligonucleotide is a DMD oligonucleotide as described herein.

Chiral control: As used herein, "chiral control" refers to control of the stereochemical designation of a chiral linkage phosphorus in a chiral internucleotidic linkage within an oligonucleotide (e.g., a DMD oligonucleotide). In some embodiments, a control is achieved through a chiral element that is absent from the sugar and base moieties of an oligonucleotide, for example, in some embodiments, a control is achieved through use of one or more chiral auxiliaries during oligonucleotide preparation as exemplified in the present disclosure, which chiral auxiliaries often are part of chiral phosphoramidites used during oligonucleotide preparation. In contrast to chiral control, a person having ordinary skill in the art appreciates that conventional oligonucleotide synthesis which does not use chiral auxiliaries cannot control stereochemistry at a chiral internucleotidic linkage if such conventional oligonucleotide synthesis is used to form the chiral internucleotidic linkage. In some embodiments, the stereochemical designation of each chiral linkage phosphorus in a chiral internucleotidic linkage within an oligonucleotide is controlled.

Chirally controlled oligonucleotide composition: The terms "chirally controlled (stereocontrolled or stereodefined) oligonucleotide composition", "chirally controlled (stereocontrolled or stereodefined) nucleic acid composition", and the like, as used herein, refers to a composition that comprises a plurality of oligonucleotides (or nucleic acids, chirally controlled oligonucleotides or chirally controlled nucleic acids) which share 1) a common base sequence, 2) a common pattern of backbone linkages; 3) a common pattern of backbone chiral centers, and 4) a common pattern of backbone phosphorus modifications (oligonucleotides of a particular type), wherein the plurality of oligonucleotides (or nucleic acids) share the same stereochemistry at one or more chiral internucleotidic linkages (chirally controlled internucleotidic linkages, whose chiral linkage phosphorus is Rp or Sp, not a random Rp and Sp mixture as non-chirally controlled internucleotidic linkages). Level of the plurality of oligonucleotides (or nucleic acids) in a chirally controlled oligonucleotide composition is non-random (predetermined, controlled). Chirally controlled oligonucleotide compositions are typically prepared through chirally controlled oligonucleotide preparation to stereoselectively form one or more chiral internucleotidic linkages (e.g., using chiral auxiliaries as exemplified in the present disclosure, compared to non-chirally controlled (stereorandom, non-stereoselective, racemic) oligonucleotide synthesis such as traditional phosphoramidite-based oligonucleotide synthesis using no chiral auxiliaries or chiral catalysts to purposefully control stereoselectivity). A chirally controlled oligonucleotide composition is enriched, relative to a substantially racemic preparation of oligonucleotides having the common base sequence, the common pattern of backbone linkages, and the common pattern of backbone phosphorus modifications, for oligonucleotides of the plurality. In some embodiments, a chirally controlled oligonucleotide composition comprises a plurality of oligonucleotides of a particular oligonucleotide type defined by: 1) base sequence; 2) pattern of backbone linkages; 3) pattern of backbone chiral centers; and 4) pattern of backbone phosphorus modifications, wherein it is enriched, relative to a substantially racemic preparation of oligonucleotides having the same base sequence, pattern of backbone linkages, and pattern of backbone phosphorus modifications, for oligonucleotides of the particular oligonucleotide type. As one having ordinary skill in the art readily appreciates, such enrichment can be characterized in that compared to a substantially racemic preparation, at each chirally controlled internucleotidic linkage, a higher level of the linkage phosphorus has the desired configuration. In some embodiments, each chirally controlled internucleotidic linkage independently has a diastereopurity of at least 80%, 85%, 90%, 91%, 92%, 93%, 94%, 95%, 96%, 97%, 98%, or 99% with respect to its chiral linkage phosphorus. In some embodiments, each independently has a diastereopurity of at least 90%. In some embodiments, each independently has a diastereopurity of at least 95%. In some embodiments, each independently has a diastereopurity of at least 97%. In some embodiments, each independently has a diastereopurity of at least 98%. In some embodiments, oligonucleotides of a plurality have the same constitution. In some embodiments, oligonucleotides of a plurality have the same constitution and stereochemistry, and are structurally identical.

In some embodiments, the plurality of oligonucleotides in a chirally controlled oligonucleotide composition share the same base sequence, the same, if any, nucleobase, sugar, and internucleotidic linkage modifications, and the same stereochemistry (Rp or Sp) independently at linkage phosphorus chiral centers of one or more chirally controlled internucleotidic linkages, though stereochemistry of certain linkage phosphorus chiral centers may differ. In some embodiments, about 0.1%-100%, (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition are oligonucleotides of the plurality. In some embodiments, about 0.1%-100%, (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence are oligonucleotides of the plurality. In some embodiments, about 0.1%-100%, (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, the common pattern of backbone linkages, and the common pattern of backbone phosphorus modifications are oligonucleotides of the plurality. In some embodiments, about 0.1%-100%, (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition, or of all oligonucleotides in a composition that share a common base sequence (e.g., of a plurality of oligonucleotide or an oligonucleotide type), or of all oligonucleotides in a composition that share a common base sequence, a common pattern of backbone linkages, and a common pattern of backbone phosphorus modifications (e.g., of a plurality of oligonucleotide or an oligonucleotide type), or of all oligonucleotides in a composition that share a common base sequence, a common patter of base modifications, a common pattern of sugar modifications, a common pattern of internucleotidic linkage types, and/or a common pattern of internucleotidic linkage modifications (e.g., of a plurality of oligonucleotide or an oligonucleotide type), or of all oligonucleotides in a composition that share the same constitution, are oligonucleotides of the plurality. In some embodiments, a percentage is at least $(DP)^{NCI}$, wherein DP is a percentage selected from 85%-100%, and NCI is the number of chirally controlled internucleotidic linkage. In some embodiments, DP is at least 85%, 90%, 91%, 92%, 93%, 94%, 95%, 96%, 97%, 98%, or 99%. In some embodiments, DP is at least 85%. In some embodiments, DP is at least 90%. In some embodiments, DP is at least 95%. In some embodiments, DP is at least 96%. In some embodiments, DP is at least 97%. In some embodiments, DP is at least 98%. In some embodiments, DP is at least 99%. In some embodiments, DP reflects diastereopurity of linkage phosphorus chiral centers chirally controlled internucleotidic linkages. In some embodiments, diastereopurity of a linkage phosphorus chiral center of an internucleotidic linkage may be typically assessed using an appropriate dimer comprising such an internucleotidic linkage and the two nucleoside units being linked by the internucleotidic linkage. In some embodiments, the plurality of oligonucleotides share the same stereochemistry at about 1-50 (e.g., about 1-10, 1-20, 5-10, 5-20, 10-15, 10-20, 10-25, 10-30, or about 1, 2, 3, 4, 5, 6, 7, 8, 9, 10, 11, 12, 13, 14, 15, 16, 17, 18, 19, or 20, or at least 1, 2, 3, 4, 5, 6, 7, 8, 9, 10, 11, 12, 13, 14, 15, 16, 17, 18, 19, or 20) chiral internucleotidic linkages. In some embodiments, the plurality of oligonucleotides share the same stereochemistry at about 0.1%-100% (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, about 5%, 10%, 15%, 20%, 25%, 30%, 35%, 40%, 45%, 50%, 55%, 60%, 65%, 70%, 75%, 80%, 85%, 90%, 95%, or 100%, or at least 5%, 10%, 15%, 20%, 25%, 30%, 35%, 40%, 45%, 50%, 55%, 60%, 65%, 70%, 75%, 80%, 85%, 90%, 95%, or 99%) of chiral internucleotidic linkages. In some embodiments, each chiral internucleotidic linkage is a chiral controlled internucleotidic linkage, and the composition is a completely chirally controlled oligonucleotide composition. In some embodiments, not all chiral internucleotidic linkages are chiral controlled internucleotidic linkages, and the composition is a partially chirally controlled oligonucleotide composition. In some embodiments, a chirally controlled oligonucleotide composition comprises predetermined levels of individual oligonucleotide or nucleic acids types. For instance, in some embodiments a chirally controlled oligonucleotide composition comprises one oligonucleotide type at a predetermined level (e.g., as described above). In some embodiments, a chirally controlled oligonucleotide composition comprises more than one oligonucleotide type, each independently at a predetermined level. In some embodiments, a chirally controlled oligonucleotide composition comprises multiple oligonucleotide types, each independently at a predetermined level. In some embodiments, a chirally controlled oligonucleotide composition is a composition of oligonucleotides of an oligonucleotide type, which composition comprises a predetermined level of a plurality of oligonucleotides of the oligonucleotide type. In some embodiments, a chirally controlled oligonucleotide composition is a chirally controlled DMD oligonucleotide composition comprising a plurality of DMD oligonucleotides. In some embodiments, a chirally controlled oligonucleotide composition is a composition of oligonucleotides of a DMD oligonucleotide type.

Chirally pure: as used herein, the phrase "chirally pure" is used to describe an oligonucleotide or compositions thereof, in which all or nearly all (the rest are impurities) of the oligonucleotide molecules exist in a single diastereomeric form with respect to the linkage phosphorus atoms. In many embodiments, as appreciated by those skilled in the art, a chirally pure oligonucleotide composition is substantially pure in that substantially all of the oligonucleotides in the composition are structurally identical (being the same stereoisomer).

Linkage phosphorus: as defined herein, the phrase "linkage phosphorus" is used to indicate that the particular phosphorus atom being referred to is the phosphorus atom present in an internucleotidic linkage, which phosphorus atom corresponds to the phosphorus atom of a natural phosphate linkage as occurs in naturally occurring DNA and RNA. In some embodiments, a linkage phosphorus atom is in a modified internucleotidic linkage. In some embodiments, a linkage phosphorus atom is chiral.

For purposes of this disclosure, the chemical elements are identified in accordance with the Periodic Table of the Elements, CAS version, *Handbook of Chemistry and Physics,* 67th Ed., 1986-87, inside cover.

Unless otherwise specified, salts, such as pharmaceutically acceptable acid or base addition salts, stereoisomeric forms, and tautomeric forms, of compounds (e.g., DMD oligonucleotides, agents, etc.) are included. Unless otherwise specified, singular forms "a", "an", and "the" include the plural reference unless the context clearly indicates otherwise (and vice versa). Thus, for example, a reference to "a compound" may include a plurality of such compounds.

DETAILED DESCRIPTION OF CERTAIN EMBODIMENTS

Synthetic oligonucleotides provide useful molecular tools in a wide variety of applications. For example, oligonucleotides are useful in therapeutic, diagnostic, research, and new nanomaterials applications. The use of naturally occurring nucleic acids (e.g., unmodified DNA or RNA) is limited, for example, by their susceptibility to endo- and exo-nucleases. As such, various synthetic counterparts have been developed to circumvent these shortcomings. These include synthetic oligonucleotides that contain chemical modification, e.g., base modifications, sugar modifications, backbone modifications, etc., which, among other things, render these molecules less susceptible to degradation and improve other properties of oligonucleotides, e.g., DMD oligonucleotides. Chemical modifications may also lead to certain undesired effects, such as increased toxicities, etc. From a structural point of view, modifications to natural phosphate linkages can introduce chirality, and certain properties of oligonucleotides may be affected by the configurations of the phosphorus atoms that form the backbone of the oligonucleotides.

In some embodiments, the present disclosure pertains to a DMD oligonucleotide or DMD oligonucleotide composition, which has a sequence at least partially complementary to a DMD target nucleic acid, and, in some embodiments, is capable of mediating skipping of a DMD exon. In some embodiments, a DMD oligonucleotide or DMD oligonucleotide composition is capable of mediating skipping of DMD exon 51 or 53.

In some embodiments, a DMD oligonucleotide or DMD oligonucleotide composition comprises any of various modifications to the internucleotidic linkages (e.g., backbone), sugars, and/or nucleobases.

In some embodiments, a DMD oligonucleotide or DMD oligonucleotide composition is any DMD oligonucleotide or DMD oligonucleotide composition disclosed herein (e.g., in Table A1).

In some embodiments, the chirality of the backbone (e.g., the configurations of the phosphorus atoms) or inclusion of natural phosphate linkages or non-natural internucleotidic linkages in the backbone and/or modifications of a sugar and/or nucleobase, and/or the addition of chemical moieties can affect properties and activities of DMD oligonucleotides, e.g., the ability of a DMD oligonucleotide (e.g., a DMD oligonucleotide antisense to a Dystrophin (DMD) DMD transcript sequence) to skip DMD exon 51 or DMD exon 53, and/or other properties of a DMD oligonucleotide, including but not limited to, increased stability, improved pharmacokinetics, and/or decreased immunogenicity, etc. Suitable assays for assessing properties and/or activities of provided compounds, e.g., DMD oligonucleotides, and compositions thereof are widely known in the art and can be utilized in accordance with the present disclosure.

In some embodiments, a DMD transcript is pre-mRNA. In some embodiments, a splicing product is mature RNA. In some embodiments, a splicing product is mRNA. In some embodiments, splicing modulation or alteration comprises skipping DMD exon 51 or DMD exon 53.

In some embodiments, provided DMD oligonucleotides in provided compositions, e.g., DMD oligonucleotides of a plurality, comprise base modifications, sugar modifications, and/or internucleotidic linkage modifications. In some embodiments, provided DMD oligonucleotides comprise base modifications and sugar modifications. In some embodiments, provided DMD oligonucleotides comprise base modifications and internucleotidic linkage modifications. In some embodiments, provided DMD oligonucleotides comprise sugar modifications and internucleotidic modifications. In some embodiments, provided compositions comprise base modifications, sugar modifications, and internucleotidic linkage modifications. Example chemical modifications, such as base modifications, sugar modifications, internucleotidic linkage modifications, etc. are widely known in the art including but not limited to those described in this disclosure. In some embodiments, a modified base is substituted A, T, C, G or U. In some embodiments, a sugar modification is 2'-modification. In some embodiments, a 2'-modification is 2—F modification. In some embodiments, a 2'-modification is 2'—OR', wherein $R^1$ is not hydrogen. In some embodiments, a 2'-modification is 2'—OR', wherein R' is optionally substituted alkyl. In some embodiments, a 2'-modification is 2'-OMe. In some embodiments, a 2'-modification is 2'-MOE. In some embodiments, a modified sugar moiety is a bridged bicyclic or polycyclic ring. In some embodiments, a modified sugar moiety is a bridged bicyclic or polycyclic ring having 5-20 ring atoms wherein one or more ring atoms are optionally and independently heteroatoms. Example ring structures are widely known in the art, such as those found in BNA, LNA, etc.

In some embodiments, provided DMD oligonucleotides comprise one or more modified internucleotidic linkages. In some embodiments, provided DMD oligonucleotides comprise one or more chiral modified internucleotidic linkages. In some embodiments, provided DMD oligonucleotides comprise one or more chirally controlled chiral modified internucleotidic linkages. In some embodiments, provided DMD oligonucleotides comprise one or more natural phosphate linkages. In some embodiments, provided DMD oligonucleotides comprise one or more modified internucleotidic linkages and one or more natural phosphate linkages. In some embodiments, a modified internucleotidic linkage is a phosphorothioate linkage. In some embodiments, each modified internucleotidic linkage is a phosphorothioate linkage.

In some embodiments, provided DMD oligonucleotides comprise both one or more modified internucleotidic linkages and one or more natural phosphate linkages. In some embodiments, DMD oligonucleotides comprising both modified internucleotidic linkage and natural phosphate linkage and compositions thereof provide improved properties, e.g., skipping of exon 51 or 53 and toxicities, etc. In some embodiments, a modified internucleotidic linkage is a chiral internucleotidic linkage. In some embodiments, a modified internucleotidic linkage is a phosphorothioate linkage. In some embodiments, a modified internucleotidic linkage is a substituted phosphorothioate linkage.

Among other things, the present disclosure encompasses the recognition that stereorandom DMD oligonucleotide preparations contain a plurality of distinct chemical entities that differ from one another, e.g., in the stereochemical structure of individual backbone linkage phosphorus chiral centers within the DMD oligonucleotide chain. Without control of stereochemistry of backbone chiral centers, stereorandom DMD oligonucleotide preparations provide uncontrolled compositions comprising undetermined levels of DMD oligonucleotide stereoisomers with respect to the uncontrolled chiral centers, e.g., chiral linkage phosphorus. Even though these stereoisomers may have the same base sequence, they are different chemical entities at least due to their different backbone stereochemistry, and they can have, as demonstrated herein, different properties, e.g., skipping of exon 51 or 53, toxicities, etc. Among other things, the present disclosure provides new DMD oligonucleotide compositions wherein stereochemistry of one or more linkage phosphorus chiral centers are independently controlled (e.g., in chirally controlled internucleotidic linkages). In some embodiments, the present disclosure provides chirally controlled DMD oligonucleotide compositions which are or contain particular stereoisomers of DMD oligonucleotides of interest.

In some embodiments, in a DMD oligonucleotide, a pattern of backbone chiral centers can provide improved activity(s) or characteristic(s), including but not limited to: improved skipping of DMD exon 51 or DMD exon 53, increased stability, increased activity, low toxicity, low immune response, improved protein binding profile, increased binding to certain proteins, and/or enhanced delivery.

In some embodiments, provided DMD oligonucleotides comprise one or more non-negatively charged internucleotidic linkages. In some embodiments, a non-negatively charged internucleotidic linkage is a positively charged internucleotidic linkage. In some embodiments, a non-negatively charged internucleotidic linkage is a neutral internucleotidic linkage. In some embodiments, a modified internucleotidic linkage (e.g., a non-negatively charged internucleotidic linkage) comprises an optionally substituted guanidine moiety. In some embodiments, a modified internucleotidic linkage comprises an optionally substituted cyclic guanidine moiety. In some embodiments, a modified internucleotidic linkage comprises an optionally substituted cyclic guanidine moiety and has the structure of

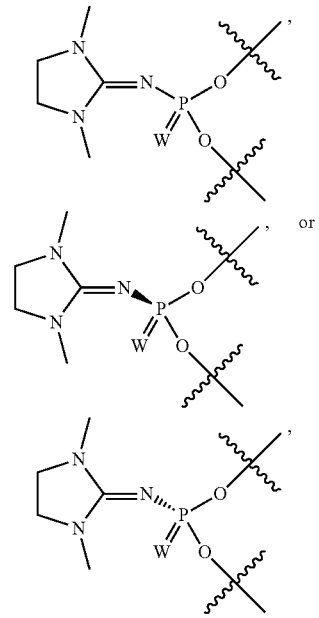

wherein W is O. In some embodiments, a non-negatively charged internucleotidic linkage is stereochemically controlled.

In some embodiments, provided DMD oligonucleotides can bind to a DMD transcript, and change the splicing pattern of the DMD transcript by inducing (e.g., mediating) skipping of exon 51 or 53. In some embodiments, provided DMD oligonucleotides provides exon-skipping of an exon, with efficiency greater than a comparable DMD oligonucleotide under one or more suitable conditions, e.g., as described herein. In some embodiments, a provided skipping efficiency is at least 10%, 20%, 30%, 40%, 50%, 60%, 70%, 80%, 90%, 100%, 110%, 120%, 130%, 140%, 150%, 160%, 170%, 180%, 190% more than, or 2, 3, 4, 5, 6, 7, 8, 9, 10, 11, 12, 13, 14, 15, 16, 17, 18, 19, 20, 30, 40, 50 or more fold of, that of a comparable DMD oligonucleotide under one or more suitable conditions, e.g., as described herein.

In some embodiments, compared to a reference condition, provided chirally controlled DMD oligonucleotide compositions are surprisingly effective. In some embodiments, skipping of exon 52 or 53 (e.g., as measured by increased levels of desired mRNA, proteins, etc., decreased levels of undesired mRNA, proteins, etc.) can be enhanced by more than 5, 10, 15, 20, 25, 30, 40, 50, or 100 fold. In some embodiments, a change is measured by increase of a desired mRNA level compared to a reference condition. In some embodiments, a change is measured by decrease of an undesired mRNA level compared to a reference condition. In some embodiments, a reference condition is absence of DMD oligonucleotide treatment. In some embodiments, a reference condition is a stereorandom composition of DMD oligonucleotides having the same base sequence and chemical modifications.

In some embodiments, a provided DMD oligonucleotide composition is characterized in that, when it is contacted with the DMD transcript in a DMD transcript splicing system, splicing of the DMD transcript is altered (e.g., exon 51 or 53 is skipped) relative to that observed under reference conditions selected from the group consisting of absence of the composition, presence of a reference composition, and combinations thereof. In some embodiments, a desired splicing product (e.g., one lacking exon 51 or 53) is increased 10%, 20%, 30%, 40%, 50%, 60%, 70%, 80%, 90%, 100%, or 2, 3, 4, 5, 6,7, 8,9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000 fold or more. In some embodiments, a desired splicing reference is absent (e.g., cannot be reliably detected by quantitative PCR) under reference conditions. In some embodiments, as exemplified in the present disclosure, levels of the plurality of DMD oligonucleotides, e.g., a plurality of DMD oligonucleotides, in provided compositions are predetermined.

In some embodiments, DMD oligonucleotides having a common base sequence may have the same pattern of nucleoside modifications, e.g., sugar modifications, base modifications, etc. In some embodiments, a pattern of nucleoside modifications may be represented by a combination of locations and modifications. In some embodiments, all non-chiral linkages (e.g., PO) may be omitted. In some embodiments, DMD oligonucleotides having the same base sequence have the same constitution.

In some embodiments, a DMD oligonucleotide composition is chirally controlled.

In some embodiments, a DMD oligonucleotide composition is not stereorandom, and is not a racemic preparation of a diastereoisomers.

As understood by a person having ordinary skill in the art, a stereorandom or racemic preparation of DMD oligonucleotides is prepared by non-stereoselective and/or low-stereoselective coupling of nucleotide monomers, typically without using any chiral auxiliaries, chiral modification reagents, and/or chiral catalysts. In some embodiments, in a substantially racemic (or chirally uncontrolled) preparation of DMD oligonucleotides, all or most coupling steps are not chirally controlled in that the coupling steps are not specifically conducted to provide enhanced stereoselectivity. An example substantially racemic preparation of DMD oligonucleotides is the preparation of phosphorothioate DMD oligonucleotides through sulfurizing phosphite triesters from commonly used phosphoramidite DMD oligonucleotide synthesis with either tetraethylthiuram disulfide or (TETD) or 3H-1, 2-bensodithiol-3-one 1, 1-dioxide (BDTD), a well-known process in the art. In some embodiments, substantially racemic preparation of DMD oligonucleotides provides substantially racemic DMD oligonucleotide compositions (or chirally uncontrolled DMD oligonucleotide compositions). In some embodiments, at least one coupling of a nucleotide monomer has a diastereoselectivity lower than about 60:40, 70:30, 80:20, 85:15, 90:10, 91:9, 92:8, 97:3, 98:2, or 99:1. In some embodiments, each internucleotidic linkage independently has a diastereoselectivity lower than about 60:40, 70:30, 80:20, 85:15, 90:10, 91:9, 92:8, 97:3, 98:2, or 99:1. In some embodiments, a diastereoselectivity is lower than about 60:40. In some embodiments, a diastereoselectivity is lower than about 70:30. In some embodiments, a diastereoselectivity is lower than about 80:20. In some embodiments, a diastereoselectivity is lower than about 90:10. In some embodiments, a diastereoselectivity is lower than about 91:9. In some embodiments, at least one internucleotidic linkage has a diastereoselectivity lower than about 90:10. In some embodiments, each internucleotidic linkage independently has a diastereoselectivity lower than about 90:10. In some embodiments, a non-chirally controlled internucleotidic linkage has a diastereomeric purity no more than 90%, 85%, 80%, 75%, 70%, 65%, 60%, or 55%. In some embodiments, the purity is no more than 90%. In some embodiments, the purity is no more than 85%. In some embodiments, the purity is no more than 80%.

In contrast, in chirally controlled DMD oligonucleotide composition, at least one and typically each chirally controlled internucleotidic linkage, such as those of DMD oligonucleotides of chirally controlled DMD oligonucleotide compositions, independently has a diastereomeric purity of 90%, 91%, 92%, 93%, 94%, 95%, 96%, 97%, 98%, 99% or more with respect to the chiral linkage phosphorus. In some embodiments, a diastereomeric purity is 95% or more. In some embodiments, a diastereomeric purity is 96% or more. In some embodiments, a diastereomeric purity is 97% or more. In some embodiments, a diastereomeric purity is 98% or more. In some embodiments, a diastereomeric purity is 99% or more. Among other things, technologies of the present disclosure routinely provide chirally controlled internucleotidic linkages with high diastereomeric purity.

As appreciated by a person having ordinary skill in the art, diastereoselectivity of a coupling or diastereomeric purity (diastereopurity) of an internucleotidic linkage can be assessed through the diastereoselectivity of a dimer formation/diastereomeric purity of the internucleotidic linkage of a dimer formed under the same or comparable conditions, wherein the dimer has the same 5'- and 3'-nucleosides and internucleotidic linkage.

In some embodiments, the present disclosure provides chirally controlled (and/or stereochemically pure) DMD oligonucleotide compositions comprising a plurality of DMD oligonucleotides defined by having:
1) a common base sequence;
2) a common pattern of backbone linkages; and
3) a common pattern of backbone chiral centers, which composition is a substantially pure preparation of a single DMD oligonucleotide in that at least about 10% of the DMD oligonucleotides in the composition have the common base sequence and length, the common pattern of backbone linkages, and the common pattern of backbone chiral centers, wherein the oligonucleotide is provided herein (e.g., in Table A1).

In some embodiments, the present disclosure provides chirally controlled DMD oligonucleotide composition of a plurality of DMD oligonucleotides, wherein the composition is enriched, relative to a substantially racemic preparation of the same DMD oligonucleotides, for DMD oligonucleotides of a single DMD oligonucleotide type. In some embodiments, the present disclosure provides chirally controlled DMD oligonucleotide composition of a plurality of DMD oligonucleotides wherein the composition is enriched, relative to a substantially racemic preparation of the same DMD oligonucleotides, for DMD oligonucleotides of a single DMD oligonucleotide type defined by:
1) base sequence;
2) pattern of backbone linkages;

3) pattern of backbone chiral centers; and
4) pattern of backbone phosphorus modifications, wherein the oligonucleotide is provided herein (e.g., in Table A1).

In some embodiments, the present disclosure provides a chirally controlled DMD oligonucleotide composition comprising a plurality of DMD oligonucleotides of a particular DMD oligonucleotide type defined by:
1) base sequence;
2) pattern of backbone linkages;
3) pattern of backbone chiral centers; and
4) pattern of backbone phosphorus modifications,
wherein the composition is enriched, relative to a substantially racemic preparation of DMD oligonucleotides having the same base sequence and length, for DMD oligonucleotides of the particular DMD oligonucleotide type, wherein the oligonucleotide is provided herein (e.g., in Table A1).

In some embodiments, DMD oligonucleotides of a DMD oligonucleotide type have a common pattern of backbone phosphorus modifications and a common pattern of sugar modifications. In some embodiments, DMD oligonucleotides of a DMD oligonucleotide type have a common pattern of backbone phosphorus modifications and a common pattern of base modifications. In some embodiments, DMD oligonucleotides of a DMD oligonucleotide type have a common pattern of backbone phosphorus modifications and a common pattern of nucleoside modifications. In some embodiments, DMD oligonucleotides of a particular type have the same constitution. In some embodiments, DMD oligonucleotides of a DMD oligonucleotide type are identical.

In some embodiments, a chirally controlled DMD oligonucleotide composition is a substantially pure preparation of a DMD oligonucleotide type in that DMD oligonucleotides in the composition that are not of the DMD oligonucleotide type are impurities form the preparation process of said DMD oligonucleotide type, in some case, after certain purification procedures.

In some embodiments, at least about 20%, 30%, 40%, 50%, 60%, 70%, 80%, 90%, or 95% of the DMD oligonucleotides in the composition have a common base sequence, a common pattern of backbone linkages, and a common pattern of backbone chiral centers.

In some embodiments, DMD oligonucleotides having a common base sequence, a common pattern of backbone linkages, and a common pattern of backbone chiral centers have a common pattern of backbone phosphorus modifications. In some embodiments, DMD oligonucleotides having a common base sequence, a common pattern of backbone linkages, and a common pattern of backbone chiral centers have a common pattern of backbone phosphorus modifications and a common pattern of nucleoside modifications. In some embodiments, DMD oligonucleotides having a common base sequence, a common pattern of backbone linkages, and a common pattern of backbone chiral centers have a common pattern of backbone phosphorus modifications and a common pattern of sugar modifications. In some embodiments, DMD oligonucleotides having a common base sequence, a common pattern of backbone linkages, and a common pattern of backbone chiral centers have a common pattern of backbone phosphorus modifications and a common pattern of base modifications. In some embodiments, DMD oligonucleotides having a common base sequence, a common pattern of backbone linkages, and a common pattern of backbone chiral centers are identical.

In some embodiments, purity of a chirally controlled DMD oligonucleotide composition of a DMD oligonucleotide type is expressed as the percentage of DMD oligonucleotides in the composition that are of the DMD oligonucleotide type. In some embodiments, at least about 10% of the DMD oligonucleotides in a chirally controlled DMD oligonucleotide composition are of the DMD oligonucleotide type. In some embodiments, at least about 20% of the DMD oligonucleotides in a chirally controlled DMD oligonucleotide composition are of the DMD oligonucleotide type. In some embodiments, at least about 30% of the DMD oligonucleotides in a chirally controlled DMD oligonucleotide composition are of the DMD oligonucleotide type. In some embodiments, at least about 40% of the DMD oligonucleotides in a chirally controlled DMD oligonucleotide composition are of the DMD oligonucleotide type. In some embodiments, at least about 50% of the DMD oligonucleotides in a chirally controlled DMD oligonucleotide composition are of the DMD oligonucleotide type. In some embodiments, at least about 60% of the DMD oligonucleotides in a chirally controlled DMD oligonucleotide composition are of the DMD oligonucleotide type. In some embodiments, at least about 70% of the DMD oligonucleotides in a chirally controlled DMD oligonucleotide composition are of the DMD oligonucleotide type. In some embodiments, at least about 80% of the DMD oligonucleotides in a chirally controlled DMD oligonucleotide composition are of the DMD oligonucleotide type. In some embodiments, at least about 90% of the DMD oligonucleotides in a chirally controlled DMD oligonucleotide composition are of the DMD oligonucleotide type. In some embodiments, at least about 92% of the DMD oligonucleotides in a chirally controlled DMD oligonucleotide composition are of the DMD oligonucleotide type. In some embodiments, at least about 94% of the DMD oligonucleotides in a chirally controlled DMD oligonucleotide composition are of the DMD oligonucleotide type. In some embodiments, at least about 95% of the DMD oligonucleotides in a chirally controlled DMD oligonucleotide composition are of the DMD oligonucleotide type. In some embodiments, at least about 96% of the DMD oligonucleotides in a chirally controlled DMD oligonucleotide composition are of the same DMD oligonucleotide type. In some embodiments, at least about 97% of the DMD oligonucleotides in a chirally controlled DMD oligonucleotide composition are of the DMD oligonucleotide type. In some embodiments, at least about 98% of the DMD oligonucleotides in a chirally controlled DMD oligonucleotide composition are of the DMD oligonucleotide type. In some embodiments, at least about 99% of the DMD oligonucleotides in a chirally controlled DMD oligonucleotide composition are of the DMD oligonucleotide type.

In some embodiments, purity of a chirally controlled DMD oligonucleotide composition can be controlled by stereoselectivity of each coupling step in its preparation process. In some embodiments, a coupling step has a stereoselectivity (e.g., diastereoselectivity) of 60% (60% of the new internucleotidic linkage formed from the coupling step has the intended stereochemistry). After such a coupling step, the new internucleotidic linkage formed may be referred to have a 60% purity. In some embodiments, each coupling step has a stereoselectivity of at least 60%. In some embodiments, each coupling step has a stereoselectivity of at least 70%. In some embodiments, each coupling step has a stereoselectivity of at least 80%. In some embodiments, each coupling step has a stereoselectivity of at least 85%. In some embodiments, each coupling step has a stereoselectivity of at least 90%. In some embodiments, each coupling step has a stereoselectivity of at least 91%. In some embodiments, each coupling step has a stereoselectivity of at least 92%. In some embodiments, each coupling step has a stereoselectivity of at least 93%. In some embodiments, each coupling step has a stereoselectivity of at least 94%. In some embodiments, each coupling step has a stereoselectivity of at least 95%. In some embodiments, each coupling step has a stereoselectivity of at least 96%. In some embodiments, each coupling step has a stereoselectivity of at least 97%. In some embodiments, each coupling step has a stereoselectivity of at least 98%. In some embodiments, each coupling step has a stereoselectivity of at least 99%. In some embodiments, each coupling step has a stereoselectivity of at least 99.5%. In some embodiments, each coupling step has a stereoselectivity of virtually 100%.

In some embodiments, in provided compositions, at least 0.5%, 1%, 2%, 3%, 4%, 5%, 6%, 7%, 8%, 9%, 10%, 20%, 30%, 40%, 50%, 60%, 70%, 75%, 80%, 81%, 82%, 83%, 84%, 85%, 86%, 87%, 88%, 89%, 90%, 91%, 92%, 93%, 94%, 95%, 96%, 97%, 97% or 99% of DMD oligonucleotides that have the base sequence of a particular DMD oligonucleotide type (defined by 1) base sequence; 2) pattern of backbone linkages; 3) pattern of backbone chiral centers; and 4) pattern of backbone phosphorus modifications) are DMD oligonucleotides of the particular DMD oligonucleotide type. In some embodiments, at least 0.5%, 1%, 2%, 3%, 4%, 5%, 6%, 7%, 8%, 9%, 10%, 20%, 30%, 40%, 50%, 60%, 70%, 75%, 80%, 81%, 82%, 83%, 84%, 85%, 86%, 87%, 88%, 89%, 90%, 91%, 92%, 93%, 94%, 95%, 96%, 97%, 97% or 99% of DMD oligonucleotides that have the base sequence, the pattern of backbone linkages, and the pattern of backbone phosphorus modifications of a particular DMD oligonucleotide type are DMD oligonucleotides of the particular DMD oligonucleotide type.

In some embodiments, a provided DMD oligonucleotide comprises one or more chiral, modified phosphate linkages. In some embodiments, provided chirally controlled (and/or stereochemically pure) preparations are of DMD oligonucleotides that include one or more modified backbone linkages, bases, and/or sugars.

In some embodiments, provided chirally controlled (and/or stereochemically pure) preparations are of a stereochemical purity of greater than about 80%. In some embodiments, provided chirally controlled (and/or stereochemically pure) preparations are of a stereochemical purity of greater than about 85%. In some embodiments, provided chirally controlled (and/or stereochemically pure) preparations are of a stereochemical purity of greater than about 90%. In some embodiments, provided chirally controlled (and/or stereochemically pure) preparations are of a stereochemical purity of greater than about 91%. In some embodiments, provided chirally controlled (and/or stereochemically pure) preparations are of a stereochemical purity of greater than about 92%. In some embodiments, provided chirally controlled (and/or stereochemically pure) preparations are of a stereochemical purity of greater than about 93%. In some embodiments, provided chirally controlled (and/or stereochemically pure) preparations are of a stereochemical purity of greater than about 94%. In some embodiments, provided chirally controlled (and/or stereochemically pure) preparations are of a stereochemical purity of greater than about 95%. In some embodiments, provided chirally controlled (and/or stereochemically pure) preparations are of a stereochemical purity of greater than about 96%. In some embodiments, provided chirally controlled (and/or stereochemically pure) preparations are of a stereochemical purity of greater than about 97%. In some embodiments, provided chirally controlled (and/or stereochemically pure) preparations are of a stereochemical purity of greater than about 98%. In some embodiments, provided chirally controlled (and/or stereochemically pure) preparations are of a stereochemical purity of greater than about 99%.

In some embodiments, one or more is one. In some embodiments, one or more is two. In some embodiments, one or more is three. In some embodiments, one or more is four. In some embodiments, one or more is five. In some embodiments, one or more is six. In some embodiments, one or more is seven. In some embodiments, one or more is eight. In some embodiments, one or more is nine. In some embodiments, one or more is ten. In some embodiments, one or more is at least one. In some embodiments, one or more is at least two. In some embodiments, one or more is at least three. In some embodiments, one or more is at least four. In some embodiments, one or more is at least five. In some embodiments, one or more is at least six. In some embodiments, one or more is at least seven. In some embodiments, one or more is at least eight. In some embodiments, one or more is at least nine. In some embodiments, one or more is at least ten.

In some embodiments, a base sequence, e.g., a common base sequence of a plurality of DMD oligonucleotide, a base sequence of a particular DMD oligonucleotide type, etc., comprises or is a sequence complementary to a gene or DMD transcript (e.g., of Dystrophin or DMD). In some embodiments, a common base sequence comprises or is a sequence 100% complementary to a gene.

In some embodiments, linkage phosphorus of chiral internucleotidic linkages are chirally controlled. In some embodiments, a chiral internucleotidic linkage is phosphorothioate internucleotidic linkage. In some embodiments, each chiral internucleotidic linkage in a DMD oligonucleotide of a provided composition is a phosphorothioate internucleotidic linkage.

As appreciated by those skilled in the art, internucleotidic linkages, natural phosphate linkages, phosphorothioate internucleotidic linkages, etc. may exist in their salt forms depending on pH of their environment. Unless otherwise indicated, such salt forms are included in the present application when such internucleotidic linkages are referred to.

In some embodiments, DMD oligonucleotides of the present disclosure comprise one or more modified sugar moieties. In some embodiments, DMD oligonucleotides of the present disclosure comprise one or more modified base moieties. As known by a person of ordinary skill in the art and described in the disclosure, various modifications can be introduced to sugar and base moieties. For example, in some embodiments, a modification is a modification described in U.S. Pat. No. 9,006,198, WO2014/012081, WO/2015/107425, and WO/2017/062862, the sugar and base modifications of each of which are incorporated herein by reference.

Dystrophin

In some embodiments, the present disclosure provides technologies, e.g., DMD oligonucleotides, compositions, methods, etc., related to the dystrophin (DMD) gene or a product encoded thereby (a DMD transcript, a protein (e.g., various variants of the dystrophin protein), etc.).

In some embodiments, the present disclosure provides technologies, including DMD oligonucleotides and compositions and methods of use thereof, for treatment of muscular dystrophy, including but not limited to, Duchenne Muscular Dystrophy (also abbreviated as DMD) and Becker Muscular Dystrophy (BMD). In some embodiments, DMD comprises one or more mutations. In some embodiments, such mutations are associated with reduced biological functions of dystrophin protein in a subject suffering from or susceptible to muscular dystrophy.

In some embodiments, the dystrophin (DMD) gene or a product thereof, or a variant or portion thereof, may be referred to as DMD, BMD, CMD3B, DXS142, DXS164, DXS206, DXS230, DXS239, DXS268, DXS269, DXS270, DXS272, MRX85, or dystrophin; External IDs: OMIM: 300377 MGI: 94909; HomoloGene: 20856; GeneCards: DMD; In Human: Entrez: 1756; Ensembl: ENSG00000198947; UniProt: P11532; RefSeq (mRNA): NM_000109; NM_004006; NM_004007; NM_004009; NM_004010; RefSeq (protein): NP_000100; NP_003997; NP_004000; NP_004001; NP_004002; Location (UCSC): Chr X: 31.1-33.34 Mb; In Mouse: Entrez: 13405; Ensembl: ENSMUSG00000045103; UniProt: P11531; RefSeq (mRNA): NM_007868; NM_001314034; NM_001314035; NM_001314036; NM_001314037; RefSeq (protein): NP_001300963; NP_001300964; NP_001300965; NP 001300966; NP_001300967; Location (UCSC): Chr X: 82.95-85.21 Mb.

The DMD gene reportedly contains 79 exons distributed over 2.3 million bp of genetic real estate on the X chromosome; however, only approximately 14,000 bp (<1%) is reported to be used for translation into protein (coding sequence). It is reported that about 99.5% of the genetic sequence, the intronic sequences, is spliced out of the 2.3 million bp initial heteronuclear RNA DMD transcript to provide a mature 14,000 bp mRNA that includes all key information for dystrophin protein production. In some embodiments, patients with DMD have mutation(s) in the DMD gene that prevent the appropriate construction of the wild-type DMD mRNA and/or the production of the wild-type dystrophin protein, and patients with DMD often show marked dystrophin deficiency in their muscle.

In some embodiments, a dystrophin DMD transcript, e.g., mRNA, or protein encompasses those related to or produced from alternative splicing. For example, sixteen alternative DMD transcripts of the dystrophin gene were reported following an analysis of splicing patterns of the DMD gene in skeletal muscle, brain and heart tissues. Sironi et al. 2002 FEBS Letters 517: 163-166.

It is reported that dystrophin has several isoforms. In some embodiments, dystrophin refers to a specific isoform. At least three full-length dystrophin isoforms have been reported, each controlled by a tissue-specific promoter. Klamut et al. 1990 Mol. Cell. Biol. 10: 193-205; Nudel et al. 1989 Nature 337: 76-78; Gorecki et al. 1992 Hum. Mol. Genet. 1: 505-510. The muscle isoform is reportedly mainly expressed in skeletal muscle but also in smooth and cardiac muscles [Bies, R. D., Phelps, S. F., Cortez, M. D., Roberts, R., Caskey, C. T. and Chamberlain, J. S. 1992 Nucleic Acids Res. 20: 1725-1731], the brain dystrophin is reportedly specific for cortical neurons but can also be detected in heart and cerebellar neurons, while the Purkinje-cell type reportedly accounts for nearly all cerebellar dystrophin [Gorecki et al. 1992 Hum. Mol. Genet. 1: 505-510]. Alternative splicing reportedly provides a means for dystrophin diversification: the 3' region of the gene reportedly undergoes alternative splicing resulting in tissue-specific DMD transcripts in brain neurons, cardiac Purkinje fibers, and smooth muscle cells [Bies et al. 1992 Nucleic Acids Res. 20: 1725-1731; and Feener et al. 1989 Nature 338: 509-511] while 12 patterns of alternative splicing have been reported in the 5' region of the gene in skeletal muscle [Surono et al. 1997 Biochem. Biophys. Res. Commun. 239: 895-899].

In some embodiments, a dystrophin mRNA, gene or protein is a revertant version. Among others, revertant dystrophins were reported in, for example: Hoffman et al. 1990 J. Neurol. Sci. 99:9-25; Klein et al. 1992 Am. J. Hum. Genet. 50: 950-959; and Chelly et al. 1990 Cell 63: 1239-1348; Arahata et al. 1998 Nature 333: 861-863; Bonilla et al. 1988 Cell 54: 447-452; Fanin et al. 1992 Neur. Disord. 2: 41-45; Nicholson et al. 1989 J. Neurol. Sci. 94: 137-146; Shimizu et al. 1988 Proc. Jpn. Acad. Sci. 64: 205-208; Sicinzki et al. 1989 Science 244: 1578-1580; and Sherratt et al. Am. J. Hum. Genet. 53: 1007-1015.

Various mutations in the DMD gene can and/or were reported to cause muscular dystrophy, including some in exon 51 or 53.

Muscular Dystrophy

Compositions comprising one or more DMD oligonucleotides described herein can be used to treat or delay onset of muscular dystrophy, or at least one symptom thereof. In some embodiments, muscular dystrophy (MD) is any of a group of muscle conditions, diseases, or disorders that results in (increasing) weakening and breakdown of skeletal muscles over time. The conditions, diseases, or disorders differ in which muscles are primarily affected, the degree of weakness, when symptoms begin, and how quickly symptoms worsen. Many MD patients will eventually become unable to walk. In many cases musuclar dystrophy is fatal. Some types are also associated with problems in other organs, including the central nervous system. In some embodiments, the muscular dystrophy is Duchenne (Duchenne's) Muscular Dystrophy (DMD) or Becker (Becker's) Muscular Dystrophy (BMD).

In some embodiments, a symptom of Duchenne Muscular Dystrophy is reportedly muscle weakness associated with muscle wasting, with the voluntary muscles being first affected, especially those of the hips, pelvic area, thighs, shoulders, and calves. Muscle weakness can reportedly also occur later, in the arms, neck, and other areas. Calves are reportedly often enlarged. Symptoms reportedly usually appear before age six and may appear in early infancy. Other physical symptoms reportedly are: awkward manner of walking, stepping, or running (in some cases, patients tend to walk on their forefeet, because of an increased calf muscle tone), frequent falls, fatigue, difficulty with motor skills (e.g., running, hopping, jumping), lumbar hyperlordosis, possibly leading to shortening of the hip-flexor muscles, unusual overall posture and/or manner of walking, stepping, or running, muscle contractures of Achilles tendon and hamstrings impair functionality, progressive difficulty walking, muscle fiber deformities, pseudohypertrophy (enlarging) of tongue and calf muscles, higher risk of neurobehavioral disorders (e.g., ADHD), learning disorders (e.g., dyslexia), and non-progressive weaknesses in specific cognitive skills (e.g., short-term verbal memory), which are believed to be the result of absent or dysfunctional dystrophin in the brain, eventual loss of ability to walk (usually by the age of 12), skeletal deformities (including scoliosis in some cases), and trouble getting up from lying or sitting position.

In some embodiments, Becker muscular dystrophy (BMD) is reportedly caused by mutations that give rise to shortened but in-frame DMD transcripts resulting in the production of truncated but partially functional protein(s). Such partially functional protein(s) were reported to retain the critical amino terminal, cysteine rich and C-terminal domains but usually lack elements of the central rod domains which were reported to be of less functional significance. England et al. 1990 Nature, 343, 180-182.

In some embodiments, BMD phenotypes range from mild DMD to virtually asymptomatic, depending on the precise mutation and the level of dystrophin produced. Yin et al. 2008 Hum. Mol. Genet. 17: 3909-3918.

In some embodiments, dystrophy patients with out-of-frame mutations are generally diagnosed with the more severe Duchenne Muscular Dystrophy, and dystrophy patients with in-frame mutations are generally diagnosed with the less severe Becker Muscular Dystrophy. However, a minority of patients with in-frame deletions are diagnosed with Duchenne Muscular Dystrophy, including those with deletion mutations starting or ending in exons 50 or 51, which encode part of the hinge region, such as deletions of exons 47 to 51, 48 to 51, and 49 to 53. Without wishing to be bound by any particular theory, the present disclosure notes that the patient-to-patient variability in disease severity despite the presence of the same exon deletion reportedly may be related to the effect of the specific deletion breakpoints on mRNA splicing efficiency and/or patterns; translation or DMD transcription efficiency after genome rearrangement; and stability or function of the truncated protein structure. Yokota et al. 2009 Arch. Neurol. 66: 32.

Exon Skipping as a Treatment for Muscular Dystrophy

In some embodiments, a treatment for muscular dystrophy comprises the use of a DMD oligonucleotide which is capable of mediating skipping of Dystrophin (DMD) exon 51 or 53. In some embodiments, the present disclosure provides methods for treatment of muscular dystrophy comprising administering to a subject suffering therefrom or susceptible thereto a DMD oligonucleotide, or a composition comprising a DMD oligonucleotide. Particularly, among other things, the present disclosure demonstrates that chirally controlled DMD oligonucleotide/chirally controlled DMD oligonucleotide compositions are unexpectedly effective for modulating exon skipping compared to otherwise identical but non-chirally controlled DMD oligonucleotide/oligonucleotide compositions. In some embodiments, the present disclosure demonstrates incorporation of one or more non-negatively charged internucleotidic linkage into a DMD oligonucleotide can greatly improve delivery and/or overall exon skipping efficiency.

In some embodiments, a treatment for muscular dystrophy employs the use of a DMD oligonucleotide, wherein the DMD oligonucleotide is capable of mediating (e.g., directing) skipping of DMD exon 51 or DMD exon 53. In some embodiments, a DMD oligonucleotide is capable of mediating the skipping of an exon which comprises a mutation (e.g., a frameshift, insertion, deletion, missense, or nonsense mutation, or other mutation), wherein translation of the mRNA with a skipped exon produces a truncated but functional (or largely functional) DMD protein.

In some embodiments, a composition comprising a DMD oligonucleotide is useful for treatment of a Dystrophin-related disorder of the central nervous system. In some embodiments, the present disclosure pertains to a method of treatment of a Dystrophin-related disorder of the central nervous system, wherein the method comprises the step of administering a therapeutically effective amount of a DMD oligonucleotide to a patient suffering from a Dystrophin-related disorder of the central nervous system. In some embodiments, a DMD oligonucleotide is administered outside the central nervous system (as non-limiting examples, intravenously or intramuscularly) to a patient suffering from a Dystrophin-related disorder of the central nervous system, and the DMD oligonucleotide is capable of passing through the blood-brain barrier into the central nervous system. In some embodiments, a DMD oligonucleotide is administered directly into the central nervous system (as non-limiting example, via intrathecal, intraventricular, intracranial, etc., delivery).

In some embodiments, a Dystrophin-related disorder of the central nervous system, or a symptom thereof, can be any one or more of: decreased intelligence, decreased long term memory, decreased short term memory, language impairment, epilepsy, autism spectrum disorder, attention deficit hyperactivity disorder (ADHD), obsessive-compulsive disorder, learning problem, behavioral problem, a decrease in brain volume, a decrease in grey matter volume, lower white matter fractional anisotropy, higher white matter radial diffusivity, an abnormality of skull shape, or a deleterious change in the volume or structure of the hippocampus, globus pallidus, caudate putamen, hypothalamus, anterior commissure, periaqueductal gray, internal capsule, amygdala, corpus callosum, septal nucleus, nucleus accumbens, fimbria, ventricle, or midbrain thalamus. In some embodiments, a patient exhibiting muscle-related symptoms of muscular dystrophy also exhibits symptoms of a Dystrophin-related disorder of the central nervous system.

In some embodiments, a Dystrophin-related disorder of the central nervous system is related to, associated with and/or caused by an abnormality in the level, activity, expression and/or distribution of a gene product of the Dystrophin gene, such as full-length Dystrophin or a smaller isoform of Dystrophin, including, but not limited to, Dp260, Dp140, Dp116, Dp71 or Dp40. In some embodiments, a DMD oligonucleotide is administered into the central nervous system of a muscular dystrophy patient in order to ameliorate one or more systems of a Dystrophin-related disorder of the central nervous system. In some embodiments, a Dystrophin-related disorder of the central nervous system is related to, associated with and/or caused by an abnormality in the level, activity, expression and/or distribution of a gene product of the Dystrophin gene, such as full-length Dystrophin or a smaller isoform of Dystrophin, including, but not limited to, Dp260, Dp140, Dp116, Dp71 or Dp40. In some embodiments, administration of a DMD oligonucleotide to a patient suffering from a Dystrophin-related disorder of the central nervous system increases the level, activity, and/or expression and/or improves the distribution of a gene product of the Dystrophin gene.

In some embodiments, the present disclosure provides technologies for modulating dystrophin pre-mRNA splicing, whereby exon 51 or exon 53 is excised to remove a mutation.

In some embodiments, in a DMD patient, a DMD gene comprises an exon comprising a mutation, and the disorder is at least partially treated by skipping of DMD exon 51 or DMD exon 53.

In some embodiments, in a DMD patient, a DMD gene or DMD transcript has a mutation in an exon(s), which is a missense or nonsense mutation and/or deletion, insertion, inversion, translocation or duplication.

In some embodiments, in a treatment for muscular dystrophy, an exon of DMD (e.g., exon 51 or 53) is skipped, wherein the exon encodes a string of amino acids not essential for DMD protein function, or whose skipping can provide a fully or at least partially functional DMD protein.

In some embodiments, in a treatment for muscular dystrophy, a DMD oligonucleotide is capable of mediating skipping of DMD exon 51 or 53, thereby creating an mRNA from which can be translated into an artificially internally truncated DMD protein variant which provides at least partially improved or fully restored biological activity.

In some embodiments, an internally truncated DMD protein variant produced from a dystrophin DMD transcript with a skipped exon 51 or skipped exon 53 is more functional than a terminally truncated DMD protein e.g., produced from a dystrophin DMD transcript with an out-of-frame deletion.

In some embodiments, an internally truncated DMD protein variant produced from a dystrophin DMD transcript with a skipped exon 51 or skipped exon 53 is more resistant to nonsense-mediated decay, which can degrade a terminally truncated DMD protein, e.g., produced from a dystrophin DMD transcript with an out-of-frame deletion.

In some embodiments, a treatment for muscular dystrophy employs the use of a DMD oligonucleotide, wherein the DMD oligonucleotide is capable of mediating skipping of DMD exon 51 or DMD exon 53.

In some embodiments, the present disclosure encompasses the recognition that the nature and location of a DMD mutation may be utilized to design an exon-skipping strategy. In some embodiments, if a DMD patient has a mutation in an exon, skipping of the mutated exon can produce an internally truncated (internally shortened) but at least partially functional DMD protein variant.

In some embodiments, a DMD patient has a mutation which alters splicing of a DMD transcript, e.g., by inactivating a site required for splicing, or activating a cryptic site so that it becomes active for splicing, or by creating an alternative (e.g., unnatural) splice site. In some embodiments, such a mutation causes production of proteins with low or no activities. In some embodiments, splicing modulation, e.g., exon skipping, suppression of such a mutation, etc., can be employed to remove or reduce effects of such a mutation, e.g., by restoring proper splicing to produce proteins with restored activities, or producing an internally truncated dystrophin protein variant with improved or restored activities, etc.

In some embodiments, restoring the reading frame can convert an out-of-frame mutation to an in-frame mutation; in some embodiments, in humans, such a change can transform severe Duchenne Muscular Dystrophy into milder Becker Muscular Dystrophy.

In some embodiments, a DMD patient or a patient suspected to have DMD is analyzed for DMD genotype prior to administration of a composition comprising a DMD oligonucleotide.

In some embodiments, a DMD patient or a patient suspected to have DMD is analyzed for DMD phenotype prior to administration of a composition comprising a DMD oligonucleotide.

In some embodiments, a DMD patient is analyzed for genotype and phenotype to determine the relationship of DMD genotype and DMD phenotype prior to administration of a composition comprising a DMD oligonucleotide.

In some embodiments, a patient is genetically verified to have dystrophy prior to administration of a composition comprising a DMD oligonucleotide.

In some embodiments, analysis of DMD genotype or genetic verification of DMD or a patient comprises determining if the patient has one or more deleterious mutations in DMD.

In some embodiments, analysis of DMD genotype or genetic verification of DMD or a patient comprises determining if the patient has one or more deleterious mutations in DMD and/or analyzing DMD splicing and/or detecting splice variants of DMD, wherein a splice variant is produced by an abnormal splicing of DMD.

In some embodiments, analysis of DMD genotype or genetic verification of DMD informs the selection of a composition comprising a DMD oligonucleotide useful for treatment.

In some embodiments, an abnormal or mutant DMD gene or a portion thereof is removed or copied from a patient or a patient's cell(s) or tissue(s) and the abnormal or mutant DMD gene, or a portion thereof comprising the abnormality or mutation, or a copy thereof, is inserted into a cell. In some embodiments, this cell can be used to test various compositions comprising a DMD oligonucleotide to predict if such a composition would be useful as a treatment for the patient. In some embodiments, the cell is a myoblast or myotubule.

In some embodiments, an individual or patient can produce, prior to treatment with a DMD oligonucleotide, one or more splice variants of DMD, often each variant being produced at a very low level. In some embodiments, any appropriate method can be used to detect low levels of splice variants being produced in a patient prior to, during or after administration of a DMD oligonucleotide.

In some embodiments, a patient and/or the tissues thereof are analyzed for production of various splicing variants of a DMD gene prior to administration of a composition comprising a DMD oligonucleotide.

In some embodiments, the present disclosure provides methods for designing a DMD oligonucleotide (e.g., a DMD oligonucleotide capable of mediating skipping of DMD exon 51 or DMD exon 53 of DMD). In some embodiments, the present disclosure utilizes rationale design described herein and optionally sequence walks to design DMD oligonucleotides, e.g., for testing exon skipping in one or more assays and/or conditions. In some embodiments, an efficacious DMD oligonucleotide is developed following rational design, including using various information of a given biological system.

In some embodiments, in a method for developing DMD oligonucleotides, DMD oligonucleotides are designed to anneal to one or more potential splicing-related motifs and then tested for their ability to mediate exon skipping.

Example Technologies for Assessing Oligonucleotides and Oligonucleotide Compositions Various technologies for assessing properties and/or activities of DMD oligonucleotides can be utilized in accordance with the present disclosure, e.g., US 20170037399, WO 2017/015555, WO 2017/015575, WO 2017/192664, WO 2017/062862, WO 2017/192679, WO 2017/210647, etc.

For example, DMD oligonucleotides can be evaluated for their ability to mediate exon skipping in various assays, including in vitro and in vivo assays, in accordance with the present disclosure. In vitro assays can be performed in various test cells described herein or known in the art, including but not limited to, A48-50 Patient-Derived Myoblast Cells. In vivo tests can be performed in test animals described herein or known in the art, including but not limited to, a mouse, rat, cat, pig, dog, monkey, or non-human primate.

As non-limiting examples, a number of assays are described below for assessing properties/activities of DMD oligonucleotides. Various other suitable assays are available and may be utilized to assess DMD oligonucleotide properties/activities, including those of DMD oligonucleotides not designed for exon skipping (e.g., for DMD oligonucleotides that may involve RNase H for reducing levels of target DMD transcripts, assays described in US 20170037399, WO 2017/015555, WO 2017/015575, WO 2017/192664, WO 2017/192679, WO 2017/210647, etc.).

A DMD oligonucleotide can be evaluated for its ability to mediate skipping of exon 51 or 53 in the Dystrophin RNA, which can be tested, as non-limiting examples, using nested PCR, qRT-PCR, and/or sequencing.

A DMD oligonucleotide can be evaluated for its ability to mediate protein restoration (e.g., production of an internally truncated Dystrophin protein variant lacking the amino acids corresponding to the codons encoded in the skipped exon, which has improved functions compared to proteins (if any) produced prior to exon skipping), which can be evaluated by a number of methods for protein detection and/or quantification, such as western blot, immunostaining, etc. Antibodies to dystrophin are commercially available or if desired, can be developed for desired purposes.

A DMD oligonucleotide can be evaluated for its ability to mediate production of a stable restored protein. Stability of restored protein can be tested, in non-limiting examples, in assays for serum and tissue stability.

A DMD oligonucleotide can be evaluated for its ability to bind protein, such as albumin. Example related technologies include those described, e.g., in WO 2017/015555, WO 2017/015575, etc.

A DMD oligonucleotide can be evaluated for immuno activity, e.g., through assays for cytokine activation, complement activation, TLR9 activity, etc. Example related technologies include those described, e.g., in WO 2017/015555, WO 2017/015575, WO 2017/192679, WO 2017/210647, etc.

In some embodiments, efficacy of a DMD oligonucleotide can be tested, e.g., in in silico analysis and prediction, a cell-free extract, a cell transfected with artificial constructs, an animal such as a mouse with a human Dystrophin transgene or portion thereof, normal and dystrophic human myogenic cell lines, and/or clinical trials. It may be desirable to utilize more than one assay, as normal and dystrophic human myogenic cell lines may sometimes produce different efficacy results under certain conditions (Mitrpant et al. 2009 Mol. Ther. 17: 1418).

In some embodiments, DMD oligonucleotides can be tested in vitro in cells. In some embodiments, testing in vitro in cells involves gymnotic delivery of the DMD oligonucleotide(s), or delivery using a delivery agent or transfectant, many of which are known in the art and may be utilized in accordance with the present disclosure.

In some embodiments, DMD oligonucleotides can be tested in vitro in normal human skeletal muscle cells (hSkMCs). See, for example, Arechavala et al. 2007 Hum. Gene Ther. 18: 798-810.

In some embodiments, DMD oligonucleotides can be tested in a muscle explant from a DMD patient. Muscle explants from DMD patients are reported in, for example, Fletcher et al. 2006 J. Gene Med. 8: 207-216; McClorey et al. 2006 Neur. Dis. 16: 583-590; and Arechavala et al. 2007 Hum. Gene Ther. 18: 798-810.

In some embodiments, cells are or comprise cultured muscle cells from DMD patients. See, for example: Aartsma-Rus et al. 2003 Hum. Mol. Genet. 8: 907-914.

In some embodiments, an individual DMD oligonucleotide may demonstrate experiment-to-experiment variability in its ability to skip exon 51 or 53 under certain circumstances. In some embodiments, an individual DMD oligonucleotide can demonstrate variability in its ability to skip exon 51 or 53 depending on which cells are used, the growth conditions, and other experimental factors. To control variations, typically DMD oligonucleotides to be tested and control DMD oligonucleotides are assayed under the same or substantially the same conditions.

In vitro experiments also include those conducted with patient-derived myoblasts. Certain results from such experiments were described herein. In certain such experiments, cells were cultured in skeletal growth media to keep them in a dividing/immature myoblast state. The media was then changed to 'differentiation' media (containing insulin and 2% horse serum) concurrent with spiking DMD oligonucleotides in the media for dosing. The cells differentiated into myotubes as they were getting dosed for a suitable period of time, e.g., a total of 4d for RNA experiments and 6d for protein experiments (such conditions referenced as '0d pre-differentiation' (0d+4d for RNA, 0d+6d for protein)).

Without wishing to be bound by any particular theory, the present disclosure notes that it may be desirable to know if DMD oligonucleotides are able to enter mature myotubes and induce skipping in these cells as well as 'immature' cells. In some embodiments, the present disclosure provided assays to test effects of DMD oligonucleotides in myotubes. In some embodiments, a dosing schedule different from the '0d pre-differentiation' was used, wherein the myoblasts were pre-differentiated into myotubes in differentiation media for several days (4d or 7d or 10d) and then DMD oligonucleotides were administered. Certain related protocols are described in Example 19.

In some embodiments, the present disclosure demonstrated that, in the pre-differentiation experiments, DMD oligonucleotides (excluding those which are PMOs) usually give about the same level of RNA skipping and dystrophin protein restoration, regardless of the number of days cells were cultured in differentiation media prior to dosing. In some embodiments, the present disclosure provides DMD oligonucleotides that may be able to enter and be active in myoblasts and in myotubes. In some embodiments, a DMD oligonucleotide is tested in vitro in A45-52 DMD patient cells (also designated D45-52 or del45-52) or A52 DMD patient cells (also designated D52 or del52) with 0, 4 or 7 days of pre-differentiation.

In some embodiments, DMD oligonucleotides can be tested in any one or more of various animal models, including non-mammalian and mammalian models; including, as non-limiting examples, Caenorhabditis, Drosophila, zebrafish, mouse, rat, cat, dog and pig. See, for example, a review in McGreevey et al. 2015 Dis. Mod. Mech. 8: 195-213.

Example use of mdx mice is reported in, for example: Lu et al. 2003 Nat. Med. 9: 1009; Jearawiriyapaisarn et al. 2008 Mol. Ther., 16, 1624-1629; Yin et al. 2008 Hum. Mol. Genet., 17, 3909-3918; Wu et al. 2009 Mol. Ther., 17, 864-871; Wu et al. 2008 Proc. Natl Acad. Sci. USA, 105, 14814-14819; Mann et al. 2001 Proc. Nat. Acad. Sci. USA 98: 42-47; and Gebski et al. 2003 Hum. Mol. Gen. 12: 1801-1811.

Efficacy of DMD oligonucleotides can be tested in dogs, such as the Golden Retriever Muscular Dystrophy (GRMD) animal model. Lu et al. 2005 Proc. Natl. Acad. Sci. USA 102:198-203; Alter et al. 2006 Nat. Med. 12:175-7; McClorey et al. 2006 Gene Ther. 13:1373-81; and Yokota et al. 2012 Nucl. Acid Ther. 22: 306.

A DMD oligonucleotide can be evaluated in vivo in a test animal for efficient delivery to various tissues (e.g., skeletal, heart and/or diaphragm muscle); this can be tested, in non-limiting examples, by hybridization ELISA and tests for distribution in animal tissue.

A DMD oligonucleotide can be evaluated in vivo in a test animal for plasma PK; this can be tested, as non-limiting examples, by assaying for AUC (area under the curve) and half-life.

In some embodiments, DMD oligonucleotides can be tested in vivo, via an intramuscular administration a muscle of a test animal.

In some embodiments, DMD oligonucleotides can be tested in vivo, via an intramuscular administration into the gastrocnemius muscle of a test animal.

In some embodiments, DMD oligonucleotides can be tested in vivo, via an intramuscular administration into the gastrocnemius muscle of a mouse.

In some embodiments, DMD oligonucleotides can be tested in vivo, via an intramuscular administration into the gastrocnemius muscle of a mouse model transgenic for the entire human dystrophin locus. See, for example: Bremmer-Bout et al. 2004 Mol. Ther. 10, 232-240.

Additional tests which can be performed to evaluate the efficacy of DMO DMD oligonucleotides include centrally nucleated fiber counts and dystrophin-positive fiber counts, and functional grip strength analysis. See, as non-limiting examples, experimental protocols reported in: Yin et al. 2009 Hum. Mol. Genet. 18: 4405-4414.

Additional methods of testing DMD oligonucleotides include, as non-limiting example, methods reported in: Kinali et al. 2009 Lancet 8: 918; Bertoni et al. 2003 Hum. Mol. Gen. 12: 1087-1099.

Certain Examples of Oligonucleotides and Compositions

In some embodiments, the present disclosure provides DMD oligonucleotides and/or DMD oligonucleotide compositions that are useful for various purposes, e.g., modulating skipping, reducing levels of DMD transcripts, improving levels of beneficial proteins, treating conditions, diseases and disorders, etc. In some embodiments, the present disclosure provides DMD oligonucleotide compositions with improved properties, e.g., increased skipping of exon 51 or 53, reduced toxicities, etc. Among other things, DMD oligonucleotides of the present disclosure comprise chemical modifications, stereochemistry, and/or combinations thereof which can improve various properties and activities of DMD oligonucleotides. Non-limiting examples are listed in Table A1. In some embodiments, a DMD oligonucleotide type is a type as defined by the base sequence, pattern of backbone linkages, pattern of backbone chiral centers and pattern of backbone phosphorus modifications of a DMD oligonucleotide in Table A1, wherein the DMD oligonucleotide comprises at least one chirally controlled internucleotidic linkage (at least one R or S in "Stereochemistry/Linkage").

In some embodiments, the present disclosure pertains to a DMD oligonucleotide described herein, e.g., in Table A1.

In the following table ID indicates identification or DMD oligonucleotide number; and Description indicates the modified sequence.

TABLE A1

Example Oligonucleotides.

| ID | Description | Naked Sequence | SEQ ID NO | Linkage/ Stereochemistry |
|---|---|---|---|---|
| WV-3152 | fU * SfC * SfA * SfA * SfG * SfG * SmAfA * SmGfA * SmUfG * SmGfC * SfA * SfU * SfU * SfU * SfC * SfU | *UCAAGGAAGAUGGCAUUUCU | 1 | SSSSS SOSOS OSOSSSSS S |
| WV-7336 | fU * fC * fA * fA * fGfG * mAfA * mGmA * fU * mGmGfC * fA * fU * fU * fU * fC * fU | UCAAGGAAGAUGGCAUUUCU | 2 | XXXXO XOXOX XOOXX XXX X |
| WV-9517 | fC * SfU * SfC * SfC * SfG * SfG * SfU * SfU * SmCfU * SmG * SfA * SmAmGfG * SfU * SfG * SfU * SfU * SfC | CUCCGGUUCUGAAGGUGUUC | 3 | SSSSS SSSOSS SOOSSSSS |
| WV-12880 | fC * SfU * SfCn001fC * SfG * SfGn001fU * SfU * SmCfU * SmG * SfA * SmAfG * SfG * SfU * SfGn001fU * SfU * SfC | CUCCGGUUCUGAAGGUGUUC | 4 | SS nX SS nX SSOSS SOSSS nX SS |
| WV-13405 | GTTGCCTCCGGTTCTGAAGGTGTTC | GTTGCCTCCGGTTCTGAAGGT GTTC | 5 | OOOOO OOOOO OOOOO OOOOO OOOO |
| WV-13406 | CTCCGGTTCTGAAGGTGTTC | CTCCGGTTCTGAAGGTGTTC | 6 | OOOOO OOOOO OOOOO OOOO |
| WV-13407 | TGCCTCCGGTTCTGAAGGTGTTCTTGTA | TGCCTCCGGTTCTGAAGGTGT T CTTGTA | 7 | OOOOO OOOOO OOOOO OOOOO OOOOO OO |
| WV-13826 | fU * SfC * SfC * SfG * SfG * SfU * SfU * SmCfU * SmG * SfA * SmAmGfG * SfU * SfG * SfU * SfU * SfC | UCCGGUUCUGAAGGUGUUC | 8 | SSSSS SSOSS SOOSSSSS |
| WV-13827 | fC * SfU * SfC * SfC * SfG * SfG * SfU * SfU * SmCfU * SmG * SfA * SmAmGfG * SfU * SfG * SfU * SfU | CUCCGGUUCUGAAGGUGUU | 9 | SSSSS SSSOSS SOOSSSS |
| WV-13835 | fU * SfC * SfC * SfG * SfG * SfU * SfU * SmCfU * SmG * SfA * SmAmGfG * SfU * SfG * SfU * SfU * SfC * SfU | UCCGGUUCUGAAGGUGUUCU | 10 | SSSSS SSOSS SOOSSSSS S |
| WV-13864 | fC * SfU * SfCn001RfC * SfG * SfGn001RfU * SfU * SmCfU * SmG * SfA * SmAfG * SfG * SfU * SfGn001RfU * SfU * SfC | CUCCGGUUCUGAAGGUGUUC | 11 | SS nR SS nR SSOSS SOSSS nR SS |

TABLE A1-continued

Example Oligonucleotides.

| ID | Description | Naked Sequence | SEQ ID NO | Linkage/ Stereochemistry |
|---|---|---|---|---|
| WV-14344 | fC * SfU * SfCn001RfC * SfG * SfGn001RfU * SfU * SmCfU * SmG * SfA * SmAfGfG * SfU * SfGn001RfU SfU * SfC | CUCCGGUUCUGAAGGUGUUC | 12 | SS nR SS nR SSOSS SOOSS nR SS |
| WV-14522 | fU * SfC * SfAn001fA * SfG * SfGn001mAfA * SmGmA * SfU * SmGmGfC * SfA * SfU * SfUn001fU * SfC * SfU | UCAAGGAAGAUGGCAUUUCU | 13 | SS nX SS nX OSOSSOOSSS nX SS |
| WV-14523 | fU * SfC * SfAn001fA * SfG * SfGn001mAfA * SmGmA * SfU * SmGmGfCn001fA * SfU * SfUn001fU * SfC * SfU | UCAAGGAAGAUGGCAUUUCU | 14 | SS nX SS nX OSOSSOO nX SS nX SS |
| WV-14791 | fU * SfC * SfCn001RfG * SfG * SfUn001RfU * SmCfU * SmG * SfA * SmAmGfG * SfU * SfGn001RfU * SfU * SfC * SfU | *UCCGGUUCUGAAGGUGUUC | 15 | SS nR SS nR SOSSSOOSS nR SSS |
| WV-15860 | fU * SfC * SfAn001fA * SfG * SfG * SmAfA * SmGmA * SfU * SmGmGfCn001fA * SfU * SfUn001fU * SfC * SfU | UCAAGGAAGAUGGCAUUUCU | 16 | SS nX SSSOSOS SOO nX SS nX SS |
| WV-15861 | fU * SfC * SfAn001fA * SfG * SfGn001mAfA * SmGmA * SfU * SmGmGfC * SfA * SfU * SfU * SfU * SfC * SfU | UCAAGGAAGAUGGCAUUUCU | 17 | SS nX SS nX OSOSSOOSSSSS S |
| WV-15862 | fU * SfC * SfA * SfA * SfG * SfG * SmAfA * SmGmA * SfU * SmGmGfCn001fA * SfU * SfUn001fU * SfC * SfU | UCAAGGAAGAUGGCAUUUCU | 18 | SSSSS SOSOS SOO nX SS nX SS |
| WV-17859 | fU * SfC * SfAn001fA * SfG * SfG * SmA * SfA * SmGmA * SfU * SmGmGfCn001fA * SfU * SfUn001fU * SfC * SfU | UCAAGGAAGAUGGCAUUUCU | 19 | SS nX SSSSS OSSOO nX SS nX SS |
| WV-17860 | fU * SfC * SfAn001fA * SfG * SfG * SmAfA * SmGmA * SfU * SmGmG * SfCn001fA * SfU * SfUn001fU * SfC * SfU | UCAAGGAAGAUGGCAUUUCU | 20 | SS nX SSSOSOS SOS nX SS nX SS |
| WV-17861 | fU * SfC * SfAn001fA * SfG * SfG * SmA * SfA * SmGmA * SfU * SmGmG * SfCn001fA * SfU * SfUn001fU * SfC * SfU | UCAAGGAAGAUGGCAUUUCU | 21 | SS nX SSSSS OSSOS nX SS nX SS |
| WV-17862 | fU * SfC * SfAn001fA * SfG * SfG * SfA * SfA * SmGmA * SfU * SmGfG * SfCn001fA * SfU * SfUn001fU * SfC * SfU | UCAAGGAAGAUGGCAUUUCU | 22 | SS nX SSSSS OSSOS nX SS nX SS |
| WV-17863 | fU * SfC * SfAn001fA * SfG * SfGn001mA * SfA * SmGmA * SfU * SmGmGfC * SfA * SfU * SfUn001fU SfC * SfU | UCAAGGAAGAUGGCAUUUCU | 23 | SS nX SS nX SSOSS OOSSS nX SS |
| WV-17864 | fU * SfC * SfAn001fA * SfG * SfGn001mAfA * SmGmA * SfU * SmGmG * SfC * SfA * SfU * SfUn001fU * SfC * SfU | UCAAGGAAGAUGGCAUUUCU | 24 | SS nX SS nX OSOSSOSS SS nX SS |
| WV-17865 | fU * SfC * SfAn001fA * SfG * SfGn001mA * SfA * SmGmA * SfU * SmGmG * SfC * SfA * SfU * SfUn001fU * SfC * SfU | UCAAGGAAGAUGGCAUUUCU | 25 | SS nX SS nX SSOSS OSSSS nX SS |
| WV-17866 | fU * SfC * SfAn001fA * SfG * SfGn001fA * SfA * SmGmA * SfU * SmGfG * SfC * SfA * SfU * SfUn001fU * SfC * SfU | UCAAGGAAGAUGGCAUUUCU | 26 | SS nX SS nX SSOSS OSSSS nX SS |
| WV-20034 | fU * SfG * SfAn001fA * SfA * SfUn001fC * SfU * SmG * SfC * SmC * SfA * SmG * SfA * SfG * SfC * SfAn001fG * SfG * SfU | UGAAAUCUGCCAGAGCAGGU | 27 | SS nX SS nX SSSSS SSSSS nX SS |
| WV-20034 | fU * SfG * SfAn001fA * SfA * SfUn001fC * SfU * SmG * SfC * SmC * SfA * SmG * SfA * SfG * SfC * SfAn001fG * SfG * SfU | UGAAAUCUGCCAGAGCAGGU | 28 | SS nX SS nX SSSSS SSSSS nX SS |
| WV-20037 | fA * SfA * SfUn001fC * SfU * SfGn001fC * SfC * SmA * SfG * SmA * SfG * SmC * SfA * SfG * SfG * SfUn001fA * SfC * SfC | AAUCUGCCAGAGCAGGUACC | 29 | SS nX SS nX SSSSS SSSSS nX SS |

TABLE A1-continued

Example Oligonucleotides.

| ID | Description | Naked Sequence | SEQ ID NO | Linkage/ Stereochemistry |
|---|---|---|---|---|
| WV-20040 | fC * SfU * SfGn001fC * SfC * SfAn001fG * SfA * SmG * SfC * SmA * SfG * SmG * SfU * SfA * SfC * SfCn001fU * SfC * SfC | CUGCCAGAGCAGGUACCUCC | 30 | SS nX SS nX SSSSS SSSSS nX SS |
| WV-20043 | fC * SfC * SfAn001fG * SfA * SfGn001fC * SfA * SmG * SfG * SmU * SfA * SmC * SfC * SfU * SfC * SfCn001fA * SfA * SfC | CCAGAGCAGGUACCUCCAAC | 31 | SS nX SS nX SSSSS SSSSS nX SS |
| WV-20046 | fG * SfA * SfGn001fC * SfA * SfGn001fG * SfU * SmA * SfC * SmC * SfU * SmC * SfC * SfA * SfA * SfCn001fA * SfU * SfC | GAGCAGGUACCUCCAACAUC | 32 | SS nX SS nX SSSSS SSSSS nX SS |
| WV-20049 | fC * SfA * SfGn001fG * SfU * SfAn001fC * SfC * SmU * SfC * SmC * SfA * SmA * SfC * SfA * SfU * SfCn001fA * SfA * SfG | CAGGUACCUCCAACAUCAAG | 33 | SS nX SS nX SSSSS SSSSS nX SS |
| WV-20050 | fA * SfG * SfGn001fU * SfA * SfCn001fC * SfU * SmC * SfC * SmA * SfA * SmC * SfA * SfU * SfC * SfAn001fA * SfG * SfG | AGGUACCUCCAACAUCAAGG | 34 | SS nX SS nX SSSSS SSSSS nX SS |
| WV-20051 | fG * SfG * SfUn001fA * SfC * SfCn001fU * SfC * SmC * SfA * SmA * SfC * SmA * SfU * SfC * SfA * SfAn001fG * SfG * SfA | GGUACCUCCAACAUCAAGGA | 35 | SS nX SS nX SSSSS SSSSS nX SS |
| WV-20052 | fG * SfU * SfAn001fC * SfC * SfUn001fC * SfC * SmA * SfA * SmC * SfA * SmU * SfC * SfA * SfA * SfGn001fG * SfA * SfA | GUACCUCCAACAUCAAGGAA | 36 | SS nX SS nX SSSSS SSSSS nX SS |
| WV-20053 | fU * SfA * SfCn001fC * SfU * SfCn001fC * SfA * SmA * SfC * SmA * SfU * SmC * SfA * SfA * SfG * SfGn001fA * SfA * SfG | UACCUCCAACAUCAAGGAAG | 37 | SS nX SS nX SSSSS SSSSS nX SS |
| WV-20054 | fA * SfC * SfCn001fU * SfC * SfCn001fA * SfA * SmC * SfA * SmU * SfC * SmA * SfA * SfG * SfG * SfAn001fA * SfG * SfA | ACCUCCAACAUCAAGGAAGA | 38 | SS nX SS nX SSSSS SSSSS nX SS |
| WV-20055 | fC * SfC * SfUn001fC * SfC * SfAn001fA * SfC * SmA * SfU * SmC * SfA * SmA * SfG * SfG * SfA * SfAn001fG * SfA * SfU | CCUCCAACAUCAAGGAAGAU | 39 | SS nX SS nX SSSSS SSSSS nX SS |
| WV-20056 | fC * SfU * SfCn001fC * SfA * SfAn001fC * SfA * SmU * SfC * SmA * SfA * SmG * SfG * SfA * SfA * SfGn001fA * SfU * SfG | CUCCAACAUCAAGGAAGAUG | 40 | SS nX SS nX SSSSS SSSSS nX SS |
| WV-20057 | fU * SfC * SfCn001fA * SfA * SfCn001fA * SfU * SmC * SfA * SmA * SfG * SmG * SfA * SfA * SfG * SfAn001fU * SfG * SfG | UCCAACAUCAAGGAAGAUGG | 41 | SS nX SS nX SSSSS SSSSS nX SS |
| WV-20058 | fC * SfC * SfAn001fA * SfC * SfAn001fU * SfC * SmA * SfA * SmG * SfG * SmA * SfA * SfG * SfA * SfUn001fG * SfG * SfC | CCAACAUCAAGGAAGAUGGC | 42 | SS nX SS nX SSSSS SSSSS nX SS |
| WV-20059 | fC * SfA * SfAn001fC * SfA * SfUn001fC * SfA * SmA * SfG * SmG * SfA * SmA * SfG * SfA * SfU * SfGn001fG * SfC * SfA | CAACAUCAAGGAAGAUGGCA | 43 | SS nX SS nX SSSSS SSSSS nX SS |
| WV-20060 | fA * SfA * SfCn001fA * SfU * SfCn001fA * SfA * SmG * SfG * SmA * SfA * SmG * SfA * SfU * SfG * SfGn001fC * SfA * SfU | AACAUCAAGGAAGAUGGCAU | 44 | SS nX SS nX SSSSS SSSSS nX SS |
| WV-20061 | fA * SfC * SfAn001fU * SfC * SfAn001fA * SfG * SmG * SfA * SmA * SfG * SmA * SfU * SfG * SfG * SfCn001fA * SfU * SfU | ACAUCAAGGAAGAUGGCAUU | 45 | SS nX SS nX SSSSS SSSSS nX SS |
| WV-20062 | fC * SfA * SfUn001fC * SfA * SfAn001fG * SfG * SmA * SfA * SmG * SfA * SmU * SfG * SfG * SfC * SfAn001fU * SfU * SfU | CAUCAAGGAAGAUGGCAUUU | 46 | SS nX SS nX SSSSS SSSSS nX SS |
| WV-20063 | fA * SfU * SfCn001fA * SfA * SfGn001fG * SfA * SmA * SfG * SmA * SfU * SmG * SfG * SfC * SfA * SfUn001fU * SfU * SfC | AUCAAGGAAGAUGGCAUUUC | 47 | SS nX SS nX SSSSS SSSSS nX SS |

TABLE A1-continued

Example Oligonucleotides.

| ID | Description | Naked Sequence | SEQ ID NO | Linkage/ Stereochemistry |
|---|---|---|---|---|
| WV-20064 | fU * SfC * SfAn001fA * SfG * SfGn001fA * SfA * SmG * SfA * SmU * SfG * SmG * SfC * SfA * SfU * SfUn001fU * SfC * SfU | UCAAGGAAGAUGGCAUUUCU | 48 | SS nX SS nX SSSSS SSSSS nX SS |
| WV-20064 | fU * SfC * SfAn001fA * SfG * SfGn001fA * SfA * SmG * SfA * SmU * SfG * SmG * SfC * SfA * SfU * SfUn001fU * SfC * SfU | UCAAGGAAGAUGGCAUUUCU | 49 | SS nX SS nX SSSSS SSSSS nX SS |
| WV-20065 | fC * SfA * SfAn001fG * SfG * SfAn001fA * SfG * SmA * SfU * SmG * SfG * SmC * SfA * SfU * SfU * SfUn001fC * SfU * SfA | CAAGGAAGAUGGCAUUUCUA | 50 | SS nX SS nX SSSSS SSSSS nX SS |
| WV-20066 | fA * SfA * SfGn001fG * SfA * SfAn001fG * SfA * SmU * SfG * SmG * SfC * SmA * SfU * SfU * SfU * SfCn001fU * SfA * SfG | AAGGAAGAUGGCAUUUCUAG | 51 | SS nX SS nX SSSSS SSSSS nX SS |
| WV-20067 | fA * SfG * SfGn001fA * SfA * SfGn001fA * SfU * SmG * SfG * SmC * SfA * SmU * SfU * SfU * SfC * SfUn001fA * SfG * SfU | AGGAAGAUGGCAUUUCUAGU | 52 | SS nX SS nX SSSSS SSSSS nX SS |
| WV-20068 | fG * SfG * SfAn001fA * SfG * SfAn001fU * SfG * SmG * SfC * SmA * SfU * SmU * SfU * SfC * SfU * SfAn001fG * SfU * SfU | GGAAGAUGGCAUUUCUAGUU | 53 | SS nX SS nX SSSSS SSSSS nX SS |
| WV-20069 | fG * SfA * SfAn001fG * SfA * SfUn001fG * SfG * SmC * SfA * SmU * SfU * SmU * SfC * SfU * SfA * SfGn001fU * SfU * SfU | GAAGAUGGCAUUUCUAGUUU | 54 | SS nX SS nX SSSSS SSSSS nX SS |
| WV-20070 | fA * SfA * SfGn001fA * SfU * SfGn001fG * SfC * SmA * SfU * SmU * SfU * SmC * SfU * SfA * SfG * SfUn001fU * SfU * SfG | AAGAUGGCAUUUCUAGUUUG | 55 | SS nX SS nX SSSSS SSSSS nX SS |
| WV-20070 | fA * SfA * SfGn001fA * SfU * SfGn001fG * SfC * SmA * SfU * SmU * SfU * SmC * SfU * SfA * SfG * SfUn001fU * SfU * SfG | AAGAUGGCAUUUCUAGUUUG | 56 | SS nX SS nX SSSSS SSSSS nX SS |
| WV-20071 | fA * SfG * SfAn001fU * SfG * SfGn001fC * SfA * SmU * SfU * SmU * SfC * SmU * SfA * SfG * SfU * SfUn001fU * SfG * SfG | AGAUGGCAUUUCUAGUUUGG | 57 | SS nX SS nX SSSSS SSSSS nX SS |
| WV-20072 | fG * SfA * SfUn001fG * SfG * SfCn001fA * SfU * SmU * SfU * SmC * SfU * SmA * SfG * SfU * SfU * SfUn001fG * SfG * SfA | GAUGGCAUUUCUAGUUUGGA | 58 | SS nX SS nX SSSSS SSSSS nX SS |
| WV-20073 | fA * SfU * SfGn001fG * SfC * SfAn001fU * SfU * SmU * SfC * SmU * SfA * SmG * SfU * SfU * SfU * SfGn001fG * SfA * SfG | AUGGCAUUUCUAGUUUGGAG | 59 | SS nX SS nX SSSSS SSSSS nX SS |
| WV-20073 | fA * SfU * SfGn001fG * SfC * SfAn001fU * SfU * SmU * SfC * SmU * SfA * SmG * SfU * SfU * SfU * SfGn001fG * SfA * SfG | AUGGCAUUUCUAGUUUGGAG | 60 | SS nX SS nX SSSSS SSSSS nX SS |
| WV-20074 | fU * SfG * SfGn001fC * SfA * SfUn001fU * SfU * SmC * SfU * SmA * SfG * SmU * SfU * SfU * SfG * SfGn001fA * SfG * SfA | UGGCAUUUCUAGUUUGGAGA | 61 | SS nX SS nX SSSSS SSSSS nX SS |
| WV-20075 | fG * SfG * SfCn001fA * SfU * SfUn001fU * SfC * SmU * SfA * SmG * SfU * SmU * SfU * SfG * SfG * SfAn001fG * SfA * SfU | GGCAUUUCUAGUUUGGAGAU | 62 | SS nX SS nX SSSSS SSSSS nX SS |
| WV-20076 | fG * SfC * SfAn001fU * SfU * SfUn001fC * SfU * SmA * SfG * SmU * SfU * SmU * SfG * SfG * SfA * SfGn001fA * SfU * SfG | GCAUUUCUAGUUUGGAGAUG | 63 | SS nX SS nX SSSSS SSSSS nX SS |
| WV-20076 | fG * SfC * SfAn001fU * SfU * SfUn001fC * SfU * SmA * SfG * SmU * SfU * SmU * SfG * SfG * SfA * SfGn001fA * SfU * SfG | GCAUUUCUAGUUUGGAGAUG | 64 | SS nX SS nX SSSSS SSSSS nX SS |
| WV-20077 | fC * SfA * SfUn001fU * SfU * SfCn001fU * SfA * SmG * SfU * SmU * SfU * SmG * SfG * SfA * SfG * SfAn001fU * SfG * SfG | CAUUUCUAGUUUGGAGAUGG | 65 | SS nX SS nX SSSSS SSSSS nX SS |

TABLE A1-continued

| Example Oligonucleotides. | | | | |
|---|---|---|---|---|
| ID | Description | Naked Sequence | SEQ ID NO | Linkage/ Stereochemistry |
| WV-20078 | fA * SfU * SfUn001fU * SfC * SfUn001fA * SfG * SmU * SfU * SmU * SfG * SmG * SfA * SfG * SfA * SfUn001fG * SfG * SfC | AUUUCUAGUUUGGAGAUGGC | 66 | SS nX SS nX SSSSS SSSSS nX SS |
| WV-20079 | fU * SfU * SfUn001fC * SfU * SfAn001fG * SfU * SmU * SfU * SmG * SfG * SmA * SfG * SfA * SfU * SfGn001fG * SfC * SfA | UUUCUAGUUUGGAGAUGGCA | 67 | SS nX SS nX SSSSS SSSSS nX SS |
| WV-20080 | fU * SfU * SfCn001fU * SfA * SfGn001fU * SfU * SmU * SfG * SmG * SfA * SmG * SfA * SfU * SfG * SfGn001fC * SfA * SfG | UUCUAGUUUGGAGAUGGCAG | 68 | SS nX SS nX SSSSS SSSSS nX SS |
| WV-20081 | fU * SfC * SfUn001fA * SfG * SfUn001fU * SfU * SmG * SfG * SmA * SfG * SmA * SfU * SfG * SfG * SfCn001fA * SfG * SfU | UCUAGUUUGGAGAUGGCAGU | 69 | SS nX SS nX SSSSS SSSSS nX SS |
| WV-20082 | fC * SfU * SfAn001fG * SfU * SfUn001fU * SfG * SmG * SfA * SmG * SfA * SmU * SfG * SfG * SfC * SfAn001fG * SfU * SfU | CUAGUUUGGAGAUGGCAGUU | 70 | SS nX SS nX SSSSS SSSSS nX SS |
| WV-20083 | fU * SfA * SfGn001fU * SfU * SfUn001fG * SfG * SmA * SfG * SmA * SfU * SmG * SfG * SfC * SfA * SfGn001fU * SfU * SfU | UAGUUUGGAGAUGGCAGUUU | 71 | SS nX SS nX SSSSS SSSSS nX SS |
| WV-20084 | fA * SfG * SfUn001fU * SfU * SfGn001fG * SfA * SmG * SfA * SmU * SfG * SmG * SfC * SfA * SfG * SfUn001fU * SfU * SfC | AGUUUGGAGAUGGCAGUUUC | 72 | SS nX SS nX SSSSS SSSSS nX SS |
| WV-20085 | fG * SfU * SfUn001fU * SfG * SfGn001fA * SfG * SmA * SfU * SmG * SfG * SmC * SfA * SfG * SfU * SfUn001fU * SfC * SfC | GUUUGGAGAUGGCAGUUUCC | 73 | SS nX SS nX SSSSS SSSSS nX SS |
| WV-20086 | fU * SfU * SfUn001fG * SfG * SfAn001fG * SfA * SmU * SfG * SmG * SfC * SmA * SfG * SfU * SfU * SfUn001fC * SfC * SfU | UUUGGAGAUGGCAGUUUCCU | 74 | SS nX SS nX SSSSS SSSSS nX SS |
| WV-20087 | fU * SfU * SfGn001fG * SfA * SfGn001fA * SfU * SmG * SfG * SmC * SfA * SmG * SfU * SfU * SfU * SfCn001fC * SfU * SfU | UUGGAGAUGGCAGUUUCCUU | 75 | SS nX SS nX SSSSS SSSSS nX SS |
| WV-20088 | fU * SfG * SfGn001fA * SfG * SfAn001fU * SfG * SmG * SfC * SmA * SfG * SmU * SfU * SfU * SfC * SfCn001fU * SfU * SfA | UGGAGAUGGCAGUUUCCUUA | 76 | SS nX SS nX SSSSS SSSSS nX SS |
| WV-20089 | fG * SfG * SfAn001fG * SfA * SfUn001fG * SfG * SmC * SfA * SmG * SfU * SmU * SfU * SfC * SfC * SfUn001fU * SfA * SfG | GGAGAUGGCAGUUUCCUUAG | 77 | SS nX SS nX SSSSS SSSSS nX SS |
| WV-20090 | fG * SfA * SfGn001fA * SfU * SfGn001fG * SfC * SmA * SfG * SmU * SfU * SmU * SfC * SfC * SfU * SfUn001fA * SfG * SfU | GAGAUGGCAGUUUCCUUAGU | 78 | SS nX SS nX SSSSS SSSSS nX SS |
| WV-20091 | fA * SfG * SfAn001fU * SfG * SfGn001fC * SfA * SmG * SfU * SmU * SfU * SmC * SfC * SfU * SfU * SfAn001fG * SfU * SfA | AGAUGGCAGUUUCCUUAGUA | 79 | SS nX SS nX SSSSS SSSSS nX SS |
| WV-20092 | fG * SfA * SfUn001fG * SfG * SfCn001fA * SfG * SmU * SfU * SmU * SfC * SmC * SfU * SfU * SfA * SfGn001fU * SfA * SfA | GAUGGCAGUUUCCUUAGUAA | 80 | SS nX SS nX SSSSS SSSSS nX SS |
| WV-20093 | fA * SfU * SfGn001fG * SfC * SfAn001fG * SfU * SmU * SfU * SmC * SfC * SmU * SfU * SfA * SfG * SfUn001fA * SfA * SfC | AUGGCAGUUUCCUUAGUAAC | 81 | SS nX SS nX SSSSS SSSSS nX SS |
| WV-20094 | fU * SfG * SfGn001fC * SfA * SfGn001fU * SfU * SmU * SfC * SmC * SfU * SmU * SfA * SfG * SfU * SfAn001fA * SfC * SfC | UGGCAGUUUCCUUAGUAACC | 82 | SS nX SS nX SSSSS SSSSS nX SS |
| WV-20095 | fG * SfG * SfCn001fA * SfG * SfUn001fU * SfU * SmC * SfC * SmU * SfU * SmA * SfG * SfU * SfA * SfAn001fC * SfC * SfA | GGCAGUUUCCUUAGUAACCA | 83 | SS nX SS nX SSSSS SSSSS nX SS |

TABLE A1-continued

Example Oligonucleotides.

| ID | Description | Naked Sequence | SEQ ID NO | Linkage/ Stereochemistry |
|---|---|---|---|---|
| WV-20096 | fG * SfC * SfAn001fG * SfU * SfUn001fU * SfC * SmC * SfU * SmU * SfA * SmG * SfU * SfA * SfA * SfCn001fC * SfA * SfC | GCAGUUUCCUUAGUAACCAC | 84 | SS nX SS nX SSSSS SSSSS nX SS |
| WV-20097 | fC * SfA * SfGn001fU * SfU * SfUn001fC * SfC * SmU * SfU * SmA * SfG * SmU * SfA * SfA * SfC * SfCn001fA * SfC * SfA | CAGUUUCCUUAGUAACCACA | 85 | SS nX SS nX SSSSS SSSSS nX SS |
| WV-20098 | fA * SfG * SfUn001fU * SfU * SfCn001fC * SfU * SmU * SfA * SmG * SfU * SmA * SfA * SfC * SfC * SfAn001fC * SfA * SfG | AGUUUCCUUAGUAACCACAG | 86 | SS nX SS nX SSSSS SSSSS nX SS |
| WV-20099 | fG * SfU * SfUn001fU * SfC * SfCn001fU * SfU * SmA * SfG * SmU * SfA * SmA * SfC * SfC * SfA * SfCn001fA * SfG * SfG | GUUUCCUUAGUAACCACAGG | 87 | SS nX SS nX SSSSS SSSSS nX SS |
| WV-20100 | fU * SfU * SfUn001fC * SfC * SfUn001fU * SfA * SmG * SfU * SmA * SfA * SmC * SfC * SfA * SfC * SfAn001fG * SfG * SfU | UUUCCUUAGUAACCACAGGU | 88 | SS nX SS nX SSSSS SSSSS nX SS |
| WV-20101 | fU * SfU * SfCn001fC * SfU * SfUn001fA * SfG * SmU * SfA * SmA * SfC * SmC * SfA * SfC * SfA * SfGn001fG * SfU * SfU | UUCCUUAGUAACCACAGGUU | 89 | SS nX SS nX SSSSS SSSSS nX SS |
| WV-20102 | fU * SfC * SfCn001fU * SfU * SfAn001fG * SfU * SmA * SfA * SmC * SfC * SmA * SfC * SfA * SfG * SfGn001fU * SfU * SfG | UCCUUAGUAACCACAGGUUG | 90 | SS nX SS nX SSSSS SSSSS nX SS |
| WV-20103 | fC * SfC * SfUn001fU * SfA * SfGn001fU * SfA * SmA * SfC * SmC * SfA * SmC * SfA * SfG * SfG * SfUn001fU * SfG * SfU | CCUUAGUAACCACAGGUUGU | 91 | SS nX SS nX SSSSS SSSSS nX SS |
| WV-20104 | fC * SfU * SfUn001fA * SfG * SfUn001fA * SfA * SmC * SfC * SmA * SfC * SmA * SfG * SfG * SfU * SfUn001fG * SfU * SfG | CUUAGUAACCACAGGUUGUG | 92 | SS nX SS nX SSSSS SSSSS nX SS |
| WV-20105 | fU * SfU * SfAn001fG * SfU * SfAn001fA * SfC * SmC * SfA * SmC * SfA * SmG * SfG * SfU * SfU * SfGn001fU * SfG * SfU | UUAGUAACCACAGGUUGUGU | 93 | SS nX SS nX SSSSS SSSSS nX SS |
| WV-20106 | fU * SfA * SfGn001fU * SfA * SfAn001fC * SfC * SmA * SfC * SmA * SfG * SmG * SfU * SfU * SfG * SfUn001fG * SfU * SfC | UAGUAACCACAGGUUGUGUC | 94 | SS nX SS nX SSSSS SSSSS nX SS |
| WV-20107 | fA * SfG * SfUn001fA * SfA * SfCn001fC * SfA * SmC * SfA * SmG * SfG * SmU * SfU * SfG * SfU * SfGn001fU * SfC * SfA | AGUAACCACAGGUUGUGUCA | 95 | SS nX SS nX SSSSS SSSSS nX SS |
| WV-20108 | fG * SfU * SfAn001fA * SfC * SfCn001fA * SfC * SmA * SfG * SmG * SfU * SmU * SfG * SfU * SfG * SfUn001fC * SfA * SfC | GUAACCACAGGUUGUGUCAC | 96 | SS nX SS nX SSSSS SSSSS nX SS |
| WV-20109 | fU * SfA * SfAn001fC * SfC * SfAn001fC * SfA * SmG * SfG * SmU * SfU * SmG * SfU * SfG * SfU * SfCn001fA * SfC * SfC | UAACCACAGGUUGUGUCACC | 97 | SS nX SS nX SSSSS SSSSS nX SS |
| WV-20110 | fA * SfA * SfCn001fC * SfA * SfCn001fA * SfG * SmG * SfU * SmU * SfG * SmU * SfG * SfU * SfC * SfAn001fC * SfC * SfA | AACCACAGGUUGUGUCACCA | 98 | SS nX SS nX SSSSS SSSSS nX SS |
| WV-20111 | fA * SfC * SfCn001fA * SfC * SfAn001fG * SfG * SmU * SfU * SmG * SfU * SmG * SfU * SfC * SfA * SfCn001fC * SfA * SfG | ACCACAGGUUGUGUCACCAG | 99 | SS nX SS nX SSSSS SSSSS nX SS |
| WV-20112 | fC * SfC * SfAn001fC * SfA * SfGn001fG * SfU * SmU * SfG * SmU * SfG * SmU * SfC * SfA * SfC * SfCn001fA * SfG * SfA | CCACAGGUUGUGUCACCAGA | 100 | SS nX SS nX SSSSS SSSSS nX SS |
| WV-20113 | fC * SfA * SfCn001fA * SfG * SfGn001fU * SfU * SmG * SfU * SmG * SfU * SmC * SfA * SfC * SfC * SfAn001fG * SfA * SfG | CACAGGUUGUGUCACCAGAG | 101 | SS nX SS nX SSSSS SSSSS nX SS |

TABLE A1-continued

Example Oligonucleotides.

| ID | Description | Naked Sequence | SEQ ID NO | Linkage/ Stereochemistry |
|---|---|---|---|---|
| WV-20114 | fA * SfC * SfAn001fG * SfG * SfUn001fU * SfG * SmU * SfG * SmU * SfC * SmA * SfC * SfC * SfA * SfGn001fA * SfG * SfU | ACAGGUUGUGUCACCAGAGU | 102 | SS nX SS nX SSSSS SSSSS nX SS |
| WV-20115 | fC * SfA * SfGn001fG * SfU * SfUn001fG * SfU * SmG * SfU * SmC * SfA * SmC * SfC * SfA * SfG * SfAn001fG * SfU * SfA | CAGGUUGUGUCACCAGAGUA | 103 | SS nX SS nX SSSSS SSSSS nX SS |
| WV-20116 | fA * SfG * SfGn001fU * SfU * SfGn001fU * SfG * SmU * SfC * SmA * SfC * SmC * SfA * SfG * SfA * SfGn001fU * SfA * SfA | AGGUUGUGUCACCAGAGUAA | 104 | SS nX SS nX SSSSS SSSSS nX SS |
| WV-20117 | fG * SfG * SfUn001fU * SfG * SfUn001fG * SfU * SmC * SfA * SmC * SfC * SmA * SfG * SfA * SfG * SfUn001fA * SfA * SfC | GGUUGUGUCACCAGAGUAAC | 105 | SS nX SS nX SSSSS SSSSS nX SS |
| WV-20118 | fG * SfU * SfUn001fG * SfU * SfGn001fU * SfC * SmA * SfC * SmC * SfA * SmG * SfA * SfG * SfU * SfAn001fA * SfC * SfA | GUUGUGUCACCAGAGUAACA | 106 | SS nX SS nX SSSSS SSSSS nX SS |
| WV-20119 | fU * SfU * SfGn001fU * SfG * SfUn001fC * SfA * SmC * SfC * SmA * SfG * SmA * SfG * SfU * SfA * SfAn001fC * SfA * SfG | UUGUGUCACCAGAGUAACAG | 107 | SS nX SS nX SSSSS SSSSS nX SS |
| WV-20120 | fU * SfG * SfUn001fG * SfU * SfCn001fA * SfC * SmC * SfA * SmG * SfA * SmG * SfU * SfA * SfA * SfCn001fA * SfG * SfU | UGUGUCACCAGAGUAACAGU | 108 | SS nX SS nX SSSSS SSSSS nX SS |
| WV-20121 | fG * SfU * SfGn001fU * SfC * SfAn001fC * SfC * SmA * SfG * SmA * SfG * SmU * SfA * SfA * SfC * SfAn001fG * SfU * SfC | GUGUCACCAGAGUAACAGUC | 109 | SS nX SS nX SSSSS SSSSS nX SS |
| WV-20122 | fU * SfG * SfUn001fC * SfA * SfCn001fC * SfA * SmG * SfA * SmG * SfU * SmA * SfA * SfC * SfA * SfGn001fU * SfC * SfU | UGUCACCAGAGUAACAGUCU | 110 | SS nX SS nX SSSSS SSSSS nX SS |
| WV-20123 | fG * SfU * SfCn001fA * SfC * SfCn001fA * SfG * SmA * SfG * SmU * SfA * SmA * SfC * SfA * SfG * SfUn001fC * SfU * SfG | GUCACCAGAGUAACAGUCUG | 111 | SS nX SS nX SSSSS SSSSS nX SS |
| WV-20124 | fU * SfC * SfAn001fC * SfC * SfAn001fG * SfA * SmG * SfU * SmA * SfA * SmC * SfA * SfG * SfU * SfCn001fU * SfG * SfA | UCACCAGAGUAACAGUCUGA | 112 | SS nX SS nX SSSSS SSSSS nX SS |
| WV-20125 | fC * SfA * SfCn001fC * SfA * SfGn001fA * SfG * SmU * SfA * SmA * SfC * SmA * SfG * SfU * SfC * SfUn001fG * SfA * SfG | CACCAGAGUAACAGUCUGAG | 113 | SS nX SS nX SSSSS SSSSS nX SS |
| WV-20126 | fA * SfC * SfCn001fA * SfG * SfAn001fG * SfU * SmA * SfA * SmC * SfA * SmG * SfU * SfC * SfU * SfGn001fA * SfG * SfU | ACCAGAGUAACAGUCUGAGU | 114 | SS nX SS nX SSSSS SSSSS nX SS |
| WV-20127 | fC * SfC * SfAn001fG * SfA * SfGn001fU * SfA * SmA * SfC * SmA * SfG * SmU * SfC * SfU * SfG * SfAn001fG * SfU * SfA | CCAGAGUAACAGUCUGAGUA | 115 | SS nX SS nX SSSSS SSSSS nX SS |
| WV-20128 | fC * SfA * SfGn001fA * SfG * SfUn001fA * SfA * SmC * SfA * SmG * SfU * SmC * SfU * SfG * SfA * SfGn001fU * SfA * SfG | CAGAGUAACAGUCUGAGUAG | 116 | SS nX SS nX SSSSS SSSSS nX SS |
| WV-20129 | fA * SfG * SfAn001fG * SfU * SfAn001fA * SfC * SmA * SfG * SmU * SfC * SmU * SfG * SfA * SfG * SfUn001fA * SfG * SfG | AGAGUAACAGUCUGAGUAGG | 117 | SS nX SS nX SSSSS SSSSS nX SS |
| WV-20130 | fG * SfA * SfGn001fU * SfA * SfAn001fC * SfA * SmG * SfU * SmC * SfU * SmG * SfA * SfG * SfU * SfAn001fG * SfG * SfA | GAGUAACAGUCUGAGUAGGA | 118 | SS nX SS nX SSSSS SSSSS nX SS |
| WV-20131 | fA * SfG * SfUn001fA * SfA * SfCn001fA * SfG * SmU * SfC * SmU * SfG * SmA * SfG * SfU * SfA * SfGn001fG * SfA * SfG | AGUAACAGUCUGAGUAGGAG | 119 | SS nX SS nX SSSSS SSSSS nX SS |

TABLE A1-continued

Example Oligonucleotides.

| ID | Description | Naked Sequence | SEQ ID NO | Linkage/ Stereochemistry |
|---|---|---|---|---|
| WV-20132 | fG * SfU * SfAn001fA * SfC * SfAn001fG * SfU * SmC * SfU * SmG * SfA * SmG * SfU * SfA * SfG * SfGn001fA * SfG * SfC | GUAACAGUCUGAGUAGGAGC | 120 | SS nX SS nX SSSSS SSSSS nX SS |
| WV-20133 | fU * SfA * SfAn001fC * SfA * SfGn001fU * SfC * SmU * SfG * SmA * SfG * SmU * SfA * SfG * SfG * SfAn001fG * SfC * SfU | UAACAGUCUGAGUAGGAGCU | 121 | SS nX SS nX SSSSS SSSSS nX SS |
| WV-20134 | fA * SfA * SfCn001fA * SfG * SfUn001fC * SfU * SmG * SfA * SmG * SfU * SmA * SfG * SfG * SfA * SfGn001fC * SfU * SfA | AACAGUCUGAGUAGGAGCUA | 122 | SS nX SS nX SSSSS SSSSS nX SS |
| WV-20135 | fA * SfC * SfAn001fG * SfU * SfCn001fU * SfG * SmA * SfG * SmU * SfA * SmG * SfG * SfA * SfG * SfCn001fU * SfA * SfA | ACAGUCUGAGUAGGAGCUAA | 123 | SS nX SS nX SSSSS SSSSS nX SS |
| WV-20136 | fC * SfA * SfGn001fU * SfC * SfUn001fG * SfA * SmG * SfU * SmA * SfG * SmG * SfA * SfG * SfC * SfUn001fA * SfA * SfA | CAGUCUGAGUAGGAGCUAAA | 124 | SS nX SS nX SSSSS SSSSS nX SS |
| WV-20137 | fA * SfG * SfUn001fC * SfU * SfGn001fA * SfG * SmU * SfA * SmG * SfG * SmA * SfG * SfC * SfU * SfAn001fA * SfA * SfA | AGUCUGAGUAGGAGCUAAAA | 125 | SS nX SS nX SSSSS SSSSS nX SS |
| WV-20138 | fG * SfU * SfCn001fU * SfG * SfAn001fG * SfU * SmA * SfG * SmG * SfA * SmG * SfC * SfU * SfA * SfAn001fA * SfA * SfU | GUCUGAGUAGGAGCUAAAAU | 126 | SS nX SS nX SSSSS SSSSS nX SS |
| WV-20139 | fU * SfC * SfUn001fG * SfA * SfGn001fU * SfA * SmG * SfG * SmA * SfG * SmC * SfU * SfA * SfA * SfAn001fA * SfU * SfA | UCUGAGUAGGAGCUAAAAUA | 127 | SS nX SS nX SSSSS SSSSS nX SS |
| WV-20140 | fC * SfU * SfGn001fA * SfG * SfUn001fA * SfG * SmG * SfA * SmG * SfC * SmU * SfA * SfA * SfA * SfAn001fU * SfA * SfU | CUGAGUAGGAGCUAAAAUAU | 128 | SS nX SS nX SSSSS SSSSS nX SS |

In Table A1:
Spaces in Table A1 are utilized for formatting and readability, e.g., OXXXXX XXXXX XXXXXX XXXX illustrates the same stereochemistry as OXXXXXXXXXXXXXXXXXXX; * S and *S both indicate phosphorothioate internucleotidic linkage wherein the linkage phosphorus has Sp configuration; etc.
All DMD oligonucleotides listed in Tables A1 are single-stranded. As described in the present application, they may be used as a single strand, or as a strand to form complexes with one or more other strands.
Some sequences, due to their length, are divided into multiple lines.
ID: Identification number for an oligonucleotide.
WV-13405, WV-13406 and WV-13407 are fully PMO (morpholino oligonucleotides).

Abbreviations in Tables:
n001: non-negatively charged linkage

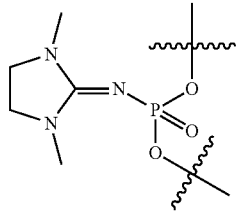 [SMILES: *OP(=O)(N=C1N(C)CCN1C)O*]

(which is stereorandom unless otherwise indicated (e.g., as n001R, or n001S));
n001R: n001 being chirally controlled and having the Rp configuration;
n001S: n001 being chirally controlled and having the Sp configuration;
nX: in Linkage/Stereochemistry, nO or nX indicates a stereorandom n001;
nR: in Linkage/Stereochemistry, nR indicates n001 being chirally controlled and having the Rp configuration;
nS: in Linkage/Stereochemistry, nS indicates n001 being chirally controlled and having the Sp configuration;
F, f: 2'-F modification on the following nucleoside (e.g., fA

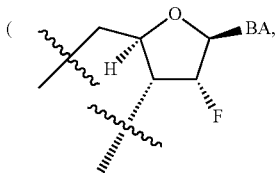

wherein BA is nucleobase A));
m: 2'-OMe modification on the following nucleoside (e.g., mA

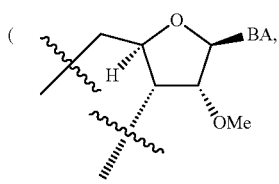

wherein BA is nucleobase A));
*, PS: Phosphorothioate;
*R, R, Rp: Phosphorothioate in Rp conformation;
*S, S, Sp: Phosphorothioate in Sp conformation;
X: Phosphorothioate stereorandom;
O, PO: phosphodiester (phosphate). When no internucleotidic linkage is specified between two nucleoside units, the internucleotidic linkage is a phosphodiester linkage (natural phosphate linkage).

In some embodiments, each phosphorothioate internucleotidic linkage of a DMD oligonucleotide is independently a chirally controlled internucleotidic linkage. In some embodiments, a provided DMD oligonucleotide composition is a chirally controlled DMD oligonucleotide composition of a DMD oligonucleotide type listed in Table A1, wherein each phosphorothioate internucleotidic linkage of the DMD oligonucleotide is independently a chirally controlled internucleotidic linkage.

In some embodiments, the present disclosure provides compositions comprising or consisting of a plurality of provided DMD oligonucleotides (e.g., chirally controlled DMD oligonucleotide compositions). In some embodiments, all DMD oligonucleotides of the plurality are of the same type, i.e., all have the same base sequence, pattern of backbone linkages, pattern of backbone chiral centers, and pattern of backbone phosphorus modifications. In some embodiments, all DMD oligonucleotides of the same type are structural identical. In some embodiments, provided compositions comprise DMD oligonucleotides of a plurality of DMD oligonucleotides types, typically in controlled amounts. In some embodiments, a provided chirally controlled DMD oligonucleotide composition comprises a combination of two or more provided DMD oligonucleotide types.

In some embodiments, a DMD oligonucleotide composition of the present disclosure is a chirally controlled DMD oligonucleotide composition, wherein the sequence of the DMD oligonucleotides of its plurality comprises or consists of a base sequence listed in Table A1.

In some embodiments, the present disclosure provides a DMD oligonucleotide composition, wherein the DMD oligonucleotide is WV-13405.

In some embodiments, the present disclosure provides a DMD oligonucleotide composition, wherein the DMD oligonucleotide is WV-13405.

In some embodiments, the present disclosure provides a DMD oligonucleotide composition, wherein the DMD oligonucleotide is WV-13406.

In some embodiments, the present disclosure provides a DMD oligonucleotide composition, wherein the DMD oligonucleotide is WV-13407.

In some embodiments, the present disclosure provides a DMD oligonucleotide composition, wherein the DMD oligonucleotide is WV-13826.

In some embodiments, the present disclosure provides a DMD oligonucleotide composition, wherein the DMD oligonucleotide is WV-13827.

In some embodiments, the present disclosure provides a DMD oligonucleotide composition, wherein the DMD oligonucleotide is WV-13835.

In some embodiments, the present disclosure provides a DMD oligonucleotide composition, wherein the DMD oligonucleotide is WV-13835.

In some embodiments, the present disclosure provides a DMD oligonucleotide composition, wherein the DMD oligonucleotide is WV-13864.

In some embodiments, the present disclosure provides a DMD oligonucleotide composition, wherein the DMD oligonucleotide is WV-14344.

In some embodiments, the present disclosure provides a DMD oligonucleotide composition, wherein the DMD oligonucleotide is WV-14522.

In some embodiments, the present disclosure provides a DMD oligonucleotide composition, wherein the DMD oligonucleotide is WV-14523.

In some embodiments, the present disclosure provides a DMD oligonucleotide composition, wherein the DMD oligonucleotide is WV-14791.

In some embodiments, the present disclosure provides a DMD oligonucleotide composition, wherein the DMD oligonucleotide is WV-15860.

In some embodiments, the present disclosure provides a DMD oligonucleotide composition, wherein the DMD oligonucleotide is WV-15860.

In some embodiments, the present disclosure provides a DMD oligonucleotide composition, wherein the DMD oligonucleotide is WV-15861.

In some embodiments, the present disclosure provides a DMD oligonucleotide composition, wherein the DMD oligonucleotide is WV-15862.

In some embodiments, the present disclosure provides a DMD oligonucleotide composition, wherein the DMD oligonucleotide is WV-17859.

In some embodiments, the present disclosure provides a DMD oligonucleotide composition, wherein the DMD oligonucleotide is WV-17860.

In some embodiments, the present disclosure provides a DMD oligonucleotide composition, wherein the DMD oligonucleotide is WV-17861.

In some embodiments, the present disclosure provides a DMD oligonucleotide composition, wherein the DMD oligonucleotide is WV-17862.

In some embodiments, the present disclosure provides a DMD oligonucleotide composition, wherein the DMD oligonucleotide is WV-17863.

In some embodiments, the present disclosure provides a DMD oligonucleotide composition, wherein the DMD oligonucleotide is WV-17864.

In some embodiments, the present disclosure provides a DMD oligonucleotide composition, wherein the DMD oligonucleotide is WV-17865.

In some embodiments, the present disclosure provides a DMD oligonucleotide composition, wherein the DMD oligonucleotide is WV-17866.

In some embodiments, the present disclosure provides a DMD oligonucleotide composition, wherein the DMD oligonucleotide is WV-20034.

In some embodiments, the present disclosure provides a DMD oligonucleotide composition, wherein the DMD oligonucleotide is WV-20037.

In some embodiments, the present disclosure provides a DMD oligonucleotide composition, wherein the DMD oligonucleotide is WV-20040.

In some embodiments, the present disclosure provides a DMD oligonucleotide composition, wherein the DMD oligonucleotide is WV-20043.

In some embodiments, the present disclosure provides a DMD oligonucleotide composition, wherein the DMD oligonucleotide is WV-20046.

In some embodiments, the present disclosure provides a DMD oligonucleotide composition, wherein the DMD oligonucleotide is WV-20049.

In some embodiments, the present disclosure provides a DMD oligonucleotide composition, wherein the DMD oligonucleotide is WV-20050.

In some embodiments, the present disclosure provides a DMD oligonucleotide composition, wherein the DMD oligonucleotide is WV-20051.

In some embodiments, the present disclosure provides a DMD oligonucleotide composition, wherein the DMD oligonucleotide is WV-20052.

In some embodiments, the present disclosure provides a DMD oligonucleotide composition, wherein the DMD oligonucleotide is WV-20053.

In some embodiments, the present disclosure provides a DMD oligonucleotide composition, wherein the DMD oligonucleotide is WV-20054.

In some embodiments, the present disclosure provides a DMD oligonucleotide composition, wherein the DMD oligonucleotide is WV-20055.

In some embodiments, the present disclosure provides a DMD oligonucleotide composition, wherein the DMD oligonucleotide is WV-20056.

In some embodiments, the present disclosure provides a DMD oligonucleotide composition, wherein the DMD oligonucleotide is WV-20057.

In some embodiments, the present disclosure provides a DMD oligonucleotide composition, wherein the DMD oligonucleotide is WV-20058.

In some embodiments, the present disclosure provides a DMD oligonucleotide composition, wherein the DMD oligonucleotide is WV-20059.

In some embodiments, the present disclosure provides a DMD oligonucleotide composition, wherein the DMD oligonucleotide is WV-20060.

In some embodiments, the present disclosure provides a DMD oligonucleotide composition, wherein the DMD oligonucleotide is WV-20061.

In some embodiments, the present disclosure provides a DMD oligonucleotide composition, wherein the DMD oligonucleotide is WV-20062.

In some embodiments, the present disclosure provides a DMD oligonucleotide composition, wherein the DMD oligonucleotide is WV-20063.

In some embodiments, the present disclosure provides a DMD oligonucleotide composition, wherein the DMD oligonucleotide is WV-20064.

In some embodiments, the present disclosure provides a DMD oligonucleotide composition, wherein the DMD oligonucleotide is WV-20065.

In some embodiments, the present disclosure provides a DMD oligonucleotide composition, wherein the DMD oligonucleotide is WV-20066.

In some embodiments, the present disclosure provides a DMD oligonucleotide composition, wherein the DMD oligonucleotide is WV-20067.

In some embodiments, the present disclosure provides a DMD oligonucleotide composition, wherein the DMD oligonucleotide is WV-20067.

In some embodiments, the present disclosure provides a DMD oligonucleotide composition, wherein the DMD oligonucleotide is WV-20068.

In some embodiments, the present disclosure provides a DMD oligonucleotide composition, wherein the DMD oligonucleotide is WV-20069.

In some embodiments, the present disclosure provides a DMD oligonucleotide composition, wherein the DMD oligonucleotide is WV-20070.

In some embodiments, the present disclosure provides a DMD oligonucleotide composition, wherein the DMD oligonucleotide is WV-20071.

In some embodiments, the present disclosure provides a DMD oligonucleotide composition, wherein the DMD oligonucleotide is WV-20072.

In some embodiments, the present disclosure provides a DMD oligonucleotide composition, wherein the DMD oligonucleotide is WV-20073.

In some embodiments, the present disclosure provides a DMD oligonucleotide composition, wherein the DMD oligonucleotide is WV-20074.

In some embodiments, the present disclosure provides a DMD oligonucleotide composition, wherein the DMD oligonucleotide is WV-20075.

In some embodiments, the present disclosure provides a DMD oligonucleotide composition, wherein the DMD oligonucleotide is WV-20076.

In some embodiments, the present disclosure provides a DMD oligonucleotide composition, wherein the DMD oligonucleotide is WV-20076.

In some embodiments, the present disclosure provides a DMD oligonucleotide composition, wherein the DMD oligonucleotide is WV-20077.

In some embodiments, the present disclosure provides a DMD oligonucleotide composition, wherein the DMD oligonucleotide is WV-20078.

In some embodiments, the present disclosure provides a DMD oligonucleotide composition, wherein the DMD oligonucleotide is WV-20079.

In some embodiments, the present disclosure provides a DMD oligonucleotide composition, wherein the DMD oligonucleotide is WV-20080.

In some embodiments, the present disclosure provides a DMD oligonucleotide composition, wherein the DMD oligonucleotide is WV-20081.

In some embodiments, the present disclosure provides a DMD oligonucleotide composition, wherein the DMD oligonucleotide is WV-20082.

In some embodiments, the present disclosure provides a DMD oligonucleotide composition, wherein the DMD oligonucleotide is WV-20083.

In some embodiments, the present disclosure provides a DMD oligonucleotide composition, wherein the DMD oligonucleotide is WV-20084.

In some embodiments, the present disclosure provides a DMD oligonucleotide composition, wherein the DMD oligonucleotide is WV-20085.

In some embodiments, the present disclosure provides a DMD oligonucleotide composition, wherein the DMD oligonucleotide is WV-20086.

In some embodiments, the present disclosure provides a DMD oligonucleotide composition, wherein the DMD oligonucleotide is WV-20087.

In some embodiments, the present disclosure provides a DMD oligonucleotide composition, wherein the DMD oligonucleotide is WV-20088.

In some embodiments, the present disclosure provides a DMD oligonucleotide composition, wherein the DMD oligonucleotide is WV-20089.

In some embodiments, the present disclosure provides a DMD oligonucleotide composition, wherein the DMD oligonucleotide is WV-20090.

In some embodiments, the present disclosure provides a DMD oligonucleotide composition, wherein the DMD oligonucleotide is WV-20091.

In some embodiments, the present disclosure provides a DMD oligonucleotide composition, wherein the DMD oligonucleotide is WV-20092.

In some embodiments, the present disclosure provides a DMD oligonucleotide composition, wherein the DMD oligonucleotide is WV-20093.

In some embodiments, the present disclosure provides a DMD oligonucleotide composition, wherein the DMD oligonucleotide is WV-20094.

In some embodiments, the present disclosure provides a DMD oligonucleotide composition, wherein the DMD oligonucleotide is WV-20095.

In some embodiments, the present disclosure provides a DMD oligonucleotide composition, wherein the DMD oligonucleotide is WV-20096.

In some embodiments, the present disclosure provides a DMD oligonucleotide composition, wherein the DMD oligonucleotide is WV-20097.

In some embodiments, the present disclosure provides a DMD oligonucleotide composition, wherein the DMD oligonucleotide is WV-20098.

In some embodiments, the present disclosure provides a DMD oligonucleotide composition, wherein the DMD oligonucleotide is WV-20099.

In some embodiments, the present disclosure provides a DMD oligonucleotide composition, wherein the DMD oligonucleotide is WV-20100.

In some embodiments, the present disclosure provides a DMD oligonucleotide composition, wherein the DMD oligonucleotide is WV-20101.

In some embodiments, the present disclosure provides a DMD oligonucleotide composition, wherein the DMD oligonucleotide is WV-20102.

In some embodiments, the present disclosure provides a DMD oligonucleotide composition, wherein the DMD oligonucleotide is WV-20103.

In some embodiments, the present disclosure provides a DMD oligonucleotide composition, wherein the DMD oligonucleotide is WV-20104.

In some embodiments, the present disclosure provides a DMD oligonucleotide composition, wherein the DMD oligonucleotide is WV-20105.

In some embodiments, the present disclosure provides a DMD oligonucleotide composition, wherein the DMD oligonucleotide is WV-20106.

In some embodiments, the present disclosure provides a DMD oligonucleotide composition, wherein the DMD oligonucleotide is WV-20107.

In some embodiments, the present disclosure provides a DMD oligonucleotide composition, wherein the DMD oligonucleotide is WV-20108.

In some embodiments, the present disclosure provides a DMD oligonucleotide composition, wherein the DMD oligonucleotide is WV-20109.

In some embodiments, the present disclosure provides a DMD oligonucleotide composition, wherein the DMD oligonucleotide is WV-20110.

In some embodiments, the present disclosure provides a DMD oligonucleotide composition, wherein the DMD oligonucleotide is WV-20111.

In some embodiments, the present disclosure provides a DMD oligonucleotide composition, wherein the DMD oligonucleotide is WV-20112.

In some embodiments, the present disclosure provides a DMD oligonucleotide composition, wherein the DMD oligonucleotide is WV-20113.

In some embodiments, the present disclosure provides a DMD oligonucleotide composition, wherein the DMD oligonucleotide is WV-20114.

In some embodiments, the present disclosure provides a DMD oligonucleotide composition, wherein the DMD oligonucleotide is WV-20115.

In some embodiments, the present disclosure provides a DMD oligonucleotide composition, wherein the DMD oligonucleotide is WV-20116.

In some embodiments, the present disclosure provides a DMD oligonucleotide composition, wherein the DMD oligonucleotide is WV-20117.

In some embodiments, the present disclosure provides a DMD oligonucleotide composition, wherein the DMD oligonucleotide is WV-20118.

In some embodiments, the present disclosure provides a DMD oligonucleotide composition, wherein the DMD oligonucleotide is WV-20119.

In some embodiments, the present disclosure provides a DMD oligonucleotide composition, wherein the DMD oligonucleotide is WV-20120.

In some embodiments, the present disclosure provides a DMD oligonucleotide composition, wherein the DMD oligonucleotide is WV-20121.

In some embodiments, the present disclosure provides a DMD oligonucleotide composition, wherein the DMD oligonucleotide is WV-20122.

In some embodiments, the present disclosure provides a DMD oligonucleotide composition, wherein the DMD oligonucleotide is WV-20123.

In some embodiments, the present disclosure provides a DMD oligonucleotide composition, wherein the DMD oligonucleotide is WV-20124.

In some embodiments, the present disclosure provides a DMD oligonucleotide composition, wherein the DMD oligonucleotide is WV-20125.

In some embodiments, the present disclosure provides a DMD oligonucleotide composition, wherein the DMD oligonucleotide is WV-20126.

In some embodiments, the present disclosure provides a DMD oligonucleotide composition, wherein the DMD oligonucleotide is WV-20127.

In some embodiments, the present disclosure provides a DMD oligonucleotide composition, wherein the DMD oligonucleotide is WV-20128.

In some embodiments, the present disclosure provides a DMD oligonucleotide composition, wherein the DMD oligonucleotide is WV-20129.

In some embodiments, the present disclosure provides a DMD oligonucleotide composition, wherein the DMD oligonucleotide is WV-20130.

In some embodiments, the present disclosure provides a DMD oligonucleotide composition, wherein the DMD oligonucleotide is WV-20131.

In some embodiments, the present disclosure provides a DMD oligonucleotide composition, wherein the DMD oligonucleotide is WV-20132.

In some embodiments, the present disclosure provides a DMD oligonucleotide composition, wherein the DMD oligonucleotide is WV-20133.

In some embodiments, the present disclosure provides a DMD oligonucleotide composition, wherein the DMD oligonucleotide is WV-20134.

In some embodiments, the present disclosure provides a DMD oligonucleotide composition, wherein the DMD oligonucleotide is WV-20135.

In some embodiments, the present disclosure provides a DMD oligonucleotide composition, wherein the DMD oligonucleotide is WV-20136.

In some embodiments, the present disclosure provides a DMD oligonucleotide composition, wherein the DMD oligonucleotide is WV-20137.

In some embodiments, the present disclosure provides a DMD oligonucleotide composition, wherein the DMD oligonucleotide is WV-20138.

In some embodiments, the present disclosure provides a DMD oligonucleotide composition, wherein the DMD oligonucleotide is WV-20139.

In some embodiments, the present disclosure provides a DMD oligonucleotide composition, wherein the DMD oligonucleotide is WV-20140.

In some embodiments, the present disclosure provides a DMD oligonucleotide composition, wherein the DMD oligonucleotide is WV-13835.

In some embodiments, the present disclosure provides a DMD oligonucleotide composition, wherein the DMD oligonucleotide is WV-13864.

In some embodiments, the present disclosure provides a DMD oligonucleotide composition, wherein the DMD oligonucleotide is WV-14344.

In some embodiments, the present disclosure provides a chirally controlled composition of DMD oligonucleotide WV-13835.

In some embodiments, the present disclosure provides a chirally controlled composition of DMD oligonucleotide WV-13864.

In some embodiments, the present disclosure provides a chirally controlled composition of DMD oligonucleotide WV-14344.

In some embodiments, the present disclosure provides a DMD oligonucleotide composition, wherein the DMD oligonucleotide is WV-13405.

In some embodiments, the present disclosure provides a DMD oligonucleotide composition, wherein the DMD oligonucleotide is WV-13406.

In some embodiments, the present disclosure provides a DMD oligonucleotide composition, wherein the DMD oligonucleotide is WV-13407.

In some embodiments, the present disclosure provides a DMD oligonucleotide composition, wherein the DMD oligonucleotide is WV-13826.

In some embodiments, the present disclosure provides a DMD oligonucleotide composition, wherein the DMD oligonucleotide is WV-13827.

In some embodiments, the present disclosure provides a DMD oligonucleotide composition, wherein the DMD oligonucleotide is WV-13835.

In some embodiments, the present disclosure provides a DMD oligonucleotide composition, wherein the DMD oligonucleotide is WV-13864.

In some embodiments, the present disclosure provides a DMD oligonucleotide composition, wherein the DMD oligonucleotide is WV-14344.

In some embodiments, the present disclosure provides a DMD oligonucleotide composition, wherein the DMD oligonucleotide is WV-14522.

In some embodiments, the present disclosure provides a DMD oligonucleotide composition, wherein the DMD oligonucleotide is WV-14523.

In some embodiments, the present disclosure provides a DMD oligonucleotide composition, wherein the DMD oligonucleotide is WV-14791.

In some embodiments, the present disclosure provides a DMD oligonucleotide composition, wherein the DMD oligonucleotide is WV-15860.

In some embodiments, the present disclosure provides a DMD oligonucleotide composition, wherein the DMD oligonucleotide is WV-15861.

In some embodiments, the present disclosure provides a DMD oligonucleotide composition, wherein the DMD oligonucleotide is WV-15862.

In some embodiments, the present disclosure provides a DMD oligonucleotide composition, wherein the DMD oligonucleotide is WV-17859.

In some embodiments, the present disclosure provides a DMD oligonucleotide composition, wherein the DMD oligonucleotide is WV-17860.

In some embodiments, the present disclosure provides a DMD oligonucleotide composition, wherein the DMD oligonucleotide is WV-17861.

In some embodiments, the present disclosure provides a DMD oligonucleotide composition, wherein the DMD oligonucleotide is WV-17862.

In some embodiments, the present disclosure provides a DMD oligonucleotide composition, wherein the DMD oligonucleotide is WV-17863.

In some embodiments, the present disclosure provides a DMD oligonucleotide composition, wherein the DMD oligonucleotide is WV-17864.

In some embodiments, the present disclosure provides a DMD oligonucleotide composition, wherein the DMD oligonucleotide is WV-17865.

In some embodiments, the present disclosure provides a DMD oligonucleotide composition, wherein the DMD oligonucleotide is WV-17866.

In some embodiments, the present disclosure provides a DMD oligonucleotide composition, wherein the DMD oligonucleotide is WV-20034.

In some embodiments, the present disclosure provides a DMD oligonucleotide composition, wherein the DMD oligonucleotide is WV-20037.

In some embodiments, the present disclosure provides a DMD oligonucleotide composition, wherein the DMD oligonucleotide is WV-20040.

In some embodiments, the present disclosure provides a DMD oligonucleotide composition, wherein the DMD oligonucleotide is WV-20043.

In some embodiments, the present disclosure provides a DMD oligonucleotide composition, wherein the DMD oligonucleotide is WV-20046.

In some embodiments, the present disclosure provides a DMD oligonucleotide composition, wherein the DMD oligonucleotide is WV-20049.

In some embodiments, the present disclosure provides a DMD oligonucleotide composition, wherein the DMD oligonucleotide is WV-20050.

In some embodiments, the present disclosure provides a DMD oligonucleotide composition, wherein the DMD oligonucleotide is WV-20051.

In some embodiments, the present disclosure provides a DMD oligonucleotide composition, wherein the DMD oligonucleotide is WV-20052.

In some embodiments, the present disclosure provides a DMD oligonucleotide composition, wherein the DMD oligonucleotide is WV-20053.

In some embodiments, the present disclosure provides a DMD oligonucleotide composition, wherein the DMD oligonucleotide is WV-20054.

In some embodiments, the present disclosure provides a DMD oligonucleotide composition, wherein the DMD oligonucleotide is WV-20055.

In some embodiments, the present disclosure provides a DMD oligonucleotide composition, wherein the DMD oligonucleotide is WV-20056.

In some embodiments, the present disclosure provides a DMD oligonucleotide composition, wherein the DMD oligonucleotide is WV-20057.

In some embodiments, the present disclosure provides a DMD oligonucleotide composition, wherein the DMD oligonucleotide is WV-20058.

In some embodiments, the present disclosure provides a DMD oligonucleotide composition, wherein the DMD oligonucleotide is WV-20059.

In some embodiments, the present disclosure provides a DMD oligonucleotide composition, wherein the DMD oligonucleotide is WV-20060.

In some embodiments, the present disclosure provides a DMD oligonucleotide composition, wherein the DMD oligonucleotide is WV-20061.

In some embodiments, the present disclosure provides a DMD oligonucleotide composition, wherein the DMD oligonucleotide is WV-20062.

In some embodiments, the present disclosure provides a DMD oligonucleotide composition, wherein the DMD oligonucleotide is WV-20063.

In some embodiments, the present disclosure provides a DMD oligonucleotide composition, wherein the DMD oligonucleotide is WV-20064.

In some embodiments, the present disclosure provides a DMD oligonucleotide composition, wherein the DMD oligonucleotide is WV-20065.

In some embodiments, the present disclosure provides a DMD oligonucleotide composition, wherein the DMD oligonucleotide is WV-20066.

In some embodiments, the present disclosure provides a DMD oligonucleotide composition, wherein the DMD oligonucleotide is WV-20067.

In some embodiments, the present disclosure provides a DMD oligonucleotide composition, wherein the DMD oligonucleotide is WV-20068.

In some embodiments, the present disclosure provides a DMD oligonucleotide composition, wherein the DMD oligonucleotide is WV-20069.

In some embodiments, the present disclosure provides a DMD oligonucleotide composition, wherein the DMD oligonucleotide is WV-20070.

In some embodiments, the present disclosure provides a DMD oligonucleotide composition, wherein the DMD oligonucleotide is WV-20071.

In some embodiments, the present disclosure provides a DMD oligonucleotide composition, wherein the DMD oligonucleotide is WV-20072.

In some embodiments, the present disclosure provides a DMD oligonucleotide composition, wherein the DMD oligonucleotide is WV-20073.

In some embodiments, the present disclosure provides a DMD oligonucleotide composition, wherein the DMD oligonucleotide is WV-20074.

In some embodiments, the present disclosure provides a DMD oligonucleotide composition, wherein the DMD oligonucleotide is WV-20075.

In some embodiments, the present disclosure provides a DMD oligonucleotide composition, wherein the DMD oligonucleotide is WV-20076.

In some embodiments, the present disclosure provides a DMD oligonucleotide composition, wherein the DMD oligonucleotide is WV-20076.

In some embodiments, the present disclosure provides a DMD oligonucleotide composition, wherein the DMD oligonucleotide is WV-20077.

In some embodiments, the present disclosure provides a DMD oligonucleotide composition, wherein the DMD oligonucleotide is WV-20078.

In some embodiments, the present disclosure provides a DMD oligonucleotide composition, wherein the DMD oligonucleotide is WV-20079.

In some embodiments, the present disclosure provides a DMD oligonucleotide composition, wherein the DMD oligonucleotide is WV-20080.

In some embodiments, the present disclosure provides a DMD oligonucleotide composition, wherein the DMD oligonucleotide is WV-20081.

In some embodiments, the present disclosure provides a DMD oligonucleotide composition, wherein the DMD oligonucleotide is WV-20082.

In some embodiments, the present disclosure provides a DMD oligonucleotide composition, wherein the DMD oligonucleotide is WV-20083.

In some embodiments, the present disclosure provides a DMD oligonucleotide composition, wherein the DMD oligonucleotide is WV-20084.

In some embodiments, the present disclosure provides a DMD oligonucleotide composition, wherein the DMD oligonucleotide is WV-20085.

In some embodiments, the present disclosure provides a DMD oligonucleotide composition, wherein the DMD oligonucleotide is WV-20086.

In some embodiments, the present disclosure provides a DMD oligonucleotide composition, wherein the DMD oligonucleotide is WV-20087.

In some embodiments, the present disclosure provides a DMD oligonucleotide composition, wherein the DMD oligonucleotide is WV-20088.

In some embodiments, the present disclosure provides a DMD oligonucleotide composition, wherein the DMD oligonucleotide is WV-20089.

In some embodiments, the present disclosure provides a DMD oligonucleotide composition, wherein the DMD oligonucleotide is WV-20090.

In some embodiments, the present disclosure provides a DMD oligonucleotide composition, wherein the DMD oligonucleotide is WV-20091.

In some embodiments, the present disclosure provides a DMD oligonucleotide composition, wherein the DMD oligonucleotide is WV-20092.

In some embodiments, the present disclosure provides a DMD oligonucleotide composition, wherein the DMD oligonucleotide is WV-20093.

In some embodiments, the present disclosure provides a DMD oligonucleotide composition, wherein the DMD oligonucleotide is WV-20094.

In some embodiments, the present disclosure provides a DMD oligonucleotide composition, wherein the DMD oligonucleotide is WV-20095.

In some embodiments, the present disclosure provides a DMD oligonucleotide composition, wherein the DMD oligonucleotide is WV-20096.

In some embodiments, the present disclosure provides a DMD oligonucleotide composition, wherein the DMD oligonucleotide is WV-20097.

In some embodiments, the present disclosure provides a DMD oligonucleotide composition, wherein the DMD oligonucleotide is WV-20098.

In some embodiments, the present disclosure provides a DMD oligonucleotide composition, wherein the DMD oligonucleotide is WV-20099.

In some embodiments, the present disclosure provides a DMD oligonucleotide composition, wherein the DMD oligonucleotide is WV-20100.

In some embodiments, the present disclosure provides a DMD oligonucleotide composition, wherein the DMD oligonucleotide is WV-20101.

In some embodiments, the present disclosure provides a DMD oligonucleotide composition, wherein the DMD oligonucleotide is WV-20102.

In some embodiments, the present disclosure provides a DMD oligonucleotide composition, wherein the DMD oligonucleotide is WV-20103.

In some embodiments, the present disclosure provides a DMD oligonucleotide composition, wherein the DMD oligonucleotide is WV-20104.

In some embodiments, the present disclosure provides a DMD oligonucleotide composition, wherein the DMD oligonucleotide is WV-20105.

In some embodiments, the present disclosure provides a DMD oligonucleotide composition, wherein the DMD oligonucleotide is WV-20106.

In some embodiments, the present disclosure provides a DMD oligonucleotide composition, wherein the DMD oligonucleotide is WV-20107.

In some embodiments, the present disclosure provides a DMD oligonucleotide composition, wherein the DMD oligonucleotide is WV-20108.

In some embodiments, the present disclosure provides a DMD oligonucleotide composition, wherein the DMD oligonucleotide is WV-20109.

In some embodiments, the present disclosure provides a DMD oligonucleotide composition, wherein the DMD oligonucleotide is WV-20110.

In some embodiments, the present disclosure provides a DMD oligonucleotide composition, wherein the DMD oligonucleotide is WV-20111.

In some embodiments, the present disclosure provides a DMD oligonucleotide composition, wherein the DMD oligonucleotide is WV-20112.

In some embodiments, the present disclosure provides a DMD oligonucleotide composition, wherein the DMD oligonucleotide is WV-20113.

In some embodiments, the present disclosure provides a DMD oligonucleotide composition, wherein the DMD oligonucleotide is WV-20114.

In some embodiments, the present disclosure provides a DMD oligonucleotide composition, wherein the DMD oligonucleotide is WV-20115.

In some embodiments, the present disclosure provides a DMD oligonucleotide composition, wherein the DMD oligonucleotide is WV-20116.

In some embodiments, the present disclosure provides a DMD oligonucleotide composition, wherein the DMD oligonucleotide is WV-20117.

In some embodiments, the present disclosure provides a DMD oligonucleotide composition, wherein the DMD oligonucleotide is WV-20118.

In some embodiments, the present disclosure provides a DMD oligonucleotide composition, wherein the DMD oligonucleotide is WV-20119.

In some embodiments, the present disclosure provides a DMD oligonucleotide composition, wherein the DMD oligonucleotide is WV-20120.

In some embodiments, the present disclosure provides a DMD oligonucleotide composition, wherein the DMD oligonucleotide is WV-20121.

In some embodiments, the present disclosure provides a DMD oligonucleotide composition, wherein the DMD oligonucleotide is WV-20122.

In some embodiments, the present disclosure provides a DMD oligonucleotide composition, wherein the DMD oligonucleotide is WV-20123.

In some embodiments, the present disclosure provides a DMD oligonucleotide composition, wherein the DMD oligonucleotide is WV-20124.

In some embodiments, the present disclosure provides a DMD oligonucleotide composition, wherein the DMD oligonucleotide is WV-20125.

In some embodiments, the present disclosure provides a DMD oligonucleotide composition, wherein the DMD oligonucleotide is WV-20126.

In some embodiments, the present disclosure provides a DMD oligonucleotide composition, wherein the DMD oligonucleotide is WV-20127.

In some embodiments, the present disclosure provides a DMD oligonucleotide composition, wherein the DMD oligonucleotide is WV-20128.

In some embodiments, the present disclosure provides a DMD oligonucleotide composition, wherein the DMD oligonucleotide is WV-20129.

In some embodiments, the present disclosure provides a DMD oligonucleotide composition, wherein the DMD oligonucleotide is WV-20130.

In some embodiments, the present disclosure provides a DMD oligonucleotide composition, wherein the DMD oligonucleotide is WV-20131.

In some embodiments, the present disclosure provides a DMD oligonucleotide composition, wherein the DMD oligonucleotide is WV-20132.

In some embodiments, the present disclosure provides a DMD oligonucleotide composition, wherein the DMD oligonucleotide is WV-20133.

In some embodiments, the present disclosure provides a DMD oligonucleotide composition, wherein the DMD oligonucleotide is WV-20134.

In some embodiments, the present disclosure provides a DMD oligonucleotide composition, wherein the DMD oligonucleotide is WV-20135.

In some embodiments, the present disclosure provides a DMD oligonucleotide composition, wherein the DMD oligonucleotide is WV-20136.

In some embodiments, the present disclosure provides a DMD oligonucleotide composition, wherein the DMD oligonucleotide is WV-20137.

In some embodiments, the present disclosure provides a DMD oligonucleotide composition, wherein the DMD oligonucleotide is WV-20138.

In some embodiments, the present disclosure provides a DMD oligonucleotide composition, wherein the DMD oligonucleotide is WV-20139.

In some embodiments, the present disclosure provides a DMD oligonucleotide composition, wherein the DMD oligonucleotide is WV-20140.

In some embodiments, such a provided oligonucleotide composition may be chirally controlled, and comprises a plurality of the oligonucleotides, wherein one or more (e.g., 1, 2, 3, 4, 5, 6, 7, 8, 9, 10, 11, 12, 13, 14, 15, 16, 17, 18, 19, 20 or more) internucleotidic linkages are chirally controlled. In some embodiments, each chiral internucleotidic linkage is independently chirally controlled. In some embodiments, a chirally controlled internucleotidic linkage is one that of S, R, nR or nS as indicated in "Linkage/Stereochemistry" in Table A1.

In some embodiments, the present disclosure provides a chirally controlled DMD oligonucleotide composition, wherein the DMD oligonucleotide is capable of mediating skipping of a DMD exon and the DMD oligonucleotide is WV-13405.

In some embodiments, the present disclosure provides a chirally controlled DMD oligonucleotide composition, wherein the DMD oligonucleotide is capable of mediating skipping of a DMD exon and the DMD oligonucleotide is WV-13406.

In some embodiments, the present disclosure provides a chirally controlled DMD oligonucleotide composition, wherein the DMD oligonucleotide is capable of mediating skipping of a DMD exon and the DMD oligonucleotide is WV-13407.

In some embodiments, the present disclosure provides a chirally controlled DMD oligonucleotide composition, wherein the DMD oligonucleotide is capable of mediating skipping of a DMD exon and the DMD oligonucleotide is WV-13826.

In some embodiments, the present disclosure provides a chirally controlled DMD oligonucleotide composition, wherein the DMD oligonucleotide is capable of mediating skipping of a DMD exon and the DMD oligonucleotide is WV-13827.

In some embodiments, the present disclosure provides a chirally controlled DMD oligonucleotide composition, wherein the DMD oligonucleotide is capable of mediating skipping of a DMD exon and the DMD oligonucleotide is WV-13835.

In some embodiments, the present disclosure provides a chirally controlled DMD oligonucleotide composition, wherein the DMD oligonucleotide is capable of mediating skipping of a DMD exon and the DMD oligonucleotide is WV-13864.

In some embodiments, the present disclosure provides a chirally controlled DMD oligonucleotide composition, wherein the DMD oligonucleotide is capable of mediating skipping of a DMD exon and the DMD oligonucleotide is WV-14344.

In some embodiments, the present disclosure provides a chirally controlled DMD oligonucleotide composition, wherein the DMD oligonucleotide is capable of mediating skipping of a DMD exon and the DMD oligonucleotide is WV-14522.

In some embodiments, the present disclosure provides a chirally controlled DMD oligonucleotide composition, wherein the DMD oligonucleotide is capable of mediating skipping of a DMD exon and the DMD oligonucleotide is WV-14523.

In some embodiments, the present disclosure provides a chirally controlled DMD oligonucleotide composition, wherein the DMD oligonucleotide is capable of mediating skipping of a DMD exon and the DMD oligonucleotide is WV-14791.

In some embodiments, the present disclosure provides a chirally controlled DMD oligonucleotide composition, wherein the DMD oligonucleotide is capable of mediating skipping of a DMD exon and the DMD oligonucleotide is WV-15860.

In some embodiments, the present disclosure provides a chirally controlled DMD oligonucleotide composition, wherein the DMD oligonucleotide is capable of mediating skipping of a DMD exon and the DMD oligonucleotide is WV-15861.

In some embodiments, the present disclosure provides a chirally controlled DMD oligonucleotide composition, wherein the DMD oligonucleotide is capable of mediating skipping of a DMD exon and the DMD oligonucleotide is WV-15862.

In some embodiments, the present disclosure provides a chirally controlled DMD oligonucleotide composition, wherein the DMD oligonucleotide is capable of mediating skipping of a DMD exon and the DMD oligonucleotide is WV-17859.

In some embodiments, the present disclosure provides a chirally controlled DMD oligonucleotide composition, wherein the DMD oligonucleotide is capable of mediating skipping of a DMD exon and the DMD oligonucleotide is WV-17860.

In some embodiments, the present disclosure provides a chirally controlled DMD oligonucleotide composition, wherein the DMD oligonucleotide is capable of mediating skipping of a DMD exon and the DMD oligonucleotide is WV-17861.

In some embodiments, the present disclosure provides a chirally controlled DMD oligonucleotide composition, wherein the DMD oligonucleotide is capable of mediating skipping of a DMD exon and the DMD oligonucleotide is WV-17862.

In some embodiments, the present disclosure provides a chirally controlled DMD oligonucleotide composition, wherein the DMD oligonucleotide is capable of mediating skipping of a DMD exon and the DMD oligonucleotide is WV-17863.

In some embodiments, the present disclosure provides a chirally controlled DMD oligonucleotide composition, wherein the DMD oligonucleotide is capable of mediating skipping of a DMD exon and the DMD oligonucleotide is WV-17864.

In some embodiments, the present disclosure provides a chirally controlled DMD oligonucleotide composition, wherein the DMD oligonucleotide is capable of mediating skipping of a DMD exon and the DMD oligonucleotide is WV-17865.

In some embodiments, the present disclosure provides a chirally controlled DMD oligonucleotide composition, wherein the DMD oligonucleotide is capable of mediating skipping of a DMD exon and the DMD oligonucleotide is WV-17866.

In some embodiments, the present disclosure provides a chirally controlled DMD oligonucleotide composition, wherein the DMD oligonucleotide is capable of mediating skipping of a DMD exon and the DMD oligonucleotide is WV-20034.

In some embodiments, the present disclosure provides a chirally controlled DMD oligonucleotide composition, wherein the DMD oligonucleotide is capable of mediating skipping of a DMD exon and the DMD oligonucleotide is WV-20037.

In some embodiments, the present disclosure provides a chirally controlled DMD oligonucleotide composition, wherein the DMD oligonucleotide is capable of mediating skipping of a DMD exon and the DMD oligonucleotide is WV-20040.

In some embodiments, the present disclosure provides a chirally controlled DMD oligonucleotide composition, wherein the DMD oligonucleotide is capable of mediating skipping of a DMD exon and the DMD oligonucleotide is WV-20043.

In some embodiments, the present disclosure provides a chirally controlled DMD oligonucleotide composition, wherein the DMD oligonucleotide is capable of mediating skipping of a DMD exon and the DMD oligonucleotide is WV-20046.

In some embodiments, the present disclosure provides a chirally controlled DMD oligonucleotide composition, wherein the DMD oligonucleotide is capable of mediating skipping of a DMD exon and the DMD oligonucleotide is WV-20049.

In some embodiments, the present disclosure provides a chirally controlled DMD oligonucleotide composition, wherein the DMD oligonucleotide is capable of mediating skipping of a DMD exon and the DMD oligonucleotide is WV-20050.

In some embodiments, the present disclosure provides a chirally controlled DMD oligonucleotide composition, wherein the DMD oligonucleotide is capable of mediating skipping of a DMD exon and the DMD oligonucleotide is WV-20051.

In some embodiments, the present disclosure provides a chirally controlled DMD oligonucleotide composition, wherein the DMD oligonucleotide is capable of mediating skipping of a DMD exon and the DMD oligonucleotide is WV-20052.

In some embodiments, the present disclosure provides a chirally controlled DMD oligonucleotide composition, wherein the DMD oligonucleotide is capable of mediating skipping of a DMD exon and the DMD oligonucleotide is WV-20053.

In some embodiments, the present disclosure provides a chirally controlled DMD oligonucleotide composition, wherein the DMD oligonucleotide is capable of mediating skipping of a DMD exon and the DMD oligonucleotide is WV-20054.

In some embodiments, the present disclosure provides a chirally controlled DMD oligonucleotide composition, wherein the DMD oligonucleotide is capable of mediating skipping of a DMD exon and the DMD oligonucleotide is WV-20055.

In some embodiments, the present disclosure provides a chirally controlled DMD oligonucleotide composition, wherein the DMD oligonucleotide is capable of mediating skipping of a DMD exon and the DMD oligonucleotide is WV-20056.

In some embodiments, the present disclosure provides a chirally controlled DMD oligonucleotide composition, wherein the DMD oligonucleotide is capable of mediating skipping of a DMD exon and the DMD oligonucleotide is WV-20057.

In some embodiments, the present disclosure provides a chirally controlled DMD oligonucleotide composition, wherein the DMD oligonucleotide is capable of mediating skipping of a DMD exon and the DMD oligonucleotide is WV-20058.

In some embodiments, the present disclosure provides a chirally controlled DMD oligonucleotide composition, wherein the DMD oligonucleotide is capable of mediating skipping of a DMD exon and the DMD oligonucleotide is WV-20059.

In some embodiments, the present disclosure provides a chirally controlled DMD oligonucleotide composition, wherein the DMD oligonucleotide is capable of mediating skipping of a DMD exon and the DMD oligonucleotide is WV-20060.

In some embodiments, the present disclosure provides a chirally controlled DMD oligonucleotide composition, wherein the DMD oligonucleotide is capable of mediating skipping of a DMD exon and the DMD oligonucleotide is WV-20061.

In some embodiments, the present disclosure provides a chirally controlled DMD oligonucleotide composition, wherein the DMD oligonucleotide is capable of mediating skipping of a DMD exon and the DMD oligonucleotide is WV-20062.

In some embodiments, the present disclosure provides a chirally controlled DMD oligonucleotide composition, wherein the DMD oligonucleotide is capable of mediating skipping of a DMD exon and the DMD oligonucleotide is WV-20063.

In some embodiments, the present disclosure provides a chirally controlled DMD oligonucleotide composition, wherein the DMD oligonucleotide is capable of mediating skipping of a DMD exon and the DMD oligonucleotide is WV-20064.

In some embodiments, the present disclosure provides a chirally controlled DMD oligonucleotide composition, wherein the DMD oligonucleotide is capable of mediating skipping of a DMD exon and the DMD oligonucleotide is WV-20065.

In some embodiments, the present disclosure provides a chirally controlled DMD oligonucleotide composition, wherein the DMD oligonucleotide is capable of mediating skipping of a DMD exon and the DMD oligonucleotide is WV-20066.

In some embodiments, the present disclosure provides a chirally controlled DMD oligonucleotide composition, wherein the DMD oligonucleotide is capable of mediating skipping of a DMD exon and the DMD oligonucleotide is WV-20067.

In some embodiments, the present disclosure provides a chirally controlled DMD oligonucleotide composition, wherein the DMD oligonucleotide is capable of mediating skipping of a DMD exon and the DMD oligonucleotide is WV-20067.

In some embodiments, the present disclosure provides a chirally controlled DMD oligonucleotide composition, wherein the DMD oligonucleotide is capable of mediating skipping of a DMD exon and the DMD oligonucleotide is WV-20068.

In some embodiments, the present disclosure provides a chirally controlled DMD oligonucleotide composition, wherein the DMD oligonucleotide is capable of mediating skipping of a DMD exon and the DMD oligonucleotide is WV-20069.

In some embodiments, the present disclosure provides a chirally controlled DMD oligonucleotide composition, wherein the DMD oligonucleotide is capable of mediating skipping of a DMD exon and the DMD oligonucleotide is WV-20070.

In some embodiments, the present disclosure provides a chirally controlled DMD oligonucleotide composition, wherein the DMD oligonucleotide is capable of mediating skipping of a DMD exon and the DMD oligonucleotide is WV-20071.

In some embodiments, the present disclosure provides a chirally controlled DMD oligonucleotide composition, wherein the DMD oligonucleotide is capable of mediating skipping of a DMD exon and the DMD oligonucleotide is WV-20072.

In some embodiments, the present disclosure provides a chirally controlled DMD oligonucleotide composition, wherein the DMD oligonucleotide is capable of mediating skipping of a DMD exon and the DMD oligonucleotide is WV-20073.

In some embodiments, the present disclosure provides a chirally controlled DMD oligonucleotide composition, wherein the DMD oligonucleotide is capable of mediating skipping of a DMD exon and the DMD oligonucleotide is WV-20074.

In some embodiments, the present disclosure provides a chirally controlled DMD oligonucleotide composition, wherein the DMD oligonucleotide is capable of mediating skipping of a DMD exon and the DMD oligonucleotide is WV-20075.

In some embodiments, the present disclosure provides a chirally controlled DMD oligonucleotide composition, wherein the DMD oligonucleotide is capable of mediating skipping of a DMD exon and the DMD oligonucleotide is WV-20076.

In some embodiments, the present disclosure provides a chirally controlled DMD oligonucleotide composition, wherein the DMD oligonucleotide is capable of mediating skipping of a DMD exon and the DMD oligonucleotide is WV-20076.

In some embodiments, the present disclosure provides a chirally controlled DMD oligonucleotide composition, wherein the DMD oligonucleotide is capable of mediating skipping of a DMD exon and the DMD oligonucleotide is WV-20077.

In some embodiments, the present disclosure provides a chirally controlled DMD oligonucleotide composition, wherein the DMD oligonucleotide is capable of mediating skipping of a DMD exon and the DMD oligonucleotide is WV-20078.

In some embodiments, the present disclosure provides a chirally controlled DMD oligonucleotide composition, wherein the DMD oligonucleotide is capable of mediating skipping of a DMD exon and the DMD oligonucleotide is WV-20079.

In some embodiments, the present disclosure provides a chirally controlled DMD oligonucleotide composition, wherein the DMD oligonucleotide is capable of mediating skipping of a DMD exon and the DMD oligonucleotide is WV-20080.

In some embodiments, the present disclosure provides a chirally controlled DMD oligonucleotide composition, wherein the DMD oligonucleotide is capable of mediating skipping of a DMD exon and the DMD oligonucleotide is WV-20081.

In some embodiments, the present disclosure provides a chirally controlled DMD oligonucleotide composition, wherein the DMD oligonucleotide is capable of mediating skipping of a DMD exon and the DMD oligonucleotide is WV-20082.

In some embodiments, the present disclosure provides a chirally controlled DMD oligonucleotide composition, wherein the DMD oligonucleotide is capable of mediating skipping of a DMD exon and the DMD oligonucleotide is WV-20083.

In some embodiments, the present disclosure provides a chirally controlled DMD oligonucleotide composition, wherein the DMD oligonucleotide is capable of mediating skipping of a DMD exon and the DMD oligonucleotide is WV-20084.

In some embodiments, the present disclosure provides a chirally controlled DMD oligonucleotide composition, wherein the DMD oligonucleotide is capable of mediating skipping of a DMD exon and the DMD oligonucleotide is WV-20085.

In some embodiments, the present disclosure provides a chirally controlled DMD oligonucleotide composition, wherein the DMD oligonucleotide is capable of mediating skipping of a DMD exon and the DMD oligonucleotide is WV-20086.

In some embodiments, the present disclosure provides a chirally controlled DMD oligonucleotide composition, wherein the DMD oligonucleotide is capable of mediating skipping of a DMD exon and the DMD oligonucleotide is WV-20087.

In some embodiments, the present disclosure provides a chirally controlled DMD oligonucleotide composition, wherein the DMD oligonucleotide is capable of mediating skipping of a DMD exon and the DMD oligonucleotide is WV-20088.

In some embodiments, the present disclosure provides a chirally controlled DMD oligonucleotide composition, wherein the DMD oligonucleotide is capable of mediating skipping of a DMD exon and the DMD oligonucleotide is WV-20089.

In some embodiments, the present disclosure provides a chirally controlled DMD oligonucleotide composition, wherein the DMD oligonucleotide is capable of mediating skipping of a DMD exon and the DMD oligonucleotide is WV-20090.

In some embodiments, the present disclosure provides a chirally controlled DMD oligonucleotide composition, wherein the DMD oligonucleotide is capable of mediating skipping of a DMD exon and the DMD oligonucleotide is WV-20091.

In some embodiments, the present disclosure provides a chirally controlled DMD oligonucleotide composition, wherein the DMD oligonucleotide is capable of mediating skipping of a DMD exon and the DMD oligonucleotide is WV-20092.

In some embodiments, the present disclosure provides a chirally controlled DMD oligonucleotide composition, wherein the DMD oligonucleotide is capable of mediating skipping of a DMD exon and the DMD oligonucleotide is WV-20093.

In some embodiments, the present disclosure provides a chirally controlled DMD oligonucleotide composition, wherein the DMD oligonucleotide is capable of mediating skipping of a DMD exon and the DMD oligonucleotide is WV-20094.

In some embodiments, the present disclosure provides a chirally controlled DMD oligonucleotide composition, wherein the DMD oligonucleotide is capable of mediating skipping of a DMD exon and the DMD oligonucleotide is WV-20095.

In some embodiments, the present disclosure provides a chirally controlled DMD oligonucleotide composition, wherein the DMD oligonucleotide is capable of mediating skipping of a DMD exon and the DMD oligonucleotide is WV-20096.

In some embodiments, the present disclosure provides a chirally controlled DMD oligonucleotide composition, wherein the DMD oligonucleotide is capable of mediating skipping of a DMD exon and the DMD oligonucleotide is WV-20102.

In some embodiments, the present disclosure provides a chirally controlled DMD oligonucleotide composition, wherein the DMD oligonucleotide is capable of mediating skipping of a DMD exon and the DMD oligonucleotide is WV-20103.

In some embodiments, the present disclosure provides a chirally controlled DMD oligonucleotide composition, wherein the DMD oligonucleotide is capable of mediating skipping of a DMD exon and the DMD oligonucleotide is WV-20104.

In some embodiments, the present disclosure provides a chirally controlled DMD oligonucleotide composition, wherein the DMD oligonucleotide is capable of mediating skipping of a DMD exon and the DMD oligonucleotide is WV-20105.

In some embodiments, the present disclosure provides a chirally controlled DMD oligonucleotide composition, wherein the DMD oligonucleotide is capable of mediating skipping of a DMD exon and the DMD oligonucleotide is WV-20106.

In some embodiments, the present disclosure provides a chirally controlled DMD oligonucleotide composition, wherein the DMD oligonucleotide is capable of mediating skipping of a DMD exon and the DMD oligonucleotide is WV-20107.

In some embodiments, the present disclosure provides a chirally controlled DMD oligonucleotide composition, wherein the DMD oligonucleotide is capable of mediating skipping of a DMD exon and the DMD oligonucleotide is WV-20108.

In some embodiments, the present disclosure provides a chirally controlled DMD oligonucleotide composition, wherein the DMD oligonucleotide is capable of mediating skipping of a DMD exon and the DMD oligonucleotide is WV-20109.

In some embodiments, the present disclosure provides a chirally controlled DMD oligonucleotide composition, wherein the DMD oligonucleotide is capable of mediating skipping of a DMD exon and the DMD oligonucleotide is WV-20110.

In some embodiments, the present disclosure provides a chirally controlled DMD oligonucleotide composition, wherein the DMD oligonucleotide is capable of mediating skipping of a DMD exon and the DMD oligonucleotide is WV-20111.

In some embodiments, the present disclosure provides a chirally controlled DMD oligonucleotide composition, wherein the DMD oligonucleotide is capable of mediating skipping of a DMD exon and the DMD oligonucleotide is WV-20112.

In some embodiments, the present disclosure provides a chirally controlled DMD oligonucleotide composition, wherein the DMD oligonucleotide is capable of mediating skipping of a DMD exon and the DMD oligonucleotide is WV-20113.

In some embodiments, the present disclosure provides a chirally controlled DMD oligonucleotide composition, wherein the DMD oligonucleotide is capable of mediating skipping of a DMD exon and the DMD oligonucleotide is WV-20114.

In some embodiments, the present disclosure provides a chirally controlled DMD oligonucleotide composition, wherein the DMD oligonucleotide is capable of mediating skipping of a DMD exon and the DMD oligonucleotide is WV-20115.

In some embodiments, the present disclosure provides a chirally controlled DMD oligonucleotide composition, wherein the DMD oligonucleotide is capable of mediating skipping of a DMD exon and the DMD oligonucleotide is WV-20116.

In some embodiments, the present disclosure provides a chirally controlled DMD oligonucleotide composition, wherein the DMD oligonucleotide is capable of mediating skipping of a DMD exon and the DMD oligonucleotide is WV-20117.

In some embodiments, the present disclosure provides a chirally controlled DMD oligonucleotide composition, wherein the DMD oligonucleotide is capable of mediating skipping of a DMD exon and the DMD oligonucleotide is WV-20118.

In some embodiments, the present disclosure provides a chirally controlled DMD oligonucleotide composition, wherein the DMD oligonucleotide is capable of mediating skipping of a DMD exon and the DMD oligonucleotide is WV-20119.

In some embodiments, the present disclosure provides a chirally controlled DMD oligonucleotide composition, wherein the DMD oligonucleotide is capable of mediating skipping of a DMD exon and the DMD oligonucleotide is WV-20120.

In some embodiments, the present disclosure provides a chirally controlled DMD oligonucleotide composition, wherein the DMD oligonucleotide is capable of mediating skipping of a DMD exon and the DMD oligonucleotide is WV-20121.

In some embodiments, the present disclosure provides a chirally controlled DMD oligonucleotide composition, wherein the DMD oligonucleotide is capable of mediating skipping of a DMD exon and the DMD oligonucleotide is WV-20122.

In some embodiments, the present disclosure provides a chirally controlled DMD oligonucleotide composition, wherein the DMD oligonucleotide is capable of mediating skipping of a DMD exon and the DMD oligonucleotide is WV-20123.

In some embodiments, the present disclosure provides a chirally controlled DMD oligonucleotide composition, wherein the DMD oligonucleotide is capable of mediating skipping of a DMD exon and the DMD oligonucleotide is WV-20124.

In some embodiments, the present disclosure provides a chirally controlled DMD oligonucleotide composition, wherein the DMD oligonucleotide is capable of mediating skipping of a DMD exon and the DMD oligonucleotide is WV-20125.

In some embodiments, the present disclosure provides a chirally controlled DMD oligonucleotide composition, wherein the DMD oligonucleotide is capable of mediating skipping of a DMD exon and the DMD oligonucleotide is WV-20126.

In some embodiments, the present disclosure provides a chirally controlled DMD oligonucleotide composition, wherein the DMD oligonucleotide is capable of mediating skipping of a DMD exon and the DMD oligonucleotide is WV-20127.

In some embodiments, the present disclosure provides a chirally controlled DMD oligonucleotide composition, wherein the DMD oligonucleotide is capable of mediating skipping of a DMD exon and the DMD oligonucleotide is WV-20128.

In some embodiments, the present disclosure provides a chirally controlled DMD oligonucleotide composition, wherein the DMD oligonucleotide is capable of mediating skipping of a DMD exon and the DMD oligonucleotide is WV-20129.

In some embodiments, the present disclosure provides a chirally controlled DMD oligonucleotide composition, wherein the DMD oligonucleotide is capable of mediating skipping of a DMD exon and the DMD oligonucleotide is WV-20130.

In some embodiments, the present disclosure provides a chirally controlled DMD oligonucleotide composition, wherein the DMD oligonucleotide is capable of mediating skipping of a DMD exon and the DMD oligonucleotide is WV-20131.

In some embodiments, the present disclosure provides a chirally controlled DMD oligonucleotide composition, wherein the DMD oligonucleotide is capable of mediating skipping of a DMD exon and the DMD oligonucleotide is WV-20132.

In some embodiments, the present disclosure provides a chirally controlled DMD oligonucleotide composition, wherein the DMD oligonucleotide is capable of mediating skipping of a DMD exon and the DMD oligonucleotide is WV-20133.

In some embodiments, the present disclosure provides a chirally controlled DMD oligonucleotide composition, wherein the DMD oligonucleotide is capable of mediating skipping of a DMD exon and the DMD oligonucleotide is WV-20134.

In some embodiments, the present disclosure provides a chirally controlled DMD oligonucleotide composition, wherein the DMD oligonucleotide is capable of mediating skipping of a DMD exon and the DMD oligonucleotide is WV-20135.

In some embodiments, the present disclosure provides a chirally controlled DMD oligonucleotide composition, wherein the DMD oligonucleotide is capable of mediating skipping of a DMD exon and the DMD oligonucleotide is WV-20136.

In some embodiments, the present disclosure provides a chirally controlled DMD oligonucleotide composition, wherein the DMD oligonucleotide is capable of mediating skipping of a DMD exon and the DMD oligonucleotide is WV-20137.

In some embodiments, the present disclosure provides a chirally controlled DMD oligonucleotide composition, wherein the DMD oligonucleotide is capable of mediating skipping of a DMD exon and the DMD oligonucleotide is WV-20138.

In some embodiments, the present disclosure provides a chirally controlled DMD oligonucleotide composition, wherein the DMD oligonucleotide is capable of mediating skipping of a DMD exon and the DMD oligonucleotide is WV-20139.

In some embodiments, the present disclosure provides a chirally controlled DMD oligonucleotide composition, wherein the DMD oligonucleotide is capable of mediating skipping of a DMD exon and the DMD oligonucleotide is WV-20140.

In some experiments, provided DMD oligonucleotides can provide surprisingly high skipping of exon 51 or 53, e.g., when compared to those of Drisapersen and/or Eteplirsen. For example, various chirally controlled DMD oligonucle- otide compositions each showed a superior capability, in some embodiments many fold higher, to mediate skipping of exon 51 or 53 in dystrophin, compared to Drisapersen and/or Eteplirsen. Certain data are provided in the present disclosure as examples.

In some embodiments, when assaying example DMD oligonucleotides in mice, DMD oligonucleotides are intra- venous injected via tail vein in male C57BL/10ScSndmdmdx mice (4-5 weeks old), at tested amounts, e.g., 10 mg/kg, 30 mg/kg, etc. In some embodiments, tissues are harvested at tested times, e.g., on Day, e.g., 2, 7 and/or 14, etc., after injection, in some embodiments, fresh-frozen in liquid nitrogen and stored in −80° C. until analysis.

Various assays can be used to assess DMD oligonucle- otide levels in accordance with the present disclosure. In some embodiments, hybrid-ELISA is used to quantify DMD oligonucleotide levels in tissues using test article serial dilution as standard curve: for example, in an example procedure, maleic anhydride activated 96-well plate (Pierce 15110) was coated with 50 µl of capture probe at 500 nM in 2.5% NaHCO3(Gibco, 25080-094) for 2 hours at 37° C. The plate was then washed 3 times with PBST (PBS+0.1% Tween-20), and blocked with 5% fat free milk-PBST at 37° C. for 1 hour. Test article DMD oligonucleotide was serial diluted into matrix. This standard together with original samples were diluted with lysis buffer (4 M Guanidine; 0.33% N-Lauryl Sarcosine; 25 mM Sodium Citrate; 10 mM DTT) so that DMD oligonucleotide amount in all samples is less than 100 ng/mL. 20 µl of diluted samples were mixed with 180 µl of 333 nM detection probe diluted in PBST, then denatured in PCR machine (65° C., 10 min, 95° C., 15 min, 4 C∞). 50 µl of denatured samples were distributed in blocked ELISA plate in triplicates, and incubated overnight at 4° C. After 3 washes of PBST, 1:2000 streptavidin-AP in PBST was added, 50 µl per well and incubated at room temperature for 1 hour. After extensive wash with PBST, 100 µl of AttoPhos (Promega S1000) was added, incubated at room temperature in dark for 10 min and read on plate reader (Molecular Device, M5) fluorescence channel: Ex435 nm, Em555 nm. Oligonucleotides in samples were calculated according to standard curve by 4-parameter regression.

In some embodiments, provided DMD oligonucleotides are stable in both plasma and tissue homogenates.

Example Dystrophin Oligonucleotides and Compositions for Exon Skipping of Exon 51

In some embodiments, the present disclosure provides DMD oligonucleotides, DMD oligonucleotide composi- tions, and methods of use thereof for mediating skipping of exon 51 in DMD (e.g., of mouse, human, etc.).

In some embodiments, a provided DMD oligonucleotide and/or composition is capable of mediating skipping of exon 51.

In some embodiments, non-limiting examples of such DMD oligonucleotides and compositions include those of:

| | | | |
|---|---|---|---|
| WV-12494, | WV-12130, | WV-12131, | WV-12132, |
| WV-12133, | WV-12134, | WV-12135, | WV-12136, |
| WV-12496, | WV-12495, | WV-12123, | WV-12124, |
| WV-12125, | WV-12126, | WV-12127, | WV-12128, |
| WV-12129, | WV-12553, | WV-12554, | WV-12555, |
| WV-12556, | WV-12557, | WV-12558, | WV-12559, |
| WV-12872, | WV-12873, | WV-12876, | WV-12877, |
| WV-12878, | WV-12879, | WV-12880, | WV-12881, |
| WV-12882, | WV-12883, | WV-3152, | WV-15860, WV-20034, |
| WV-20037, | WV-20040, | WV-20043, | WV-20046, |
| WV-20049, | WV-20050, | WV-20051, | WV-20052, |
| WV-20053, | WV-20054, | WV-20055, | WV-20056, |
| WV-20057, | WV-20058, | WV-20059, | WV-20060, |

WV-20061, WV-20062, WV-20063, WV-20064, WV-20065, WV-20066, WV-20067, WV-20068, WV-20069, WV-20070, WV-20071, WV-20072, WV-20073, WV-20074, WV-20075, WV-20076, WV-20077, WV-20078, WV-20079, WV-20080, WV-20081, WV-20082, WV-20083, WV-20084, WV-20085, WV-20086, WV-20087, WV-20088, WV-20089, WV-20090, WV-20091, WV-20092, WV-20093, WV-20094, WV-20095, WV-20096, WV-20097, WV-20098, WV-20099, WV-20100, WV-20101, WV-20102, WV-20103, WV-20104, WV-20105, WV-20106, WV-20107, WV-20108, WV-20109, WV-20110, WV-20111, WV-20112, WV-20113, WV-20114, WV-20115, WV-20116, WV-20117, WV-20118, WV-20119, WV-20120, WV-20121, WV-20122, WV-20123, WV-20124, WV-20125, WV-20126, WV-20127, WV-20128, WV-20129, WV-20130, WV-20131, WV-20132, WV-20133, WV-20134, WV-20135, WV-20136, WV-20137, WV-20138, WV-20139, WV-20140, and other DMD oligonucleotides having a base sequence which comprises at least 15 contiguous bases of any of these DMD oligonucleotides.

In some embodiments, the sequence of the region of interest for exon 51 skipping differs between the mouse and human.

Various assays can be utilized to assess DMD oligonucleotides for exon skipping in accordance with the present disclosure. In some embodiments, in order to test the efficacy of a particular combination of chemistry and stereochemistry of a DMD oligonucleotide intended for exon 51 skipping in human, a corresponding DMD oligonucleotide can be prepared which has the mouse sequence, and then tested in mouse. The present disclosure recognizes that in the human and mouse homologs of exon 51, a few differences exist (underlined below):

M
(SEQ ID NO: 129)
GTGGTTACTAAGGAAACTGTCATCTCCAAACTAGAAATGCCATCTTCTTT
GCTGTTGGAG

H
(SEQ ID NO: 130)
GTGGTTACTAAGGAAACTGCCATCTCCAAACTAGAAATGCCATCTTCCTT
GATGTTGGAG where M is Mouse, nt 7571-7630; and H is Human, nt 7665-7724.

Because of these differences, slightly different DMD oligonucleotides for skipping exon 51 can be prepared for testing in mouse and human. As a non-limiting example, the following DMD oligonucleotide sequences can be used for testing in human and mouse:

```
HUMAN DMD oligonucleotide sequence:
                         (SEQ ID NO: 131)
UCAAGGAAGAUGGCAUUUCU MOUSE DMD oligonucleotide sequence:
                         (SEQ ID NO: 132)
GCAAAGAAGAUGGCAUUUCU
```

Mismatches between human and mouse are underlined.

A DMD oligonucleotide intended for treating a human subject can be constructed with a particular combination of base sequence (e.g., UCAAGGAAGAUGGCAUUUCU) (SEQ ID NO: 131), and a particular pattern of chemistry, internucleotidic linkages, stereochemistry, and additional chemical moieties (if any). Such a DMD oligonucleotide can be tested in vitro in human cells or in vivo in human subjects, but may have limited suitability for testing in mouse, for example, because base sequences of the two have mismatches.

A corresponding DMD oligonucleotide can be constructed with the corresponding mouse base sequence (GCAAAGAAGAUGGCAUUUCU)(SEQ ID NO: 132) and the same pattern of chemistry, internucleotidic linkages, stereochemistry, and additional chemical moieties (if any). Such a DMD oligonucleotide can be tested in vivo in mouse. Several DMD oligonucleotides comprising the mouse base sequence were constructed and tested.

In some embodiments, a human DMD exon skipping DMD oligonucleotide can be tested in a mouse which has been modified to comprise a DMD gene comprising the human sequence.

Various DMD oligonucleotides comprising various patterns of modifications are described herein. The Tables below show test results of certain DMD oligonucleotides. Generally, numbers indicate the amount of skipping, wherein 100 would indicate 100% skipping and 0 would indicate no skipping, unless otherwise indicated. To assay exon skipping of DMD, DMD oligonucleotides were tested in vitro in A52 human patient-derived myoblast cells and/or Δ45-52 human patient-derived myoblast cells (human cells wherein the exon 52 or exons 45-52 were already deleted). Unless noted otherwise, in various experiments, DMD oligonucleotides were delivered gymnotically.

TABLE 1

Activity of certain DMD oligonucleotides
Activity of various DMD exon 51 DMD oligonucleotides was tested in vitro.
Numbers indicate amount of skipping DMD exon 23 (as a percentage of total mRNA, where 100 would represent 100% skipped).
Amounts tested were: 10, 3.3 and 1.1 uM.

| Conc. | 10 | 3.3 | 1.1 | Conc. | 10 | 3.3 | 1.1 |
|---|---|---|---|---|---|---|---|
| WV-3152 | 20.8 | 9 | 4.1 | WV-14522 | 36.9 | 10.4 | 4.7 |
|  | 22 | 10 | 4.9 |  | 27.4 | 10.4 | 4.2 |
|  | 17.3 | 9.3 | 3.2 |  | 21 | 12.6 | 5.6 |
|  | 21.3 | 7.2 | 4.4 |  | 26.5 | 10.4 | 5.7 |
| WV-15860 | 27.4 | 13.2 | 12.7 | WV-14523 | 27.2 | 8.1 | 6.2 |
|  | 30.4 | 15.4 | 9 |  | 28.3 | 8.5 | 4.9 |
|  | 33 | 14.2 | 6 |  | 18.4 | 9.1 | 3.6 |
|  | 33.4 | 16.9 | 5.9 |  | 18.7 | 9.6 | 4.4 |
| WV-15861 | 26.6 | 9.2 | 5.6 | Mock | 0.21 |  |  |
|  | 28.5 | 6.1 | 5.4 |  | 0.35 |  |  |
|  | 34.1 | 8.2 | 5.2 |  | 0.48 |  |  |
|  | 29.9 | 11.1 | 4 |  | 0.24 |  |  |
| WV-15862 | 30.7 |  | 7.8 |  |  |  |  |
|  | 33.3 |  | 7.2 |  |  |  |  |
|  | 21.9 | 15.1 | 6.8 |  |  |  |  |
|  | 26.4 | 13.2 | 7.2 |  |  |  |  |

TABLE 2

Activity of certain DMD oligonucleotides
Oligonucleotides for skipping DMD exon 51 were tested in vitro.
Numbers indicate amount of skipping DMD exon 23 (as a percentage of total mRNA, where 100 would represent 100% skipped).
Concentrations of DMD oligonucleotides used: 10, 3.3 and 1.1 uM.

|  | 10 uM | 3.3 uM | 1.1 uM |  | 10 uM | 3.3 uM | 1.1 uM |
|---|---|---|---|---|---|---|---|
| Mock | 0.2 | 0.3 | 0.2 | WV-17861 | 37.6 | 22.6 | 9 |
|  | 0.3 | 0.2 | 0.3 |  | 38.8 | 22.5 | 8.9 |

TABLE 2-continued

Activity of certain DMD oligonucleotides
Oligonucleotides for skipping DMD exon 51 were tested in vitro.
Numbers indicate amount of skipping DMD exon 23 (as a percentage of total mRNA, where 100 would represent 100% skipped).
Concentrations of DMD oligonucleotides used: 10, 3.3 and 1.1 uM.

|  | 10 uM | 3.3 uM | 1.1 uM |
|---|---|---|---|
|  | 0.2 | 0 | 0.2 |
|  | 0.2 | 0.6 | 0.2 |
| WV-7336 | 3.1 | 1.6 | 0.7 |
|  | 8.9 | 1.8 | 0.1 |
|  | 5.4 | 1.4 | 0.9 |
|  | 4.9 | 1.5 | 0.7 |
| WV-3152 | 32.4 | 26.5 | 7.5 |
|  | 27.2 | 22.2 | 8.4 |
|  | 28 | 14.5 | 7.6 |
|  | 26.8 | 14.8 | 7.3 |
| WV-15860 | 43.3 | 25.7 | 10.2 |
|  | 37.9 | 23.8 | 9.6 |
|  | 38.4 | 24.5 | 11.2 |
|  | 42.4 | 21.9 | 11 |
| WV-17859 | 42.3 | 26.7 | 16.3 |
|  | 41.3 | 26 | 16.8 |
|  | 39.9 | 22.9 | 15.5 |
|  | 48.6 | 23.6 | 14.9 |
| WV-17860 | 38.1 | 19.3 | 11.7 |
|  | 35.3 | 19.2 | 12 |
|  | 41 | 28.2 | 16.4 |
|  | 40.4 | 21.9 | 11.1 |
|  | 40.7 | 24.4 | 13.2 |
|  | 41.7 | 25.4 | 11.6 |
| WV-17862 | 38.4 | 18.9 | 8.1 |
|  | 34.1 | 19.6 | 9 |
|  | 34.8 | 26 | 10 |
|  | 36.1 | 21.4 | 9.5 |
| WV-17863 | 32.7 | 18.2 | 9.2 |
|  | 35.1 | 18.9 | 9.3 |
|  | 34.8 | 18.2 | 8.6 |
|  | 30.7 | 17 | 9 |
| WV-17864 | 37.3 | 23.6 | 11.7 |
|  | 41.4 | 23.3 | 10.6 |
|  | 39.9 | 20.6 | 17.5 |
|  | 38.8 | 21.7 | 10.2 |
| WV-17865 | 35.9 | 16.5 | 9.3 |
|  | 34 | 16.7 | 7.5 |
|  | 34.4 | 17.5 | 11.9 |
|  | 34.1 | 17.8 | 9.8 |
| WV-17866 | 48.7 | 28.4 | 17.7 |
|  | 43.3 | 28.6 | 13.1 |
|  | 44.5 | 24.8 | 15.4 |
|  | 45.1 | 30.5 | 16.3 |

TABLE 3

Activity of certain DMD oligonucleotides
Oligonucleotides for skipping DMD exon 51 were tested in vitro.
Numbers indicate amount of skipping DMD exon 23 (as a percentage of total mRNA, where 100 would represent 100% skipped).
Concentrations of DMD oligonucleotides used: 10 and 3.3 uM.

|  | 10 uM | 3.3 uM |
|---|---|---|
| Mock | 0 | 0 |
|  | 0 | 0 |
|  | 0 | 0 |
|  | 0 | 0 |
| WV-20034 | 15.9 | 7 |
|  | 17.1 | 8.4 |
|  | 16.1 | 7.3 |
|  | 15.3 | 7.2 |
| WV-20037 | 29.7 | 18.3 |
|  | 27.2 | 17.5 |
|  | 26.6 | 19.4 |
|  | 29.2 | 18.4 |
| WV-20040 | 9.6 | 4.9 |
|  | 9.1 | 5.2 |
|  | 11.4 | 3.5 |
|  | 10.9 | 2.9 |
| WV-20043 | 20.2 | 9.6 |
|  | 20.4 | 9.8 |
|  | 18.9 | 9.8 |
|  | 21 | 10.4 |
| WV-20046 | 28.5 | 14.7 |
|  | 29.8 | 14.2 |
|  | 29.2 | 15.8 |
|  | 26.6 | 14.5 |
| WV-20049 | 20.9 | 11.6 |
|  | 18.6 | 12.2 |
|  | 18.4 | 11.7 |
| WV-20052 | 28.8 | 18.8 |
|  | 30.1 | 18.6 |
|  | 29.6 | 20.1 |
| WV-20055 | 26.8 | 17 |
|  | 25.3 | 16.6 |
|  | 24.1 | 17 |
| WV-20058 | 14.6 | 4.8 |
|  | 12 | 3.7 |
|  | 12.6 | 3.5 |
| WV-20061 | 35.8 | 26.5 |
|  | 39.3 | 24.2 |
|  | 39.9 | 22.8 |
| WV-20064 | 26.5 | 17.6 |
|  | 24.5 | 16.4 |
|  | 27.5 | 17.1 |
| WV-20067 | 15.7 | 8.3 |
|  | 16.8 | 9.3 |
|  | 17.3 | 8.6 |
|  | 16.3 | 8.7 |
| WV-20070 | 41.3 | 26.4 |
|  | 31.7 | 22.3 |
|  | 39.7 | 27.2 |
|  | 38.4 | 26.9 |
| WV-20073 | 30.9 | 21.1 |
|  | 26.9 | 17.9 |
|  | 31.1 | 20.2 |
|  | 30.7 | 22.2 |
| WV-20076 | 23.2 | 16.8 |
|  | 18.9 | 11.4 |
|  | 21.8 | 16.9 |
|  | 22.8 | 15.8 |
| WV-3152 | 35.7 | 24.8 |
|  | 33.5 | 24.9 |
|  | 32.1 | 25.3 |
| WV-15860 | 41.9 | 27.5 |
|  | 43.6 | 30.7 |
|  | 42.4 | 30 |

TABLE 4A

Activity of certain DMD oligonucleotides
Oligonucleotides for skipping DMD exon 51 were tested in vitro.
Oligonucleotides were dosed 4 d at 10 uM.
Numbers indicate amount of skipping DMD exon 51 (as a percentage of total mRNA, where 100 would represent 100% skipped).

| | | | | |
|---|---|---|---|---|
| WV-3152 | 19 | 20 | 12 | 14 |
| WV-15860 | 29 | 31 | 26 | 23 |
| WV-20140 | 1 | 1 | 1 | 1 |
| WV-20139 | 3 | 3 | 2 | 2 |
| WV-20138 |  |  | 2 | 3 |
| WV-20137 | 4 | 5 |  |  |
| WV-20136 |  |  |  |  |
| WV-20135 | 5 | 5 | 5 | 5 |
| WV-20134 | 5 | 6 | 5 | 4 |
| WV-20133 | 17 | 17 | 13 | 13 |
| WV-20132 | 8 | 8 | 6 | 6 |
| WV-20131 | 14 | 16 | 12 | 12 |
| WV-20130 | 10 | 9 | 8 | 8 |
| WV-20129 | 12 | 14 | 11 | 11 |
| WV-20128 | 9 | 9 | 8 | 8 |
| WV-20127 |  |  | 8 | 8 |
| WV-20126 | 7 | 8 | 8 | 7 |
| WV-20125 | 8 | 8 | 8 | 8 |
| WV-20124 | 22 | 21 | 21 | 21 |
| WV-20123 | 13 | 13 | 14 | 12 |
| WV-20122 | 11 | 12 | 12 | 11 |
| WV-20121 | 21 | 22 | 22 | 21 |
| WV-20120 | 28 | 30 | 32 | 33 |
| WV-20119 | 52 | 50 |  |  |
| WV-20118 | 39 | 37 | 27 | 26 |
| WV-20117 | 18 | 17 | 15 | 18 |
| WV-20116 | 20 | 20 | 17 | 17 |
| WV-20115 | 8 | 8 | 8 | 6 |
| WV-20114 | 19 | 20 | 15 | 14 |
| WV-20113 | 20 | 18 | 17 | 15 |
| WV-20112 | 16 | 15 | 12 | 12 |
| WV-20111 | 31 | 30 | 33 | 31 |

TABLE 4A-continued

Activity of certain DMD oligonucleotides
Oligonucleotides for skipping DMD exon 51 were tested in vitro.
Oligonucleotides were dosed 4 d at 10 uM.
Numbers indicate amount of skipping DMD exon 51 (as a percentage
of total mRNA, where 100 would represent 100% skipped).

| | | | | |
|---|---|---|---|---|
| WV-20110 | 14 | 14 | 14 | 12 |
| WV-20109 | 20 | 21 | 25 | 24 |
| WV-20108 | 27 | 25 | 22 | 22 |
| WV-20107 | 20 | 19 | 16 | 14 |
| WV-20106 | 44 | 42 | 34 | 37 |
| WV-20105 | 23 | 22 | 18 | 18 |
| WV-20104 | 41 | 40 | 33 | 28 |
| WV-20103 | 48 | 52 | 53 | 53 |
| WV-20102 | 54 | 52 | 55 | 59 |
| WV-20101 | 38 | 39 | 38 | 43 |
| WV-20100 | 52 | 51 | 48 | 50 |
| WV-20099 | 53 | 51 | 47 | 48 |
| WV-20098 | 46 | 44 | 45 | 46 |
| WV-20097 | 47 | 46 | 51 | 48 |
| WV-20096 | 45 | 41 | 42 | 43 |
| WV-20095 | 43 | 41 | 50 | 47 |
| WV-20094 | 55 | 50 | 57 | 55 |
| WV-20093 | 35 | 34 | 35 | 38 |
| WV-20092 | 25 | 26 | 25 | 25 |
| WV-20091 | 28 | 27 | 30 | 32 |
| WV-20090 | 21 | 19 | 22 | 22 |
| WV-20089 | 8 | 7 | 8 | 9 |
| WV-20088 | 22 | 21 | 26 | 25 |
| WV-20087 | 28 | 28 | 33 | 32 |
| WV-20086 | 25 | 25 | 27 | 26 |
| WV-20085 | 33 | 31 | 30 | 31 |
| WV-20084 | 21 | 22 | 21 | 21 |
| WV-20083 | 21 | 21 | 19 | 17 |
| WV-20082 | 42 | 37 | 32 | 30 |
| WV-20081 | 41 | 41 | 30 | 30 |
| WV-20080 | 49 | 44 | 26 | 25 |
| WV-20079 | 42 | 38 | 53 | 51 |
| WV-20078 | 27 | 28 | 36 | 35 |
| WV-20077 | 10 | 10 | 10 | 10 |
| WV-20076 | 45 | 45 | 45 | 41 |
| WV-20075 | 40 | 31 | 37 | 42 |
| WV-20074 | 55 | 57 | 53 | 56 |
| WV-20073 | 51 | 55 | 51 | 50 |
| WV-20072 | 41 | 36 | 37 | 36 |
| WV-20071 | 42 | 40 | 44 | 46 |
| WV-20070 | 18 | 18 | 25 | 25 |
| WV-20069 | 11 | 11 | 10 | 9 |
| WV-20068 | 20 | 17 | 20 | 18 |
| WV-20067 | 12 | 9 | 11 | 11 |
| WV-20066 | 12 | 11 | 13 | 12 |
| WV-20065 | 16 | 15 | 16 | 14 |
| WV-20064 | 37 | 35 | 37 | 36 |
| WV-20063 | 19 | | 24 | 22 |
| WV-20062 | 6 | 6 | 7 | 7 |
| WV-20061 | 24 | 23 | 26 | 24 |
| WV-20060 | 16 | 17 | 16 | 17 |
| WV-20059 | 55 | 42 | 62 | 67 |
| WV-20058 | 28 | 30 | 33 | 33 |
| WV-20057 | 37 | 38 | 37 | 34 |
| WV-20056 | 35 | 34 | 33 | 35 |
| WV-20055 | | | 40 | 40 |
| WV-20054 | 25 | 25 | 35 | 36 |
| WV-20053 | 43 | 45 | 46 | 46 |
| WV-20052 | 47 | 47 | 53 | 46 |
| WV-20051 | 30 | 33 | 30 | 30 |
| WV-20050 | 29 | 28 | 28 | 26 |
| WV-20049 | 41 | 41 | 38 | 38 |
| WV-20049 | 24 | 23 | 22 | 21 |

TABLE 4B

Activity of certain DMD oligonucleotides
Patient Δ48-50 cells were dosed for 4 d with oligonucleotides in
differentiation media. RNA was harvested by Trizol extraction.
TaqMan signal was normalized to SFSR9 internal control.
Numbers indicate amount of skipping DMD exon 51 (as a
percentage of total mRNA, where 100 would
represent 100% skipped).

| | 10 uM | 3.3 uM |
|---|---|---|
| Mock | 0 | 0 |
| | 0 | 0 |
| | 0 | 0 |
| | 0 | 0 |
| WV-20034 | 15.9 | 7 |
| | 17.1 | 8.4 |
| | 16.1 | 7.3 |
| | 15.3 | 7.2 |
| WV-20037 | 29.7 | 18.3 |
| | 27.2 | 17.5 |
| | 26.6 | 19.4 |
| | 29.2 | 18.4 |
| WV-20040 | 9.6 | 4.9 |
| | 9.1 | 5.2 |
| | 11.4 | 3.5 |
| | 10.9 | 2.9 |
| WV-20043 | 20.2 | 9.6 |
| | 20.4 | 9.8 |
| | 18.9 | 9.8 |
| | 21 | 10.4 |
| WV-20046 | 28.5 | 14.7 |
| | 29.8 | 14.2 |
| | 29.2 | 15.8 |
| | 26.6 | 14.5 |
| WV-20049 | 20.9 | 11.6 |
| | 18.6 | 12.2 |
| | 18.4 | 11.7 |
| WV-20052 | 28.8 | 18.8 |
| | 30.1 | 18.6 |
| | 29.6 | 20.1 |
| WV-20055 | 26.8 | 17 |
| | 25.3 | 16.6 |
| | 24.1 | 17 |
| WV-20058 | 14.6 | 4.8 |
| | 12 | 3.7 |
| | 12.6 | 3.5 |
| WV-20061 | 35.8 | 26.5 |
| | 39.3 | 24.2 |
| | 39.9 | 22.8 |
| WV-20064 | 26.5 | 17.6 |
| | 24.5 | 16.4 |
| | 27.5 | 17.1 |
| WV-20067 | 15.7 | 8.3 |
| | 16.8 | 9.3 |
| | 17.3 | 8.6 |
| | 16.3 | 8.7 |
| WV-20070 | 41.3 | 26.4 |
| | 31.7 | 22.3 |
| | 39.7 | 27.2 |
| | 38.4 | 26.9 |
| WV-20073 | 30.9 | 21.1 |
| | 26.9 | 17.9 |
| | 31.1 | 20.2 |
| | 30.7 | 22.2 |
| WV-20076 | 23.2 | 16.8 |
| | 18.9 | 11.4 |
| | 21.8 | 16.9 |
| | 22.8 | 15.8 |
| WV-3152 | 35.7 | 24.8 |
| | 33.5 | 24.9 |
| | 32.1 | 25.3 |
| WV-15860 | 41.9 | 27.5 |
| | 43.6 | 30.7 |
| | 42.4 | 30 |

TABLE 4C

Activity of certain DMD oligonucleotides
Patient-derived Δ48-50 cells were dosed with oligonucleotide
in differentiation media under free-uptake conditions for
4 days. RNA harvested by Trizol extraction. TaqMan
signal for DMD 'skipped' and DMD 'total' transcripts
were normalized to SFSR9 internal control. Numbers
indicate amount of skipping DMD exon 51 (as a percentage
of total mRNA, where 100 would represent 100% skipped).

|  | 10 uM | 3.3 uM | 1.1 uM |
|---|---|---|---|
| Mock | 0.2 | 0.3 | 0.2 |
|  | 0.3 | 0.2 | 0.3 |
|  | 0.2 | 0 | 0.2 |
|  | 0.2 | 0.6 | 0.2 |
| WV-7336 | 3.1 | 1.6 | 0.7 |
|  | 8.9 | 1.8 | 0.1 |
|  | 5.4 | 1.4 | 0.9 |
|  | 4.9 | 1.5 | 0.7 |
| WV-3152 | 32.4 | 26.5 | 7.5 |
|  | 27.2 | 22.2 | 8.4 |
|  | 28 | 14.5 | 7.6 |
|  | 26.8 | 14.8 | 7.3 |
| WV-15860 | 43.3 | 25.7 | 10.2 |
|  | 37.9 | 23.8 | 9.6 |
|  | 38.4 | 24.5 | 11.2 |
|  | 42.4 | 21.9 | 11 |
| WV-17859 | 42.3 | 26.7 | 16.3 |
|  | 41.3 | 26 | 16.8 |
|  | 39.9 | 22.9 | 15.5 |
|  | 48.6 | 23.6 | 14.9 |
| WV-17860 | 38.1 | 19.3 | 11.7 |
|  | 35.3 | 19.2 | 12 |
|  | 41 | 28.2 | 16.4 |
|  | 40.4 | 21.9 | 11.1 |
| WV-17861 | 37.6 | 22.6 | 9 |
|  | 38.8 | 22.5 | 8.9 |
|  | 40.7 | 24.4 | 13.2 |
|  | 41.7 | 25.4 | 11.6 |
| WV-17862 | 38.4 | 18.9 | 8.1 |
|  | 34.1 | 19.6 | 9 |
|  | 34.8 | 26 | 10 |
|  | 36.1 | 21.4 | 9.5 |
| WV-17863 | 32.7 | 18.2 | 9.2 |
|  | 35.1 | 18.9 | 9.3 |
|  | 34.8 | 18.2 | 8.6 |
|  | 30.7 | 17 | 9 |
| WV-17864 | 37.3 | 23.6 | 11.7 |
|  | 41.4 | 23.3 | 10.6 |
|  | 39.9 | 20.6 | 17.5 |
|  | 38.8 | 21.7 | 10.2 |
| WV-17865 | 35.9 | 16.5 | 9.3 |
|  | 34 | 16.7 | 7.5 |
|  | 34.4 | 17.5 | 11.9 |
|  | 34.1 | 17.8 | 9.8 |
| WV-17866 | 48.7 | 28.4 | 17.7 |
|  | 43.3 | 28.6 | 13.1 |
|  | 44.5 | 24.8 | 15.4 |
|  | 45.1 | 30.5 | 16.3 |

TABLE 4D

Activity of certain DMD oligonucleotides
Patient-derived Δ48-50 cells were dosed with
oligonucleotide in differentiation media
under free-uptake conditions for 4 days.
RNA from 24WP harvested by bead-based extraction.
TaqMan signal for DMD 'skipped' and DMD 'total'
transcripts were normalized to SFSR9 internal control.
Numbers indicate amount of skipping DMD exon 51 (as a
percentage of total mRNA, where 100 would represent
100% skipped).

|  | 10 uM | 3.3 uM |
|---|---|---|
| Mock | 0 | 0 |
|  | 0 | 0 |
|  | 0 | 0 |
|  | 0 | 0 |
| WV-20034 | 15.9 | 7 |
|  | 17.1 | 8.4 |
|  | 16.1 | 7.3 |
|  | 15.3 | 7.2 |
| WV-20037 | 29.7 | 18.3 |
|  | 27.2 | 17.5 |
|  | 26.6 | 19.4 |
|  | 29.2 | 18.4 |
| WV-20040 | 9.6 | 4.9 |
|  | 9.1 | 5.2 |
|  | 11.4 | 3.5 |
|  | 10.9 | 2.9 |
| WV-20043 | 20.2 | 9.6 |
|  | 20.4 | 9.8 |
|  | 18.9 | 9.8 |
|  | 21 | 10.4 |
| WV-20046 | 28.5 | 14.7 |
|  | 29.8 | 14.2 |
|  | 29.2 | 15.8 |
|  | 26.6 | 14.5 |
| WV-20049 | 20.9 | 11.6 |
|  | 18.6 | 12.2 |
|  | 18.4 | 11.7 |
| WV-20052 | 28.8 | 18.8 |
|  | 30.1 | 18.6 |
|  | 29.6 | 20.1 |
| WV-20055 | 26.8 | 17 |
|  | 25.3 | 16.6 |
|  | 24.1 | 17 |
| WV-20058 | 14.6 | 4.8 |
|  | 12 | 3.7 |
|  | 12.6 | 3.5 |
| WV-20061 | 35.8 | 26.5 |
|  | 39.3 | 24.2 |
|  | 39.9 | 22.8 |
| WV-20064 | 26.5 | 17.6 |
|  | 24.5 | 16.4 |
|  | 27.5 | 17.1 |
| WV-20067 | 15.7 | 8.3 |
|  | 16.8 | 9.3 |
|  | 17.3 | 8.6 |
|  | 16.3 | 8.7 |
| WV-20070 | 41.3 | 26.4 |
|  | 31.7 | 22.3 |
|  | 39.7 | 27.2 |
|  | 38.4 | 26.9 |
| WV-20073 | 30.9 | 21.1 |
|  | 26.9 | 17.9 |
|  | 31.1 | 20.2 |
|  | 30.7 | 22.2 |
| WV-20076 | 23.2 | 16.8 |
|  | 18.9 | 11.4 |
|  | 21.8 | 16.9 |
|  | 22.8 | 15.8 |
| WV-3152 | 35.7 | 24.8 |
|  | 33.5 | 24.9 |
|  | 32.1 | 25.3 |
| WV-15860 | 41.9 | 27.5 |
|  | 43.6 | 30.7 |
|  | 42.4 | 30 |

TABLE 4E

Activity of certain DMD oligonucleotides
Conditions and parameters: Δ48-50 cells (Delta 48-50) (no pre-differentiation) in 96WP in biological duplicate at 10 uM for 4 days
Samples were lysed and baked in bead lysis buffer, frozen at −80
Bead-based extraction with manual (vs Bravo) washes
Numbers indicate amount of skipping DMD exon 51 (as a percentage of total mRNA, where 100 would represent 100% skipped).

| | | | | |
|---|---|---|---|---|
| WV-3152 | 19 | 20 | 12 | 14 |
| WV-15860 | 29 | 31 | 26 | 23 |
| WV-20140 | 1 | 1 | 1 | 1 |
| WV-20139 | 3 | 3 | 2 | 2 |
| WV-20138 | | | 2 | 3 |
| WV-20137 | 4 | 5 | | |
| WV-20136 | | | | |
| WV-20135 | 5 | 5 | 5 | 5 |
| WV-20134 | 5 | 6 | 5 | 4 |
| WV-20133 | 17 | 17 | 13 | 13 |
| WV-20132 | 8 | 8 | 6 | 6 |
| WV-20131 | 14 | 16 | 12 | 12 |
| WV-20130 | 10 | 9 | 8 | 8 |
| WV-20129 | 12 | 14 | 11 | 11 |
| WV-20128 | 9 | 9 | 8 | 8 |
| WV-20127 | | | 8 | 8 |
| WV-20126 | 7 | 8 | 8 | 7 |
| WV-20125 | 8 | 8 | 8 | 8 |
| WV-20124 | 22 | 21 | 21 | 21 |
| WV-20123 | 13 | 13 | 14 | 12 |
| WV-20122 | 11 | 12 | 12 | 11 |
| WV-20121 | 21 | 22 | 22 | 21 |
| WV-20120 | 28 | 30 | 32 | 33 |
| WV-20119 | 52 | 50 | | |
| WV-20118 | 39 | 37 | 27 | 26 |
| WV-20117 | 18 | 17 | 15 | 18 |
| WV-20116 | 20 | 20 | 17 | 17 |
| WV-20115 | 8 | 8 | 8 | 6 |
| WV-20114 | 19 | 20 | 15 | 14 |
| WV-20113 | 20 | 18 | 17 | 15 |
| WV-20112 | 16 | 15 | 12 | 12 |
| WV-20111 | 31 | 30 | 33 | 31 |
| WV-20110 | 14 | 14 | 14 | 12 |
| WV-20109 | 20 | 21 | 25 | 24 |
| WV-20108 | 27 | 25 | 22 | 22 |
| WV-20107 | 20 | 19 | 16 | 14 |
| WV-20106 | 44 | 42 | 34 | 37 |
| WV-20105 | 23 | 22 | 18 | 18 |
| WV-20104 | 41 | 40 | 33 | 28 |
| WV-20103 | 48 | 52 | 53 | 53 |
| WV-20102 | 54 | 52 | 55 | 59 |
| WV-20101 | 38 | 39 | 38 | 43 |
| WV-20100 | 52 | 51 | 48 | 50 |
| WV-20099 | 53 | 51 | 47 | 48 |
| WV-20098 | 46 | 44 | 45 | 46 |
| WV-20097 | 47 | 46 | 51 | 48 |
| WV-20096 | 45 | 41 | 42 | 43 |
| WV-20095 | 43 | 41 | 50 | 47 |
| WV-20094 | 55 | 50 | 57 | 55 |
| WV-20093 | 35 | 34 | 35 | 38 |
| WV-20092 | 25 | 26 | 25 | 25 |
| WV-20091 | 28 | 27 | 30 | 32 |
| WV-20090 | 21 | 19 | 22 | 22 |
| WV-20089 | 8 | 7 | 8 | 9 |
| WV-20088 | 22 | 21 | 26 | 25 |
| WV-20087 | 28 | 28 | 33 | 32 |
| WV-20086 | 25 | 25 | 27 | 26 |
| WV-20085 | 33 | 31 | 30 | 31 |
| WV-20084 | 21 | 22 | 21 | 21 |
| WV-20083 | 21 | 21 | 19 | 17 |
| WV-20082 | 42 | 37 | 32 | 30 |
| WV-20081 | 41 | 41 | 30 | 30 |
| WV-20080 | 49 | 44 | 26 | 25 |
| WV-20079 | 42 | 38 | 53 | 51 |
| WV-20078 | 27 | 28 | 36 | 35 |
| WV-20077 | 10 | 10 | 10 | 10 |
| WV-20076 | 45 | 45 | 45 | 41 |
| WV-20075 | 40 | 31 | 37 | 42 |
| WV-20074 | 55 | 57 | 53 | 56 |
| WV-20073 | 51 | 55 | 51 | 50 |
| WV-20072 | 41 | 36 | 37 | 36 |
| WV-20071 | 42 | 40 | 44 | 46 |
| WV-20070 | 18 | 18 | 25 | 25 |
| WV-20069 | 11 | 11 | 10 | 9 |
| WV-20068 | 20 | 17 | 20 | 18 |
| WV-20067 | 12 | 9 | 11 | 11 |
| WV-20066 | 12 | 11 | 13 | 12 |
| WV-20065 | 16 | 15 | 16 | 14 |
| WV-20064 | 37 | 35 | 37 | 36 |
| WV-20063 | 19 | | 24 | 22 |
| WV-20062 | 6 | 6 | 7 | 7 |
| WV-20061 | 24 | 23 | 26 | 24 |
| WV-20060 | 16 | 17 | 16 | 17 |
| WV-20059 | 55 | 42 | 62 | 67 |
| WV-20058 | 28 | 30 | 33 | 33 |
| WV-20057 | 37 | 38 | 37 | 34 |
| WV-20056 | 35 | 34 | 33 | 35 |
| WV-20055 | | | 40 | 40 |
| WV-20054 | 25 | 25 | 35 | 36 |
| WV-20053 | 43 | 45 | 46 | 46 |
| WV-20052 | 47 | 47 | 53 | 46 |
| WV-20051 | 30 | 33 | 30 | 30 |
| WV-20050 | 29 | 28 | 28 | 26 |
| WV-20049 | 41 | 41 | 38 | 38 |
| WV-20049 | 24 | 23 | 22 | 21 |

TABLE 4F

Activity of certain DMD oligonucleotides
Delta 48-50 cells were treated under free uptake conditions with 10 uM of oligonucleotide in differentiation media for four days. RNA was extracted with Agilent bead-based protocol and reverse transcribed with random hexamers. TaqMan assays were targeted toward the total DMD transcript or the exon-junction corresponding to the skipped transcript, each run in multiplex with hSFSR9 internal control.
Numbers indicate amount of skipping DMD exon 51 (as a percentage of total mRNA, where 100 would represent 100% skipped).

| | | | | |
|---|---|---|---|---|
| WV-3152 | 19 | 20 | 12 | 14 |
| WV-15860 | 29 | 31 | 26 | 23 |
| WV-20140 | 1 | 1 | 1 | 1 |
| WV-20139 | 3 | 3 | 2 | 2 |
| WV-20138 | | | 2 | 3 |
| WV-20137 | 4 | 5 | | |
| WV-20136 | | | | |
| WV-20135 | 5 | 5 | 5 | 5 |
| WV-20134 | 5 | 6 | 5 | 4 |
| WV-20133 | 17 | 17 | 13 | 13 |
| WV-20132 | 8 | 8 | 6 | 6 |
| WV-20131 | 14 | 16 | 12 | 12 |
| WV-20130 | 10 | 9 | 8 | 8 |
| WV-20129 | 12 | 14 | 11 | 11 |
| WV-20128 | 9 | 9 | 8 | 8 |
| WV-20127 | | | 8 | 8 |
| WV-20126 | 7 | 8 | 8 | 7 |
| WV-20125 | 8 | 8 | 8 | 8 |
| WV-20124 | 22 | 21 | 21 | 21 |
| WV-20123 | 13 | 13 | 14 | 12 |
| WV-20122 | 11 | 12 | 12 | 11 |
| WV-20121 | 21 | 22 | 22 | 21 |
| WV-20120 | 28 | 30 | 32 | 33 |
| WV-20119 | 52 | 50 | | |
| WV-20118 | 39 | 37 | 27 | 26 |
| WV-20117 | 18 | 17 | 15 | 18 |
| WV-20116 | 20 | 20 | 17 | 17 |
| WV-20115 | 8 | 8 | 8 | 6 |
| WV-20114 | 19 | 20 | 15 | 14 |
| WV-20113 | 20 | 18 | 17 | 15 |
| WV-20112 | 16 | 15 | 12 | 12 |
| WV-20111 | 31 | 30 | 33 | 31 |
| WV-20110 | 14 | 14 | 14 | 12 |

TABLE 4F-continued

Activity of certain DMD oligonucleotides
Delta 48-50 cells were treated under free uptake conditions with 10
uM of oligonucleotide in differentiation media for four days. RNA
was extracted with Agilent bead-based protocol and reverse
transcribed with random hexamers. TaqMan assays were targeted
toward the total DMD transcript or the exon-junction corresponding to the
skipped transcript, each run in multiplex with hSFSR9 internal control.
Numbers indicate amount of skipping DMD exon 51 (as a percentage
of total mRNA, where 100 would represent 100% skipped).

| | | | | |
|---|---|---|---|---|
| WV-20109 | 20 | 21 | 25 | 24 |
| WV-20108 | 27 | 25 | 22 | 22 |
| WV-20107 | 20 | 19 | 16 | 14 |
| WV-20106 | 44 | 42 | 34 | 37 |
| WV-20105 | 23 | 22 | 18 | 18 |
| WV-20104 | 41 | 40 | 33 | 28 |
| WV-20103 | 48 | 52 | 53 | 53 |
| WV-20102 | 54 | 52 | 55 | 59 |
| WV-20101 | 38 | 39 | 38 | 43 |
| WV-20100 | 52 | 51 | 48 | 50 |
| WV-20099 | 53 | 51 | 47 | 48 |
| WV-20098 | 46 | 44 | 45 | 46 |
| WV-20097 | 47 | 46 | 51 | 48 |
| WV-20096 | 45 | 41 | 42 | 43 |
| WV-20095 | 43 | 41 | 50 | 47 |
| WV-20094 | 55 | 50 | 57 | 55 |
| WV-20093 | 35 | 34 | 35 | 38 |
| WV-20092 | 25 | 26 | 25 | 25 |
| WV-20091 | 28 | 27 | 30 | 32 |
| WV-20090 | 21 | 19 | 22 | 22 |
| WV-20089 | 8 | 7 | 8 | 9 |
| WV-20088 | 22 | 21 | 26 | 25 |
| WV-20087 | 28 | 28 | 33 | 32 |
| WV-20086 | 25 | 25 | 27 | 26 |
| WV-20085 | 33 | 31 | 30 | 31 |
| WV-20084 | 21 | 22 | 21 | 21 |
| WV-20083 | 21 | 21 | 19 | 17 |
| WV-20082 | 42 | 37 | 32 | 30 |
| WV-20081 | 41 | 41 | 30 | 30 |
| WV-20080 | 49 | 44 | 26 | 25 |
| WV-20079 | 42 | 38 | 53 | 51 |
| WV-20078 | 27 | 28 | 36 | 35 |
| WV-20077 | 10 | 10 | 10 | 10 |
| WV-20076 | 45 | 45 | 45 | 41 |
| WV-20075 | 40 | 31 | 37 | 42 |
| WV-20074 | 55 | 57 | 53 | 56 |
| WV-20073 | 51 | 55 | 51 | 50 |
| WV-20072 | 41 | 36 | 37 | 36 |
| WV-20071 | 42 | 40 | 44 | 46 |
| WV-20070 | 18 | 18 | 25 | 25 |
| WV-20069 | 11 | 11 | 10 | 9 |
| WV-20068 | 20 | 17 | 20 | 18 |
| WV-20067 | 12 | 9 | 11 | 11 |
| WV-20066 | 12 | 11 | 13 | 12 |
| WV-20065 | 16 | 15 | 16 | 14 |
| WV-20064 | 37 | 35 | 37 | 36 |
| WV-20063 | 19 | | 24 | 22 |
| WV-20062 | 6 | 6 | 7 | 7 |
| WV-20061 | 24 | 23 | 26 | 24 |
| WV-20060 | 16 | 17 | 16 | 17 |
| WV-20059 | 55 | 42 | 62 | 67 |
| WV-20058 | 28 | 30 | 33 | 33 |
| WV-20057 | 37 | 38 | 37 | 34 |
| WV-20056 | 35 | 34 | 33 | 35 |
| WV-20055 | | | 40 | 40 |
| WV-20054 | 25 | 25 | 35 | 36 |
| WV-20053 | 43 | 45 | 46 | 46 |
| WV-20052 | 47 | 47 | 53 | 46 |
| WV-20051 | 30 | 33 | 30 | 30 |
| WV-20050 | 29 | 28 | 28 | 26 |
| WV-20049 | 41 | 41 | 38 | 38 |
| WV-20049 | 24 | 23 | 22 | 21 |

TABLE 4G

Activity of certain DMD oligonucleotides
Delta 48-50 cells were treated under free uptake conditions with 10
uM of oligonucleotide in differentiation media for four days. RNA
was extracted with Agilent bead-based protocol and reverse
transcribed with random hexamers. TaqMan assays were targeted
toward the total DMD transcript or the exon-junction corresponding to
the skipped transcript, each run in multiplex with hSFSR9 internal control.
Numbers indicate amount of skipping DMD exon 51 (as a percentage
of total mRNA, where 100 would represent 100% skipped).

| | | | | |
|---|---|---|---|---|
| WV-3152 | 19 | 20 | 12 | 14 |
| WV-15860 | 29 | 31 | 26 | 23 |
| WV-20140 | 1 | 1 | 1 | 1 |
| WV-20139 | 3 | 3 | 2 | 2 |
| WV-20138 | | | 2 | 3 |
| WV-20137 | 4 | 5 | | |
| WV-20136 | | | | |
| WV-20135 | 5 | 5 | 5 | 5 |
| WV-20134 | 5 | 6 | 5 | 4 |
| WV-20133 | 17 | 17 | 13 | 13 |
| WV-20132 | 8 | 8 | 6 | 6 |
| WV-20131 | 14 | 16 | 12 | 12 |
| WV-20130 | 10 | 9 | 8 | 8 |
| WV-20129 | 12 | 14 | 11 | 11 |
| WV-20128 | 9 | 9 | 8 | 8 |
| WV-20127 | | | 8 | 8 |
| WV-20126 | 7 | 8 | 8 | 7 |
| WV-20125 | 8 | 8 | 8 | 8 |
| WV-20124 | 22 | 21 | 21 | 21 |
| WV-20123 | 13 | 13 | 14 | 12 |
| WV-20122 | 11 | 12 | 12 | 11 |
| WV-20121 | 21 | 22 | 22 | 21 |
| WV-20120 | 28 | 30 | 32 | 33 |
| WV-20119 | 52 | 50 | | |
| WV-20118 | 39 | 37 | 27 | 26 |
| WV-20117 | 18 | 17 | 15 | 18 |
| WV-20116 | 20 | 20 | 17 | 17 |
| WV-20115 | 8 | 8 | 8 | 6 |
| WV-20114 | 19 | 20 | 15 | 14 |
| WV-20113 | 20 | 18 | 17 | 15 |
| WV-20112 | 16 | 15 | 12 | 12 |
| WV-20111 | 31 | 30 | 33 | 31 |
| WV-20110 | 14 | 14 | 14 | 12 |
| WV-20109 | 20 | 21 | 25 | 24 |
| WV-20108 | 27 | 25 | 22 | 22 |
| WV-20107 | 20 | 19 | 16 | 14 |
| WV-20106 | 44 | 42 | 34 | 37 |
| WV-20105 | 23 | 22 | 18 | 18 |
| WV-20104 | 41 | 40 | 33 | 28 |
| WV-20103 | 48 | 52 | 53 | 53 |
| WV-20102 | 54 | 52 | 55 | 59 |
| WV-20101 | 38 | 39 | 38 | 43 |
| WV-20100 | 52 | 51 | 48 | 50 |
| WV-20099 | 53 | 51 | 47 | 48 |
| WV-20098 | 46 | 44 | 45 | 46 |
| WV-20097 | 47 | 46 | 51 | 48 |
| WV-20096 | 45 | 41 | 42 | 43 |
| WV-20095 | 43 | 41 | 50 | 47 |
| WV-20094 | 55 | 50 | 57 | 55 |
| WV-20093 | 35 | 34 | 35 | 38 |
| WV-20092 | 25 | 26 | 25 | 25 |
| WV-20091 | 28 | 27 | 30 | 32 |
| WV-20090 | 21 | 19 | 22 | 22 |
| WV-20089 | 8 | 7 | 8 | 9 |
| WV-20088 | 22 | 21 | 26 | 25 |
| WV-20087 | 28 | 28 | 33 | 32 |
| WV-20086 | 25 | 25 | 27 | 26 |
| WV-20085 | 33 | 31 | 30 | 31 |
| WV-20084 | 21 | 22 | 21 | 21 |
| WV-20083 | 21 | 21 | 19 | 17 |
| WV-20082 | 42 | 37 | 32 | 30 |
| WV-20081 | 41 | 41 | 30 | 30 |
| WV-20080 | 49 | 44 | 26 | 25 |
| WV-20079 | 42 | 38 | 53 | 51 |
| WV-20078 | 27 | 28 | 36 | 35 |
| WV-20077 | 10 | 10 | 10 | 10 |
| WV-20076 | 45 | 45 | 45 | 41 |
| WV-20075 | 40 | 31 | 37 | 42 |
| WV-20074 | 55 | 57 | 53 | 56 |
| WV-20073 | 51 | 55 | 51 | 50 |

TABLE 4G-continued

Activity of certain DMD oligonucleotides
Delta 48-50 cells were treated under free uptake conditions with 10
uM of oligonucleotide in differentiation media for four days. RNA
was extracted with Agilent bead-based protocol and reverse
transcribed with random hexamers. TaqMan assays were targeted
toward the total DMD transcript or the exon-junction corresponding to
the skipped transcript, each run in multiplex with hSFSR9 internal control.
Numbers indicate amount of skipping DMD exon 51 (as a percentage
of total mRNA, where 100 would represent 100% skipped).

| | | | | |
|---|---|---|---|---|
| WV-20072 | 41 | 36 | 37 | 36 |
| WV-20071 | 42 | 40 | 44 | 46 |
| WV-20070 | 18 | 18 | 25 | 25 |
| WV-20069 | 11 | 11 | 10 | 9 |
| WV-20068 | 20 | 17 | 20 | 18 |
| WV-20067 | 12 | 9 | 11 | 11 |
| WV-20066 | 12 | 11 | 13 | 12 |
| WV-20065 | 16 | 15 | 16 | 14 |
| WV-20064 | 37 | 35 | 37 | 36 |
| WV-20063 | 19 | | 24 | 22 |
| WV-20062 | 6 | 6 | 7 | 7 |
| WV-20061 | 24 | 23 | 26 | 24 |
| WV-20060 | 16 | 17 | 16 | 17 |
| WV-20059 | 55 | 42 | 62 | 67 |
| WV-20058 | 28 | 30 | 33 | 33 |
| WV-20057 | 37 | 38 | 37 | 34 |
| WV-20056 | 35 | 34 | 33 | 35 |
| WV-20055 | | | 40 | 40 |
| WV-20054 | 25 | 25 | 35 | 36 |
| WV-20053 | 43 | 45 | 46 | 46 |
| WV-20052 | 47 | 47 | 53 | 46 |
| WV-20051 | 30 | 33 | 30 | 30 |
| WV-20050 | 29 | 28 | 28 | 26 |
| WV-20049 | 41 | 41 | 38 | 38 |
| WV-20049 | 24 | 23 | 22 | 21 |

Example Dystrophin Oligonucleotides and Compositions for Exon Skipping of Exon 53

In some embodiments, the present disclosure provides DMD oligonucleotides, DMD oligonucleotide compositions, and methods of use thereof for mediating skipping of exon 53 in DMD (e.g., of mouse, human, etc.).

In some embodiments, a DMD oligonucleotide, e.g., a human DMD exon 53 skipping DMD oligonucleotide can be tested in a mouse which has been modified to comprise a DMD gene comprising the human exon 53 sequence.

In some embodiments, a DMD oligonucleotide, e.g., a DMD oligonucleotide, is capable of mediating skipping of exon 53. Non-limiting examples of such DMD oligonucleotides include: WV-12880, WV-13826, WV-13827, WV-14791, WV-9517, WV-13835, WV-13864, WV-14344, and other DMD oligonucleotides having a base sequence which comprises at least 15 contiguous bases of any of these DMD oligonucleotides.

Results of various experiments for skipping Dystrophin exon 53 are described in the present disclosure. For example, data from a sequence identification screen are shown below, in Table 5.

Additional DMD oligonucleotides were tested for their ability to mediate skipping of a DMD exon, as shown below. Full PMO (Morpholino) DMD oligonucleotides have the following sequences:

| | | | SEQ ID NO |
|---|---|---|---|
| PMO SR | WV-13405 | GTTGCCTCCGGTTCTGAAGGTGTTC | 5 |
| PMO WV | WV-13406 | CTCCGGTTCTGAAGGTGTTC | 6 |
| PMO | WV-13407 | TGCCTCCGGTTCTGAAGGTGTTCTTGTA | 7 |

WV-13407 is also designated PMO NS.

TABLE 5

Example data of certain DMD oligonucleotides.
Numbers indicate amount of skipping relative to control.

| Oligonucleotide Conc [uM] | WV-9517 | WV-13826 | WV-13827 | WV-13835 | Mock |
|---|---|---|---|---|---|
| 10 uM | 45.7 | 46.5 | 23.1 | 40.5 | 1.2 |
| | 46.3 | 45.8 | 22.9 | 58.8 | 1.1 |
| | 49.3 | 46.8 | 26.8 | 54.5 | 1.3 |
| | 48.5 | 50.3 | 28.1 | 55.2 | 1.2 |
| 3.3 uM | 18.1 | 20.3 | 7.9 | 24.6 | 1 |
| | 17 | 19.5 | 8.3 | 25.3 | 1.1 |
| | 22.6 | 19.7 | 8.8 | 26.6 | 1.1 |
| | 22.8 | 20.2 | 8.3 | 27.2 | 1.1 |
| 1.1 uM | 6 | 7 | 2.9 | 7.9 | 1 |
| | 6 | 6.2 | 2.7 | 7.4 | 1.2 |
| | 6.9 | 7.3 | 0.7 | 9.6 | 0.9 |
| | 6.6 | 6.8 | 0.9 | 9.1 | 0.7 |

| | WV-9517 | WV-12880 | WV-13864 | WV-14344 | MOCK |
|---|---|---|---|---|---|
| 10 uM | 36.1 | 60.2 | 66.8 | 47.9 | 0.9 |
| | 38.3 | 62.0 | 67.0 | 46.8 | 1.0 |
| | 44.5 | 60.9 | 68.7 | 56.8 | 1.2 |
| | 43.9 | 59.2 | 69.6 | 56.3 | 1.0 |
| 3.3 uM | 15.4 | 38.3 | 45.3 | 25.1 | 0.9 |
| | 15.8 | 37.3 | 45.6 | 27.0 | 0.9 |
| | 18.8 | 37.9 | 50.5 | 39.2 | 1.0 |
| | 18.8 | 39.6 | 49.3 | 38.9 | 1.0 |
| 1.1 uM | 4.7 | 15.8 | 21.5 | 12.2 | 0.6 |
| | 4.9 | 14.4 | 22.6 | 12.4 | 0.9 |
| | 6.4 | 18.5 | 24.9 | 17.2 | 1.1 |
| | 6.2 | 16.2 | 13.2 | 17.1 | 0.9 |
| 0.3 uM | 2.2 | 5.0 | 6.6 | 5.7 | 0.8 |
| | 1.8 | 5.0 | 5.9 | 5.7 | 0.9 |
| | 2.7 | 7.4 | 8.2 | 7.2 | 1.0 |
| | 2.7 | 7.5 | 8.2 | 6.9 | 1.0 |

TABLE 6

Example data of certain DMD oligonucleotides.
Skipping efficiency of various DMD oligonucleotides, tested
for skipping of DMD exon 53. Numbers represent skipping of exon 53.
Δ45-52 patient myoblasts were differentiated for 7 days, then treated
with DMD oligonucleotide for 4 d under gymnotic conditions
in differentiation media. RNA was harvested by Trizol extraction
and skipping analyzed by TaqMan.

| Conc. | 10 uM | 3.3 uM | 1.1 uM | 0.3 uM | 0.1 uM |
|---|---|---|---|---|---|
| Mock | 1.1 | 1.2 | | 0.8 | 1.0 |
| | 1.0 | 1.1 | 2.0 | 0.9 | 1.0 |
| | 1.1 | 0.7 | 1.1 | 1.0 | 1.1 |
| | 1.2 | 0.7 | 1.1 | 0.9 | 1.0 |
| WV-13405 (PMO) | 44.8 | 28.6 | 18.1 | 9.5 | 4.0 |
| | 44.8 | 23.4 | 17.4 | 8.7 | 4.0 |
| | 51.2 | 26.5 | 11.4 | 5.1 | 3.7 |
| | 50.8 | 25.6 | 11.2 | 5.5 | 3.6 |
| WV-9517 | 35.9 | 18.3 | 6.5 | 2.2 | 1.9 |
| | 36.6 | 17.3 | 6.4 | 2.1 | 1.9 |
| | 40.2 | 23.4 | 5.5 | 2.7 | 1.7 |
| | 38.7 | 25.6 | 5.9 | 2.2 | 1.8 |
| Wv-12880 | 57.3 | 36.3 | 16.4 | 4.8 | 7.5 |
| | 55.8 | 37.0 | 18.1 | 2.8 | 4.7 |
| | 57.5 | 35.9 | 16.6 | 8.0 | 7.4 |
| | 58.9 | 33.0 | 16.5 | 7.2 | 6.8 |
| WV-13864 | 68.1 | 45.1 | 22.6 | 10.5 | 7.4 |
| | 68.0 | 44.5 | 23.0 | 12.0 | 5.6 |
| | 67.5 | 43.1 | 24.3 | 8.4 | 6.0 |
| | 64.8 | 44.5 | 19.9 | 3.3 | 6.1 |
| WV-13835 | 40.2 | 21.5 | 6.3 | 2.8 | 2.0 |
| | 39.4 | 20.3 | 9.7 | 2.5 | 2.0 |
| | 50.0 | 21.0 | 5.5 | 3.2 | 2.0 |
| | 47.7 | 20.6 | 6.0 | 3.3 | 2.2 |

TABLE 6-continued

Example data of certain DMD oligonucleotides.
Skipping efficiency of various DMD oligonucleotides, tested
for skipping of DMD exon 53. Numbers represent skipping of exon 53.
Δ45-52 patient myoblasts were differentiated for 7 days, then treated
with DMD oligonucleotide for 4 d under gymnotic conditions
in differentiation media. RNA was harvested by Trizol extraction
and skipping analyzed by TaqMan.

| Conc. | 10 uM | 3.3 uM | 1.1 uM | 0.3 uM | 0.1 uM |
|---|---|---|---|---|---|
| WV-14791 | 41.4 | 25.9 | 7.4 | 4.7 | 0.7 |
|  | 40.3 | 24.8 | 5.8 | 4.0 | 0.5 |
|  | 40.1 | 24.9 | 9.1 | 4.3 | 3.9 |
|  | 41.3 | 27.2 | 8.9 | 4.6 | 3.5 |
| WV-14344 | 50.1 | 28.6 | 13.6 | 6.4 | 3.8 |
|  | 47.4 | 28.6 | 8.8 | 5.8 | 4.7 |
|  | 54.9 | 46.1 | 18.0 | 11.4 | 6.6 |
|  | 55.7 | 38.3 | 18.7 | 11.8 | 6.0 |

TABLE 7

Example data of certain DMD oligonucleotides.
Skipping efficiency of various DMD oligonucleotides, tested for
skipping of DMD exon 53. Numbers represent skipping of exon 53.
Δ45-52 patient myoblasts were treated with DMD oligonucleotide
for 4 d (4 days) under gymnotic conditions in differentiation media. RNA
was harvested by Trizol extraction and skipping analyzed by TaqMan.

|  | 10 uM | 3.3 uM | 1.1 uM | 0.3 uM | 0.1 uM |
|---|---|---|---|---|---|
| Mock | 0.7 | 0.6 | 0.6 | 0.6 | 0.7 |
|  | 0.7 | 0.7 | 0.6 | 0.6 | 0.7 |
|  | 0.6 | 0.6 | 0.6 | 0.7 | 0.7 |
|  | 0.5 | 0.5 | 0.7 | 0.6 | 0.7 |
| Wv-13405 (PMO) | 9.4 | 1.5 | 3.4 | 1.1 | 0.8 |
|  | 9.3 | 1.4 | 3.1 | 1.1 | 0.8 |
|  | 6.6 | 2.8 | 1.5 | 0.9 | 0.8 |
|  | 6.3 | 2.6 | 1.5 | 1.0 | 0.8 |
| WV-9517 | 29.3 | 8.4 | 2.6 | 1.0 | 0.7 |
|  | 28.7 | 9.2 | 3.0 | 1.1 | 0.8 |
|  | 16.6 | 6.6 | 2.3 | 1.1 | 0.7 |
|  | 16.9 | 6.8 | 2.2 | 1.1 | 0.9 |
| WV-12880 | 37.9 | 17.7 | 9.6 | 3.4 | 1.3 |
|  | 38.8 | 19.9 | 9.1 | 3.3 | 1.4 |
|  | 31.4 | 16.1 | 7.9 | 3.3 | 1.6 |
|  | 31.6 | 16.8 | 8.0 | 3.0 | 1.5 |
| WV-13864 | 55.9 | 28.6 | 11.7 | 4.3 | 2.0 |
|  | 54.3 | 27.8 | 11.6 | 4.6 | 2.0 |
|  | 43.4 | 22.2 | 10.7 | 4.2 | 2.0 |
|  | 43.0 | 22.7 | 9.8 | 3.8 | 2.1 |
| WV-13835 | 38.7 | 11.6 | 2.9 | 1.3 | 0.9 |
|  | 37.2 | 11.0 | 2.9 | 1.3 | 0.8 |
|  | 42.3 | 13.1 | 3.5 | 1.2 | 0.9 |
|  | 41.5 | 10.0 | 3.1 | 1.3 | 0.9 |
| WV-14791 | 26.3 | 12.1 | 5.2 | 1.9 | 1.3 |
|  | 24.8 | 11.2 | 4.7 | 2.1 | 1.1 |
|  | 28.0 | 13.0 | 5.2 | 2.2 | 1.2 |
|  | 27.6 | 12.4 | 4.9 | 2.1 | 1.4 |
| WV-14344 | 36.2 | 17.8 | 8.0 | 2.7 | 1.7 |
|  | 37.4 | 17.0 | 7.1 | 2.7 | 1.8 |
|  | 37.4 | 22.3 | 9.8 | 3.7 | 1.7 |
|  | 36.6 | 22.6 | 9.9 | 3.7 | 1.5 |

Several DMD oligonucleotides (including WV-9517, WV-13864, WV-13835, and WV-14791) were tested at various concentrations up to 30 uM for TLR9 activation in vitro in HEK-blue-TLR9 cells (16 hour gymnotic uptake). WV-13864 and WV-14791 comprise a chirally controlled non-negatively charged internucleotidic linkage in the Rp configuration. WV-9517, WV-13864, WV-13835, and WV-14791 did not exhibit significant TLR9 activation (less than 2-fold TLR9 induction; data not shown). WV-13864 and WV-14791 also exhibited negligible signal up to 30 uM in PBMC cytokine release assay compared to water (data not shown).

Example Methods for Preparing Oligonucleotides and Compositions

Among other things, the present disclosure provides technologies (methods, reagents, conditions, purification processes, etc.) for preparing oligonucleotides and oligonucleotide compositions, including chirally controlled oligonucleotides and chirally controlled oligonucleotide nucleotides. Various technologies (methods, reagents, conditions, purification processes, etc.), as described herein, can be utilized to prepare provided oligonucleotides and compositions thereof in accordance with the present disclosure, including but not limited to those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/223056, WO 2018/237194, and/or WO 2019/055951, the preparation technologies of each of which are incorporated herein by reference.

In some embodiments, the present disclosure provides chirally controlled oligonucleotides, e.g., chirally controlled DMD oligonucleotides. In some embodiments, a provided chirally controlled DMD oligonucleotide is over 50% pure. In some embodiments, a provided chirally controlled DMD oligonucleotide is over about 55% pure. In some embodiments, a provided chirally controlled DMD oligonucleotide is over about 60% pure. In some embodiments, a provided chirally controlled DMD oligonucleotide is over about 65% pure. In some embodiments, a provided chirally controlled DMD oligonucleotide is over about 70% pure. In some embodiments, a provided chirally controlled DMD oligonucleotide is over about 75% pure. In some embodiments, a provided chirally controlled DMD oligonucleotide is over about 80% pure. In some embodiments, a provided chirally controlled DMD oligonucleotide is over about 85% pure. In some embodiments, a provided chirally controlled DMD oligonucleotide is over about 90% pure. In some embodiments, a provided chirally controlled DMD oligonucleotide is over about 91% pure. In some embodiments, a provided chirally controlled DMD oligonucleotide is over about 92% pure. In some embodiments, a provided chirally controlled DMD oligonucleotide is over about 93% pure. In some embodiments, a provided chirally controlled DMD oligonucleotide is over about 94% pure. In some embodiments, a provided chirally controlled DMD oligonucleotide is over about 95% pure. In some embodiments, a provided chirally controlled DMD oligonucleotide is over about 96% pure. In some embodiments, a provided chirally controlled DMD oligonucleotide is over about 97% pure. In some embodiments, a provided chirally controlled DMD oligonucleotide is over about 98% pure. In some embodiments, a provided chirally controlled DMD oligonucleotide is over about 99% pure. In some embodiments, a provided chirally controlled DMD oligonucleotide is over about 99.5% pure. In some embodiments, a provided chirally controlled DMD oligonucleotide is over about 99.6% pure. In some embodiments, a provided chirally controlled DMD oligonucleotide is over about 99.7% pure. In some embodiments, a provided chirally controlled DMD oligonucleotide is over about 99.8% pure. In some embodiments, a provided chirally controlled DMD oligonucleotide is over about 99.9% pure. In some embodiments, a provided chirally controlled DMD oligonucleotide is over at least about 99% pure.

In some embodiments, a chirally controlled oligonucleotide composition, e.g., a chirally controlled DMD oligonucleotide composition, is a composition designed to comprise a single oligonucleotide type. In certain embodiments, such compositions are about 50% diastereomerically pure. In some embodiments, such compositions are about 50% diastereomerically pure. In some embodiments, such compositions are about 50% diastereomerically pure. In some embodiments, such compositions are about 55% diastereomerically pure. In some embodiments, such compositions are about 60% diastereomerically pure. In some embodiments, such compositions are about 65% diastereomerically pure. In some embodiments, such compositions are about 70% diastereomerically pure. In some embodiments, such compositions are about 75% diastereomerically pure. In some embodiments, such compositions are about 80% diastereomerically pure. In some embodiments, such compositions are about 85% diastereomerically pure. In some embodiments, such compositions are about 90% diastereomerically pure. In some embodiments, such compositions are about 91% diastereomerically pure. In some embodiments, such compositions are about 92% diastereomerically pure. In some embodiments, such compositions are about 93% diastereomerically pure. In some embodiments, such compositions are about 94% diastereomerically pure. In some embodiments, such compositions are about 95% diastereomerically pure. In some embodiments, such compositions are about 96% diastereomerically pure. In some embodiments, such compositions are about 97% diastereomerically pure. In some embodiments, such compositions are about 98% diastereomerically pure. In some embodiments, such compositions are about 99% diastereomerically pure. In some embodiments, such compositions are about 99.5% diastereomerically pure. In some embodiments, such compositions are about 99.6% diastereomerically pure. In some embodiments, such compositions are about 99.7% diastereomerically pure. In some embodiments, such compositions are about 99.8% diastereomerically pure. In some embodiments, such compositions are about 99.9% diastereomerically pure. In some embodiments, such compositions are at least about 99% diastereomerically pure.

Among other things, the present disclosure recognizes the challenge of stereoselective (rather than stereorandom or racemic) preparation of oligonucleotides, e.g., DMD oligonucleotides. Among other things, the present disclosure provides methods and reagents for stereoselective preparation of oligonucleotides comprising multiple (e.g., more than 5, 6, 7, 8, 9, or 10) internucleotidic linkages, and particularly for DMD oligonucleotides comprising multiple (e.g., more than 5, 6, 7, 8, 9, or 10) chiral internucleotidic linkages. In some embodiments, in a stereorandom or racemic preparation of oligonucleotides such as DMD oligonucleotides, at least one chiral internucleotidic linkage is formed with less than 90:10, 95:5, 96:4, 97:3, or 98:2 diastereoselectivity. In some embodiments, for a stereoselective or chirally controlled preparation of oligonucleotides such as DMD oligonucleotides, each chiral internucleotidic linkage is formed with greater than 90:10, 95:5, 96:4, 97:3, or 98:2 diastereoselectivity. In some embodiments, for a stereoselective or chirally controlled preparation of DMD oligonucleotides, each chiral internucleotidic linkage is formed with greater than 95:5 diastereoselectivity. In some embodiments, for a stereoselective or chirally controlled preparation of DMD oligonucleotides, each chiral internucleotidic linkage is formed with greater than 96:4 diastereoselectivity. In some embodiments, for a stereoselective or chirally controlled preparation of DMD oligonucleotides, each chiral internucleotidic linkage is formed with greater than 97:3 diastereoselectivity. In some embodiments, for a stereoselective or chirally controlled preparation of DMD oligonucleotides, each chiral internucleotidic linkage is formed with greater than 98:2 diastereoselectivity. In some embodiments, for a stereoselective or chirally controlled preparation of DMD oligonucleotides, each chiral internucleotidic linkage is formed with greater than 99:1 diastereoselectivity. In some embodiments, diastereoselectivity of a chiral internucleotidic linkage in an oligonucleotide, e.g., a DMD oligonucleotide may be measured through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage.

In some embodiments, a chirally controlled DMD oligonucleotide composition is a composition designed to comprise multiple DMD oligonucleotide types. In some embodiments, methods of the present disclosure allow for the generation of a library of chirally controlled DMD oligonucleotides such that a pre-selected amount of any one or more chirally controlled DMD oligonucleotide types can be mixed with any one or more other chirally controlled DMD oligonucleotide types to create a chirally controlled DMD oligonucleotide composition. In some embodiments, the pre-selected amount of a DMD oligonucleotide type is a composition having any one of the above-described diastereomeric purities.

In some embodiments, the present disclosure provides methods for making a chirally controlled oligonucleotide (e.g., a DMD oligonucleotide) comprising steps of:
(1) coupling;
(2) capping;
(3) optionally modifying;
(4) deblocking; and
(5) repeating steps (1)-(4) until a desired length is achieved.

In some embodiments, the present disclosure provides a method, e.g., for preparing a DMD oligonucleotide, comprising one or more cycles, each of which independently comprises: (1) a coupling step;
(2) optionally a pre-modification capping step;
(3) a modification step;
(4) optionally a post-modification capping step; and
(5) optionally a de-blocking step.

In some embodiments, a cycle comprises one or more pre-modification capping steps. In some embodiments, a cycle comprises one or more post-modification capping steps. In some embodiments, a cycle comprises one or more pre- and post-modification capping steps. In some embodiments, a cycle comprises one or more de-blocking steps. In some embodiments, a cycle comprises a coupling step, a pre-modification capping step, a modification step, a post-modification capping step, and a de-blocking step. In some embodiments, a cycle comprises a coupling step, a pre-modification capping step, a modification step, and a de-blocking step. In some embodiments, a cycle comprises a coupling step, a modification step, a post-modification capping step and a de-blocking step. In some embodiments, comprise a coupling step, a pre-modification capping step, a modification step, a post-modification capping step, and a de-blocking step. In some embodiments, one or more cycles comprise a coupling step, a pre-modification capping step, a modification step, and a de-blocking step. In some embodiments, one or more cycles comprise a coupling step, a modification step, a post-modification capping step and a de-blocking step.

When describing the provided methods, the word "cycle" has its ordinary meaning as understood by a person of ordinary skill in the art. In some embodiments, one round of steps (1)-(4) is referred to as a cycle. In some embodiments, some cycles comprise modifying. In some embodiments, some cycles do not comprise modifying. In some embodiments, some cycles comprise and some cycles do not comprise modifying. In some embodiments, each cycle independently comprises a modifying step. In some embodiments, each cycle does not comprise a cycling step.

In some embodiments, to form a chirally controlled internucleotidic linkage, a chirally pure phosphoramidite comprising a chiral auxiliary is utilized to stereoselectively form the chirally controlled internucleotidic linkage. Various phosphoramidite and chiral auxiliaries, e.g., those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/223056, WO 2018/237194, and/or WO 2019/055951, the phosphoramidite and chiral auxiliaries of each of which are incorporated herein by reference, may be utilized in accordance with the present disclosure.

In some embodiments, such an internucleotidic linkage is a neutral internucleotidic linkage. In some embodiments, such an internucleotidic linkage is a chirally controlled internucleotidic linkage. In some embodiments, such an internucleotidic linkage comprises a chiral auxiliary moiety. In some embodiments, such an internucleotidic linkage comprises no chiral auxiliary moiety. In some embodiments, a chiral auxiliary moiety falls off during modification.

Provided technologies provide various advantages. Among other things, as demonstrated herein, provided technologies can greatly improve oligonucleotide synthesis crude purity and yield, particularly for modified and/or chirally pure oligonucleotides such as DMD oligonucleotides that provide a number of properties and activities that are critical for therapeutic purposes. With the capability to provide unexpectedly high crude purity and yield for therapeutically important DMD oligonucleotides, provided technologies can significantly reduce manufacturing costs (through, e.g., simplified purification, greatly improved overall yields, etc.). In some embodiments, provided technologies can be readily scaled up to produce DMD oligonucleotides in sufficient quantities and qualities for clinical purposes. In some embodiments, provided technologies comprising chiral auxiliaries that comprise electron-withdrawing groups in $G^2$ (e.g., PSM chiral auxiliaries) are particularly useful for preparing chirally controlled internucleotidic linkages comprising P—N bonds (e.g., non-negatively charged internucleotidic linkages such as n001) and can significantly simplify manufacture operations, reduce cost, and/or facilitate downstream formation.

In some embodiments, provided technologies provides improved reagents compatibility. For example, as demonstrated in the present disclosure, provided technologies provide flexibility to use different reagent systems for oxidation, sulfurization and/or azide reactions, particularly for chirally controlled DMD oligonucleotide synthesis.

Among other things, the present disclosure provides DMD oligonucleotide compositions of high crude purity. In some embodiments, the present disclosure provides chirally controlled DMD oligonucleotide composition of high crude purity. In some embodiments, the present disclosure provides chirally controlled DMD oligonucleotide of high crude purity. In some embodiments, the present disclosure provides DMD oligonucleotide of high crude purity and/or high stereopurity.

Support and Linkers

In some embodiments, oligonucleotides can be prepared in solution. In some embodiments, oligonucleotides can be prepared using a support. In some embodiments, oligonucleotides are prepared using a solid support. Suitable support that can be utilized in accordance with the present disclosure include, e.g., solid support described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/223056, WO 2018/237194, and/or WO 2019/055951, the solid support of each of which is incorporated herein by reference.

In some embodiments, a linker moiety is utilized to connect an oligonucleotide chain to a support during synthesis. Suitable linkers are widely utilized in the art, and include those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/223056, WO 2018/237194, and/or WO 2019/055951, the linker of each of which is incorporated herein by reference In some embodiments, the linking moiety is a succinamic acid linker, or a succinate linker (—CO—CH$_2$—CH$_2$—CO—), or an oxalyl linker (—CO—CO—). In some embodiments, the linking moiety and the nucleoside are bonded together through an ester bond. In some embodiments, a linking moiety and a nucleoside are bonded together through an amide bond. In some embodiments, a linking moiety connects a nucleoside to another nucleotide or nucleic acid. Suitable linkers are disclosed in, for example, Oligonucleotides And Analogues A Practical Approach, Ekstein, F. Ed., IRL Press, N.Y., 1991, Chapter 1 and Solid-Phase Supports for Oligonucleotide Synthesis, Pon, R. T., Curr. Prot. Nucleic Acid Chem., 2000, 3.1.1-3.1.28. In some embodiments, a universal linker (UnyLinker) is used to attached the oligonucleotide to the solid support (Ravikumar et al., Org. Process Res. Dev., 2008, 12 (3), 399-410). In some embodiments, other universal linkers are used (Pon, R. T., Curr. Prot. Nucleic Acid Chem., 2000, 3.1.1-3.1.28). In some embodiments, various orthogonal linkers (such as disulfide linkers) are used (Pon, R. T., Curr. Prot. Nucleic Acid Chem., 2000, 3.1.1-3.1.28).

Among other things, the present disclosure recognizes that a linker can be chosen or designed to be compatible with a set of reaction conditions employed in oligonucleotide synthesis. In some embodiments, to avoid degradation of oligonucleotides and to avoid desulfurization, auxiliary groups are selectively removed before de-protection. In some embodiments, DPSE group can selectively be removed by F$^-$ ions. In some embodiments, the present disclosure provides linkers that are stable under a DPSE de-protection condition, e.g., 0.1M TBAF in MeCN, 0.5M HF-Et$_3$N in THF or MeCN, etc. In some embodiments, a provided linker is a linker as exemplified below:

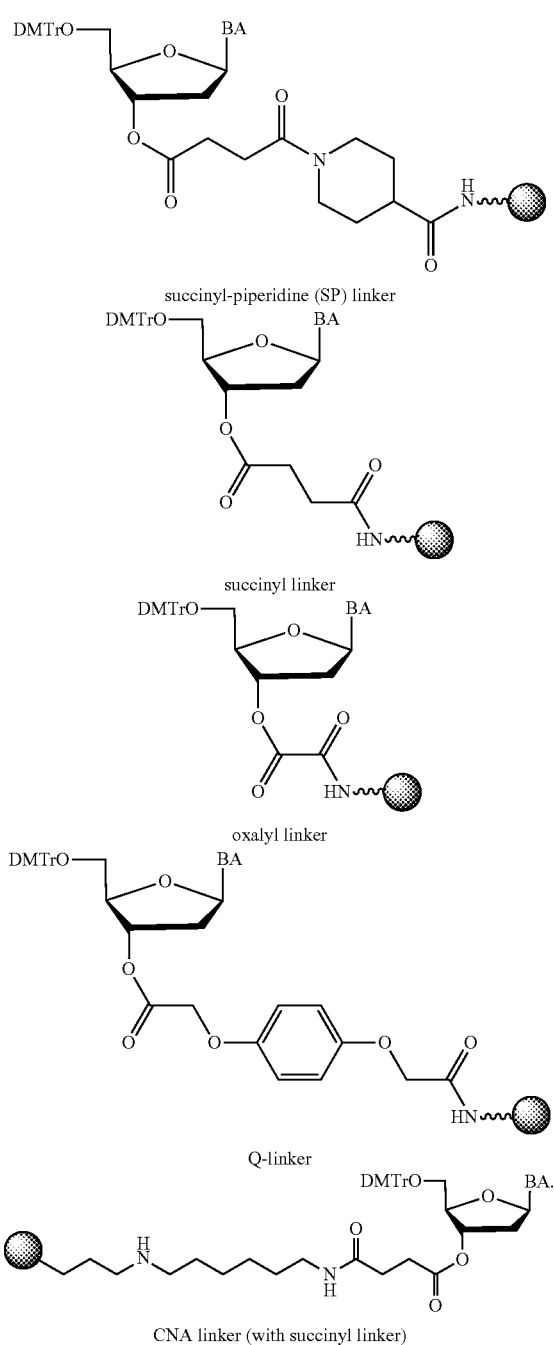

succinyl-piperidine (SP) linker succinyl linker oxalyl linker

Q-linker

CNA linker (with succinyl linker)

Solvents

Syntheses of oligonucleotides are generally performed in aprotic organic solvents. In some embodiments, a solvent is a nitrile solvent such as, e.g., acetonitrile. In some embodiments, a solvent is a basic amine solvent such as, e.g., pyridine. In some embodiments, a solvent is an ethereal solvent such as, e.g., tetrahydrofuran. In some embodiments, a solvent is a halogenated hydrocarbon such as, e.g., dichloromethane. In some embodiments, a mixture of solvents is used. In certain embodiments a solvent is a mixture of any one or more of the above-described classes of solvents.

In some embodiments, when an aprotic organic solvent is not basic, a base is present in the reacting step. In some embodiments where a base is present, the base is an amine base such as, e.g., pyridine, quinoline, or N,N-dimethylaniline. Example other amine bases include pyrrolidine, piperidine, N-methyl pyrrolidine, pyridine, quinoline, N,N-dimethylaminopyridine (DMAP), or N,N-dimethylaniline.

In some embodiments, a base is other than an amine base.

In some embodiments, an aprotic organic solvent is anhydrous. In some embodiments, an anhydrous aprotic organic solvent is freshly distilled. In some embodiments, a freshly distilled anhydrous aprotic organic solvent is a basic amine solvent such as, e.g., pyridine. In some embodiments, a freshly distilled anhydrous aprotic organic solvent is an ethereal solvent such as, e.g., tetrahydrofuran. In some embodiments, a freshly distilled anhydrous aprotic organic solvent is a nitrile solvent such as, e.g., acetonitrile.

Chiral Reagents/Chiral Auxiliaries

In some embodiments, chiral reagents (may also be referred to as chiral auxiliaries) are used to confer stereoselectivity in the production of chirally controlled oligonucleotides. Many chiral reagents, also referred to by those of skill in the art and herein as chiral auxiliaries, may be used in accordance with methods of the present disclosure. Examples of such chiral reagents are described herein and in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/098264, WO 2018/223056, WO 2018/237194, and/or WO 2019/055951, the chiral auxiliaries of each of which is incorporated by reference.

In some embodiments, a chiral reagent is a compound of Formula 3-AA:

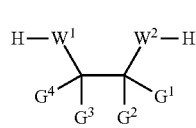

Formula 3-AA wherein each variable is independently as described herein.

In some embodiments of Formula 3-AA, $W^1$ and $W^2$ are independently -$NG^5$-, —O—, or —S—; $G^1$, $G^2$, $G^3$, $G^4$, and $G^S$ are independently hydrogen, or an optionally substituted group selected from aliphatic, alkyl, aralkyl, cycloalkyl, cycloalkylalkyl, heteroaliphatic, heterocyclyl, heteroaryl, or aryl; or two of $G^1$, $G^2$, $G^3$, $G^4$, and $G^5$ are $G^6$ (taken together to form an optionally substituted saturated, partially unsaturated or unsaturated carbocyclic or heteroatom-containing ring of up to about 20 ring atoms which is monocyclic or polycyclic, fused or unfused), and no more than four of $G^1$, $G^2$, $G^3$, $G^4$, and $G^S$ are $G^6$. Similarly to the compounds of Formula 3-I, any of $G^1$, $G^2$, $G^3$, $G^4$, or $G^5$ are optionally substituted by oxo, thioxo, alkyl, alkenyl, alkynyl, heteroaryl, or aryl moieties. In some embodiments, such substitution induces stereoselectivity in chirally controlled oligonucleotide production. In some embodiments, a heteroatom-containing moiety, e.g., heteroaliphatic, heterocyclyl, heteroaryl, etc., has 1-5 heteroatoms. In some embodiments, the heteroatoms are selected from nitrogen, oxygen, sulfur and silicon. In some embodiments, at least one heteroatom is nitrogen. In some embodiments, aliphatic, alkyl, aralkyl, cycloalkyl, cycloalkylalkyl, heteroaliphatic, heterocyclyl, heteroaryl, or aryl groups have 1-20, 1-15, 1-10, 1-9, 1-8, 1-7 or 1-6 carbon atoms.

In some embodiments, $W^1$ is -$NG^5$—O—. In some embodiments, $W^1$ is -$NG^5$—O—, wherein the —O— is bonded to —H. In some embodiments, $W^1$ is $-NG^5-$. In some embodiments, $G^S$ and one of $G^3$ and $G^4$ are taken together to form an optionally substituted 3-10 membered ring having 0-3 heteroatoms in addition to the nitrogen atom of $W^1$. In some embodiments, $G^5$ and $G^3$ are taken together to form an optionally substituted 3-10 membered ring having 0-3 heteroatoms in addition to the nitrogen atom of $W^1$. In some embodiments, $G^5$ and $G^4$ are taken together to form an optionally substituted 3-10 membered ring having 0-3 heteroatoms in addition to the nitrogen atom of $W^1$. In some embodiments, a formed ring is an optionally substituted 4, 5, 6, 7, or 8 membered ring. In some embodiments, a formed ring is an optionally substituted 4-membered ring. In some embodiments, a formed ring is an optionally substituted 5-membered ring. In some embodiments, a formed ring is an optionally substituted 6-membered ring. In some embodiments, a formed ring is an optionally substituted 7-membered ring.

In some embodiments, a provided chiral reagent has the structure of

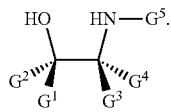

In some embodiments, a provided chiral reagent has the structure of

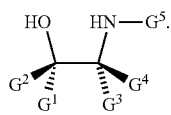

In some embodiments, a provided chiral reagent has the structure of

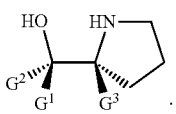

In some embodiments, a provided chiral reagent has the structure of

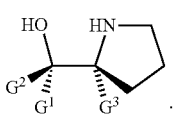

In some embodiments, a provided chiral reagent has the structure of

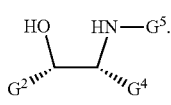

In some embodiments, a provided chiral reagent has the structure of

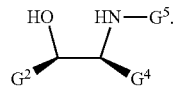

In some embodiments, a provided chiral reagent has the structure of

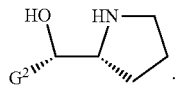

In some embodiments, a provided chiral reagent has the structure of

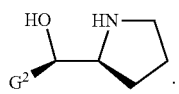

In some embodiments, $W^1$ is $-NG^5$, $W^2$ is O, each of $G^1$ and $G^3$ is independently hydrogen or an optionally substituted group selected from $C_{1-10}$ aliphatic, heterocyclyl, heteroaryl and aryl, $G^2$ is $-C(R)_2Si(R)_3$, and $G^4$ and $G^5$ are taken together to form an optionally substituted saturated, partially unsaturated or unsaturated heteroatom-containing ring of up to about 20 ring atoms which is monocyclic or polycyclic, fused or unfused. In some embodiments, each R is independently hydrogen, or an optionally substituted group selected from $C_1$-$C_6$ aliphatic, carbocyclyl, aryl, heteroaryl, and heterocyclyl. In some embodiments, $G^2$ is $-C(R)_2Si(R)_3$, wherein $-C(R)_2-$ is optionally substituted $-CH_2-$, and each R of $-Si(R)_3$ is independently an optionally substituted group selected from $C_{1-10}$ aliphatic, heterocyclyl, heteroaryl and aryl. In some embodiments, at least one R of $-Si(R)_3$ is independently optionally substituted $C_{1-10}$ alkyl. In some embodiments, at least one R of $-Si(R)_3$ is independently optionally substituted phenyl. In some embodiments, one R of $-Si(R)_3$ is independently optionally substituted phenyl, and each of the other two R is independently optionally substituted $C_{1-10}$ alkyl. In some embodiments, one R of $-Si(R)_3$ is independently optionally substituted $C_{1-10}$ alkyl, and each of the other two R is independently optionally substituted phenyl. In some embodiments, $G^2$ is optionally substituted $-CH_2Si(Ph)(Me)_2$. In some embodiments, $G^2$ is optionally substituted $-CH_2Si(Me)(Ph)_2$. In some embodiments, $G^2$ is $-CH_2Si(Me)(Ph)_2$. In some embodiments, $G^4$ and $G^5$ are taken together to form an optionally substituted saturated 5-6 membered ring containing one nitrogen atom (to which $G^5$ is attached). In some embodiments, $G^4$ and $G^5$ are taken together to form an optionally substituted saturated 5-membered ring containing one nitrogen atom. In some embodiments, $G^1$ is hydrogen. In some embodiments, $G^3$ is hydrogen. In some embodiments, both $G^1$ and $G^3$ are hydrogen.

In some embodiments, $W^1$ is $-NG^5$, $W^2$ is 0, each of $G^1$ and $G^3$ is independently $R^1$, $G^2$ is $-R^1$, and $G^4$ and $G^5$ are taken together to form an optionally substituted saturated, partially unsaturated or unsaturated heteroatom-containing ring of up to about 20 ring atoms which is monocyclic or polycyclic, fused or unfused, wherein $R^1$ is an optionally substituted group selected from $C_{1-20}$ aliphatic, $C_{1-20}$ aliphatic having 1-5 heteroatoms, $C_{6-20}$ aryl, $C_{5-20}$ heteroaryl having 1-5 heteroatoms and combinations thereof (e.g., aliphatic-aryl/heteroaryl, heteroaliphatic-aryl/heteroaryl). In some embodiments, each of $G^1$ and $G^3$ is independently R. In some embodiments, each of $G^1$ and $G^3$ is independently —H. In some embodiments, $G^2$ is connected to the rest of the molecule through a carbon atom, and the carbon atom is substituted with one or more electron-withdrawing groups. In some embodiments, $G^2$ is methyl substituted with one or more electron-withdrawing groups. In some embodiments, $G^2$ is methyl substituted with one and no more than one electron-withdrawing group. In some embodiments, $G^2$ is methyl substituted with two or more electron-withdrawing groups. Among other things, a chiral auxiliary having $G^2$ comprising an electron-withdrawing group can be readily removed by a base (base-labile, e.g., under an anhydrous condition substantially free of water; in many instances, preferably before oligonucleotides comprising internucleotidic linkages comprising such chiral auxiliaries are exposed to conditions/reagent systems comprising a substantial amount of water, particular in the presence of a base(e.g., cleavage conditions/reagent systems using $NH_4OH$)) and provides various advantages as described herein, e.g., high crude purity, high yield, high stereoselectivity, more simplified operation, fewer steps, further reduced manufacture cost, and/or more simplified downstream formulation (e.g., low amount of salt(s) after cleavage), etc. In some embodiments, as described in the Examples, such auxiliaries may provide alternative or additional chemical compatibility with other functional and/or protection groups. In some embodiments, as demonstrated in the Examples, base-labile chiral auxiliaries are particularly useful for construction of chirally controlled non-negatively charged internucleotidic linkages (e.g., neutral internucleotidic linkages such as n001); in some instances, as demonstrated in the Examples, they can provide significantly improved yield and/or crude purity with high stereoselectivity, e.g., when utilized with removal using a base under an anhydrous condition. In some embodiments, such a chiral auxiliary is bonded to a linkage phosphorus via an oxygen atom (e.g., which corresponds to a —OH group in a corresponding chiral auxiliary compound), the carbon atom in the chiral auxiliary to which the oxygen is bonded (the alpha carbon) also bonds to —H (in addition to other groups; in some embodiments, a secondary carbon), and the next carbon atom (the beta carbon) in the chiral auxiliary is boned to one or two electron-withdrawing groups. In some embodiments, —$W^2$—H is —OH. In some embodiments, $G^1$ is —H. In some embodiments, $G^2$ comprises one or two electron-withdrawing groups or can otherwise facilitate remove of the chiral auxiliary by a base. In some embodiments, $G^1$ is —H, $G^2$ comprises one or two electron-withdrawing groups, —$W^2$—H is —OH. In some embodiments, $G^1$ is —H, $G^2$ comprises one or two electron-withdrawing groups, —$W^2$—H is —OH, —$W^1$—H is -N$G^5$-H, and one of $G^3$ and $G^4$ is taken together with $G^5$ to form with their intervening atoms a ring as described herein (e.g., an optionally substituted 3-20 membered monocyclic, bicyclic or polycyclic ring having in addition to the nitrogen atom to which $G^5$ is on, 0-5 heteroatoms (e.g., an optionally substituted 3, 4, 5, or 6-membered monocyclic saturated ring having in addition to the nitrogen atom to which $G^5$ is on no other heteroatoms)).

As appreciated by those skilled in the art, various electron-withdrawing groups are known in the art and can be utilized in accordance with the present disclosure. In some embodiments, an electronic-withdrawing group comprises and/or is connected to the carbon atom through, e.g., —S(O)—, —S(O)$_2$—, —P(O)(R$^1$)—, —P(S)R$^1$—, or —C(O)—. In some embodiments, an electron-withdrawing group is —CN, —NO$_2$, halogen, —C(O)R$^1$, —C(O)OR', —C(O)N(R')$_2$, —S(O)R$^1$, —S(O)$_2$R$^1$, —P(W)(R$^1$)$_2$, —P(O)(R$^1$)$_2$, —P(O)(OR')$_2$, or —P(S)(R$^1$)$_2$. In some embodiments, an electron-withdrawing group is aryl or heteroaryl, e.g., phenyl, substituted with one or more of —CN, —NO$_2$, halogen, —C(O)R$^1$, —C(O)OR', —C(O)N(R')$_2$, —S(O)R$^1$, —S(O)$_2$R$^1$, —P(W)(R$^1$)$_2$, —P(O)(R')$_2$, —P(O)(OR')$_2$, or —P(S)(R$^1$)$_2$.

In some embodiments, $G^2$ is -L'-L"-R', wherein L' is —C(R)$_2$— or optionally substituted —CH$_2$—, and L" is —P(O)(R')—, —P(O)(R')O—, —P(O)(OR')—, —P(O)(OR')O—, —P(O)[N(R')]—, —P(O)[N(R')]O—, —P(O)[N(R')][N(R')]—, —P(S)(R')—, —S(O)$_2$—, —S(O)$_2$—, —S(O)$_2$O—, —S(O)—, —C(O)—, —C(O)N(R')—, or —S—, wherein each R' is independently R$^1$ as described herein. In some embodiments, L' is —C(R)$_2$—. In some embodiments, L' is optionally substituted —CH$_2$—.

In some embodiments, L' is —C(R)$_2$—. In some embodiments, each R is independently hydrogen, or an optionally substituted group selected from $C_1$-$C_6$ aliphatic, carbocyclyl, aryl, heteroaryl, and heterocyclyl. In some embodiments, L' is —CH$_2$—. In some embodiments, L" is —P(O)(R')—, —P(S)(R')—, —S(O)$_2$—. In some embodiments, $G^2$ is -L'-C(O)N(R')$_2$. In some embodiments, $G^2$ is -L'-P(O)(R')$_2$. In some embodiments, $G^2$ is -L'-P(S)(R')$_2$. In some embodiments, each R' is independently optionally substituted aliphatic, heteroaliphatic, aryl, or heteroaryl as described in the present disclosure (e.g., those embodiments described for R). In some embodiments, each R' is independently optionally substituted phenyl. In some embodiments, each R' is independently optionally substituted phenyl wherein one or more substituents are independently selected from —CN, -OMe, —Cl, —Br, and —F. In some embodiments, each R' is independently substituted phenyl wherein one or more substituents are independently selected from —CN, -OMe, —Cl, —Br, and —F. In some embodiments, each R' is independently substituted phenyl wherein the substituents are independently selected from —CN, -OMe, —Cl, —Br, and —F. In some embodiments, each R' is independently mono-substituted phenyl, wherein the substituent is independently selected from —CN, -OMe, —Cl, —Br, and —F. In some embodiments, two R' are the same. In some embodiments, two R' are different. In some embodiments, $G^2$ is -L'-S(O)R'. In some embodiments, $G^2$ is -L'-C(O)N(R')$_2$. In some embodiments, $G^2$ is -L'-S(O)$_2$R'. In some embodiments, R' is optionally substituted aliphatic, heteroaliphatic, aryl, or heteroaryl as described in the present disclosure (e.g., those embodiments described for R). In some embodiments, R' is optionally substituted phenyl. In some embodiments, R' is optionally substituted phenyl wherein one or more substituents are independently selected from —CN, -OMe, —Cl, —Br, and —F. In some embodiments, R' is substituted phenyl wherein one or more substituents are independently selected from —CN, -OMe, —Cl, —Br, and —F. In some embodiments, R' is substituted phenyl wherein each substituent is independently selected from —CN, -OMe, —Cl, —Br, and —F. In some embodiments, R' is mono-substituted phenyl. In some embodiments, R' is mono-substituted phenyl, wherein the substituent is independently selected from —CN, -OMe, —Cl, —Br, and —F. In some embodiments, a substituent is an electron-withdrawing group. In some embodiments, an electron-withdrawing group is —CN, —NO$_2$, halogen, —C(O)R$^1$, —C(O)OR', —C(O)N(R')$_2$, —S(O)R$^1$, —S(O)$_2$R$^1$, —P(W)(R$^1$)$_2$, —P(O)(R$^1$)$_2$, —P(O)(OR')$_2$, or —P(S)(R$^1$)$_2$.

In some embodiments, $G^2$ is optionally substituted —CH$_2$-L"-R, wherein each of L" and R is independently as described in the present disclosure. In some embodiments, $G^2$ is optionally substituted —CH(-L"-R)$_2$, wherein each of L" and R is independently as described in the present disclosure. In some embodiments, $G^2$ is optionally substituted —CH(—S—R)$_2$. In some embodiments, $G^2$ is optionally substituted —CH$_2$—S—R. In some embodiments, the two R groups are taken together with their intervening atoms to form a ring. In some embodiments, a formed ring is an optionally substituted 5, 6, 7-membered ring having 0-2 heteroatoms in addition to the intervening heteroatoms. In some embodiments, $G^2$ is optionally substituted

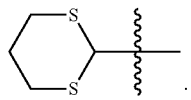

In some embodiments, $G^2$ is

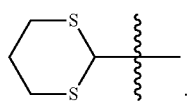

In some embodiments, —S— may be converted to —S(O)— or —S(O)$_2$—, e.g., by oxidation, e.g., to facilitate removal by a base.

In some embodiments, $G^2$ is -L'-R', wherein each variable is as described in the present disclosure. In some embodiments, $G^2$ is —CH$_2$—R'. In some embodiments, $G^2$ is —CH(R')$_2$. In some embodiments, $G^2$ is —C(R')$_3$. In some embodiments, R' is optionally substituted aryl or heteroaryl. In some embodiments, R' is substituted aryl or heteroaryl wherein one or more substituents are independently an electron-withdrawing group. In some embodiments, -L'- is optionally substituted —CH$_2$—, and R' is R, wherein R is optionally substituted aryl or heteroaryl. In some embodiments, R is substituted aryl or heteroaryl wherein one or more substituents are independently an electron-withdrawing group. In some embodiments, R is substituted aryl or heteroaryl wherein each substituent is independently an electron-withdrawing group. In some embodiments, R is aryl or heteroaryl substituted with two or more substituents, wherein each substituent is independently an electron-withdrawing group. In some embodiments, an electron-withdrawing group is —CN, —NO$_2$, halogen, —C(O)R$^1$, —C(O)OR', —C(O)N(R')$_2$, —S(O)R$^1$, —S(O)$_2$R$^1$, —P(W)(R$^1$)$_2$, —P(O)(R$^1$)$_2$, —P(O)(OR')$_2$, or —P(S)(R$^1$)$_2$. In some embodiments, R' is

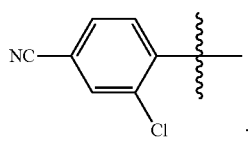 [SMILES: *c1ccc(C#N)cc1Cl]

In some embodiments, R' is p-NO$_2$Ph-. In some embodiments, R' is

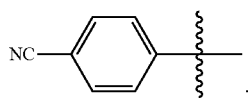 [SMILES: *c1ccc(C#N)cc1]

In some embodiments, R' is

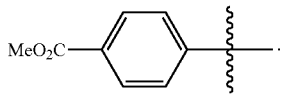

In some embodiments, R' is

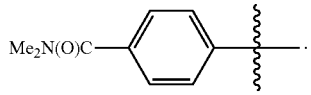

In some embodiments, R' is

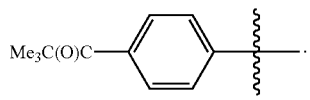

In some embodiments, R' is

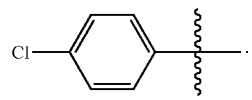

In some embodiments, $G^2$ is

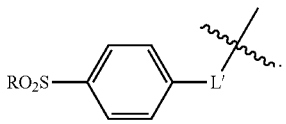

In some embodiments, R' is

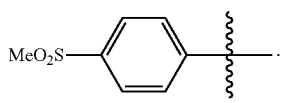

In some embodiments, R' is

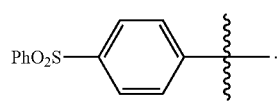

In some embodiments, R' is 2,4,6-trichlorophenyl. In some embodiments, R' is 2,4,6-trifluorophenyl. In some embodiments, $G^2$ is —CH(4-chlorophenyl)$_2$. In some embodiments, $G^2$ is —CH(R')$_2$, wherein each R' is

113

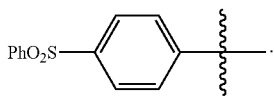

In some embodiments, G² is —CH(R')₂, wherein each R' is

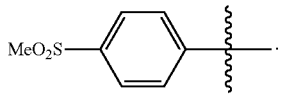

In some embodiments, R' is —C(O)R. In some embodiments, R' is CH₃C(O)—.

In some embodiments, G² is -L'-S(O)₂R', wherein each variable is as described in the present disclosure. In some embodiments, G² is —CH₂—S(O)₂R'. In some embodiments, G² is -L'-S(O)R', wherein each variable is as described in the present disclosure. In some embodiments, G² is —CH₂—S(O)R'. In some embodiments, G² is -L'-C(O)₂R', wherein each variable is as described in the present disclosure. In some embodiments, G² is —CH₂—C(O)₂R'. In some embodiments, G² is -L'-C(O)R', wherein each variable is as described in the present disclosure. In some embodiments, G² is —CH₂—C(O)R'. In some embodiments, -L'- is optionally substituted —CH₂—, and R' is R. In some embodiments, R is optionally substituted aryl or heteroaryl. In some embodiments, R is optionally substituted aliphatic. In some embodiments, R is optionally substituted heteroaliphatic. In some embodiments, R is optionally substituted heteroaryl. In some embodiments, R is optionally substituted aryl. In some embodiments, R is optionally substituted phenyl. In some embodiments, R is not phenyl, or mono-, di- or tri-substituted phenyl, wherein each substituent is selected from —NO₂, halogen, —CN, —C₁₋₃ alkyl, and C₁₋₃ alkyloxy. In some embodiments, R is substituted aryl or heteroaryl wherein one or more substituents are independently an electron-withdrawing group. In some embodiments, R is substituted aryl or heteroaryl wherein each substituent is independently an electron-withdrawing group. In some embodiments, R is aryl or heteroaryl substituted with two or more substituents, wherein each substituent is independently an electron-withdrawing group. In some embodiments, an electron-withdrawing group is —CN, —NO₂, halogen, —C(O)R¹, —C(O)OR', —C(O)N(R')₂, —S(O)R¹, —S(O)₂R¹, —P(W)(R¹)₂, —P(O)(R¹)₂, —P(O)(OR')₂, or —P(S)(R¹)₂. In some embodiments, R' is phenyl. In some embodiments, R' is substituted phenyl. In some embodiments, R' is

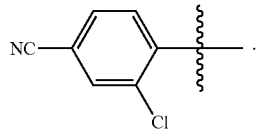 [SMILES: *c1ccc(C#N)cc1Cl]

In some embodiments, R' is

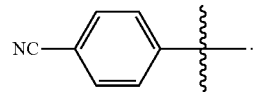

114

In some embodiments, R' is

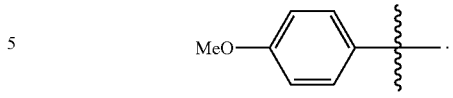

In some embodiments, R' is optionally substituted C₁₋₆ aliphatic. In some embodiments, R' is t-butyl. In some embodiments, R' is isopropyl. In some embodiments, R' is methyl. In some embodiments, G² is —CH₂C(O)OMe. In some embodiments, G² is —CH₂C(O)Ph. In some embodiments, G² is —CH₂C(O)—tBu.

In some embodiments, G² is -L'-NO₂. In some embodiments, G² is —CH₂—NO₂. In some embodiments, G² is -L'-S(O)₂N(R')₂. In some embodiments, G² is —CH₂—S(O)₂N(R')₂. In some embodiments, G² is -L'-S(O)₂NHR'. In some embodiments, G² is —CH₂—S(O)₂NHR'. In some embodiments, R' is methyl. In some embodiments, G² is —CH₂—S(O)₂NH(CH₃). In some embodiments, R' is —CH₂Ph. In some embodiments, G² is —CH₂—S(O)₂NH(CH₂Ph). In some embodiments, G² is —CH₂—S(O)₂N(CH₂Ph)₂. In some embodiments, R' is phenyl. In some embodiments, G² is —CH₂—S(O)₂NHPh. In some embodiments, G² is —CH₂—S(O)₂N(CH₃)Ph. In some embodiments, G² is —CH₂—S(O)₂N(CH₃)₂. In some embodiments, G² is —CH₂—S(O)₂NH(CH₂Ph). In some embodiments, G² is —CH₂—S(O)₂NHPh. In some embodiments, G² is —CH₂—S(O)₂NH(CH₂Ph). In some embodiments, G² is —CH₂—S(O)₂N(CH₃)₂. In some embodiments, G² is —CH₂—S(O)₂N(CH₃)Ph. In some embodiments, G² is -L'-S(O)₂N(R')(OR'). In some embodiments, G² is —CH₂—S(O)₂N(R')(OR'). In some embodiments, each R' is methyl. In some embodiments, G² is —CH₂—S(O)₂N(CH₃)(OCH₃). In some embodiments, G² is —CH₂—S(O)₂N(Ph)(OCH₃). In some embodiments, G² is —CH₂—S(O)₂N(CH₂Ph)(OCH₃). In some embodiments, G² is —CH₂—S(O)₂N(CH₂Ph)(OCH₃). In some embodiments, G² is -L'-S(O)₂OR'. In some embodiments, G² is —CH₂—S(O)₂OR'. In some embodiments, G² is —CH₂—S(O)₂OPh. In some embodiments, G² is —CH₂—S(O)₂OCH₃. In some embodiments, G² is —CH₂—S(O)₂OCH₂Ph.

In some embodiments, G² is -L'-P(O)(R¹)₂. In some embodiments, G² is —CH₂—P(O)(R¹)₂. In some embodiments, G² is -L'-P(O)[N(R')₂]₂. In some embodiments, G² is —CH₂—P(O)[N(R')₂]₂. In some embodiments, G² is -L'-P(O)[O(R')₂]₂. In some embodiments, G² is —CH₂—P(O)[O(R')₂]₂. In some embodiments, G² is -L'-P(O)(R')[N(R')₂]₂. In some embodiments, G² is —CH₂—P(O)(R')[N(R')₂]. In some embodiments, G² is -L'-P(O)(R')[O(R')]. In some embodiments, G² is —CH₂—P(O)(R')[O(R')]. In some embodiments, G² is -L'-P(O)(OR')[N(R')₂]. In some embodiments, G² is —CH₂—P(O)(OR')[N(R')₂]. In some embodiments, G² is -L'-C(O)N(R')₂, wherein each variable is as described in the present disclosure. In some embodiments, G² is —CH₂—C(O)N(R')₂. In some embodiments, each R' is independently R. In some embodiments, one R' is optionally substituted aliphatic, and one R is optionally substituted aryl. In some embodiments, one R' is optionally substituted C₁₋₆ aliphatic, and one R is optionally substituted phenyl. In some embodiments, each R' is independently optionally substituted C₁₋₆ aliphatic. In some embodiments, G² is —CH₂—P(O)(CH₃)Ph. In some embodiments, G² is —CH₂—P(O)(CH₃)₂. In some embodiments, G² is —CH₂—P(O)(Ph)₂. In some embodiments, G² is —CH₂—

P(O)(OCH$_3$)$_2$. In some embodiments, G$^2$ is —CH$_2$—P(O)(CH$_2$Ph)$_2$. In some embodiments, G$^2$ is —CH$_2$—P(O)[N(CH$_3$)Ph]$_2$. In some embodiments, G$^2$ is —CH$_2$—P(O)[N(CH$_3$)$_2$]$_2$. In some embodiments, G$^2$ is —CH$_2$—P(O)[N(CH$_2$Ph)$_2$]$_2$. In some embodiments, G$^2$ is —CH$_2$—P(O)(OCH$_3$)$_2$. In some embodiments, G$^2$ is —CH$_2$—P(O)(OPh)$_2$.

In some embodiments, G$^2$ is -L'-SR'. In some embodiments, G$^2$ is —CH$_2$—SR'. In some embodiments, R' is optionally substituted phenyl. In some embodiments, R' is phenyl.

In some embodiments, a provided chiral reagent has the structure of

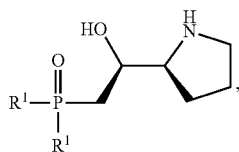

wherein each R$^1$ is independently as described in the present disclosure. In some embodiments, a provided chiral reagent has the structure of

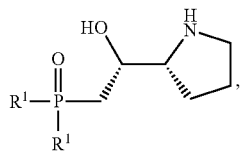

wherein each R$^1$ is independently as described in the present disclosure. In some embodiments, each R$^1$ is independently R as described in the present disclosure. In some embodiments, each R$^1$ is independently R, wherein R is optionally substituted aliphatic, aryl, heteroaliphatic, or heteroaryl as described in the present disclosure. In some embodiments, each R$^1$ is phenyl. In some embodiments, R$^1$ is -L-R'. In some embodiments, R$^1$ is -L-R', wherein L is —O—, —S—, or —N(R'). In some embodiments, a provided chiral reagent has the structure of

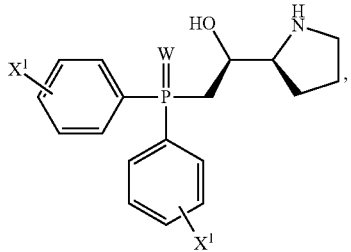

wherein each X$^1$ is independently —H, an electron-withdrawing group, —NO$_2$, —CN, —OR, —Cl, —Br, or —F, and W is O or S. In some embodiments, a provided chiral reagent has the structure of

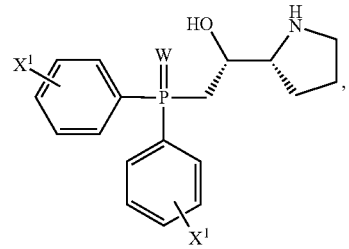

wherein each X$^1$ is independently —H, an electron-withdrawing group, —NO$_2$, —CN, —OR, —Cl, —Br, or —F, and W is O or S. In some embodiments, each X$^1$ is independently —CN, —OR, —Cl, —Br, or —F, wherein R is not —H. In some embodiments, R is optionally substituted C$_{1-6}$ aliphatic. In some embodiments, R is optionally substituted C$_{1-6}$ alkyl. In some embodiments, R is —CH$_3$. In some embodiments, one or more X$^1$ are independently electron-withdrawing groups (e.g., —CN, —NO$_2$, halogen, —C(O)R$^1$, —C(O)OR', —C(O)N(R')$_2$, —S(O)R$^1$, —S(O)$_2$R$^1$, —P(W)(R$^1$)$_2$, —P(O)(R$^1$)$_2$, —P(O)(OR')$_2$, —P(S)(R$^1$)$_2$, etc.).

In some embodiments, a provided chiral reagent has the structure of

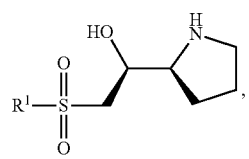

wherein R$^1$ is as described in the present disclosure. In some embodiments, a provided chiral reagent has the structure of

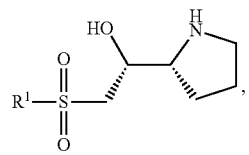

wherein R$^1$ is as described in the present disclosure. In some embodiments, R$^1$ is R as described in the present disclosure. In some embodiments, R$^1$ is R, wherein R is optionally substituted aliphatic, aryl, heteroaliphatic, or heteroaryl as described in the present disclosure. In some embodiments, R$^1$ is -L-R'. In some embodiments, R$^1$ is -L-R', wherein L is —O—, —S—, or —N(R'). In some embodiments, a provided chiral reagent has the structure of

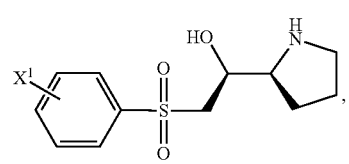

wherein X$^1$ is —H, an electron-withdrawing group, —NO$_2$, —CN, —OR, —Cl, —Br, or —F, and W is O or S.

In some embodiments, a provided chiral reagent has the structure of

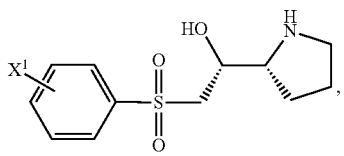

wherein $X^1$ is —H, an electron-withdrawing group, —NO$_2$, —CN, —OR, —Cl, —Br, or —F, and W is O or S. In some embodiments, $X^1$ is —CN, —OR, —Cl, —Br, or —F, wherein R is not —H. In some embodiments, R is optionally substituted $C_{1-6}$ aliphatic. In some embodiments, R is optionally substituted $C_{1-6}$ alkyl. In some embodiments, R is —CH$_3$. In some embodiments, $X^1$ is an electron-withdrawing group (e.g., —CN, —NO$_2$, halogen, —C(O)R$^1$, —C(O)OR', —C(O)N(R')$_2$, —S(O)R$^1$, —S(O)$_2$R$^1$, —P(W)(R$^1$)$_2$, —P(O)(R$^1$)$_2$, —P(O)(OR')$_2$,—P(S)(R$^1$)$_2$, etc.). In some embodiments, $X^1$ is an electron-withdrawing group that is not —CN, —NO$_2$, or halogen. In some embodiments, $X^1$ is not —H, —CN, —NO$_2$, halogen, or $C_{1-3}$ alkyloxy.

In some embodiments, $^G$ is —CH(R$^{21}$)—CH(R$^{22}$)=C(R$^{23}$)(R$^{24}$), wherein each of R$^{21}$, R$^{22}$, R$^{23}$, and R$^{24}$ is independently R. In some embodiments, R$^{22}$ and R$^{23}$ are both R, and the two R groups are taken together with their intervening atoms to form an optionally substituted aryl or heteroaryl ring as described herein. In some embodiments, one or more substituents are independently electron-withdrawing groups. In some embodiments, R$^{21}$ and R$^{24}$ are both R, and the two R groups are taken together with their intervening atoms to form an optionally substituted ring as described herein. In some embodiments, R$^{21}$ and R$^{24}$ are both R, and the two R groups are taken together with their intervening atoms to form an optionally substituted saturated or partially saturated ring as described herein. In some embodiments, R$^{22}$ and R$^{23}$ are both R, and the two R groups are taken together with their intervening atoms to form an optionally substituted aryl or heteroaryl ring as described herein, and R$^{21}$ and R$^{24}$ are both R, and the two R groups are taken together with their intervening atoms to form an optionally substituted partially saturated ring as described herein. In some embodiments, R$^2$ is —H. In some embodiments, R$^{24}$ is —H. In some embodiments, G$^2$ is optionally substituted

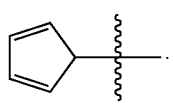 [SMILES: *C1C=CC=C1]

In some embodiments, G$^2$ is optionally substituted

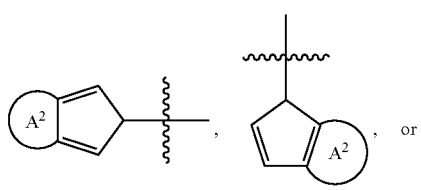

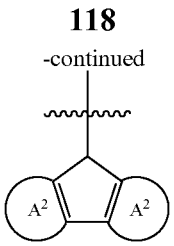

wherein each Ring A$^2$ is independently a 3-15 membered monocyclic, bicyclic or polycyclic ring as described herein. In some embodiments, Ring A$^2$ is an optionally substituted 5-10 membered monocyclic aryl or heteroaryl ring having 1-5 heteroatoms as described herein. In some embodiments, Ring A$^2$ is an optionally substituted phenyl ring as described herein. In some embodiments, In some embodiments, G$^2$ is optionally substituted

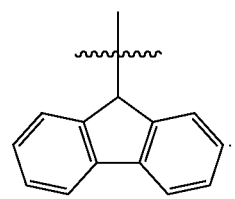 [SMILES: *C1c2ccccc2-c2ccccc21]

In some embodiments, G$^2$ is

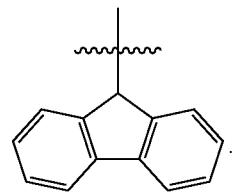 [SMILES: *C1c2ccccc2-c2ccccc21]

In some embodiments, G$^2$ is

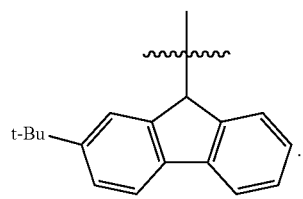 [SMILES: *C1c2ccccc2-c2ccc(C(C)(C)C)cc21]

In some embodiments, G$^2$ is

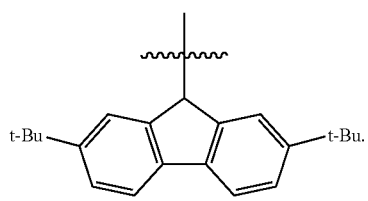 [SMILES: *C1c2cc(C(C)(C)C)ccc2-c2ccc(C(C)(C)C)cc21]

In some embodiments, a chiral auxiliary is a DPSE auxiliary. In some embodiments, a chiral auxiliary is a PSM auxiliary.

In some embodiments, when contacted with a base, a chiral auxiliary moiety, e.g., of an internucleotidic linkage, whose corresponding compound is a compound of Formula 3-I or 3-AA may be released as an alkene, which has the same structure as a product formed by elimination of a water molecule from the corresponding compound (elimination of —$W^2$—H=—OH and an alpha-H of $G^2$). In some embodiments, such an alkene has the structure of (electron-withdrawing group)$_2$=C($R^1$)-L-N($R^5$)($R^6$), (electron-withdrawing group)H=C($R^1$)-L-N($R^5$)($R^6$), CH(-L"-R')=C($R^1$)-L-N($R^5$)($R^6$) wherein the CH group is optionally substituted, or $C^x$=C($R^1$)-L-N($R^5$)($R^6$), wherein $C^x$ is optionally substituted

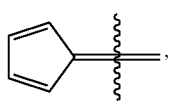

and may be optionally fused with one or more optionally substituted rings, and each other variable is independently as described herein. In some embodiments, $C^x$ is optionally substituted

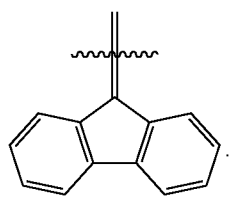 [SMILES: *=C1c2ccccc2-c2ccccc21]

In some embodiments, $C^x$ is

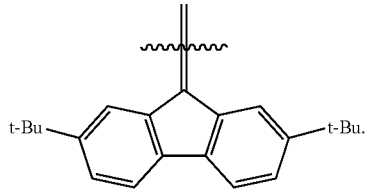 [SMILES: *=C1c2cc(C(C)(C)C)ccc2-c2ccc(C(C)(C)C)cc21]

In some embodiments, such an alkene is

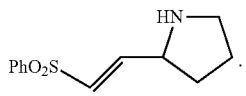

In some embodiments, such an alkene is

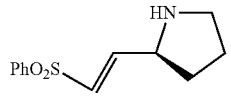

In some embodiments, such an alkene is

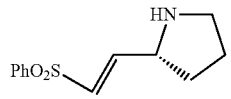

In some embodiments, a chiral reagent is an aminoalcohol. In some embodiments, a chiral reagent is an aminothiol. In some embodiments, a chiral reagent is an aminophenol. In some embodiments, a chiral reagent is (S)- and (R)-2-methylamino-1-phenylethanol, (1R, 2S)-ephedrine, or (1R, 2S)-2-methylamino-1,2-diphenylethanol.

In some embodiments of the disclosure, a chiral reagent is a compound of one of the following formulae:

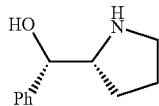
Formula O

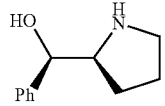
Formula P

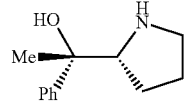
Formula Q

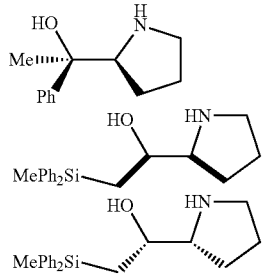
Formula R (DPSE)

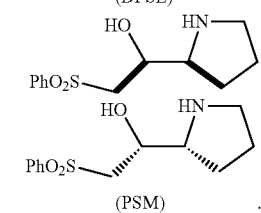

(PSM)

As appreciated by those skilled in the art, chiral reagents are typically stereopure or substantially stereopure, and are typically utilized as a single stereoisomer substantially free of other stereoisomers. In some embodiments, compounds of the present disclosure are stereopure or substantially stereopure.

As demonstrated herein, when used for preparing a chiral internucleotidic linkage, to obtain stereoselectivity generally stereochemically pure chiral reagents are utilized. Among other things, the present disclosure provides stereochemically pure chiral reagents, including those having structures described.

The choice of chiral reagent, for example, the isomer represented by Formula Q or its stereoisomer, Formula R, permits specific control of chirality at a linkage phosphorus. Thus, either an Rp or Sp configuration can be selected in each synthetic cycle, permitting control of the overall three dimensional structure of a chirally controlled DMD oligonucleotide. In some embodiments, a chirally controlled DMD oligonucleotide has all Rp stereocenters. In some embodiments of the disclosure, a chirally controlled DMD oligonucleotide has all Sp stereocenters. In some embodiments of the disclosure, each linkage phosphorus in the chirally controlled DMD oligonucleotide is independently Rp or Sp. In some embodiments of the disclosure, each linkage phosphorus in the chirally controlled DMD oligonucleotide is independently Rp or Sp, and at least one is Rp and at least one is Sp. In some embodiments, the selection of Rp and Sp centers is made to confer a specific three dimensional superstructure to a chirally controlled DMD oligonucleotide. Examples of such selections are described in further detail herein.

In some embodiments, a provided DMD oligonucleotide comprise a chiral auxiliary moiety, e.g., in an internucleotidic linkage. In some embodiments, a chiral auxiliary is connected to a linkage phosphorus. In some embodiments, a chiral auxiliary is connected to a linkage phosphorus through $W^2$. In some embodiments, a chiral auxiliary is connected to a linkage phosphorus through $W^2$, wherein $W^2$ is O. Optionally, $W^1$, e.g., when $W^1$ is $-NG^5-$, is capped during DMD oligonucleotide synthesis. In some embodiments, $W^1$ in a chiral auxiliary in a DMD oligonucleotide is capped, e.g., by a capping reagent during DMD oligonucleotide synthesis. In some embodiments, $W^1$ may be purposeful capped to modulate DMD oligonucleotide property. In some embodiments, $W^1$ is capped with $-R^1$. In some embodiments, $R^1$ is $-C(O)R'$. In some embodiments, R' is optionally substituted $C_{1-6}$ aliphatic. In some embodiments, R' is methyl.

In some embodiments, a chiral reagent for use in accordance with the present disclosure is selected for its ability to be removed at a particular step in the above-depicted cycle. For example, in some embodiments it is desirable to remove a chiral reagent during the step of modifying the linkage phosphorus. In some embodiments, it is desirable to remove a chiral reagent before the step of modifying the linkage phosphorus. In some embodiments, it is desirable to remove a chiral reagent after the step of modifying the linkage phosphorus. In some embodiments, it is desirable to remove a chiral reagent after a first coupling step has occurred but before a second coupling step has occurred, such that a chiral reagent is not present on the growing DMD oligonucleotide during the second coupling (and likewise for additional subsequent coupling steps). In some embodiments, a chiral reagent is removed during the "deblock" reaction that occurs after modification of the linkage phosphorus but before a subsequent cycle begins. Example methods and reagents for removal are described herein.

In some embodiments, removal of chiral auxiliary is achieved when performing the modification and/or deblocking step, as illustrated in Scheme I. It can be beneficial to combine chiral auxiliary removal together with other transformations, such as modification and deblocking. A person of ordinary skill in the art would appreciate that the saved steps/transformation could improve the overall efficiency of synthesis, for instance, with respect to yield and product purity, especially for longer DMD oligonucleotides. One example wherein the chiral auxiliary is removed during modification and/or deblocking is illustrated in Scheme I.

In some embodiments, a chiral reagent for use in accordance with methods of the present disclosure is characterized in that it is removable under certain conditions. For instance, in some embodiments, a chiral reagent is selected for its ability to be removed under acidic conditions. In certain embodiments, a chiral reagent is selected for its ability to be removed under mildly acidic conditions. In certain embodiments, a chiral reagent is selected for its ability to be removed by way of an E1 elimination reaction (e.g., removal occurs due to the formation of a cation intermediate on the chiral reagent under acidic conditions, causing the chiral reagent to cleave from the DMD oligonucleotide). In some embodiments, a chiral reagent is characterized in that it has a structure recognized as being able to accommodate or facilitate an E1 elimination reaction. One of skill in the relevant arts will appreciate which structures would be envisaged as being prone toward undergoing such elimination reactions.

In some embodiments, a chiral reagent is selected for its ability to be removed with a nucleophile. In some embodiments, a chiral reagent is selected for its ability to be removed with an amine nucleophile. In some embodiments, a chiral reagent is selected for its ability to be removed with a nucleophile other than an amine.

In some embodiments, a chiral reagent is selected for its ability to be removed with a base. In some embodiments, a chiral reagent is selected for its ability to be removed with an amine. In some embodiments, a chiral reagent is selected for its ability to be removed with a base other than an amine.

In some embodiments, chirally pure phosphoramidites comprising chiral auxiliaries may be isolated before use. In some embodiments, chirally pure phosphoramidites comprising chiral auxiliaries may be used without isolation—in some embodiments, they may be used directly after formation.

Activation

As appreciated by those skilled in the art, DMD oligonucleotide preparation may use various conditions, reagents, etc. to active a reaction component, e.g., during phosphoramidite preparation, during one or more steps during in the cycles, during post-cycle cleavage/deprotection, etc. Various technologies for activation can be utilized in accordance with the present disclosure, including but not limited to those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/223056, WO 2018/237194, and/or WO 2019/055951, the activation technologies of each of which are incorporated by reference. Certain activation technologies, e.g., reagents, conditions, methods, etc. are illustrated in the Examples.

Coupling

In some embodiments, cycles of the present disclosure comprise stereoselective condensation/coupling steps to form chirally controlled internucleotidic linkages. For condensation, often an activating reagent is used, such as 4,5-dicyanoimidazole (DCI), 4,5-dichloroimidazole, 1-phenylimidazolium triflate (PhIMT), benzimidazolium triflate (BIT), benztriazole, 3-nitro-1,2,4-triazole (NT), tetrazole, 5-ethylthiotetrazole (ETT), 5-benzylthiotetrazole (BTT), 5-(4-nitrophenyl)tetrazole, N-cyanomethylpyrrolidinium triflate (CMPT), N-cyanomethylpiperidinium triflate, N-cyanomethyldimethylammonium triflate, etc. Suitable conditions and reagents, including chiral phosphoramidites, include those described in U.S. Pat. Nos. 9,695,211, 9,605, 019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/223056, WO 2018/237194, and/or WO 2019/055951, the condensation reagents, conditions and methods of each of which are incorporated by reference. Certain coupling technologies, e.g., reagents, conditions, methods, etc. are illustrated in the Examples.

In some embodiments, a chiral phosphoramidite for coupling has the structure of

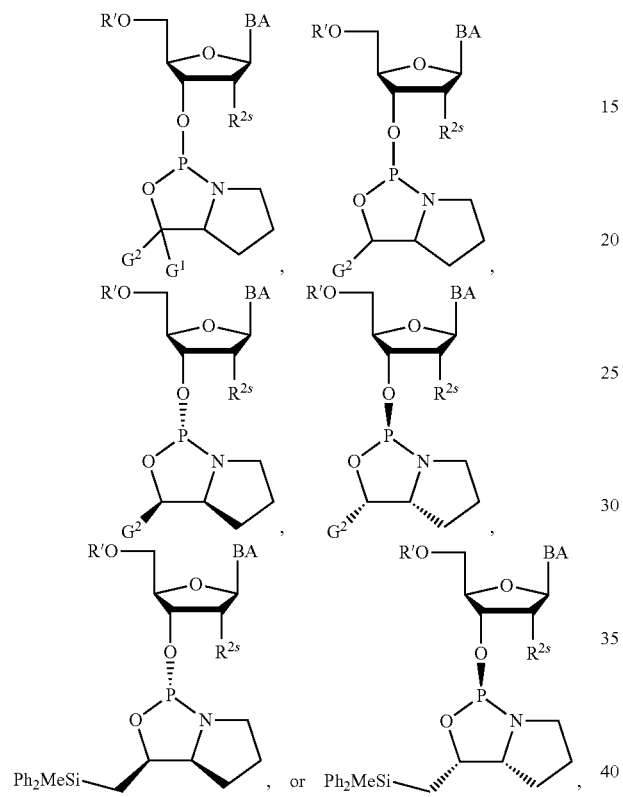

wherein $R^{2s}$ is —H, —F, or —OR, and each other variable is independently as described in the present disclosure. In some embodiments, $G^1$ or $G^2$ comprises an electron-withdrawing group as described in the present disclosure. In some embodiments, a chiral phosphoramidite for coupling has the structure of

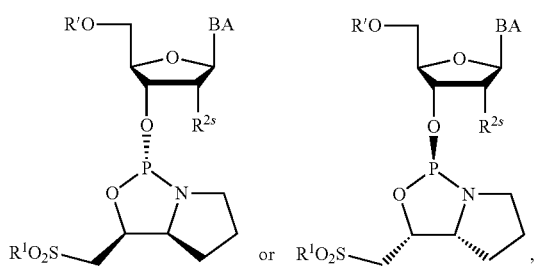

wherein each variable is independently as described in the present disclosure. In some embodiments, $R^1$ is R' as described in the present disclosure. In some embodiments, $R^1$ is R as described in the present disclosure. In some embodiments, R is optionally substituted phenyl as described in the present disclosure. In some embodiments, R is phenyl. In some embodiments, R is optionally substituted $C_{1-6}$ aliphatic as described in the present disclosure. In some embodiments, R is optionally substituted $C_{1-6}$ alkyl as described in the present disclosure. For example, in some embodiments, R is methyl; in some embodiments, R is isopropyl; in some embodiments, R is t-butyl; etc. In some embodiments, R' is a 5'-blocking group in oligonucleotide synthesis, e.g., DMTr. In some embodiments, BA is an optionally protected nucleobase as described herein. In some embodiments, BA is optionally substituted A, T, G, C, U or a tautomer thereof. In some embodiments, BA is a protected nucleobase. In some embodiments, BA is optionally substituted protected A, T, G, C, U or a tautomer thereof. In some embodiments, R' is a protection group. In some embodiments, R' is DMTr. In some embodiments, $R^{2s}$ is —H, —F, or -OMe. In some embodiments, $R^{2s}$ is —H. In some embodiments, $R^{2s}$ is —F. In some embodiments, $R^{2s}$ is -OMe.

In some embodiments, an internucleotidic linkage formed in a coupling step comprising,

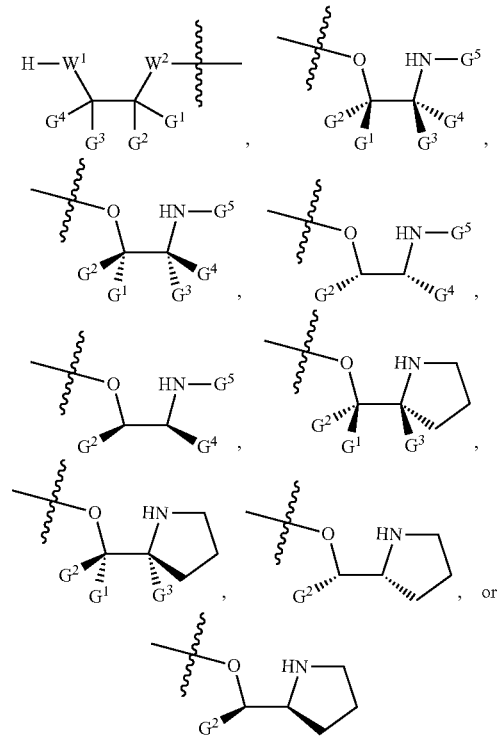

bonded to the linkage phosphorus, wherein each variable is independently in accordance with the present disclosure.

In some embodiments, a coupling forms an internucleotidic linkage with a stereoselectivity of 80%, 85%, 90%, 91%, 92%, 93%, 94%, 95%, 96%, 97%, 98%, 99% or more. In some embodiments, the stereoselectivity is 85% or more. In some embodiments, the stereoselectivity is 85% or more. In some embodiments, the stereoselectivity is 90% or more. In some embodiments, the stereoselectivity is 91% or more. In some embodiments, the stereoselectivity is 92% or more. In some embodiments, the stereoselectivity is 93% or more. In some embodiments, the stereoselectivity is 94% or more. In some embodiments, the stereoselectivity is 95% or more. In some embodiments, the stereoselectivity is 96% or more. In some embodiments, the stereoselectivity is 97% or more.

In some embodiments, the stereoselectivity is 98% or more. In some embodiments, the stereoselectivity is 99% or more.

Capping

If the final nucleic acid is larger than a dimer, the unreacted —OH moiety is generally capped with a blocking/capping group. Chiral auxiliaries in oligonucleotides may also be capped with a blocking group to form a capped condensed intermediate. Suitable capping technologies (e.g., reagents, conditions, etc.) include those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/223056, WO 2018/237194, and/or WO 2019/055951, the capping technologies of each of which are incorporated by reference. In some embodiments, a capping reagent is a carboxylic acid or a derivate thereof. In some embodiments, a capping reagent is R'COOH. In some embodiments, a capping step introduces R'COO— to unreacted 5'-OH group and/or amino groups in chiral auxiliaries. In some embodiments, a cycle may comprise two or more capping steps. In some embodiments, a cycle comprises a first capping before modification of a coupling product (e.g., converting P(III) to P(V)), and another capping after modification of a coupling product. In some embodiments, a first capping is performed under an amidation condition, e.g., which comprises an acylating reagent (e.g., an anhydride having the structure of (RC(O))$_2$O, (e.g., Ac$_2$O)) and a base (e.g., 2,6-lutidine). In some embodiments, a first capping caps an amino group, e.g., that of a chiral auxiliary in an internucleotidic linkage. In some embodiments, an internucleotidic linkage formed in a capping step comprises

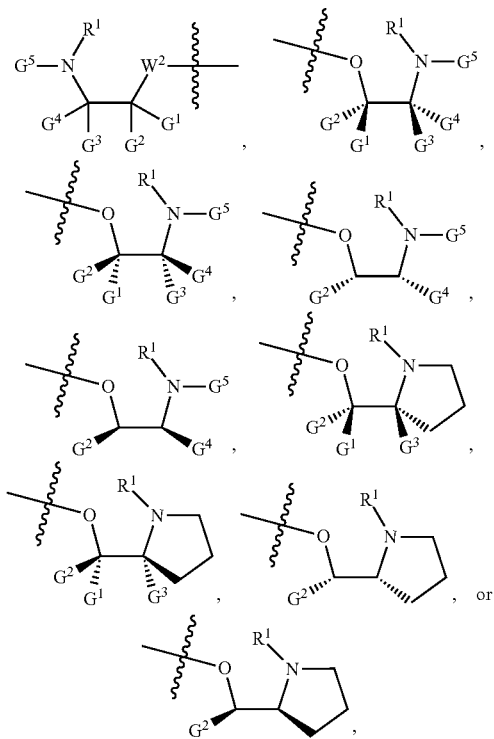

wherein each variable is independently in accordance with the present disclosure. In some embodiments, R' is R—C(O)—. In some embodiments, R is CH$_3$—. In some embodiments, each chirally controlled coupling (e.g., using a chiral auxiliary) is followed with a first capping. Typically, cycles for non-chirally controlled coupling using traditional phosphoramidite to construct natural phosphate linkages do not contain a first capping. In some embodiments, a second capping is performed, e.g., under an esterification condition (e.g., capping conditions of traditional phosphoramidite oligonucleotide synthesis) wherein free 5'-OH are capped.

Certain capping technologies, e.g., reagents, conditions, methods, etc. are illustrated in the Examples.

Modifying

In some embodiments, an internucleotidic linkage wherein its linkage phosphorus exists as P(III) is modified to form another modified internucleotidic linkage. In many embodiments, P(III) is modified by reaction with an electrophile. Various types of reactions suitable for P(III) may be utilized in accordance with the present disclosure. Suitable modifying technologies (e.g., reagents (e.g., sulfurization reagent, oxidation reagent, etc.), conditions, etc.) include those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/223056, WO 2018/237194, and/or WO 2019/055951, the modifying technologies of each of which are incorporated by reference.

In some embodiments, as illustrated in the Examples, the present disclosure provides modifying reagents for introducing non-negatively charged internucleotidic linkages including neutral internucleotidic linkages.

In some embodiments, modifying is within a cycle. In some embodiments, modifying can be outside of a cycle. For example, in some embodiments, one or more modifying steps can be performed after the DMD oligonucleotide chain has been reached to introduce modifications simultaneously at one or more internucleotidic linkages and/or other locations.

In some embodiments, modifying comprises use of click chemistry, e.g., wherein an alkyne group of a DMD oligonucleotide, e.g., of an internucleotidic linkage, is reacted with an azide. Various reagents and conditions for click chemistry can be utilized in accordance with the present disclosure. In some embodiments, an azide has the structure of R$^1$—N$_3$, wherein R$^1$ is as described in the present disclosure. In some embodiments, R$^1$ is optionally substituted C$_{1-6}$ alkyl. In some embodiments, R$^1$ is isopropyl.

In some embodiments, as demonstrated in the examples, a P(III) linkage can be converted into a non-negatively charged internucleotidic linkage by reacting the P(III) linkage with an azide or an azido imidazolinium salt (e.g., a compound comprising

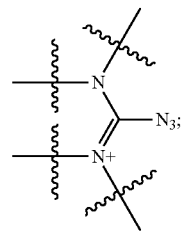 [SMILES: *N(*)C(N=[N+]=[N-])=[N+](*)*]

in some embodiments, referred to as an azide reaction) under suitable conditions. In some embodiments, an azido imidazolinium salt is a salt of PF$_6^-$. In some embodiments, an azido imidazolinium salt is a salt of

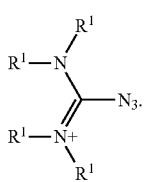

In some embodiments, a useful reagent is a salt of

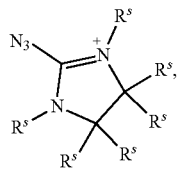

wherein each $R^s$ is independently $R^1$. In some embodiments, a useful reagent is a salt of

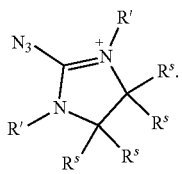

Such reagents comprising nitrogen cations also contain counter anions (e.g., $Q^-$ as described in the present disclosure), which are widely known in the art and are contained in various chemical reagents. In some embodiments, a useful reagent is $Q^+Q^-$, wherein $Q^+$ is

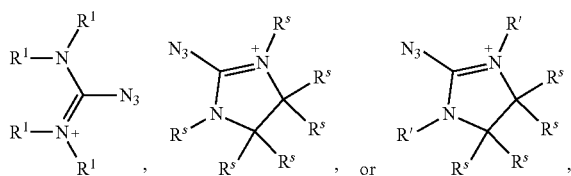

and $Q^-$ is a counter anion. In some embodiments, $Q^+$ is

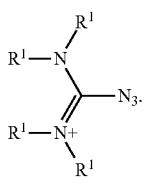

In some embodiments, $Q^+$ is

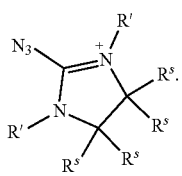

In some embodiments, $Q^+$ is

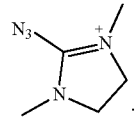

As appreciated by those skilled in the art, in a compound having the structure of $Q^+Q^-$, typically the number of positive charges in $Q^+$ equals the number of negative charges in Q-. In some embodiments, $Q^+$ is a monovalent cation and $Q^-$ is a monovalent anion. In some embodiments, $Q^-$ is $F^-$, $Cl^-$, $Br$, $BF_4^-$, $PF_6^-$, $TfO^-$, $Tf_2N^-$, $AsF_6^-$, $ClO_4^-$, or $SbF_6^-$. In some embodiments, $Q^-$ is $PF_6^-$. Those skilled in the art readily appreciate that many other types of counter anions are available and can be utilized in accordance with the present disclosure. In some embodiments, an azido imidazolinium salt is 2-azido-1,3-dimethylimidazolinium hexafluorophosphate.

In some embodiments, a P(III) linkage is reacted with an electrophile having the structure of $R-G^Z$, wherein R is as described in the present disclosure, and $G^Z$ is a leaving group, e.g., —Cl, —Br, —I, -OTf, -Oms, -OTosyl, etc. In some embodiments, R is —$CH_3$. In some embodiments, R is —$CH_2CH_3$. In some embodiments, R is —$CH_2CH_2CH_3$. In some embodiments, R is —$CH_2OCH_3$. In some embodiments, R is $CH_3CH_2OCH_2$—. In some embodiments, R is $PhCH_2OCH_2$—. In some embodiments, R is HC≡C—$CH_2$—. In some embodiments, R is $H_3C$—C≡C—$CH_2$—. In some embodiments, R is $CH_2$=$CHCH_2$—. In some embodiments, R is $CH_3SCH_2$—. In some embodiments, R is —$CH_2COOCH_3$. In some embodiments, R is —$CH_2COOCH_2CH_3$. In some embodiments, R is —$CH_2CONHCH_3$.

In some embodiments, after a modifying step, a P(III) linkage phosphorus is converted into a P(V) internucleotidic linkage. In some embodiments, a P(III) linkage phosphorus is converted into a P(V) internucleotidic linkage, and all groups bounded to the linkage phosphorus remain unchanged. In some embodiments, a linkage phosphorus is converted from P into P(=O). In some embodiments, a linkage phosphorus is converted from P into P(=S). In some embodiments, a linkage phosphorus is converted from P into P(=N-L-$R^5$). In some embodiments, a linkage phosphorus is converted from P into

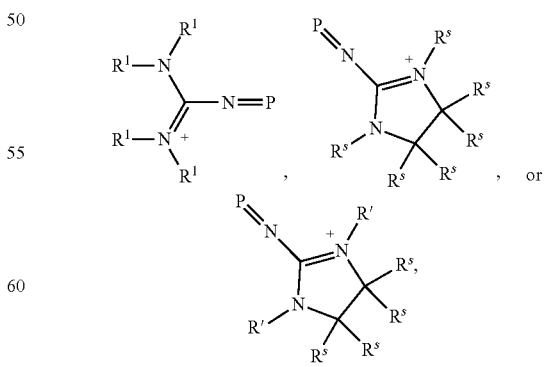

wherein each variable is independently as described in the present disclosure. In some embodiments, P is converted into

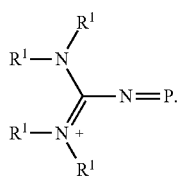

In some embodiments, P is converted into

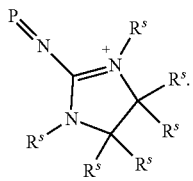

In some embodiments, P is converted into

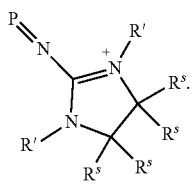

In some embodiments, P is converted into

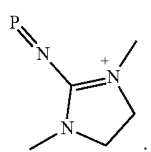

As appreciated by those skilled in the art, for each cation there typically exists a counter anion so that the total number of positive charges equals the total number of negative charges in a system (e.g., compound, composition, etc.). In some embodiments, a counter anion is $Q^-$ as described in the present disclosure (e.g., $F^-$, $Cl^-$, $Br^-$, $BF_4^-$, $PF_6^-$, $TfO^-$, $Tf_2N^-$, $AsF_6^-$, $ClO_4^-$, $SbF_6^-$, etc.).

In some embodiments, such an internucleotidic linkage is chirally controlled. In some embodiments, all such internucleotidic linkages are chirally controlled. In some embodiments, linkage phosphorus of at least one of such internucleotidic linkages is Rp. In some embodiments, linkage phosphorus of at least one of such internucleotidic linkages is Sp. In some embodiments, linkage phosphorus of at least one of such internucleotidic linkages is Rp, and linkage phosphorus of at least one of such internucleotidic linkages is Sp. In some embodiments, DMD oligonucleotides of the present disclosure comprises one or more (e.g., 1-5, 1-10, 1-15, 1-20, 1-25, 1-30, 1-40, 1-50, 1, 2, 3, 4, 5, 6, 7, 8, 9, 10, 11, 12, 13, 14, 15, 16, 17, 18, 19, 20, 21, 22, 23, 24, 25, etc.) such internucleotidic linkages. In some embodiments, such DMD oligonucleotide further comprise one or more other types of internucleotidic linkages, e.g., one or more natural phosphate linkages, and/or one or more phosphorothioate internucleotidic linkages (e.g., in some embodiments, one or more of which are independently chirally controlled; in some embodiments, each of which is independently chirally controlled; in some embodiments, at least one is Rp; in some embodiments, at least one is Sp; in some embodiments, at least one is Rp and at least one is Sp; etc.) In some embodiments, such DMD oligonucleotides are stereopure (substantially free of other stereoisomers). In some embodiments, the present disclosure provides chirally controlled DMD oligonucleotide compositions of such DMD oligonucleotides. In some embodiments, the present disclosure provides chirally pure DMD oligonucleotide compositions of such DMD oligonucleotides.

In some embodiments, modifying proceeds with a stereoselectivity of 80%, 85%, 90%, 91%, 92%, 93%, 94%, 95%, 96%, 97%, 98%, 99% or more. In some embodiments, the stereoselectivity is 85% or more. In some embodiments, the stereoselectivity is 85% or more. In some embodiments, the stereoselectivity is 90% or more. In some embodiments, the stereoselectivity is 91% or more. In some embodiments, the stereoselectivity is 92% or more. In some embodiments, the stereoselectivity is 93% or more. In some embodiments, the stereoselectivity is 94% or more. In some embodiments, the stereoselectivity is 95% or more. In some embodiments, the stereoselectivity is 96% or more. In some embodiments, the stereoselectivity is 97% or more. In some embodiments, the stereoselectivity is 98% or more. In some embodiments, the stereoselectivity is 99% or more. In some embodiments, modifying is stereospecific.

Deblocking

In some embodiments, a cycle comprises a cycle step. In some embodiments, the 5' hydroxyl group of the growing DMD oligonucleotide is blocked (i.e., protected) and must be deblocked in order to subsequently react with a nucleoside coupling partner.

In some embodiments, acidification is used to remove a blocking group. Suitable deblocking technologies (e.g., reagents, conditions, etc.) include those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/223056, WO 2018/237194, and/or WO 2019/055951, the deblocking technologies of each of which are incorporated by reference. Certain deblocking technologies, e.g., reagents, conditions, methods, etc. are illustrated in the Examples.

Cleavage and Deprotection

At certain stage, e.g., after the desired DMD oligonucleotide lengths have been achieved, cleavage and/or deprotection are performed to deprotect blocked nucleobases etc. and cleave the DMD oligonucleotide products from support. In some embodiments, cleavage and deprotection are performed separately. In some embodiments, cleavage and deprotection are performed in one step, or in two or more steps but without separation of products in between. In some embodiments, cleavage and/or deprotection utilizes basic conditions and elevated temperature. In some embodiments, for certain chiral auxiliaries, a fluoride condition is required (e.g., TBAF, HF-ET$_3$N, etc., optionally with additional base). Suitable cleavage and deprotection technologies (e.g., reagents, conditions, etc.) include those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/223056, WO 2018/237194, and/or WO 2019/055951, the cleavage and deprotection technologies of each of which are incorporated by reference. Certain cleavage and deprotection technologies, e.g., reagents, conditions, methods, etc. are illustrated in the Examples.

In some embodiments, certain chiral auxiliaries are removed under basic conditions. In some embodiments, DMD oligonucleotides are contacted with a base, e.g., an amine having the structure of N(R)$_3$, to remove certain chiral auxiliaries (e.g., those comprising an electronic-withdrawing group in G$^2$ as described in the present disclosure). In some embodiments, a base is NHR$_2$. In some embodiments, each R is independently optionally substituted C$_{1-6}$ aliphatic. In some embodiments, each R is independently optionally substituted C$_{1-6}$ alkyl. In some embodiments, an amine is DEA. In some embodiments, an amine is TEA. In some embodiments, an amine is provided as a solution, e.g., an acetonitrile solution. In some embodiments, such contact is performed under anhydrous conditions. In some embodiments, such a contact is performed immediately after desired DMD oligonucleotide lengths are achieved (e.g., first step post synthesis cycles). In some embodiments, such a contact is performed before removal of chiral auxiliaries and/or protection groups and/or cleavage of DMD oligonucleotides from a solid support. In some embodiments, contact with a base may remove cyanoethyl groups utilized in standard DMD oligonucleotide synthesis, providing an natural phosphate linkage which may exist in a salt form (with the cation being, e.g., an ammonium salt).

Cycles

Suitable cycles for preparing DMD oligonucleotides of the present disclosure include those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647 (e.g., Schemes I, I-b, I-c, I-d, I-e, I-f, etc.), WO 2018/223056, WO 2018/237194, and/or WO 2019/055951, the cycles of each of which are incorporated by reference. For example, in some embodiments, an example cycle is Scheme I-f Certain cycles are illustrated in the Examples (e.g., for preparation of natural phosphate linkages, utilizing other chiral auxiliaries, etc.).

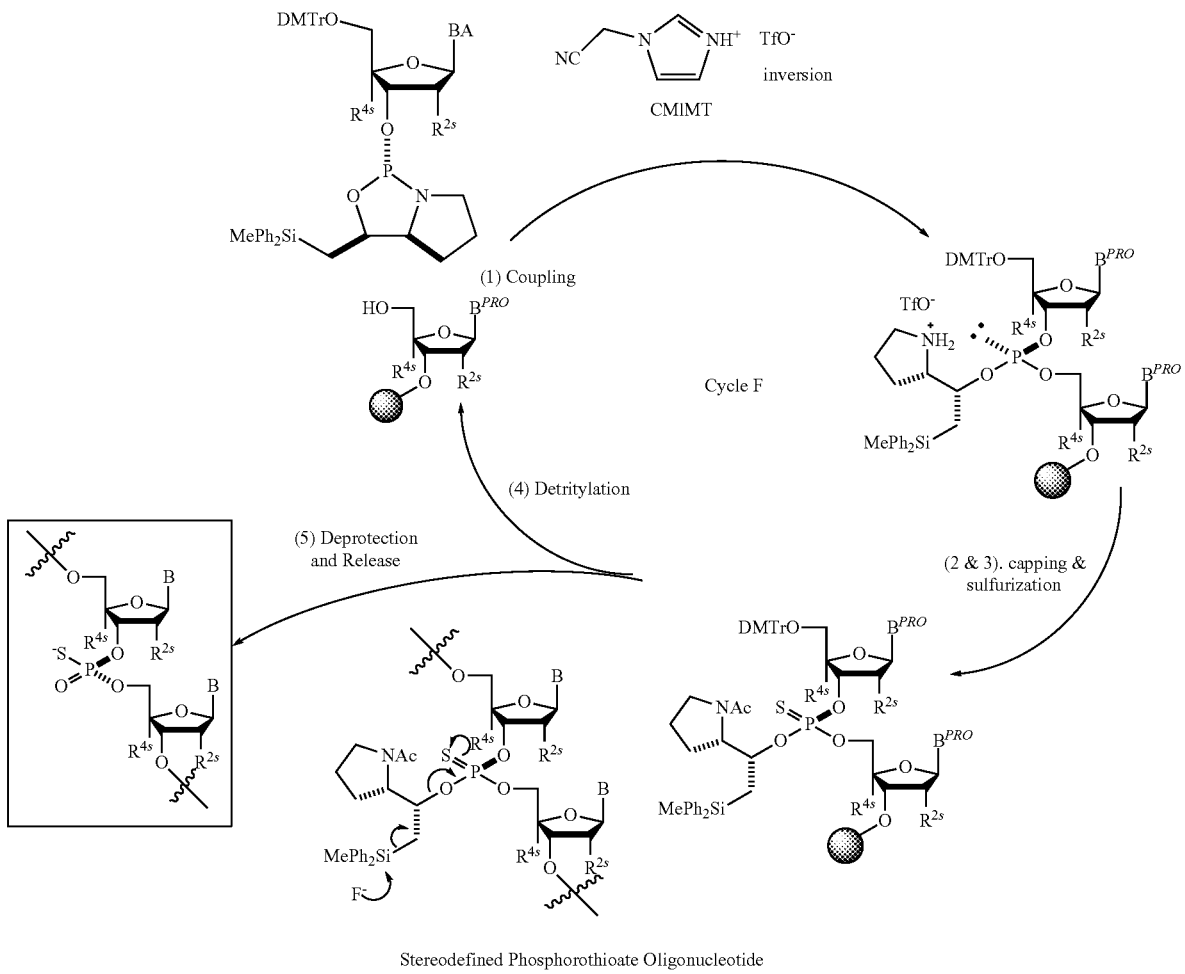

Scheme I-e. Example cycle using DPSE chiral auxiliary.

Stereodefined Phosphorothioate Oligonucleotide

In some embodiments, R$^{2s}$ is H or —OR$^1$, wherein R$^1$ is not hydrogen. In some embodiments, R$^{2s}$ is H or —OR$^1$, wherein R$^1$ is optionally substituted C$_{1-6}$ alkyl. In some embodiments, R$^{2s}$ is H. In some embodiments, R$^{2s}$ is -OMe. In some embodiments, R$^{2s}$ is —OCH$_2$CH$_2$OCH$_3$. In some embodiments, R$^{2s}$ is —F. In some embodiments, R$^{4s}$ is —H. In some embodiments, R$^{4s}$ and R$^{2s}$ are taken together to form a bridge -L-O— as described in the present disclosure. In some embodiments, the —O— is connected to the carbon at the 2' position. In some embodiments, L is —CH$_2$—. In some embodiments, L is —CH(Me)-. In some embodiments, L is —(R)—CH(Me)-. In some embodiments, L is —(S)—CH(Me)-.

Purification and Characterization

Various purification and/or characterization technologies (methods, instruments, protocols, etc.) can be utilized to purify and/or characterize DMD oligonucleotides and DMD oligonucleotide compositions in accordance with the present disclosure. In some embodiments, purification is performed using various types of HPLC/UPLC technologies. In some embodiments, characterization comprises MS, NMR, UV, etc. In some embodiments, purification and characterization may be performed together, e.g., HPLC-MS, UPLC-MS, etc. Example purification and characterization technologies include those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/223056, WO 2018/237194, and/or WO 2019/055951, the purification and characterization technologies of each of which are incorporated by reference.

In some embodiments, the present disclosure provides methods for preparing provided DMD oligonucleotide and DMD oligonucleotide compositions. In some embodiments, a provided method comprises providing a provided chiral reagent having the structure of formula 3-AA as described herein. In some embodiments, a provided method comprises providing a provided chiral reagent having the structure of

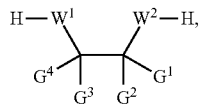

wherein $W^1$ is -$NG^5$, $W^2$ is O, each of $G^1$ and $G^3$ is independently hydrogen or an optionally substituted group selected from $C_{1-10}$ aliphatic, heterocyclyl, heteroaryl and aryl, $G^2$ is —$C(R)_2Si(R)_3$ or —$C(R)_2SO_2R^1$, and $G^4$ and $G^5$ are taken together to form an optionally substituted saturated, partially unsaturated or unsaturated heteroatom-containing ring of up to about 20 ring atoms which is monocyclic or polycyclic, fused or unfused, wherein each R is independently hydrogen, or an optionally substituted group selected from $C_1$-$C_6$ aliphatic, carbocyclyl, aryl, heteroaryl, and heterocyclyl.

In some embodiments, a provided chiral reagent has the structure of

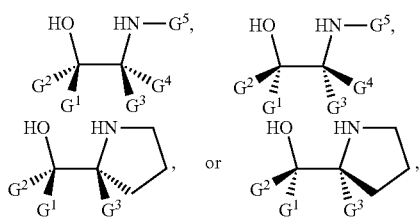

wherein each variable is independently as described in the present disclosure. In some embodiments, a provided methods comprises providing a phosphoramidite comprising a moiety from a chiral reagent having the structure of

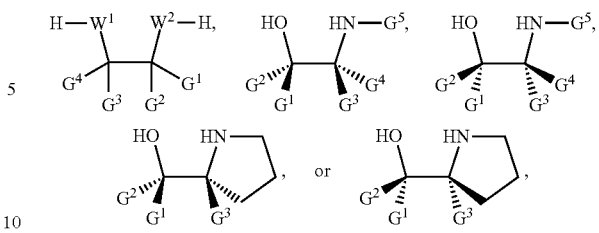

wherein —$W^1$H and —$W^2$H, or the hydroxyl and amino groups, form bonds with the phosphorus atom of the phosphoramidite. In some embodiments, —$W^1$H and —$W^2$H, or the hydroxyl and amino groups, form bonds with the phosphorus atom of the phosphoramidite, e.g., in

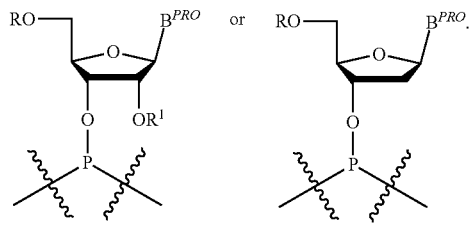

In some embodiments, a phosphoramidite has the structure of

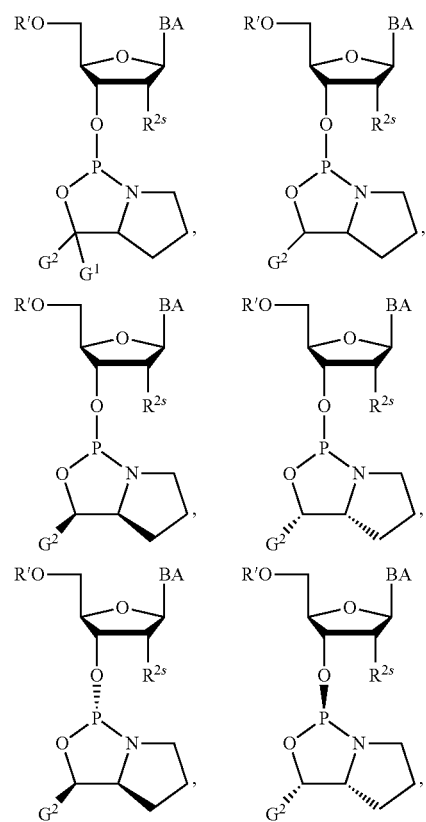

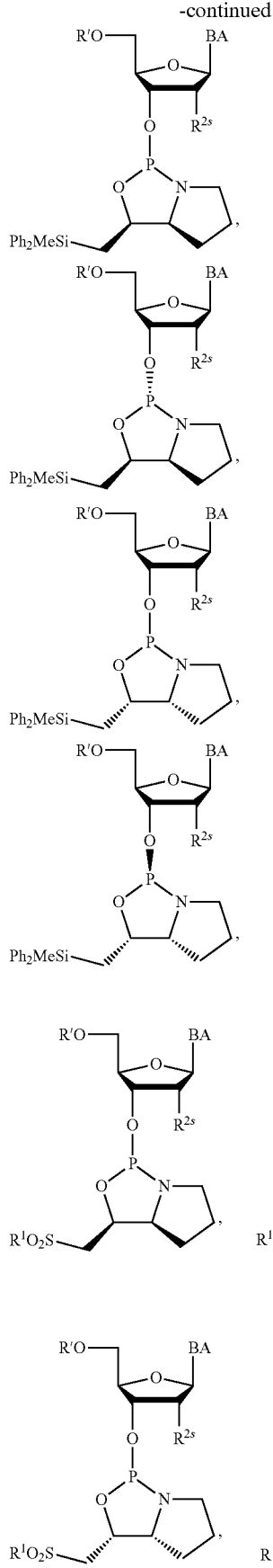

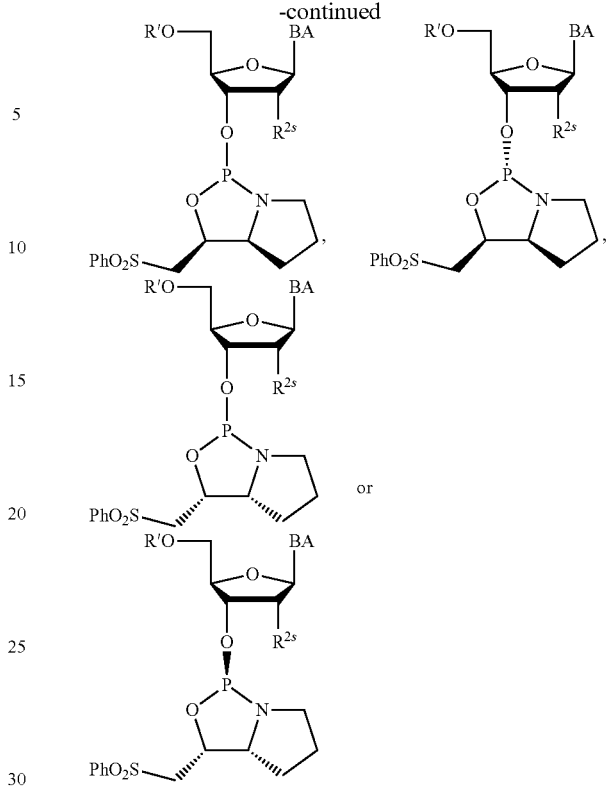

wherein each other variable is independently as described in the present disclosure. In some embodiments, $R^{2s}$ is —H. In some embodiments, $R^{2s}$ is —F. In some embodiments, $R^{2s}$ is -OMe. In some embodiments, R' is DMTr. In some embodiments, BA is optionally substituted A, T, C, G, U or an optionally substituted tautomer of A, T, C, G, or U.

In some embodiments, $G^2$ is —$C(R)_2Si(R)_3$, wherein —$C(R)_2$— is optionally substituted —$CH_2$—, and each R of —$Si(R)_3$ is independently an optionally substituted group selected from $C_{1-10}$ aliphatic, heterocyclyl, heteroaryl and aryl. In some embodiments, at least one R of —$Si(R)_3$ is independently optionally substituted $C_{1-10}$ alkyl. In some embodiments, at least one R of —$Si(R)_3$ is independently optionally substituted phenyl. In some embodiments, one R of —$Si(R)_3$ is independently optionally substituted phenyl, and each of the other two R is independently optionally substituted $C_{1-10}$ alkyl. In some embodiments, one R of —$Si(R)_3$ is independently optionally substituted $C_{1-10}$ alkyl, and each of the other two R is independently optionally substituted phenyl. In some embodiments, $G^2$ is optionally substituted —$CH_2Si(Ph)(Me)_2$. In some embodiments, $G^2$ is optionally substituted —$CH_2Si(Me)(Ph)_2$. In some embodiments, $G^2$ is —$CH_2Si(Me)(Ph)_2$. In some embodiments, $G^4$ and $G^5$ are taken together to form an optionally substituted saturated 5-6 membered ring containing one nitrogen atom (to which $G^5$ is attached). In some embodiments, $G^4$ and $G^5$ are taken together to form an optionally substituted saturated 5-membered ring containing one nitrogen atom. In some embodiments, $G^1$ is hydrogen. In some embodiments, $G^3$ is hydrogen. In some embodiments, both $G^1$ and $G^3$ are hydrogen. In some embodiments, both $G^1$ and $G^3$ are hydrogen, $G^2$ is —$C(R)_2Si(R)_3$, wherein —$C(R)_2$— is optionally substituted —$CH_2$—, and each R of —$Si(R)_3$ is independently an optionally substituted group selected from $C_{1-10}$ aliphatic, heterocyclyl, heteroaryl and aryl, and $G^4$ and $G^5$ are taken together to form an optionally substituted saturated 5-membered ring containing one nitrogen atom. In some embodiments, a provided method further comprises providing a fluoro-containing reagent. In some embodiments, a provided fluoro-containing reagent removes a chiral reagent, or a product formed from a chiral reagent, from oligonucleotides after synthesis. Various known fluoro-containing reagents, including those F⁻ sources for removing —SiR₃ groups, can be utilized in accordance with the present disclosure, for example, TBAF, HF₃-Et₃N etc. In some embodiments, a fluoro-containing reagent provides better results, for example, shorter treatment time, lower temperature, less de-sulfurization, etc, compared to traditional methods, such as concentrated ammonia. In some embodiments, for certain fluoro-containing reagent, the present disclosure provides linkers for improved results, for example, less cleavage of DMD oligonucleotides from support during removal of chiral reagent (or product formed therefrom during DMD oligonucleotide synthesis). In some embodiments, a provided linker is an SP linker. In some embodiments, the present disclosure demonstrated that a HF-base complex can be utilized, such as HF—NR₃, to control cleavage during removal of chiral reagent (or product formed therefrom during DMD oligonucleotide synthesis). In some embodiments, HF—NR₃ is HF-NEt₃. In some embodiments, HF—NR₃ enables use of traditional linkers, e.g., succinyl linker.

In some embodiments, as described herein, $G^2$ comprises an electron-withdrawing group, e.g., at its α position. In some embodiments, $G^2$ is methyl substituted with one or more electron-withdrawing groups. In some embodiments, an electronic-withdrawing group comprises and/or is connected to the carbon atom through, e.g., —S(O)—, —S(O)₂—, —P(O)(R¹)—, —P(S)R¹—, or —C(O)—. In some embodiments, an electron-withdrawing group is —CN, —NO₂, halogen, —C(O)R¹, —C(O)OR', —C(O)N(R')₂, —S(O)R¹, —S(O)₂R¹, —P(W)(R¹)₂, —P(O)(R¹)₂, —P(O)(OR')₂, or —P(S)(R¹)₂. In some embodiments, an electron-withdrawing group is aryl or heteroaryl, e.g., phenyl, substituted with one or more of —CN, —NO₂, halogen, —C(O)R¹, —C(O)OR', —C(O)N(R')₂, —S(O)R¹, —S(O)₂R¹, —P(W)(R¹)₂, —P(O)(R¹)₂, —P(O)(OR')₂, or —P(S)(R¹)₂. In some embodiments, $G^2$ is —CH₂S(O)R'. In some embodiments, $G^2$ is —CH₂S(O)₂R'. In some embodiments, $G^2$ is —CH₂P(O)(R¹)₂. Additional example embodiments are described, e.g., as for chiral reagents/auxiliaries.

Confirmation that a stereocontrolled oligonucleotide (e.g., one prepared by a method described herein or in the art) comprises the intended stereocontrolled (chirally controlled) internucleotidic linkage can be performed using a variety of suitable technologies. A stereocontrolled (chirally controlled) oligonucleotide comprises at least one stereocontrolled internucleotidic linkage, which can be, e.g., a stereocontrolled internucleotidic linkage comprising a phosphorus, a stereocontrolled phosphorothioate internucleotidic linkage (PS) in the Rp configuration, a PS in the Sp configuration, etc. Useful technologies include, as non-limiting examples: NMR (e.g., 1D (one-dimensional) and/or 2D (two-dimensional)¹H-³¹P HETCOR (heteronuclear correlation spectroscopy)), HPLC, RP-HPLC, mass spectrometry, LC-MS, and/or stereospecific nucleases. In some embodiments, stereospecific nucleases include: benzonase, micrococcal nuclease, and svPDE (snake venome phosphodiesterase), which are specific for internucleotidic linkages in the Rp configuration (e.g., a PS in the Rp configuration); and nuclease P1, mung bean nuclease, and nuclease S1, which are specific for internucleotidic linkages in the Sp configuration (e.g., a PS in the Sp configuration).

In some embodiments, the present disclosure pertains to a method of confirming or identifying the stereochemistry pattern of the backbone of an oligonucleotide, e.g., a DMD oligonucleotide and/or stereochemistry of particular internucleotidic linkages. In some embodiments, a DMD oligonucleotide comprises a stereocontrolled internucleotidic linkage comprising a phosphorus, a stereocontrolled phosphorothioate (PS) in the Rp configuration, or a PS in the Sp configuration. In some embodiments, a DMD oligonucleotide comprises at least one stereocontrolled internucleotidic linkage and at least one internucleotidic linkage which is not stereocontrolled. In some embodiments, a method comprises digestion of a DMD oligonucleotide with a stereospecific nuclease. In some embodiments, a stereospecific nuclease is selected from: benzonase, micrococcal nuclease, and svPDE (snake venom phosphodiesterase), which are specific for internucleotidic linkages in the Rp configuration (e.g., a PS in the Rp configuration); and nuclease P1, mung bean nuclease, and nuclease S1, which are specific for internucleotidic linkages in the Sp configuration (e.g., a PS in the Sp configuration). In some embodiments, a DMD oligonucleotide or fragments thereof produced by digestion with a stereospecific nuclease are analyzed. In some embodiments, a DMD oligonucleotide or fragments thereof (e.g., produced by digestion with a stereospecific nuclease) are analyzed by NMR, 1D (one-dimensional) and/or 2D (two-dimensional) ¹H—³¹P HETCOR (heteronuclear correlation spectroscopy), HPLC, RP-HPLC, mass spectrometry, LC-MS, UPLC, etc. In some embodiments, a DMD oligonucleotide or fragments thereof are compared with chemically synthesized fragments of the DMD oligonucleotide having a known pattern of stereochemistry.

Without wishing to be bound by any particular theory, the present disclosure notes that, in at least some cases, stereospecificity of a particular nuclease may be altered by a modification (e.g., 2'-modification) of a sugar, by a base sequence, or by a stereochemical context. For example, in some embodiments, benzonase and micrococcal nuclease, which are specific for Rp internucleotidic linkages, were both unable to cleave an isolated PS Rp internucleotidic linkage flanked by PS Sp internucleotidic linkages.

Various techniques and materials can be utilized. In some embodiments, the present disclosure provides useful combinations of technologies. For example, in some embodiments, stereochemistry of one or more particular internucleotidic linkages of a DMD oligonucleotide can be confirmed by digestion of the DMD oligonucleotide with a stereospecific nuclease and analysis of the resultant fragments (e.g., nuclease digestion products) by any of a variety of techniques (e.g., separation based on mass-to-charge ratio, NMR, HPLC, mass spectrometry, etc.). In some embodiments, stereochemistry of products of digesting a DMD oligonucleotide with a stereospecific nuclease can be confirmed by comparison (e.g., NMR, HPLC, mass spectrometry, etc.) with chemically synthesized fragments (e.g., dimers, trimers, tetramers, etc.) produced, e.g., via technologies that control stereochemistry.

In yet another example, a different DMD oligonucleotide was tested to confirm that the internucleotidic linkages were in the intended configurations. The DMD oligonucleotide is capable of skipping exon 51 of DMD; the majority of the nucleotides in the DMD oligonucleotide were 2'—F and the remainder were 2'-OMe; the majority of the internucleotidic linkages in the DMD oligonucleotide were PS in the Sp configuration and the remainder were PO. This DMD oligonucleotide was tested by digestion with stereospecific nucleases, and the resultant digestion fragments were analyzed (e.g., by LC-MS and by comparison with chemically synthesized fragments of known stereochemistry). The results confirmed that the DMD oligonucleotide had the intended pattern of stereocontrolled internucleotidic linkages.

In some embodiments, NMR is useful for characterization and/or confirming stereochemistry. In a set of example experiments, a set of DMD oligonucleotides comprising a stereocontrolled CpG motif were tested to confirm the intended stereochemistry of the CpG motif. Oligonucleotides of the set comprise a motif having the structure of pCpGp, wherein C is Cytosine, G is Guanine, and p is a phosphorothioate which is stereorandom or stereocontrolled (e.g., in the Rp or Sp configuration). For example, one DMD oligonucleotide comprises a pCpGp structure, wherein the pattern of stereochemistry of the phosphorothioates (e.g., the ppp) was RRR; in another DMD oligonucleotide, the pattern of stereochemistry of the ppp was RSS; in another DMD oligonucleotide, the pattern of stereochemistry of the ppp was RSR; etc. In the set, all possible patterns of stereochemistry of the ppp were represented. In the portion of the DMD oligonucleotide outside the pCpGp structure, all the internucleotidic linkages were PO; all nucleosides in the DMD oligonucleotides were 2'-deoxy. These various DMD oligonucleotides were tested in NMR, without digestion with a stereospecific nuclease, and distinctive patterns of peaks were observed, indicating that each PS which was Rp or Sp produced a unique peak, and confirming that the DMD oligonucleotides comprised stereocontrolled PS internucleotidic linkages of the intended stereochemistry.

Stereochemistry patterns of the internucleotidic linkages of various other stereocontrolled DMD oligonucleotides were confirmed, wherein the DMD oligonucleotides comprise a variety of chemical modifications and patterns of stereochemistry.

Biological Applications, Example Use, and Dosing Regimens

As described herein, provided compositions and methods are useful for various purposes, e.g., those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, and/or WO 2017/210647.

In some embodiments, provided technologies skip exon 51 or 53 in a target DMD transcript. A number of DMD oligonucleotides comprising various types of modified internucleotidic linkages, including many comprising non-negatively charged internucleotidic linkages (e.g., n001), which have various base sequences and/or target various nucleic acids (e.g., DMD transcripts of various genes) were prepared, and various useful properties, activities, and/or advantages were demonstrated.

In some embodiments, the present disclosure provides methods for modulating level of a DMD transcript or a product encoded thereby in a system, comprising administering an effective amount of a provided DMD oligonucleotide or a composition thereof. In some embodiments, the present disclosure provides methods for modulating level of a DMD transcript or a product encoded thereby in a system, comprising contacting the DMD transcript a provided DMD oligonucleotide or a composition thereof. In some embodiments, a system is an in vitro system. In some embodiments, a system is a cell. In some embodiments, a system is a tissue. In some embodiments, a system is an organ. In some embodiments, a system is an organism. In some embodiments, a system is a subject. In some embodiments, a system is a human. In some embodiments, modulating level of a DMD transcript decreases level of the DMD transcript. In some embodiments, modulating level of a DMD transcript increases level of the DMD transcript.

In some embodiments, the present disclosure provides methods for preventing or treating a condition, disease, or disorder associated with a nucleic acid sequence or a product encoded thereby, comprising administering to a subject suffering therefrom or susceptible thereto an effective amount of a provided DMD oligonucleotide or composition thereof, wherein the DMD oligonucleotide or composition thereof modulate level of a DMD transcript of the nucleic acid sequence. In some embodiments, a nucleic acid sequence is a gene. In some embodiments, modulating level of a DMD transcript decreases level of the DMD transcript. In some embodiments, modulating level of a DMD transcript increases level of the DMD transcript.

In some embodiments, change of the level of a modulated DMD transcript, e.g., through knock-down, exon skipping, etc., is at least 1.1, 1.2, 1.3, 1.4, 1.5, 2, 3, 4, 5, 6, 7, 8, 9, 10, 15, 20, 25, 30, 40, 50, 100, 200, 500, or 1000 fold.

In some embodiments, provided DMD oligonucleotides and DMD oligonucleotide compositions modulate splicing. In some embodiments, provided DMD oligonucleotides and DMD oligonucleotide compositions promote exon skipping, thereby produce a level of a DMD transcript which has increased beneficial functions that the DMD transcript prior to exon skipping. In some embodiments, a beneficial function is encoding a protein that has increased biological functions. In some embodiments, the present disclosure provides methods for modulating splicing, comprising administering to a splicing system a provided DMD oligonucleotide or DMD oligonucleotide composition, wherein splicing of at least one DMD transcript is altered (e.g., skipping of exon 51 or 53 is increased). In some embodiments, level of at least one splicing product is increased at least 1.1, 1.2, 1.3, 1.4, 1.5, 2, 3, 4, 5, 6, 7, 8, 9, 10, 15, 20, 25, 30, 40, 50, 100, 200, 500, or 1000 fold. In some embodiments, the present disclosure provides methods for modulating DMD splicing, comprising administering to a splicing system a provided DMD oligonucleotide or composition thereof.

In some embodiments, the present disclosure provides methods for preventing or treating DMD, comprising administering to a subject susceptible thereto or suffering therefrom a pharmaceutical composition comprising an effective amount of a provided DMD oligonucleotide or DMD oligonucleotide composition.

In some embodiments, provided compositions and methods provide improved splicing patterns of DMD transcripts compared to a reference pattern, which is a pattern from a reference condition selected from the group consisting of absence of the composition, presence of a reference composition, and combinations thereof. An improvement can be an improvement of any desired biological functions. In some embodiments, for example, in DMD, an improvement is production of an mRNA from which a dystrophin protein with improved biological activities is produced.

In some embodiments, particularly useful and effective are chirally controlled DMD oligonucleotides and chirally controlled DMD oligonucleotide compositions, wherein the DMD oligonucleotides (or DMD oligonucleotides of a plurality in chirally controlled DMD oligonucleotide compositions) optionally comprises one or more non-negatively charged internucleotidic linkages. Among other things, such DMD oligonucleotides and DMD oligonucleotide compositions can provide greatly improved effects, better delivery, lower toxicity, etc.

In some embodiments, exon 53 of DMD is skipped.

In some embodiments, a provided DMD oligonucleotide composition is administered at a dose and/or frequency lower than that of an otherwise comparable reference DMD oligonucleotide composition with comparable effect in altering the splicing of a target DMD transcript. In some embodiments, a stereocontrolled (chirally controlled) DMD oligonucleotide composition is administered at a dose and/or frequency lower than that of an otherwise comparable stereorandom reference DMD oligonucleotide composition with comparable effect in altering the splicing of the target DMD transcript. If desired, a provided composition can also be administered at higher dose/frequency due to its lower toxicities.

In some embodiments, provided DMD oligonucleotides, compositions and methods have low toxicities, e.g., when compared to a reference composition. As widely known in the art, DMD oligonucleotides can induce toxicities when administered to, e.g., cells, tissues, organism, etc. In some embodiments, DMD oligonucleotides can induce undesired immune response. In some embodiments, DMD oligonucleotide can induce complement activation. In some embodiments, DMD oligonucleotides can induce activation of the alternative pathway of complement. In some embodiments, DMD oligonucleotides can induce inflammation. Among other things, the complement system has strong cytolytic activity that can damages cells and should therefore be modulated to reduce potential injuries. In some embodiments, DMD oligonucleotide-induced vascular injury is a recurrent challenge in the development of DMD oligonucleotides for e.g., pharmaceutical use. In some embodiments, a primary source of inflammation when high doses of DMD oligonucleotides are administered involves activation of the alternative complement cascade. In some embodiments, complement activation is a common challenge associated with phosphorothioate-containing DMD oligonucleotides, and there is also a potential of some sequences of phosphorothioates to induce innate immune cell activation. In some embodiments, cytokine release is associated with administration of DMD oligonucleotides. For example, in some embodiments, increases in interleukin-6 (IL-6) monocyte chemoattractant protein (MCP-1) and/or interleukin-12 (IL-12) is observed. See, e.g., Frazier, Antisense Oligonucleotide Therapies: The Promise and the Challenges from a Toxicologic Pathologist's Perspective. *Toxicol Pathol.*, 43: 78-89, 2015; and Engelhardt, et al., Scientific and Regulatory Policy Committee Points-to-consider Paper: Drug-induced Vascular Injury Associated with Nonsmall Molecule Therapeutics in Preclinical Development: Part 2. Antisense Oligonucleotides. *Toxicol Pathol.* 43: 935-944, 2015.

Oligonucleotide compositions as provided herein can be used as agents for modulating a number of cellular processes and machineries, including but not limited to, DMD transcription, translation, immune responses, epigenetics, etc. In addition, DMD oligonucleotide compositions as provided herein can be used as reagents for research and/or diagnostic purposes. One of ordinary skill in the art will readily recognize that the present disclosure disclosure herein is not limited to particular use but is applicable to any situations where the use of synthetic oligonucleitides is desirable. Among other things, provided compositions are useful in a variety of therapeutic, diagnostic, agricultural, and/or research applications.

Various dosing regimens can be utilized to administer provided chirally controlled DMD oligonucleotide compositions, e.g., those described in in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, and/or WO 2017/210647, the dosing regimens of each of which is incorporated herein by reference.

In some embodiments, with their low toxicity, provided DMD oligonucleotides and compositions can be administered in higher dosage and/or with higher frequency. In some embodiments, with their improved delivery (and other properties), provided compositions can be administered in lower dosages and/or with lower frequency to achieve biological effects, for example, clinical efficacy.

A single dose can contain various amounts of DMD oligonucleotides. In some embodiments, a single dose can contain various amounts of a type of chirally controlled DMD oligonucleotide, as desired suitable by the application. In some embodiments, a single dose contains about 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 or more (e.g., about 350, 400, 450, 500, 550, 600, 650, 700, 750, 800, 850, 900, 950, 1000 or more) mg of a type of chirally controlled DMD oligonucleotide. In some embodiments, a chirally controlled DMD oligonucleotide is administered at a lower amount in a single dose, and/or in total dose, than a chirally uncontrolled DMD oligonucleotide. In some embodiments, a chirally controlled DMD oligonucleotide is administered at a lower amount in a single dose, and/or in total dose, than a chirally uncontrolled DMD oligonucleotide due to improved efficacy. In some embodiments, a chirally controlled DMD oligonucleotide is administered at a higher amount in a single dose, and/or in total dose, than a chirally uncontrolled DMD oligonucleotide. In some embodiments, a chirally controlled DMD oligonucleotide is administered at a higher amount in a single dose, and/or in total dose, than a chirally uncontrolled DMD oligonucleotide due to improved safety.

Pharmaceutical Compositions

When used as therapeutics, a provided DMD oligonucleotide or DMD oligonucleotide composition described herein is administered as a pharmaceutical composition. In some embodiments, the pharmaceutical composition comprises a therapeutically effective amount of a provided DMD oligonucleotides, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers. In some embodiments, in provided compositions provided DMD oligonucleotides may exist as salts, preferably pharmaceutically acceptable salts, e.g., sodium salts, ammonium salts, etc. In some embodiments, a salt of a provided DMD oligonucleotide comprises two or more cations, for example, in some embodiments, up to the number of negatively charged acidic groups (e.g., phosphate, phosphorothioate, etc.) in a DMD oligonucleotide. As appreciated by those skilled in the art, DMD oligonucleotides described herein may be provided and/or utilized in a salt form, particularly a pharmaceutically acceptable salt form.

In some embodiments, the present disclosure provides salts of provided DMD oligonucleotides, e.g., chirally controlled DMD oligonucleotides, and pharmaceutical compositions thereof. In some embodiments, a salt is a pharmaceutically acceptable salt. In some embodiments, each hydrogen ion that may be donated to a base (e.g., under conditions of an aqueous solution, a pharmaceutical composition, etc.) is replaced by a non-$H^+$ cation. For example, in some embodiments, a pharmaceutically acceptable salt of a DMD oligonucleotide is an all-metal ion salt, wherein each hydrogen ion (for example, of —OH, —SH, etc., acidic enough in water) of each internucleotidic linkage (e.g., a natural phosphate linkage, a phosphorothioate diester linkage, etc.) is replaced by a metal ion. In some embodiments, a provided salt is an all-sodium salt. In some embodiments, a provided pharmaceutically acceptable salt is an all-sodium salt. In some embodiments, a provided salt is an all-sodium salt, wherein each internucleotidic linkage which is a natural phosphate linkage (acid form —O—P(O)(OH)—O—), if any, exists as its sodium salt form (—O—P(O)(ONa)—O—), and each internucleotidic linkage which is a phosphorothioate diester linkage (phosphorothioate internucleotidic linkage; acid form —O—P(O)(SH)—O—), if any, exists as its sodium salt form (—O—P(O)(SNa)—O—).

In some embodiments, the pharmaceutical composition is formulated for intravenous injection, oral administration, buccal administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the present disclosure provides a pharmaceutical composition comprising chirally controlled DMD oligonucleotide, or composition thereof, in admixture with a pharmaceutically acceptable excipient. One of skill in the art will recognize that the pharmaceutical compositions include the pharmaceutically acceptable salts of the chirally controlled DMD oligonucleotide, or composition thereof, described above.

A variety of supramolecular nanocarriers can be used to deliver nucleic acids. Example nanocarriers include, but are not limited to liposomes, cationic polymer complexes and various polymeric. Complexation of nucleic acids with various polycations is another approach for intracellular delivery; this includes use of PEGlyated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, polymer micelles, quantum dots and lipoplexes. In some embodiments, a DMD oligonucleotide is conjugated to another molecular.

Additional nucleic acid delivery strategies are known in addition to the example delivery strategies described herein.

In therapeutic and/or diagnostic applications, the compounds of the disclosure can be formulated for a variety of modes of administration, including systemic and topical or localized administration. Techniques and formulations generally may be found in Remington, The Science and Practice of Pharmacy, (20th ed. 2000).

Provided DMD oligonucleotides, and compositions thereof, are effective over a wide dosage range. For example, in the treatment of adult humans, dosages from about 0.01 to about 1000 mg, from about 0.5 to about 100 mg, from about 1 to about 50 mg per day, and from about 5 to about 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

As appreciated by a person having oridinary skill in the art, DMD oligonucleotides may be formulated as a number of salts for, e.g., pharmaceutical uses. In some embodiments, a salt is a metal cation salt and/or ammonium salt. In some embodiments, a salt is a metal cation salt of a DMD oligonucleotide. In some embodiments, a salt is an ammonium salt of a DMD oligonucleotide. Representative alkali or alkaline earth metal salts include sodium, lithium, potassium, calcium, magnesium, and the like. In some embodiments, a salt is a sodium salt of a DMD oligonucleotide. In some embodiments, pharmaceutically acceptable salts include, when appropriate, nontoxic ammonium, quaternary ammonium, and amine cations formed with DMD oligonucleotides. As appreciated by a person having oridinary skill in the art, a salt of a DMD oligonucleotide may contain more than one cations, e.g., sodium ions, as there may be more than one anions within a DMD oligonucleotide.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection.

Compounds, e.g., DMD oligonucleotides, can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

In certain embodiments, DMD oligonucleotides and compositions are delivered to the CNS. In certain embodiments, DMD oligonucleotides and compositions are delivered to the cerebrospinal fluid. In certain embodiments, DMD oligonucleotides and compositions are administered to the brain parenchyma. In certain embodiments, DMD oligonucleotides and compositions are delivered to an animal/subject by intrathecal administration, or intracerebroventricular administration. Broad distribution of DMD oligonucleotides and compositions, described herein, within the central nervous system may be achieved with intraparenchymal administration, intrathecal administration, or intracerebroventricular administration.

In certain embodiments, parenteral administration is by injection, by, e.g., a syringe, a pump, etc. In certain embodiments, the injection is a bolus injection. In certain embodiments, the injection is administered directly to a tissue, such as striatum, caudate, cortex, hippocampus and cerebellum.

In certain embodiments, methods of specifically localizing a pharmaceutical agent, such as by bolus injection, decreases median effective concentration (EC50) by a factor of 20, 25, 30, 35, 40, 45 or 50. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, a DMD oligonucleotide is delivered by injection or infusion once every month, every two months, every 90 days, every 3 months, every 6 months, twice a year or once a year.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of an active compound into preparations which can be used pharmaceutically. The preparations formulated for oral administration may be in the form of tablets, dragees, capsules, or solutions.

Pharmaceutical preparations for oral use can be obtained by combining an active compound with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, an active compound may be dissolved or suspended in suitable liquids, such as fatty oils, liquid paraffin, or liquid polyethylene glycols (PEGs). In addition, stabilizers may be added.

In some embodiments, any DMD oligonucleotide, or combination thereof, described herein, or any composition comprising a DMD oligonucleotide described herein, can be combined with any pharmaceutical preparation described herein or known in the art.

Combination Therapy

In some embodiments, a subject is administered an additional treatment (including, but not limited to, a therapeutic agent or method) in additional to provided DMD oligonucleotide or DMD oligonucleotide composition, e.g., a composition comprising a DMD oligonucleotide. In some embodiments, a composition comprising a DMD oligonucleotide(s) (or two or more compositions, each comprising a DMD oligonucleotide) is administered to a patient along with an additional treatment.

In some embodiments, the present disclosure pertains to a method for treating muscular dystrophy, Duchenne (Duchenne's) muscular dystrophy (DMD), or Becker (Becker's) muscular dystrophy (BMD), comprising (a) administering to a subject susceptible thereto or suffering therefrom a composition comprising a provided DMD oligonucleotide, and (b) administering to the subject an additional treatment which is capable of preventing, treating, ameliorating or slowing the progress of muscular dystrophy. In some embodiments, an additional treatment is a composition comprising a second DMD oligonucleotide.

In some embodiments, an additional treatment is capable of preventing, treating, ameliorating or slowing the progress of muscular dystrophy by itself. In some embodiments, an additional treatment is capable of preventing, treating, ameliorating or slowing the progress of muscular dystrophy when administered with a provided DMD oligonucleotide.

In some embodiments, an additional treatment is administered to the subject prior to, after or simultaneously with a composition comprising a provided DMD oligonucleotide, e.g., a provided DMD oligonucleotide. In some embodiments, a composition comprises both a DMD oligonucleotide(s) and an additional treatment. In some embodiments, a DMD oligonucleotide(s) and an additional treatment(s) are in separate compositions. In some embodiments, the present disclosure provides technologies (e.g., compositions, methods, etc.) for combination therapy, for example, with other therapeutic agents and/or medical procedures. In some embodiments, provided DMD oligonucleotides and/or compositions may be used together with one or more other therapeutic agents. In some embodiments, provided compositions comprise provided DMD oligonucleotides, and one or more other therapeutic agents. In some embodiments, the one or more other therapeutic agents may have one or more different targets, and/or one or more different mechanisms toward targets, when compared to provided DMD oligonucleotides in the composition. In some embodiments, a therapeutic agent is a DMD oligonucleotide. In some embodiments, a therapeutic agent is a small molecule drug. In some embodiments, a therapeutic agent is a protein. In some embodiments, a therapeutic agent is an antibody. A number of therapeutic agents may be utilized in accordance with the present disclosure. For example, DMD oligonucleotides for DMD may be used together with one or more therapeutic agents that modulate utrophin production (utrophin modulators). In some embodiments, a utrophin modulator promotes production of utrophin. In some embodiments, a utrophin modulator is ezutromid. In some embodiments, a utrophin modulator is

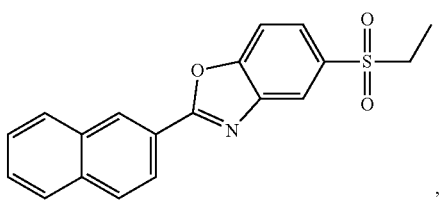 [SMILES: CCS(=O)(=O)c1ccc2oc(-c3ccc4ccccc4c3)nc2c1]

, or a pharmaceutically acceptable salt thereof. In some embodiments, provided DMD oligonucleotides or compositions thereof are administered prior to, concurrently with, or subsequent to one or more other therapeutic agents and/or medical procedures. In some embodiments, provided DMD oligonucleotides or compositions thereof are administered concurrently with one or more other therapeutic agents and/or medical procedures. In some embodiments, provided DMD oligonucleotides or compositions thereof are administered prior to one or more other therapeutic agents and/or medical procedures. In some embodiments, provided DMD oligonucleotides or compositions thereof are administered subsequent to one or more other therapeutic agents and/or medical procedures. In some embodiments, provide compositions comprise one or more other therapeutic agents.

In some embodiments, a composition comprising a DMD oligonucleotide is co-administered with an additional agent in order to improve skipping of a DMD exon of interest. In some embodiments, an additional agent is an antibody, DMD oligonucleotide, protein or small molecule. In some embodiments, an additional agent interferes with a protein involved in splicing. In some embodiments, an additional agent interferes with a protein involved in splicing, wherein the protein is a SR protein.

In some embodiments, an additional agent interferes with a protein involved in splicing, wherein the protein is a SR protein, which contains a protein domain with one or more long repeats of serine (S) and arginine (R) amino acid residues. SR proteins are reportedly heavily phosphorylated in cells and are involved in constitutive and alternative splicing. Long et al. 2009 Biochem. J. 417: 15-27; Shepard et al. 2009 Genome Biol. 10: 242. In some embodiments, an additional agent is a chemical compound that inhibits or decreases a SR protein kinase. In some embodiments, a chemical compound that inhibits or decreases a SR protein kinase is SRPIN340. SRPIN340 is reported in, for example, Fukuhura et al. 2006 Proc. Natl. Acad. Sci. USA 103: 11329-11333. In some embodiments, a chemical compound is a kinase inhibitor specific for Cdc-like kinases (Clks) that are also able to phosphorylate SR proteins. In some embodiments, a kinase inhibitor specific for Cdc-like kinases (Clks) that are also able to phosphorylate SR proteins is TG003. TG003 reportedly affected splicing both in vitro and in vivo. Nowak et al. 2010 J. Biol. Chem. 285: 5532-5540; Muraki et al. 2004 J. Biol. Chem. 279: 24246-24254; Yomoda et al. 2008 Genes Cells 13: 233-244; and Nishida et al. 2011 Nat Commun. 2:308.

In some embodiments, in a patient afflicted with muscular dystrophy, muscle tissue is replaced by fat and connective tissue, and affected muscles may look larger due to increased fat content, a condition known as pseudohypertrophy. In some embodiments, a composition comprising a DMD oligonucleotide(s) is administered along with a treatment which reduces or prevents development of fat or fibrous or connective tissue, or replacement of muscle tissue by fat or fibrous or connective tissue.

In some embodiments, a composition comprising a DMD oligonucleotide(s) is administered along with a treatment which reduces or prevents development of fat or fibrous or connective tissue, or replacement of muscle tissue by fat or fibrous or connective tissue, wherein the treatment is an antibody to connective tissue growth factor (CTGF), a central mediator of fibrosis (e.g., FG-3019). In some embodiments, a composition comprising a DMD oligonucleotide(s) is administered along with an agent which reduces the fat content of the human body.

Additional treatments include: slowing the progression of the disease by immune modulators (eg, steroids and transforming growth factor-beta inhibitors), inducing or introducing proteins that may compensate for dystrophin deficiency in the myofiber (eg, utrophin, biglycan, and laminin), or bolstering the muscle's regenerative response (eg, myostatin and activin 2B).

In some embodiments, an additional treatment is a small molecule capable of restoring normal balance of calcium within muscle cells.

In some embodiments, an additional treatment is a small molecule capable of restoring normal balance of calcium within muscle cells by correcting the activity of a type of channel called the ryanodine receptor calcium channel complex (RyR). In some embodiments, such a small molecule is Rycal ARM210 (ARMGO Pharma, Tarry Town, NY).

In some embodiments, an additional treatment is a flavonoid.

In some embodiments, an additional treatment is a flavonoid such as Epicatechin. Epicatechin is a flavonoid found in dark chocolate harvested from the cacao tree which has been reported in animals and humans to increase the production of new mitochondria in heart and muscle (e.g., mitochondrial biogenesis) while concurrently stimulating the regeneration of muscle tissue.

In some embodiments, an additional treatment is follistatin gene therapy.

In some embodiments, an additional treatment is adeno-associated virus delivery of follistatin 344 to increase muscle strength and prevent muscle wasting and fibrosis.

In some embodiments, an additional treatment is glucocorticoid.

In some embodiments, an additional treatment is prednisone.

In some embodiments, an additional treatment is deflazacort.

In some embodiments, an additional treatment is vamorolone (VBP15).

In some embodiments, an additional treatment is delivery of an exogenous Dystrophin gene or synthetic version or portion thereof, such as a microdystrophin gene.

In some embodiments, an additional treatment is delivery of an exogenous Dystrophin gene or portion thereof, such as a microdystrophin gene, such as SGT-001, an adeno-associated viral (AAV) vector-mediated gene transfer system for delivery of a synthetic dystrophin gene or microdystrophin (Solid BioSciences, Cambridge, Mass.).

In some embodiments, an additional treatment is stem cell treatment.

In some embodiments, an additional treatment is a steroid.

In some embodiments, an additional treatment is a corticosteroid.

In some embodiments, an additional treatment is prednisone.

In some embodiments, an additional treatment is a beta-2 agonist.

In some embodiments, an additional treatment is an ion channel inhibitor.

In some embodiments, an additional treatment is a calcium channel inhibitor.

In some embodiments, an additional treatment is a calcium channel inhibitor which is a xanthin. In some embodiments, an additional treatment is a calcium channel inhibitor which is methylxanthine. In some embodiments, an additional treatment is a calcium channel inhibitor which is pentoxifylline. In some embodiments, an additional treatment is a calcium channel inhibitor which is a methylxanthine derivative selected from: pentoxifylline, furafylline, lisofylline, propentofylline, pentifylline, theophylline, torbafylline, albifylline, enprofylline and derivatives thereof.

In some embodiments, an additional treatment is a treatment for heart disease or cardiovascular disease.

In some embodiments, an additional treatment is a blood pressure medicine.

In some embodiments, an additional treatment is surgery.

In some embodiments, an additional treatment is surgery to fix shortened muscles, straighten the spine, or treat a heart or lung problem.

In some embodiments, an additional treatment is a brace, walker, standing walker, or other mechanical aid for walking.

In some embodiments, an additional treatment is exercise and/or physical therapy.

In some embodiments, an additional treatment is assisted ventilation.

In some embodiments, an additional treatment is anticonvulsant, immunosuppressant or treatment for constipation.

In some embodiments, an additional treatment is an inhibitor of NF-κB.

In some embodiments, an additional treatment comprises salicylic acid and/or docosahexaenoic acid (DHA).

In some embodiments, an additional treatment is edasalonexent (CAT-1004, Catabasis), a conjugate of salicylic acid and docosahexaenoic acid (DHA).

In some embodiments, an additional treatment is a cell-based therapeutic.

In some embodiments, an additional treatment is comprises allogeneic cardiosphere-derived cells.

In some embodiments, an additional treatment is CAP-1002 (Capricor).

In some embodiments, y, t, n and m, e.g., in a stereochemistry pattern, each are independently 1-20 as described in the present disclosure. In some embodiments, y is 1. In some embodiments, y is at least 2, 3, 4, 5, 6, 7, 8, 9, 10, 11, 12, 13, 14, or 15. In some embodiments, y is 2, 3, 4, 5, 6, 7, 8, 9, 10, 11, 12, 13, 14, or 15. In some embodiments, y is 1, 2, 3, 4, 5, 6, 7, 8, 9, or 10. In some embodiments, y is 1. In some embodiments, y is 2. In some embodiments, y is 3. In some embodiments, y is 4. In some embodiments, y is 5. In some embodiments, y is 6. In some embodiments, y is 7. In some embodiments, y is 8. In some embodiments, y is 9. In some embodiments, y is 10.

In some embodiments, n is 1. In some embodiments, n is at least 2, 3, 4, 5, 6, 7, 8, 9, 10, 11, 12, 13, 14, or 15. In some embodiments, n is 2, 3, 4, 5, 6, 7, 8, 9, 10, 11, 12, 13, 14, or 15. In some embodiments, n is 1-10. In some embodiments, n is 1, 2, 3, 4, 5, 6, 7 or 8. In some embodiments, n is 1. In some embodiments, n is 2, 3, 4, 5, 6, 7 or 8. In some embodiments, n is 3, 4, 5, 6, 7 or 8. In some embodiments, n is 4, 5, 6, 7 or 8. In some embodiments, n is 5, 6, 7 or 8. In some embodiments, n is 6, 7 or 8. In some embodiments, n is 7 or 8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, m is 0-50. In some embodiments, m is 1-50. In some embodiments, m is 1. In some embodiments, m is 2-50. In some embodiments, m is at least 2, 3, 4, 5, 6, 7, 8, 9, 10, 11, 12, 13, 14, or 15. In some embodiments, m is 2, 3, 4, 5, 6, 7 or 8. In some embodiments, m is 3, 4, 5, 6, 7 or 8. In some embodiments, m is 4, 5, 6, 7 or 8. In some embodiments, m is 5, 6, 7 or 8. In some embodiments, m is 6, 7 or 8. In some embodiments, m is 7 or 8. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20. In some embodiments, m is 21. In some embodiments, m is 22. In some embodiments, m is 23. In some embodiments, m is 24. In some embodiments, m is 25. In some embodiments, m is at least 2. In some embodiments, m is at least 3. In some embodiments, m is at least 4. In some embodiments, m is at least 5. In some embodiments, m is at least 6. In some embodiments, m is at least 7. In some embodiments, m is at least 8. In some embodiments, m is at least 9. In some embodiments, m is at least 10. In some embodiments, m is at least 11. In some embodiments, m is at least 12. In some embodiments, m is at least 13. In some embodiments, m is at least 14. In some embodiments, m is at least 15. In some embodiments, m is at least 16. In some embodiments, m is at least 17. In some embodiments, m is at least 18. In some embodiments, m is at least 19. In some embodiments, m is at least 20. In some embodiments, m is at least 21. In some embodiments, m is at least 22. In some embodiments, m is at least 23. In some embodiments, m is at least 24. In some embodiments, m is at least 25. In some embodiments, m is at least greater than 25.

In some embodiments, t is 1-20. In some embodiments, t is 1. In some embodiments, t is at least 2, 3, 4, 5, 6, 7, 8, 9, 10, 11, 12, 13, 14, or 15. In some embodiments, t is 2, 3, 4, 5, 6, 7, 8, 9, 10, 11, 12, 13, 14, or 15. In some embodiments, t is 1-5. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 11. In some embodiments, t is 12. In some embodiments, t is 13. In some embodiments, t is 14. In some embodiments, t is 15. In some embodiments, t is 16. In some embodiments, t is 17. In some embodiments, t is 18. In some embodiments, t is 19. In some embodiments, t is 20.

In some embodiments, each of t and m is independently at least 2, 3, 4, 5, 6, 7, 8, 9, 10, 11, 12, 13, 14, or 15. In some embodiments, each of t and m is independently at least 3. In some embodiments, each of t and m is independently at least 4. In some embodiments, each of t and m is independently at least 5. In some embodiments, each of t and m is independently at least 6. In some embodiments, each of t and m is independently at least 7. In some embodiments, each of t and m is independently at least 8. In some embodiments, each of t and m is independently at least 9. In some embodiments, each of t and m is independently at least 10.

As used in the present disclosure, in some embodiments, "one or more" is 1-200, 1-150, 1-100, 1-90, 1-80, 1-70, 1-60, 1-50, 1-40, 1-30, or 1, 2, 3, 4, 5, 6, 7, 8, 9, 10, 11, 12, 13, 14, 15, 16, 17, 18, 19, 20, 21, 22, 23, 24, or 25. In some embodiments, "one or more" is one. In some embodiments, "one or more" is two. In some embodiments, "one or more" is three. In some embodiments, "one or more" is four. In some embodiments, "one or more" is five. In some embodiments, "one or more" is six. In some embodiments, "one or more" is seven. In some embodiments, "one or more" is eight. In some embodiments, "one or more" is nine. In some embodiments, "one or more" is ten. In some embodiments, "one or more" is at least one. In some embodiments, "one or more" is at least two. In some embodiments, "one or more" is at least three. In some embodiments, "one or more" is at least four. In some embodiments, "one or more" is at least five. In some embodiments, "one or more" is at least six. In some embodiments, "one or more" is at least seven. In some embodiments, "one or more" is at least eight. In some embodiments, "one or more" is at least nine. In some embodiments, "one or more" is at least ten. As used in the present disclosure, in some embodiments, "at least one" is 1-200, 1-150, 1-100, 1-90, 1-80, 1-70, 1-60, 1-50, 1-40, 1-30, or 1, 2, 3, 4, 5, 6, 7, 8, 9, 10, 11, 12, 13, 14, 15, 16, 17, 18, 19, 20, 21, 22, 23, 24, or 25. In some embodiments, "at least one" is one. In some embodiments, "at least one" is two. In some embodiments, "at least one" is three. In some embodiments, "at least one" is four. In some embodiments, "at least one" is five. In some embodiments, "at least one" is six. In some embodiments, "at least one" is seven. In some embodiments, "at least one" is eight. In some embodiments, "at least one" is nine. In some embodiments, "at least one" is ten.

Among other things, the present disclosure provides the following Example Embodiments:

1. An oligonucleotide having the structure of WV-14791 (SEQ ID NO: 15):
   fU * SfC * SfCn001RfG * SfG * SfUn001RfU * SmCfU * SmG * SfA * SmAmGfG * SfU * SfGn001RfU * SfU * SfC * SfU,
   or a pharmaceutically acceptable salt form thereof, wherein:
   f represents a 2'—F modified nucleoside;
   *S represents a Sp phosphorothioate;
   m represents a 2'-OMe modified nucleoside; and
   n001R is

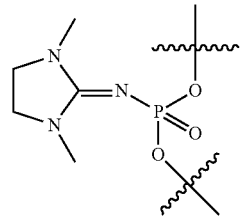 [SMILES: *OP(=O)(N=C1N(C)CCN1C)O*]

wherein the phosphorus is of the Rp configuration.

2. An oligonucleotide having the structure of WV-13826 (SEQ ID NO: 8):
   fU * SfC * SfC * SfG * SfG * SfU * SfU * SmCfU * SmG * SfA * SmAmGfG * SfU * SfG * SfU * SfU * SfC,
   or a pharmaceutically acceptable salt form thereof, wherein:
   f represents a 2'—F modified nucleoside;
   *S represents a Sp phosphorothioate;
   m represents a 2'-OMe modified nucleoside.

3. An oligonucleotide having the structure of WV-13864 (SEQ ID NO: 11):
   fC * SfU * SfCn001RfC * SfG * SfGn001RfU * SfU * SmCfU * SmG * SfA * SmAfG * SfG * SfU * SfGn001RfU * SfU * SfC,
   or a pharmaceutically acceptable salt form thereof, wherein:
   f represents a 2'—F modified nucleoside;
   *S represents a Sp phosphorothioate;
   m represents a 2'-OMe modified nucleoside; and
   n001R is

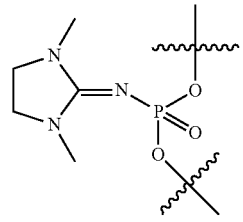 [SMILES: *OP(=O)(N=C1N(C)CCN1C)O*]

wherein the phosphorus is of the Rp configuration.

4. An oligonucleotide having the structure of WV-13835 (SEQ ID NO: 10):
   fU * SfC * SfC * SfG * SfG * SfU * SfU * SmCfU * SmG * SfA * SmAmGfG * SfU * SfG * SfU * SfU * SfC * SfU,
   or a pharmaceutically acceptable salt form thereof, wherein:
   f represents a 2'—F modified nucleoside;
   *S represents a Sp phosphorothioate; and
   m represents a 2'-OMe modified nucleoside.

5. An oligonucleotide having the structure of WV-143444 (SEQ ID NO: 12):
   fC * SfU * SfCn001RfC * SfG * SfGn001RfU * SfU * SmCfU * SmG * SfA * SmAfGfG * SfU * SfGn001RfU * SfU * SfC,
   or a pharmaceutically acceptable salt form thereof, wherein:
   f represents a 2'—F modified nucleoside;
   *S represents a Sp phosphorothioate;
   m represents a 2'-OMe modified nucleoside; and
   n001R is

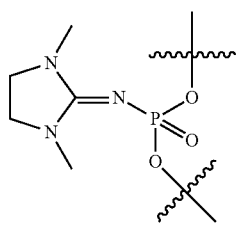 [SMILES: *OP(=O)(N=C1N(C)CCN1C)O*]

wherein the phosphorus is of the Rp configuration.

6. The oligonucleotide of any one of Embodiments 1-5, wherein the oligonucleotide is in a salt form.

7. The oligonucleotide of Embodiment 6, wherein the salt form is a sodium salt.

8. The oligonucleotide of Embodiment 7, wherein the number of sodium ions in the sodium salt equals the total number of phosphorothioate and phosphate linkages in the oligonucleotide.

9. A chirally controlled oligonucleotide composition comprising a plurality of the oligonucleotide of any one of Embodiments 1-8, wherein it is enriched, relative to a substantially racemic preparation of oligonucleotides of the same base sequence of the oligonucleotide for the oligonucleotide.

10. A pharmaceutical composition, comprising a therapeutically effective amount of the oligonucleotide of any one of Embodiments 1-8 and a pharmaceutically acceptable inactive ingredient selected from pharmaceutically acceptable diluents, pharmaceutically acceptable excipients, and pharmaceutically acceptable carriers.

11. The pharmaceutical composition of Embodiment 10, wherein the pharmaceutical composition is a solution.

12. An oligonucleotide composition for use in treatment of a disease, said use comprising altering splicing of a target transcript, wherein: the oligonucleotide composition being characterized in that, when it is contacted with the target transcript in a transcript splicing system, splicing of the transcript is altered relative to that observed under reference conditions selected from the group consisting of absence of the composition, presence of a reference composition, and combinations thereof.

13. The oligonucleotide composition for use of Embodiment 12, wherein
  (a) the splicing of the target transcript is altered relative to absence of the composition, preferably wherein the target transcript is pre-mRNA of dystrophin, and wherein the alteration is that one or more exon is skipped at an increased level relative to absence of the composition, more preferably wherein exon 53 of dystrophin is skipped at an increased level relative to absence of the composition; or
  (b) wherein the oligonucleotide composition is a composition of any one of Embodiments 9-11.

14. An oligonucleotide of any one of Embodiments 1 to 8, or a composition of any one of Embodiments 9-13 for use in treating Duchenne muscular dystrophy, said use comprising administering to a subject susceptible thereto or suffering therefrom an oligonucleotide of any one of Embodiments 1 to 8, or a composition of any one of Embodiments 9-13.

15. A method for preventing or treating DMD, comprising administering to a subject susceptible thereto or suffering therefrom an effective amount of a DMD oligonucleotide.

16. The method of Embodiment 15, wherein the subject is has a mutation of the DMD gene that is amenable to exon 51 skipping, and the DMD oligonucleotide can provide exon 51 skipping.

17. The method of Embodiment 15, wherein the subject is has a mutation of the DMD gene that is amenable to exon 53 skipping, and the DMD oligonucleotide can provide exon 53 skipping.

18. The method of Embodiment 15, wherein the oligonucleotide is an oligonucleotide of any one of Embodiments 1-8.

19. The method of Embodiment 15, wherein the oligonucleotide is administered in a composition of any one of Embodiments 9-13.

20. A method for preparing an oligonucleotide, comprising using of a chiral auxiliary, phosphoramidite or an azide reagent, or a condition described in the specification.

21. An oligonucleotide, chiral auxiliary, phosphoramidite, composition or method described in the specification.

EXEMPLIFICATION

The foregoing has been a description of certain non-limiting embodiments of the disclosure. Accordingly, it is to be understood that embodiments of the disclosure herein described are merely illustrative of applications of principles of the disclosure. Reference herein to details of illustrated embodiments is not intended to limit the scope of any claims.

Certain methods for preparing, and for assessing properties and/or activities of, oligonucleotides and oligonucleotide compositions are widely known in the art, including but not limited to those described in U.S. Pat. Nos. 9,394,333, 9,744,183, 9,605,019, 9,598,458, US 2015/0211006, US 2017/0037399, WO 2017/015555, WO 2017/192664, WO 2017/015575, WO2017/062862, WO 2017/160741, WO 2017/192679, and WO 2017/210647, the methods and reagents of each of which are incorporated herein by reference. Applicant describes herein example methods for preparing provided DMD oligonucleotides and DMD oligonucleotide compositions.

Functions and advantage of certain embodiments of the present disclosure may be more fully understood from the examples described below. The following examples are intended to illustrate certain benefits of such embodiments.

Example 1. Example Synthesis of DMD Oligonucleotide Compositions

Certain technologies for preparing DMD oligonucleotide and compositions thereof are widely known in the art. In some embodiments, DMD oligonucleotides and DMD oligonucleotide compositions of the present disclosure were prepared using technologies, e.g., reagents (e.g., solid supports, coupling reagents, cleavage reagents, phosphoramidites, etc.), chiral auxiliaries, solvents (e.g., for reactions, washing, etc.), cycles, reaction conditions (e.g., time, temperature, etc.), etc., described in one or more of U.S. Pat. Nos. 9,394,333, 9,744,183, 9,605,019, 9,598,458, US 2015/0211006, US 2017/0037399, WO 2017/015555, WO 2017/192664, WO 2017/015575, WO2017/062862, WO 2017/160741, WO 2017/192679, WO 2017/210647, PCT/US18/35687, PCT/US18/38835, and PCT/US18/51398.

Example 2. Example Synthesis of Phosphoramidate Internucleotidic Linkages Comprising a Cyclic Guanidine Moiety As illustrated herein, phosphoramidate internucleotidic linkages can be readily prepared from phosphite internucleotidic linkages, including stereopure phosphite internucleotidic linkages, in accordance with the present disclosure.

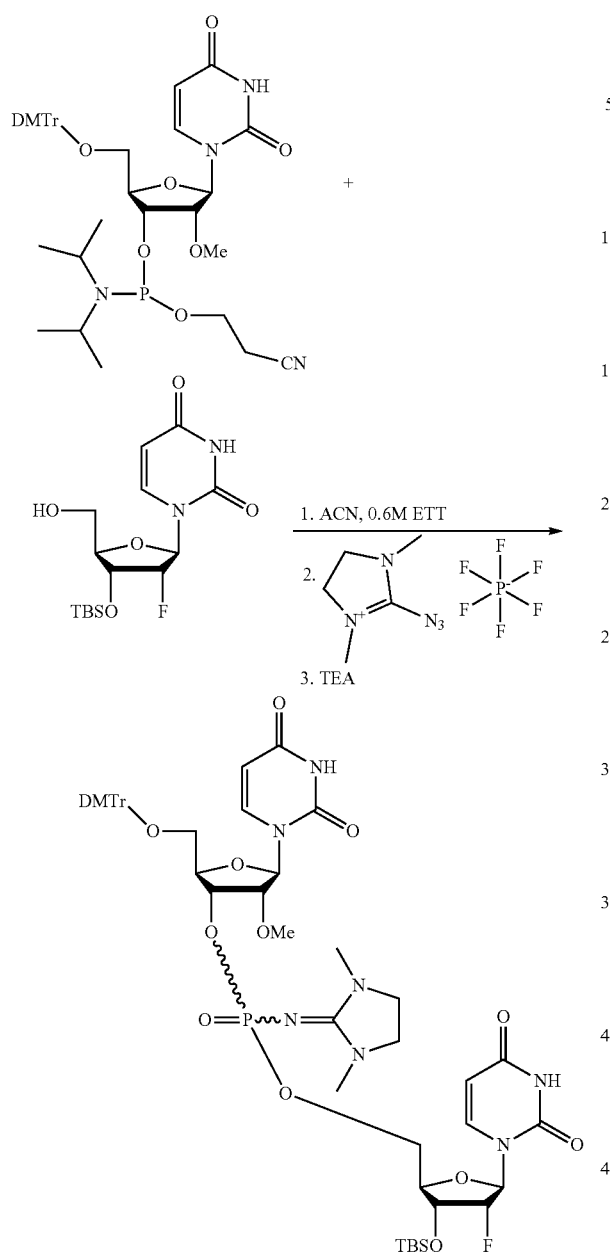

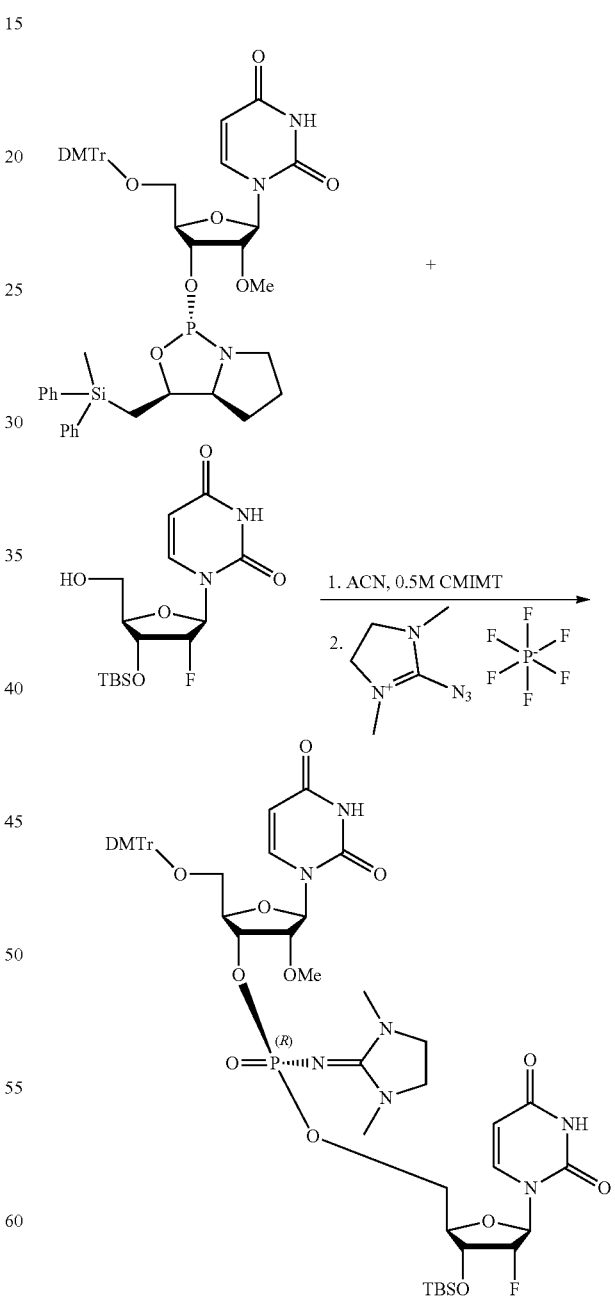

To a stirred solution of amidite (474 mg, 0.624 mmol, 1.5 equiv., pre-dried by co-evaporation with dry acetonitrile and under vacuum for a minimum of 12 h) and TBS protected alcohol (150 mg, 0.41 mmol, pre-dried by co-evaporation with dry acetonitrile and under vacuum for a minimum of 12 h) in dry acetonitrile (5.2 ml) was added 5-(et hylthio)-1H-tetrazole (ETT, 2.08 ml, 0.6M, 3 equiv.) under argon atmosphere at room temperature. The reaction mixture was stirred for 5 mins then monitored by LCMS and then a solution of 2-azido-1,3-dimethylimidazolinium hexafluorophosphate (356 mg, 1.24 mmol, 3 equiv.) in acetonitrile (1 ml) was added. Once the reaction was completed (after ~5 mins, monitored by LCMS) then triethylamine (0.17 ml, 1.24 mmol, 3 equiv) was added and the reaction was monitored by LCMS. The reaction mixture was concentrated under reduced pressure and then redissolved in dichloromethane (50 ml), washed with water (25 ml), saturated aq. sodium bicarbonate (25 ml), and brine (25 ml), and dried with magnesium sulfate. The solvent was removed under reduced pressure. The crude product was purified by silica gel column (80 g) using DCM (5% triethyl amine) and MeOH as eluent. Product-containing fractions were collected and the solvent was evaporated. The resulted product may contain TEA.HCl salt. To remove the salt, the product was re-dissolved in DCM (50 ml) and washed with saturated aq. sodium bicarbonate (20 ml) and brine (20 ml) then dried with magnesium sulfate and the the solvent was evaporated. A pale yellow solid was obtained. Yield: 440 mg (89%). $^{31}$P NMR (162 MHz, CDCl$_3$) δ −1.34, −1.98. MS calculated for $C_{51}H_{65}FN_7O_{14}PSi$ $[M]^+$ 1078.17, Observed: 1078.57 $[M+H]^+$.

Synthesis of Stereopure (Rp) Dimer.

To a stirred solution of L-DPSE chiral amidite (1.87 g, 2.08 mmol, 1.5 equiv., pre-dried by co-evaporation with dry acetonitrile and under vacuum for a minimum of 12 h) and TBS protected alcohol (500 mg, 1.38 mmol, pre-dried by co-evaporation with dry acetonitrile and under vacuum for a minimum of 12 h) in dry acetonitrile (18 mL) was added 2-(1H-imidazol-1-yl) acetonitrile trifluoromethanesulfonate (CMIMT, 5.54 mL, 0.5M, 2 equiv.) under argon atmosphere at room temperature. The resulting reaction mixture was stirred for 5 mins then monitored by LCMS and then a solution of 2-azido-1,3-dimethylimidazolinium hexafluorophosphate (1.18 g, 4.16 mmol, 3 equiv.) in acetonitrile (2 mL) was added. Once the reaction was completed (after ~5 mins, monitored by LCMS), the reaction mixture was concentrated under reduced pressure and then redissolved in dichloromethane (70 mL), washed with water (40 mL), saturated aq. sodium bicarbonate (40 mL) and brine (40 mL), and dried with magnesium sulfate. The solvent was removed under reduced pressure. The crude product was purified by silica gel column (120 g) using DCM (5% triethyl amine) and MeOH as eluent. Product containing fractions were collected and the solvent was evaporated. The resulted product contained TEA.HCl salt. To remove the salt, the product was re-dissolved in DCM (50 mL) and washed with saturated aq. sodium bicarbonate (20 mL) and brine (20 mL) and then dried with magnesium sulfate and the solvent was evaporated. A pale yellow foamy solid was obtained. Yield: 710 mg (47%). $^{31}$P NMR (162 MHz, CDCl$_3$) δ −1.38. MS calculated for $C_{51}H_{65}FN_7O_{14}PSi$ [M]$^+$ 1078.17, Observed: 1078.19.

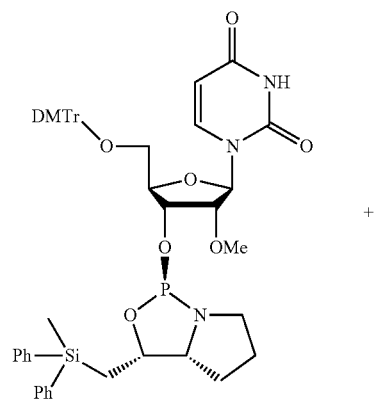

+

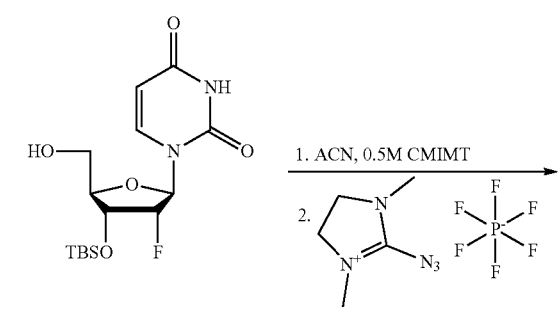

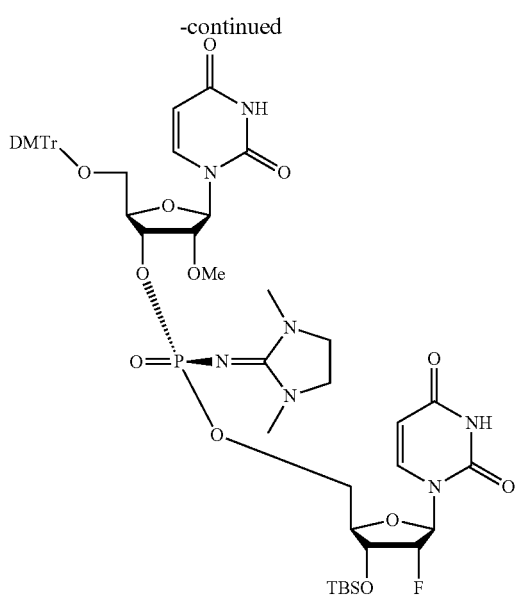

Synthesis of Stereopure (Sp) Dimer

The same procedure was followed as for the Rp dimer. In place of L-DPSE chiral amidite, D-DPSE chiral amidite was used. A pale yellow foamy solid was obtained. Yield: 890 mg (59%). $^{31}$P NMR (162 MHz, CDCl$_3$) δ −1.93. MS calculated for $C_{51}H_{65}FN_7O_{14}PSi$ [M]$^+$1078.17, Observed: 1078.00.

In an example $^{31}$P NMR (internal standard of phosphoric acid at δ 0.0), the stereorandom preparation showed two peaks at −1.34 and −1.98, respectively; the stereopure Rp preparation showed a peak at −1.93, and the stereopure Sp preparation showed a peak at −1.38.

Example 3. Preparation of DMD Oligonucleotides with Internucleotidic Linkages Comprising Neutral Guanidinium Group In accordance with technologies described in the present disclosure, DMD oligonucleotides with various neutral and/or cationic internucleotidic linkages (e.g., at physiological pH) can be prepared. Illustrated below are preparation of DMD oligonucleotides comprising representative such internucleotidic linkages.

WV-11237 is a DMD oligonucleotide comprising four internucleotidic linkages having the structure of

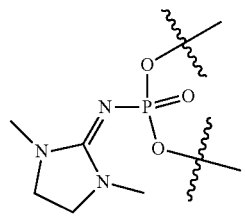 [SMILES: *OP(=O)(N=C1N(C)CCN1C)O*]

(n001) to introduce a neutral nature to the backbone and reduce the overall negative charges of the backbone. Expected molecular weight: 7113.4.

As an example, one preparation of WV-11237, including certain synthetic conditions and analytical results, is described below. Briefly, stereopure internucleotidic linkages were constructed using L-DPSE amidites and typical DPSE coupling cycles comprising Detritylation→Coupling→Pre-Cap→Thiolation→Post-Cap. Cycles for the n001 internucleotidic linkages were modified and comprised Detritylation→Coupling→Dimethyl imidazolium treatment→Post-cap. Compared to certain oxidation cycles, oxidation steps of oxidizing the P(III), e.g., with $I_2$-Pyridine-water, was replaced with the dimethyl imidazolium treatment.

Certain conditions and/or results of an example preparation.
Synthetic Scale: 127 μMol
Synthetic Conditions (Stereopure Internucleotidic Linkages)

| Synthetic Steps | Conditions |
| --- | --- |
| Detritylation | 3% DCA in Toluene; 300 cm/hr, 436 UV watch |
| Coupling | 2.5 eq. of 0.2M chiral amidite, 67% of 0.6M CMIMT Recycle time: 10 min |
| Pre-Cap B | Reagent: 20:30:50::Acetic anhydride: Lutidine: Acetonitrile 1.5 CV, 3 min CT |
| Thiolation | Reagent: 0.2M Xanthane Hydride 0.6 CV, 6 min CT |
| Capping (1:1 Cap A + Cap B) | 0.4 CV, 0.8 min CT |

Cap A = 20%:80% = NMI:ACN (v/v)
Cap B = 20%:30%:50% = $Ac_2O$:2,6-Lutidine:ACN (v/v/v)

Synthetic Conditions (Stereorandom n001)

| Synthetic Steps | Conditions |
| --- | --- |
| Detritylation | 3% DCA in Toluene; 300 cm/hr, 436 UV watch |
| Coupling | 2.5 eq. of 0.2M standard amidite, 67% of 0.6M ETT Recycle time: 8 min |
| Dimethyl imidazolium treatment: | 2.30 CV, 5 min CT, 3.5 eq. |
| Capping (1:1 Cap A + Cap B) | 0.4 CV, 0.8 min CT |

Synthesis Process Parameters:
  Synthesizer: AKTA Oligopilot 100
  Solid Support: CPG 2'Fluoro-U, (85 umol/g)
  Synthetic scale: 127 umol; 1.5 gm
  Column diameter: 20 mm
  Column volume: 6.3 mL
Stereopure Coupling Reagents:
  Monomer: 0.2M in MeCN (2'Fluoro-dA-L-DPSE, 2'Fluoro-dG-L-DPSE, 2'-OMe-A-L-DPSE); 0.2M in 20% isobutyronitrle/MeCN (2'Fluoro-dC-L-DPSE, 2'Fluoro-U-L-DPSE)
  Deblocking: 3% DCA in Toluene
  Activator: 0.6M CMIMT in MeCN
  Sulfurization: 0.2M Xanthane Hydride in pyridine
  Cap A: 20% NMI in MeCN
  Cap B: Acetic anhydride, Lutidine, MeCN (20:30:50)
  Pre-Cap: Neat Cap B
Stereorandom Coupling Reagents:
  Monomer: 0.2M in MeCN (2'OMeA and 2'OMeG)
  Deblocking: 3% DCA in Toluene
  Activator: 0.6M ETT in MeCN
  2-Azido-1,3-dimethylimidazolinium-hexafluorophosphate: 0.1M in MeCN
  Cap A: 20% NMI in MeCN
  Cap B: Acetic anhydride, Lutidine, MeCN Deprotection Condition:

One pot deprotection by first treating the support with 5M TEA.HF in DMSO, $H_2O$, Triethylamine (pH 6.8). Incubation: 3 h, room temperature, 80 μL/μmol. Followed by addition of aqueous ammonia (200 μL/μmol). Incubation: 24 h, 35° C. The deprotected material was sterile filtered using 0.45 μm filters. Yield: 72 O.D./μmol Recipe for 5X Solution of TEA.HF in DMSO/Water, 5/1, v/v:

| Reagent | Solvents/Reagents | Volume (mL) | Total Volume (mL) |
| --- | --- | --- | --- |
| (5X) TEA.HF in DMSO/Water, 5/1, v/v | DMSO | 55.0 | 100 |
| | Water | 11.0 | |
| | Triethylamine (TEA) | 9.0 | |
| | Triethylamine trihydrofluoride (TEA.3HF) | 25.0 | |

In an example crude UPLC chromatogram, there were four distinct peaks all having same desired molecular weight of 7113.2:

| | RT | Area | % Area | Height |
| --- | --- | --- | --- | --- |
| 9 | 7.843 | 402732 | 16.75 | 212901 |
| 10 | 7.884 | 941388 | 39.14 | 327190 |
| 11 | 7.968 | 595232 | 24.75 | 275741 |
| 12 | 8.025 | 353090 | 14.68 | 150141 |

The example final QC UPLC chromatogram showed four distinct peaks all having the desired molecular weight of 7113.2 (% Purity 95.32). Crude LC-MS showed a single peak of desired molecular weight of 7113.2 (data not shown). The example final QC LC-MS showed a major peak with the desired molecular weight of 7113.1.

Other DMD oligonucleotides may be prepared using similar cycle conditions or variants thereof depending on specific chemistries of each DMD oligonucleotides.

Example 4. Chirally Controlled Non-Negatively Charged Internucleotidic Linkages

Dimer Synthesis.

This procedure is to make stereopure dimer phosphate backbone followed by incorporating it to the selective sites of DMD oligonucleotides (e.g., antisense DMD oligonucleotide or ASO, single-stranded RNAi agent or ssRNA, etc.). A second approach is to synthesize molecules using an automated DMD oligonucleotide synthesizer to introduce a non-negatively charged internucleotidic linkage, e.g., a neutral internucleotidic linkage, at a specific site or full DMD oligonucleotide.

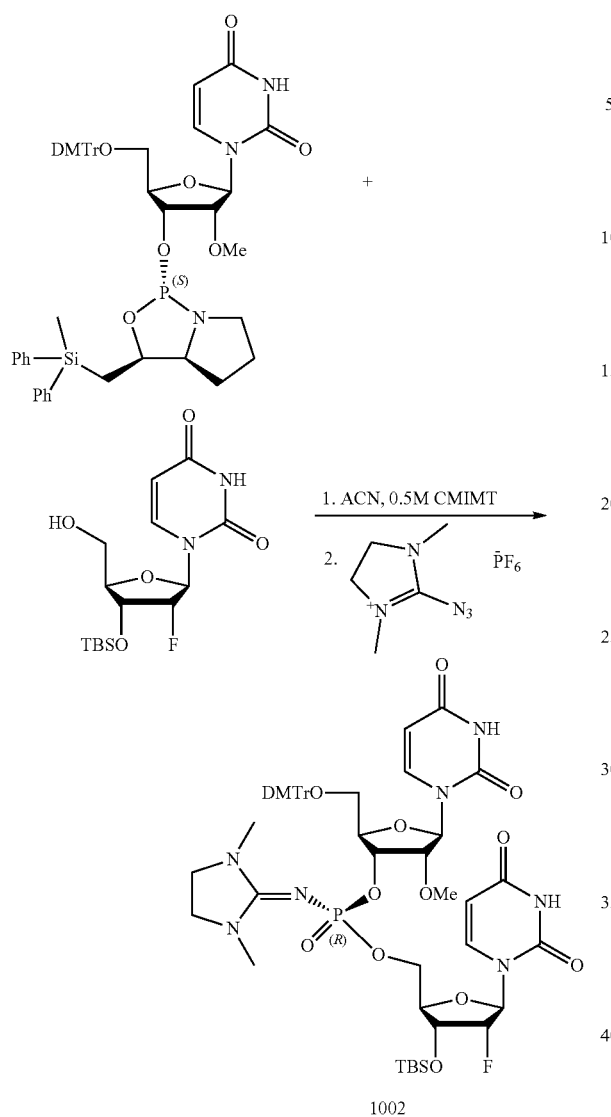

1002

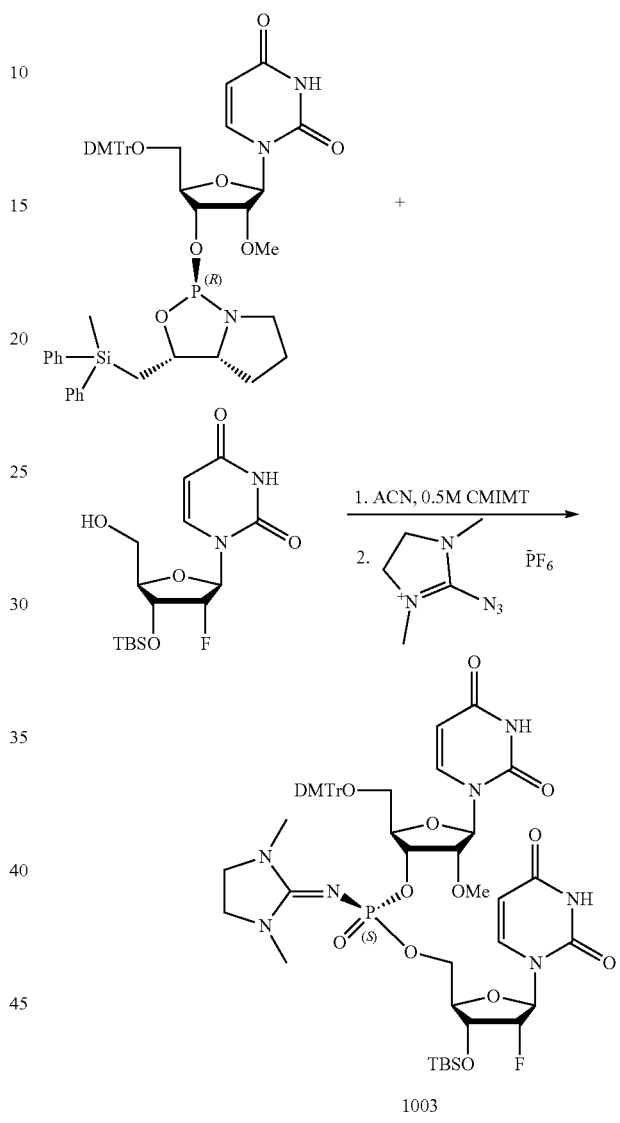

1003

General experimental procedure (B) for stereopure (Rp) dimer: To a stirred solution of L (or) D-DPSE chiral amidite (1.87 g, 2.08 mmol, 1.5 equiv., pre-dried by co-evaporation with dry acetonitrile and kept it under vacuum for minimum 12 h) and TBS protected alcohol (500 mg, 1.38 mmol, pre-dried by co-evaporation with dry acetonitrile and kept it under vacuum for minimum 12 h) in dry acetonitrile (18 mL) was added 2-(1H-imidazol-1-yl) acetonitrile trifluoromethanesulfonate (CMIMT, 5.54 mL, 0.5M, 2 equiv.) under argon atmosphere at room temperature. Resulting reaction mixture was stirred for 5 mins then monitored by LCMS and then a solution of 2-azido-1,3-dimethylimidazolinium hexafluorophosphate (1.18 g, 4.16 mmol, 3 equiv.) in acetonitrile (2 mL) was added. Once the reaction was completed (after ~5 mins, monitored by LCMS) then the reaction mixture was concentrated under reduced pressure and then redissolved in dichloromethane (70 mL) washed with water (40 mL), saturated aq. sodium bicarbonate (40 mL) and brine (40 mL) dried with magnesium sulfate. Solvent was removed under reduced pressure. The crude product was purified by silica gel column (120 g) using DCM (2% triethyl amine) and MeOH as eluent. Product containing fractions are evaporated. Pale yellow foamy solid 1002 was obtained. Yield: 710 mg (47%). $^{31}$P NMR (162 MHz, CDCl$_3$) δ -1.38. MS (ES) m z calculated for C$_{51}$H$_{65}$FN$_7$O$_{14}$PSi [M]$^+$1077.40, Observed: 1078.19 [M+H]$^+$.

Stereopure (Sp) dimer 1003: The procedure B was followed as shown above. D-DPSE chiral amidite was used. Pale yellow foamy solid was obtained. Yield: 890 mg (59%). $^{31}$P NMR (162 MHz, CDCl$_3$) δ -1.93. MS (ES) m z calculated for C$_{51}$H$_{65}$FN$_7$O$_{14}$PSi [M]$^+$1077.40, Observed: 1078.00 [M+H]+.

General experimental procedure (C) for deprotection of TBS group: To a stirred solution of TBS protected compound (9.04 mmol) in THF (70 mL), was added TBAF (1.0 M, 13.6 mmol) at rt. The reaction mixture was stirred at room temperature for 2-4 h. LCMS showed there was no starting material left, then concentrated followed by purification using ISCO-combiflash system (330 g gold rediSep high performance silica column pre-equilibrated 3 CV with 2% TEA in DCM) and DCM/Methanol/2% TEA as a gradient eluent. Product containing column fractions were pooled together and evaporated followed by drying under high vacuum afforded the pure product.

General experimental procedure (D) for chiral amidites: The TBS deprotected compound (2.5 mmol) was dried by co-evaporation with 80 mL of anhydrous toluene (30 mL×2) at 35° C. and dried under at high vacuum for overnight. Then dried it was dissolved in dry THF (30 mL), followed by the addition of triethylamine (17.3 mmol) then the reaction mixture was cooled to −65° C. [for Guanine flavors: TMS-Cl, 2.5 mmol was added at −65° C., for non-Guanine flavors no TMS-Cl was added]. The THF solution of [(1R,3S,3aS)-1-chloro-3-((methyldiphenylsilyl)methyl)tetrahydro-1H,3H-pyrrolo1[1,2-c][1,3,2]oxazaphosphole (or) (1S,3R,3aR)-1-chloro-3-((methyldiphenylsilyl)methyl)tetrahydro-1H,3H-pyrrolo[1,2-c][1,3,2]oxazaphosphole (1.8 equiv.) was added through syringe to the above reaction mixture over 2 min then gradually warmed to room temperature. After 20-30 min, at rt, TLC as well as LCMS indicated starting material was converted to product (reaction time: 1 h). Then the reaction mixture was filtered under argon using air free filter tube, washed with THF and dried under rotary evaporation at 26° C. afforded crude solid material, which was purified by ISCO-combiflash system (40 g gold rediSep high performance silica column (pre-equilibrated 3 CV with $CH_3CN$/5% TEA then 3 CV with DCM/5% TEA) using DCM/$CH_3CN$/5% TEA as a solvent (compound eluted at 10-40 DCM/$CH_3CN$/5% TEA). After evaporation of column fractions pooled together was dried under high vacuum afforded white solid to give isolated yield.

$^{31}$P NMR (internal standard of Phosphoric acid at δ 0.0): 1001: −1.34 and −1.98. 1002: −1.93. 1003: −1.38. $^{1}$H NMR of 1001, 1002, and 1003 demonstrated different chemical shifts for multiple hydrogens of the diastereomers. LCMS showed different retention times for the two diastereomers as well. Under one condition, the following retention times were observed: 1.90 and 2.15 for 1001, 1.92 for one diastereomer, and 2.17 for the other.

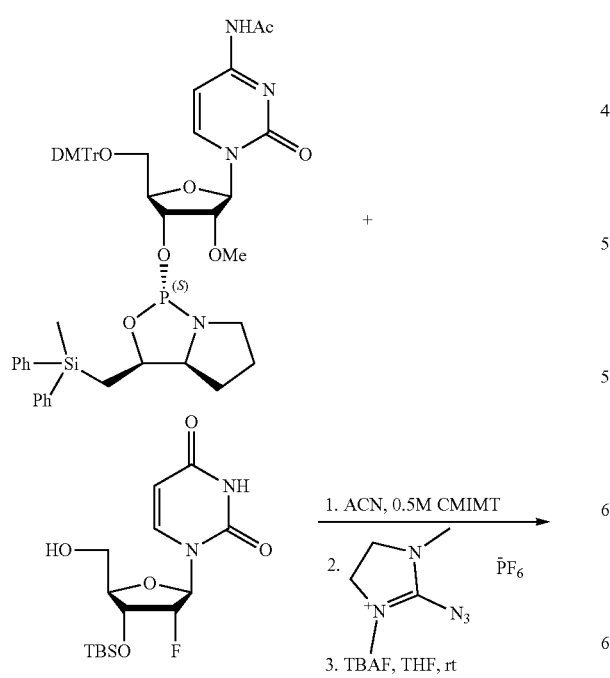

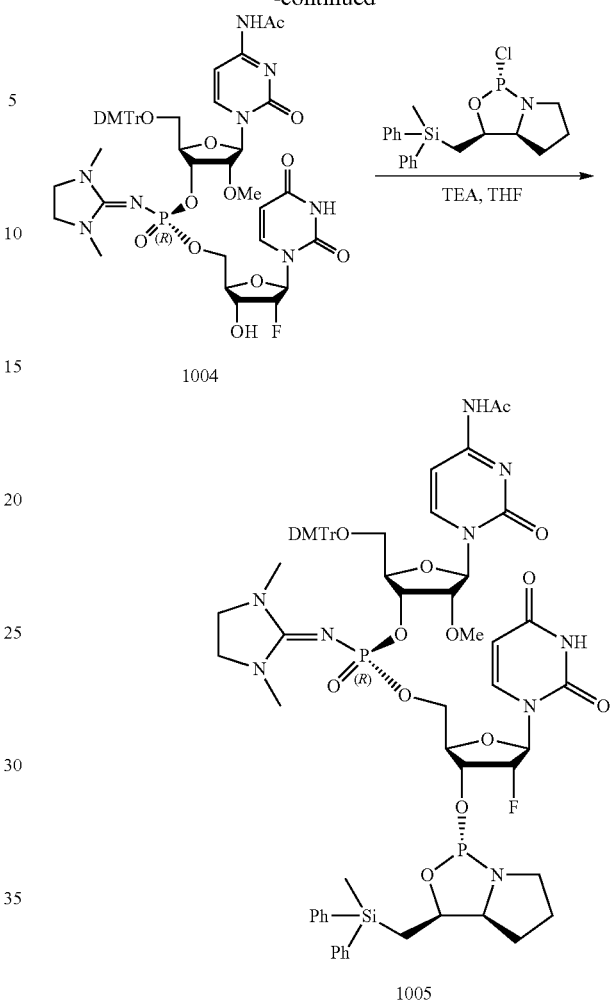

1004

1005

Compound 1004: Procedures B and C followed, Off-white foamy solid, Yield: (36%). $^{31}$P NMR (162 MHz, $CDCl_3$) δ −1.23. MS (ES) m z calculated for $C_{47}H_{54}FN_8O_{14}P$ [M]$^+$1004.34, Observed: 1043.21 [M+K]$^+$.

Compound 1005: Procedure D used, Off-white foamy solid, Yield: (81%). $^{31}$P NMR (162 MHz, $CDCl_3$) δ 154.43, -2.52. MS (ES) m z calculated for $C_{66}H_{76}FN_9O_{15}P_2Si$ [M]$^+$1343.46, Observed: 1344.85 [M+H]$^+$.

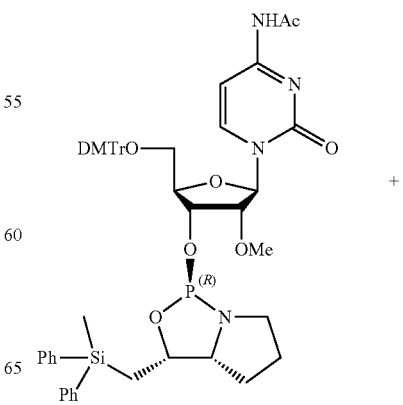

165
-continued
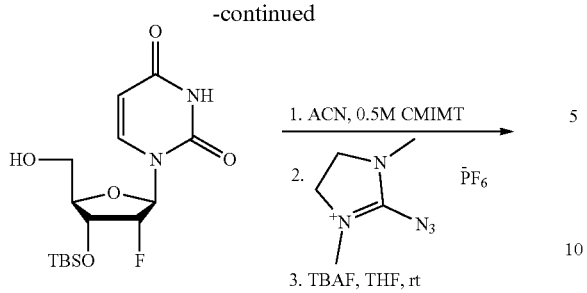
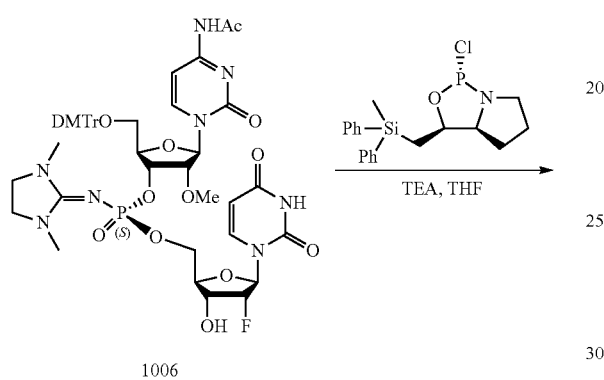
166
-continued
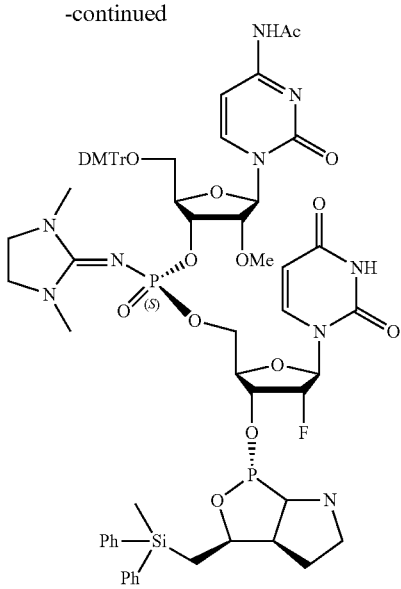
Compound 1006: Procedures B, and C followed, Off-white foamy solid, Yield: (47%). $^{31}$P NMR (162 MHz, CDCl$_3$) δ −2.54. MS (ES) m z calculated for C$_{47}$H$_{54}$FN$_8$O$_{14}$P [M]$^+$1004.34, Observed: 1043.12 [M+K]$^+$.
Compound 1007: Procedure D used, Off-white foamy solid, Yield: (81%). $^{31}$P NMR (162 MHz, CDCl$_3$) δ 153.55, −2.20. MS (ES) m z calculated for C$_{66}$H$_{76}$FN$_9$O$_{15}$P$_2$Si [M]$^+$1343.46, Observed: 1344.75 [M+H]$^+$.
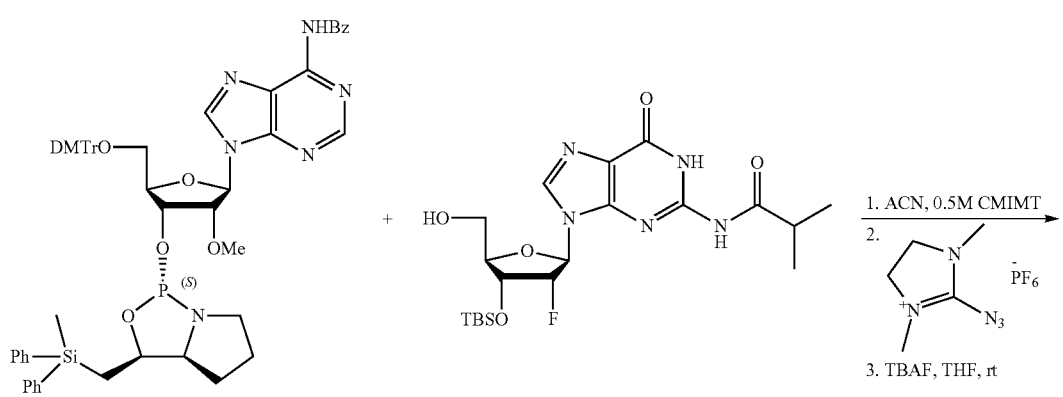
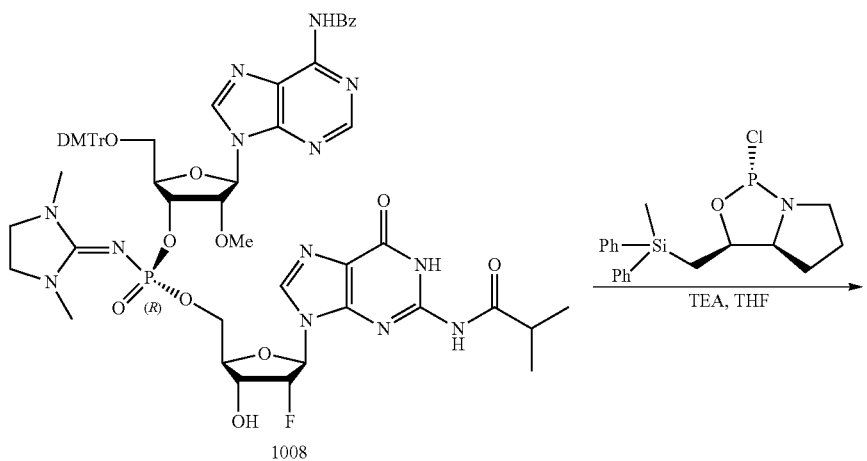

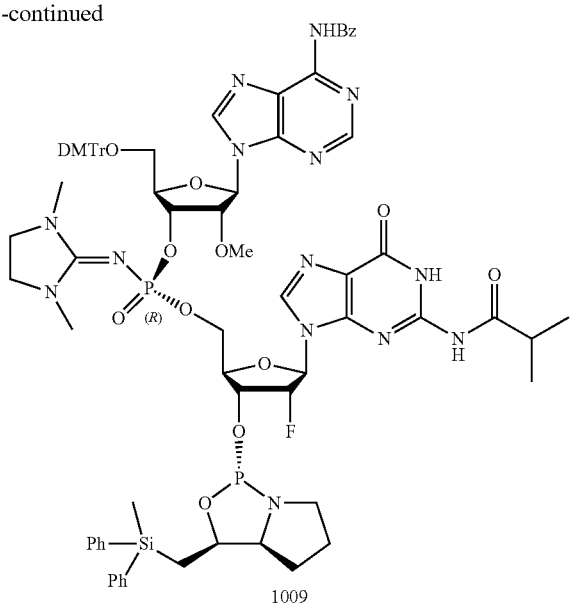
1009
Compound 1008: Procedures B and C followed, Off-white foamy solid, Yield: (36%). $^{31}$P NMR (162 MHz, CDCl$_3$) δ −1.38. MS (ES) m z calculated for C$_{58}$H$_{63}$FN$_{13}$O$_{13}$P [M]$^+$1199.43, Observed: 1200.76 [M+H]$^+$.
Compound 1009: Procedure D used, Off-white foamy solid, Yield: (60%). $^{31}$P NMR (162 MHz, CDCl$_3$) δ 157.26, −2.86. MS (ES) m z calculated for C$_{77}$H$_{85}$FN$_{14}$O$_{14}$P$_2$Si [M]$^+$1538.55, Observed: 1539.93 [M+H]$^+$.
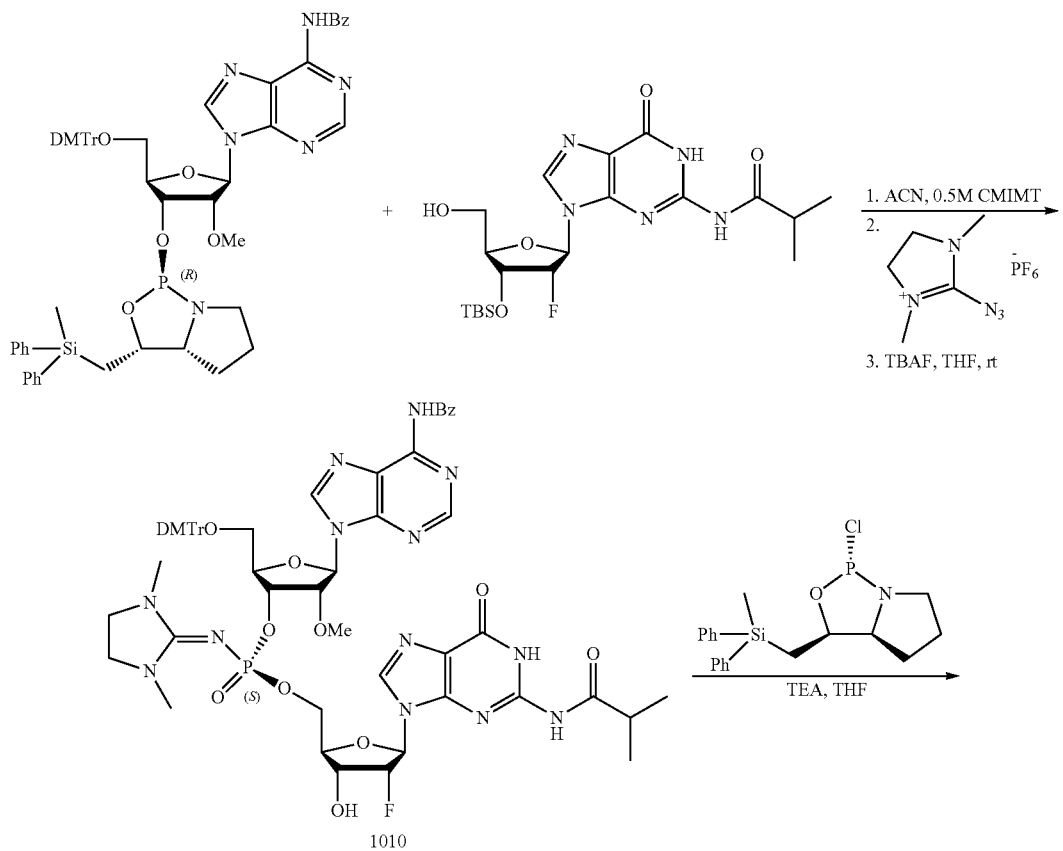
1010

-continued
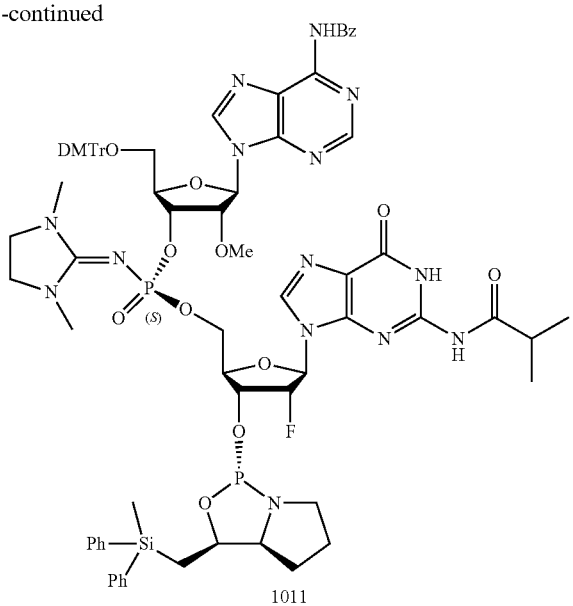
Compound 1010: Procedures B and C followed, Off-white foamy solid, Yield: (36%). $^{31}$P NMR (162 MHz, CDCl$_3$) δ −2.82. MS (ES) m z calculated for C$_{58}$H$_{63}$FN$_{13}$O$_{13}$P [M]$^+$1199.43, Observed: 1200.19 [M+H]$^+$.
Compound 1011: Procedure D used, Off-white foamy solid, Yield: (63%). $^{31}$P NMR (162 MHz, CDCl$_3$) δ 159.56, −2.99. MS (ES) m z calculated for C$_{77}$H$_{85}$FN$_{14}$O$_{14}$P2Si [M]$^+$1538.55, Observed: 1539.83 [M+H]$^+$.
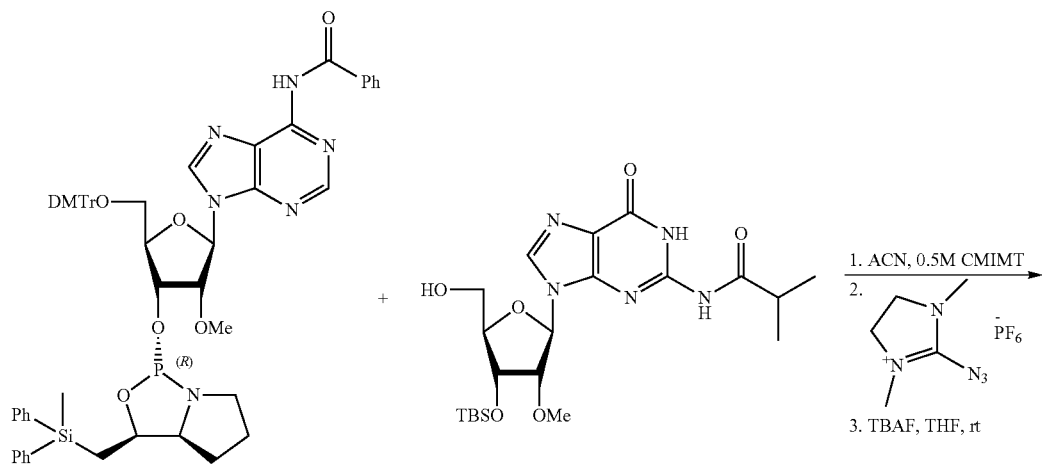

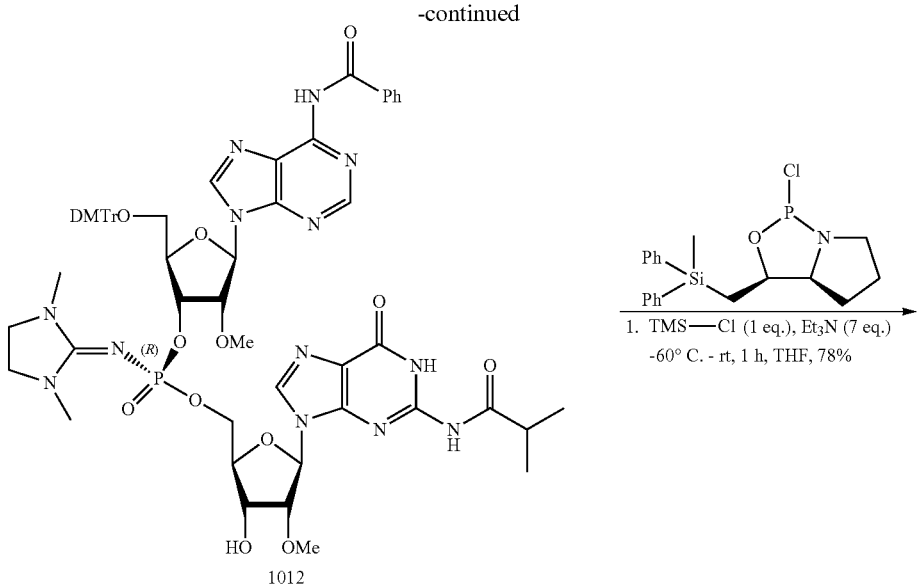

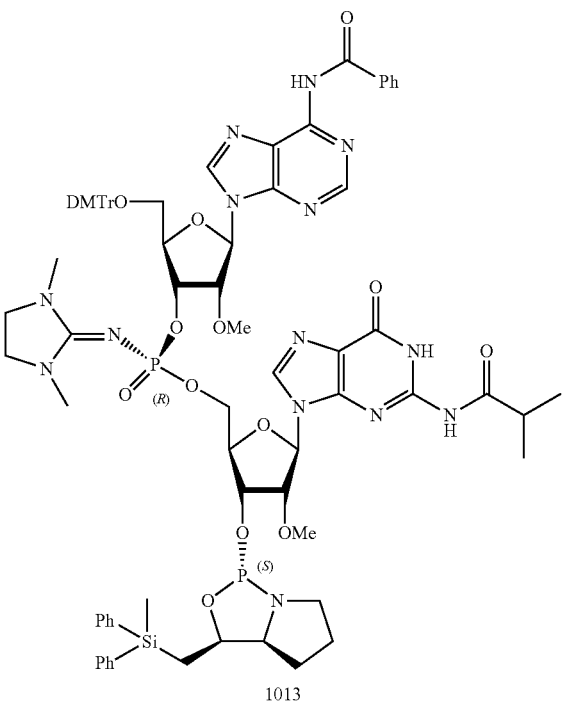

Compound 1012: Procedures B and C followed, Off-white foamy solid, Yield: (36%). $[\alpha]_D^{23}=-25.74$ (c 1.06, $CHCl_3$). $^{31}P$ NMR (162 MHz, Chloroform-d) δ −1.83. $^1H$ NMR (400 MHz, Chloroform-d) δ 12.14 (s, 1H), 11.28 (s, 1H), 9.15 (s, 1H), 8.56 (s, 1H), 8.25-7.94 (m, 2H), 7.90 (s, 1H), 7.72-7.48 (m, 2H), 7.44 (dd, J=8.2, 6.7 Hz, 2H), 7.35-7.26 (m, 2H), 7.24-7.02 (m, 8H), 6.81-6.56 (m, 4H), 6.04 (d, J=5.2 Hz, 1H), 5.67 (d, J=5.5 Hz, 1H), 4.83 (dt, J=8.6, 4.4 Hz, 1H), 4.71-4.54 (m, 2H), 4.49 (dt, J=14.2, 4.8 Hz, 2H), 4.35 (ddt, J=11.0, 5.1, 3.2 Hz, 1H), 4.28-4.09 (m, 2H), 3.68 (s, 6H), 3.37 (d, J=3.3 Hz, 7H), 3.33-3.17 (m, 5H), 2.82 (s, 5H), 2.74-2.60 (m, 1H), 1.92 (s, 2H), 1.72-1.50 (m, 1H), 1.08 (d, J=6.9 Hz, 3H), 0.94 (d, J=6.9 Hz, 3H). MS (ES) m z calculated for $C_{59}H_{66}N_{13}O_{14}P$ 1211.45 $[M]^+$, Observed: 1212.42 $[M+H]^+$.

Compound 1013: Procedure D used, Off-white foamy solid, Yield: (78%). $[\alpha]_D^{23}$ −15.48 (c 0.96, $CHCl_3$). $^{31}P$ NMR (162 MHz, Chloroform-d) δ 159.42, −2.47. MS (ES) m z calculated for $C_{78}H_{88}N_{14}O_{15}P_2Si$ 1550.57 $[M]^+$, Observed: 1551.96 $[M+H]^+$.

173 174
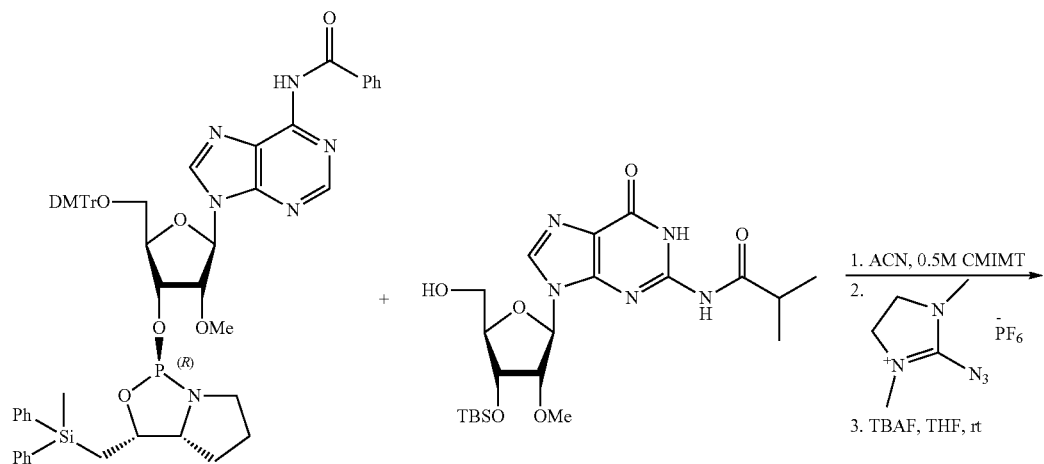
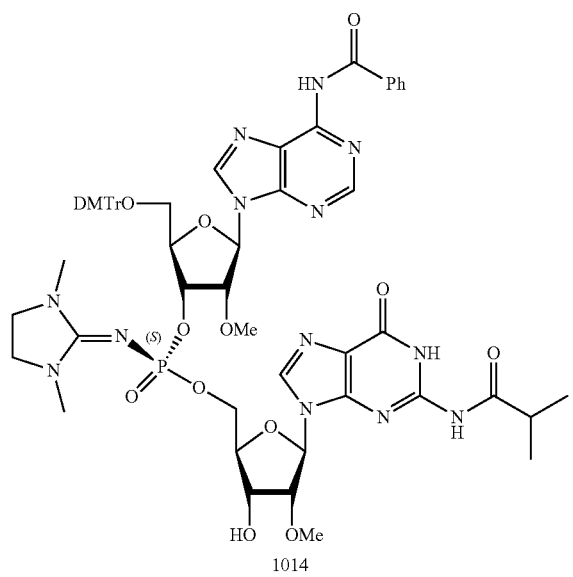
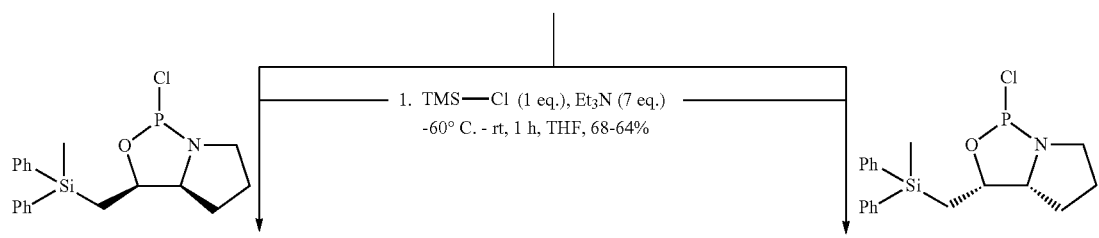

175
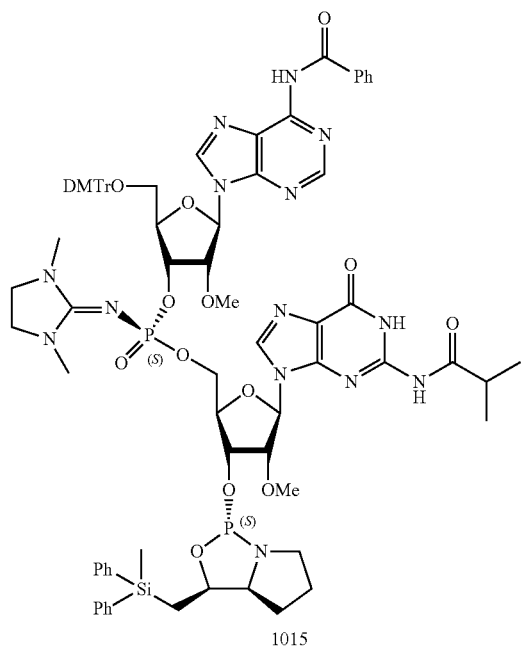
1015
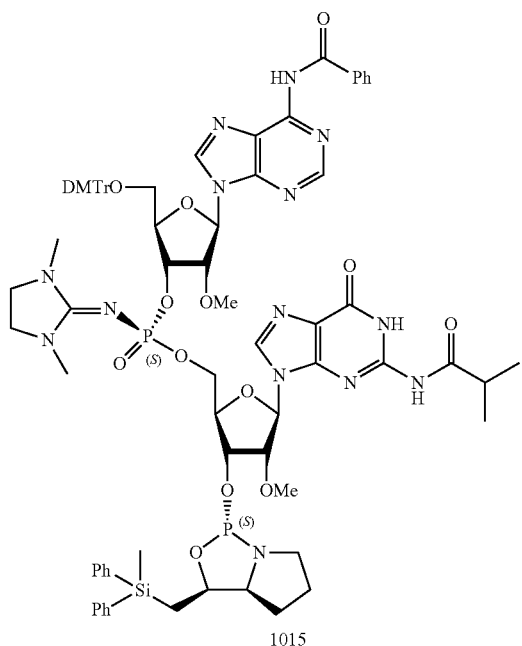
1015
Compound 1014: Procedures B and C followed, Off-white foamy solid, Yield: (30%). [α]2=—21.45 (c 0.55, CHCl$_3$). MS (ES) m z calculated for C$_{59}$H$_{66}$N$_{13}$O$_{14}$P 1211.45 [M]$^+$, Observed: 1212.80 [M+H]$^+$.
176
-continued
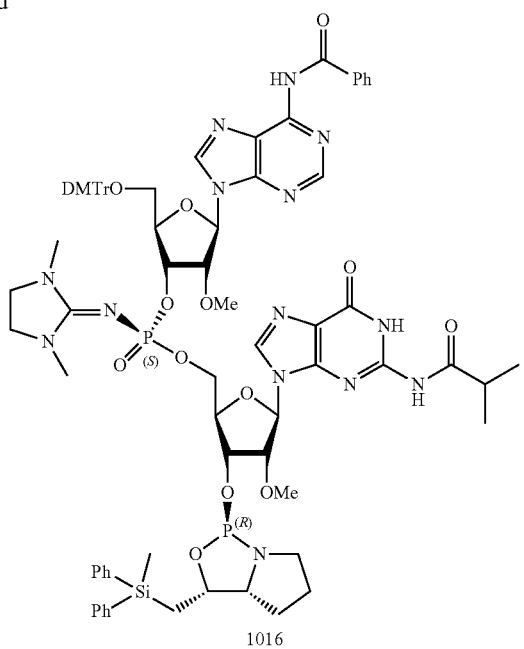
1016
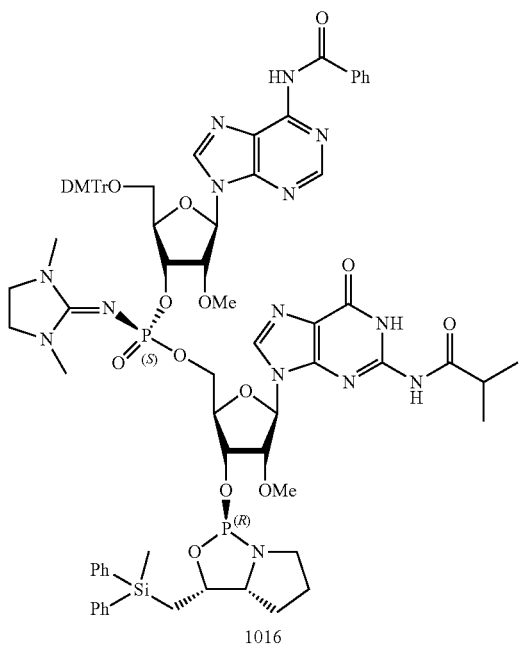
1016
Compound 1015: Procedure D used, Off-white foamy solid, Yield: (68%). [α]$_D^{23}$=−15.63 (c 1.44, CHCl$_3$). MS (ES) m z Calculated for C$_{78}$H$_{88}$N$_{14}$O$_{15}$P$_2$Si 1550.57 [M]$^+$, Observed: 1551.77 [M+H]$^+$.

Compound 1016: Procedure D used, Off-white foamy solid, Yield: (64%). $^{31}$P NMR (162 MHz, CDCl$_3$) δ 156.64, −2.67. MS (ES) m z Calculated for $C_{78}H_{88}N_{14}O_{15}P_2Si$ 1550.57 [M]$^+$, Observed: 1551.77 [M+H]$^+$.

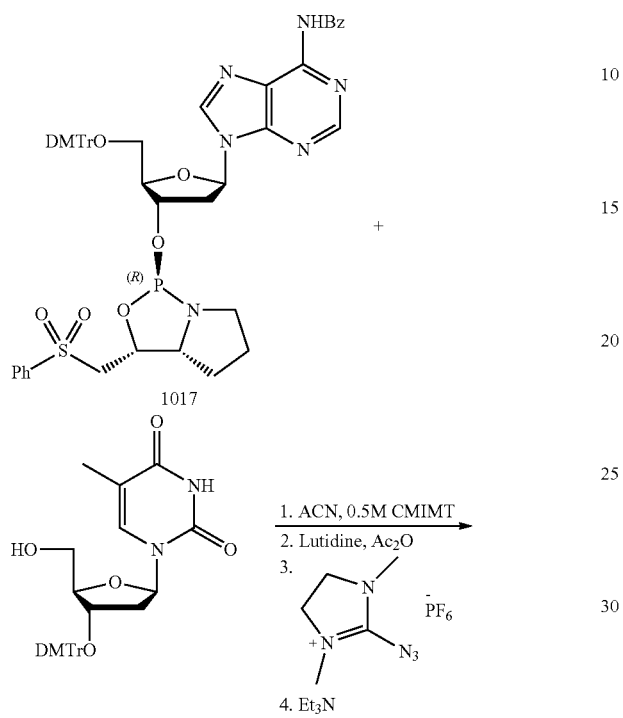

General experimental procedure (E) for stereopure dimer using sulfonyl amidite: To a stirred solution of stereopure sulfonyl amidite 1017 (259 mg, 0.275 mmol, 1.5 equiv) and TBS protected alcohol (100 mg, 0.18 mmol) in dry acetonitrile (2 mL) was added 2-(1H-imidazol-1-yl) acetonitrile trifluoromethanesulfonate (CMIMT, 0.73 mL, 0.36 mmol, 0.5M, 2 equiv.) under argon atmosphere at room temperature. Resulting reaction mixture was stirred for 5 mins and monitored by LCMS then a mixture of acetic anhydride (2M in ACN, 0.18 ml, 0.36 mmol, 2 equ) and lutidine (2M in ACN, 0.18 ml, 0.36 mmol, 2 equ) was added then stirred for ~5 mins then a solution of 2-azido-1,3-dimethylimidazolinium hexafluorophosphate (104.7 mg, 0.367 mmol, 2 equiv.) in acetonitrile (1 mL) was added. Once the reaction was completed (after ~5 mins, monitored by LCMS) then triethylamine (0.13 mL, 0.91 mmol, 5 equiv.) was added and monitored by LCMS. Once the reaction was completed, it was concentrated under reduced pressure and then re-dissolved in dichloromethane (50 mL) washed with water (25 mL), saturated aq. Sodium bicarbonate (25 mL) and brine (25 mL) dried with magnesium sulfate. Solvent was removed under reduced pressure. The crude product was purified by silica gel column (80 g) using DCM (2% triethylamine) and MeOH as eluent. Product containing fractions collected and evaporated. Off white solid 1018 obtained. Yield: 204 mg (82%). $^{31}$P NMR (162 MHz, CDCl$_3$) δ −1.87. MS (ES) m z calculated for $C_{74}H_{75}FN_{10}O_{14}P$ [M]$^+$ 1359.44, Observed: 1360.39 [M+H]$^+$.

Additional phosphoramidites that may be utilized for synthesis include:

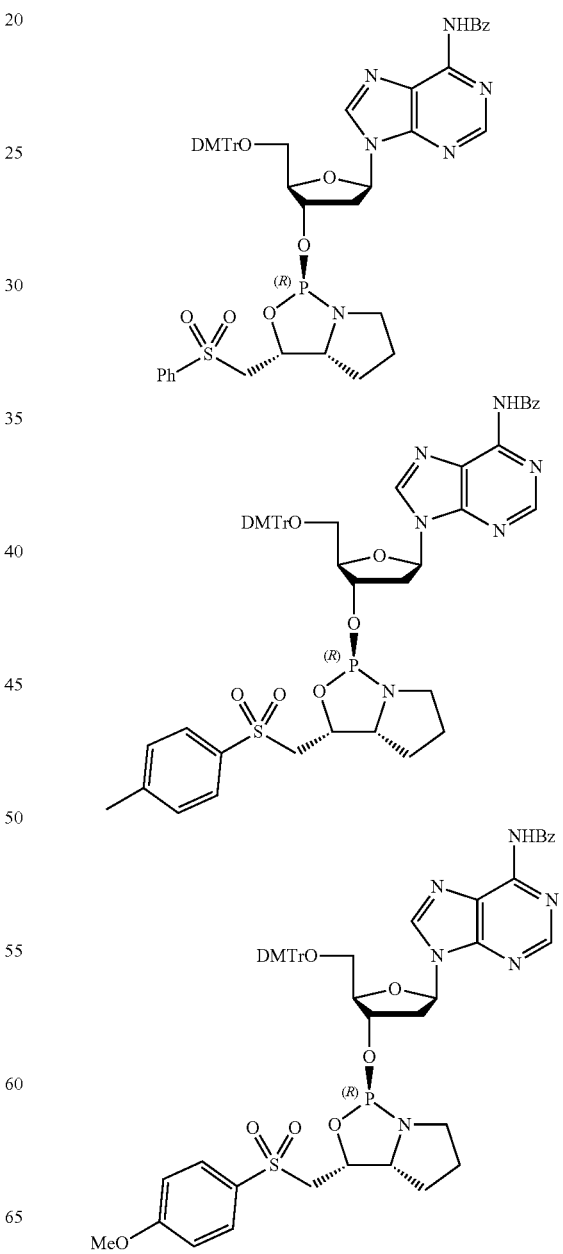

-continued

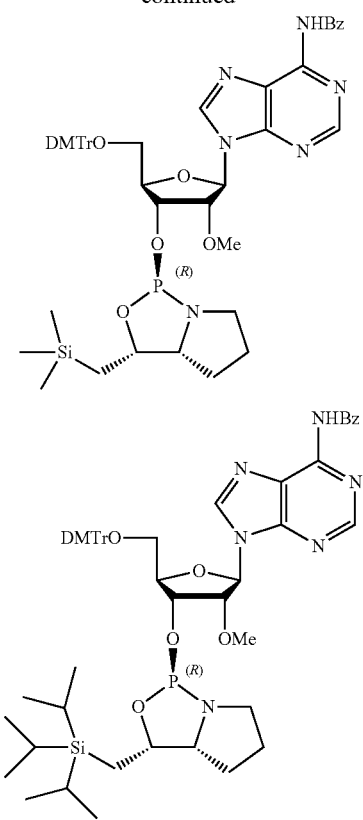

Additional useful chiral auxiliaries include:

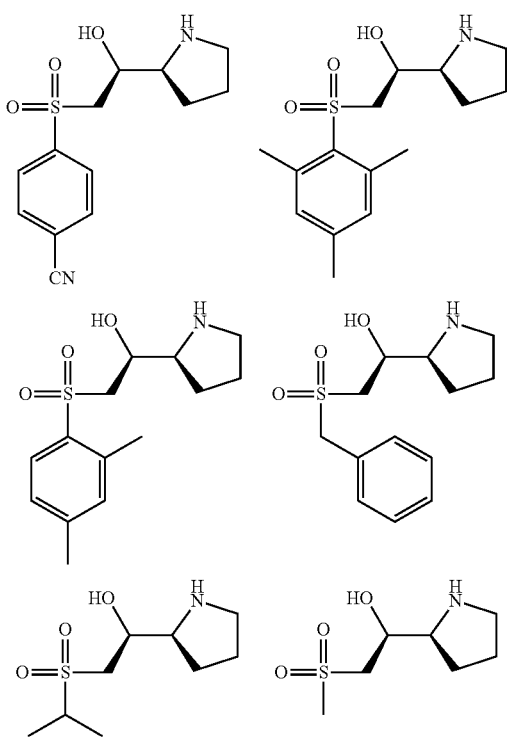

-continued

Other phosphoramidites and chiral auxiliaries, such as those described in U.S. Pat. Nos. 9,695,211, 9,605,019, 9,598,458, US 2013/0178612, US 20150211006, US 20170037399, WO 2017/015555, WO 2017/062862, WO 2017/160741, WO 2017/192664, WO 2017/192679, WO 2017/210647, WO 2018/098264, PCT/US18/35687, and/or PCT/US18/38835, the chiral auxiliaries and phosphoramidites of each of which is incorporated by reference.

Example 5. Example Technologies for Chirally Controlled Oligonucleotide Preparation—Example Useful Chiral Auxiliaries Among other things, the present disclosure provides technologies (e.g., chiral auxiliaries, phosphoramidites, cycles, conditions, reagents, etc.) that are useful for preparing chirally controlled internucleotidic linkages. In some embodiments, provided technologies are particularly useful for preparing certain internucleotidic linkages, e.g., non-negatively charged internucleotidic linkages, neutral internucleotidic linkages, etc., comprising P—N=, wherein P is the linkage. In some embodiments, the linkage phosphorus is trivalent. Certain example technologies (chiral auxiliaries and their preparations, phosphoramidites and their preparations, cycles, conditions, reagents, etc.) are described in the Examples herein. Among other things, such chiral auxiliaries provide milder reaction conditions, higher functional group compatibility, alternative deprotection and/or cleavage conditions, higher crude and/or purified yields, higher crude purity, higher product purity, and/or higher (or substantially the same or comparable) stereoselectivity when compared to a reference chiral auxiliary (e.g., of formula O, P, Q, R or DPSE).

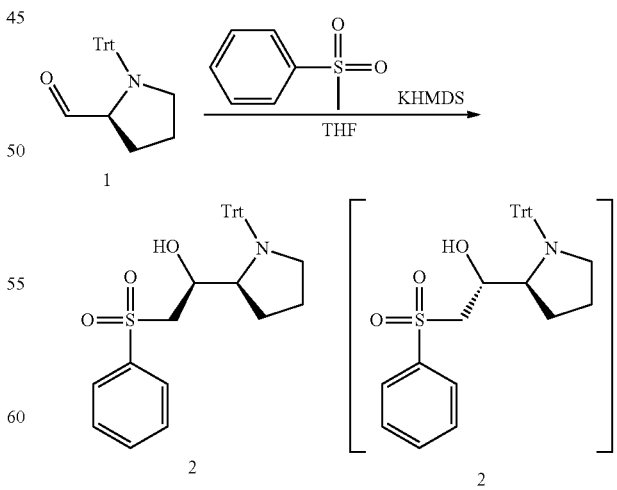

Two batches in parallel: To a solution of methylsulfonylbenzene (102.93 g, 658.96 mmol, 1.5 eq.) in THF (600 mL) was added KHMDS (1 M, 658.96 mL, 1.5 eq.) dropwise at −70° C., and warmed to −30° C. slowly over 30 min. The mixture was then cooled to −70° C. A solution of compound 1 (150 g, 439.31 mmol, 1 eq.) in THF (400 mL) was added dropwise at −70° C. The mixture was stirred at −70° C. for 3 hr. TLC (Petroleum ether: Ethyl acetate=3:1, Rf=0.1) indicated compound 1 was consumed completely and one major new spot with larger polarity was detected. Combined 2 batches. The reaction mixture was quenched by added to the sat. NH$_4$Cl (aq. 1000 mL), and then extracted with EtOAc (1000 mL×3). The combined organic layers were dried over Na$_2$SO$_4$, filtered, and concentrated under reduced pressure to give 1000 mL solution. Then added the MeOH (600 mL), concentrated under reduced pressure to give 1000 mL solution, then filtered the residue and washed with MeOH (150 mL); the residue was dissolved with THF (1000 mL) and MeOH (600 mL), then concentrated under reduced pressure to give 1000 mL solution. Then filtered to give a residue and washed with MeOH (150 mL). And repeat one more time. Compound 2 (248 g, crude) was obtained as a white solid. And the combined mother solution was concentrated under reduced pressure to give compound 3 (200 g, crude) as yellow oil.

Compound 2: $^1$H NMR (400 MHz, CHLOROFORM-d) δ=7.80 (d, J=7.5 Hz, 2H), 7.74-7.66 (m, 1H), 7.61-7.53 (m, 2H), 7.47 (d, J=7.5 Hz, 6H), 7.24-7.12 (m, 9H), 4.50-4.33 (m, 1H), 3.33 (s, 1H), 3.26 (ddd, J=2.9, 5.2, 8.2 Hz, 1H), 3.23-3.10 (m, 2H), 3.05-2.91 (m, 2H), 1.59-1.48 (m, 1H), 1.38-1.23 (m, 1H), 1.19-1.01 (m, 1H), 0.31-0.12 (m, 1H).

Preparation of Compound WV-CA-108.

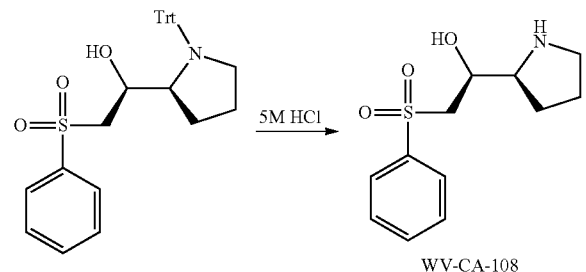

To a solution of compound 2 (248 g, 498.35 mmol, 1 eq.) in THF (1 L) was added HCl (5 M, 996.69 mL, 10 eq.). The mixture was stirred at 15° C. for 1 hr. TLC (Petroleum ether: Ethyl acetate=3:1, Rf=0.03) indicated compound 2 was consumed completely and one major new spot with larger polarity was detected. The resulting mixture was washed with MTBE (500 mL×3). The combined organic layers were back-extracted with water (100 mL). The combined aqueous layer was adjusted to pH 12 with 5M NaOH aq. and extracted with DCM (500 mL×3). The combined organic layers were dried over anhydrous Na$_2$SO$_4$, filtered and concentrated to afford a white solid. WV-CA-108 (122.6 g, crude) was obtained as a white solid.

$^1$H NMR (400 MHz, CHLOROFORM-d) δ=7.95 (d, J=7.5 Hz, 2H), 7.66 (t, J=7.5 Hz, 1H), 7.57 (t, J=7.7 Hz, 2H), 4.03 (ddd, J=2.6, 5.3, 8.3 Hz, 1H), 3.37-3.23 (m, 2H), 3.20-3.14 (m, 1H), 2.91-2.75 (m, 3H), 2.69 (br s, 1H), 1.79-1.54 (m, 5H); $^{13}$C NMR (101 MHz, CHLOROFORM-d) δ=139.58, 133.83, 129.28, 127.90, 67.90, 61.71, 59.99, 46.88, 25.98, 25.84; LCMS [M+H]f: 256.1. LCMS purity: 100%. SFC 100% purity.

Preparation of Compound WV-CA-237.

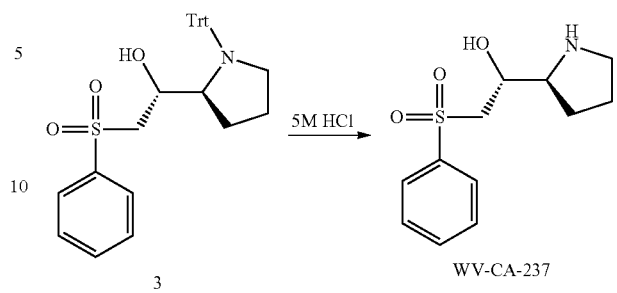

To a solution of compound 3 (400.00 g, 803.78 mmol) in THF (1.5 L) was added HCl (5 M, 1.61 L). The mixture was stirred at 15° C. for 2 hr. TLC indicated compound 3 was consumed completely and one major new spot with larger polarity was detected. The resulting mixture was washed with MTBE (500 mL×3). The combined aqueous layer was adjusted to pH 12 with 5M NaOH aq. and extracted with DCM (500 mL×1) and EtOAc (1000 mL×2). The combined organic layers were dried over anhydrous Na$_2$SO$_4$, filtered, and concentrated to afford as a brown solid. WV-CA-237 (100 g, crude) was obtained as a brown solid.

The residue was purified by column chromatography (SiO$_2$, Petroleum ether/Ethyl acetate=3/1 to Ethyl acetate: Methanol=1: 2) to give 24 g crude. Then the 4 g residue was purified by prep-HPLC (column: Phenomenex luna C18 250×50 mm×10 um; mobile phase: [water (0.05% HCl)-ACN]; B %: 2%→20%, 15 min) to give desired compound (2.68 g, yield 65%,) as a white solid. WV-CA-237 (2.68 g) was obtained as a white solid. WV-CA-237: $^1$H NMR (400 MHz, CHLOROFORM-d) δ=7.98-7.88 (m, 2H), 7.68-7.61 (m, 1H), 7.60-7.51 (m, 2H), 4.04 (dt, J=2.4, 5.6 Hz, 1H), 3.85 (ddd, J=3.1, 5.6, 8.4 Hz, 1H), 3.37-3.09 (m, 3H), 2.95-2.77 (m, 3H), 1.89-1.53 (m, 4H), 1.53-1.39 (m, 1H); $^{13}$C NMR (101 MHz, CHLOROFORM-d) δ=139.89, 133.81, 133.70, 129.26, 129.16, 128.05, 127.96, 68.20, 61.77, 61.61, 61.01, 60.05, 46.67, 28.02, 26.24, 25.93; LCMS [M+H]f:256.1. LCMS purity: 80.0%. SFC dr=77.3: 22.7.

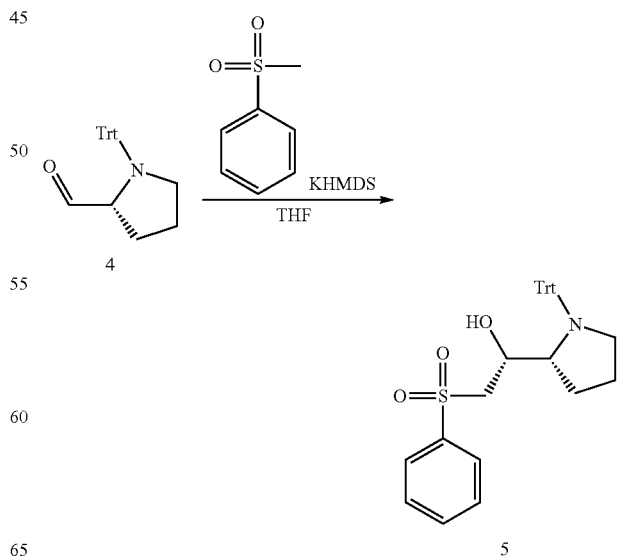

To a solution of compound 4 (140 g, 410.02 mmol) in THF (1400 mL) was added methylsulfonylbenzene (96.07 g, 615.03 mmol), then added KHMDS (1 M, 615.03 mL) in 0.5 hr. The mixture was stirred at -70~-40° C. for 3 hr. TLC indicated compound 4 was consumed and one new spot formed. The reaction mixture was quenched by addition sat. NH$_4$Cl aq. 3000 mL at 0° C., and then diluted with EtOAc (3000 mL) and extracted with EtOAc (2000 mL×3). Dried over Na$_2$SO$_4$, filtered, and concentrated under reduced pressure to give a residue. To the crude was added THF (1000 mL) and MeOH (1500 mL), concentrated under reduced pressure at 45° C. until about 1000 mL residue remained, filtered the solid. Repeat 3 times. Compound 5 (590 g, 72.29% yield) was obtained as a yellow solid. $^1$H NMR (400 MHz, CHLOROFORM-d) δ=7.81 (d, J=7.5 Hz, 2H), 7.75-7.65 (m, 1H), 7.62-7.53 (m, 2H), 7.48 (br d, J=7.2 Hz, 6H), 7.25-7.11 (m, 9H), 4.50-4.37 (m, 1H), 3.31-3.11 (m, 3H), 3.04-2.87 (m, 2H), 1.60-1.48 (m, 1H), 1.39-1.24 (m, 1H), 1.11 (dtd, J=4.5, 8.8, 12.8 Hz, 1H), 0.32-0.12 (m, 1H).
Preparation of Compound WV-CA-236.

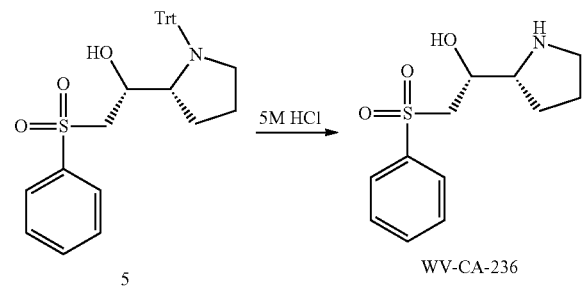

5    WV-CA-236

To a solution of compound 5 (283 g, 568.68 mmol) in THF (1100 mL) was added HCl (5 M, 1.14 L). The mixture was stirred at 25° C. for 2 hr. TLC indicated compound 5 was consumed and two new spots formed. The reaction mixture was washed with MTBE (1000 mL×3), then the aqueous phase was basified by addition NaOH (5M) until pH=12 at 0° C., and then extracted with DCM (1000 mL×3) to give a residue, dried over Na$_2$SO$_4$, filtered, and concentrated under reduced pressure to give a residue. Compound WV-CA-236 (280 g, 1.10 mol, 96.42% yield) was obtained as a yellow solid.

The crude product was added HCl/EtOAc (1400 mL, 4M) at 0° C., 2 hr later, filtered the white solid and washed the solid with MeOH (1000 mL×3). LCMS showed the solid contained another peak (MS=297). Then the white solid was added H$_2$O (600 mL) and washed with DCM (300 mL×3). The aqueous phase was added NaOH (5 M) until pH=12. Then diluted with DCM (800 mL) and extracted with DCM (800 mL×4). The combined organic layer was dried over Na$_2$SO$_4$, filtered, and concentrated under reduced pressure to give the product. Compound WV-CA-236 (280 g) was obtained as a yellow solid. $^1$H NMR (400 MHz, CHLOROFORM-d) δ=8.01-7.89 (m, 2H), 7.69-7.62 (m, 1H), 7.61-7.51 (m, 2H), 4.05 (ddd, J=2.8, 5.2, 8.4 Hz, 1H), 3.38-3.22 (m, 2H), 3.21-3.08 (m, 1H), 2.95-2.72 (m, 4H), 1.85-1.51 (m, 4H); $^{13}$C NMR (101 MHz, CHLOROFORM-d) δ=139.75, 133.76, 129.25, 127.94, 67.57, 61.90, 60.16, 46.86, 25.86. LCMS [M+H]+: 256. LCMS purity: 95.94. SFC purity: 99.86%.

Example 6. Example Technologies for Chirally Controlled Oligonucleotide Preparation—Example Useful Phosphoramidites Among other things, the present disclosure provides phosphoramidites useful for oligonucleotide synthesis. In some embodiments, provided phosphoramidites are particularly useful for preparation of chirally controlled internucleotidic linkages. In some embodiments, provided phosphoramidites are particularly useful for preparing chirally controlled internucleotidic linkages, e.g., non-negatively charged internucleotidic linkages or neutral internucleotidic linkages, etc., that comprise P—N=. In some embodiments, the linkage phosphorus is trivalent. In some embodiments, the linkage phosphorus is pentavalent.

General Procedure I for Chloroderivative: In some embodiments, in an example procedure, a chiral auxiliary (174.54 mmol) was dried by azeotropic evaporation with anhydrous toluene (80 mL×3) at 35° C. in a rota-evaporator and dried under high vacuum for overnight. A solution of this dried chiral auxiliary (174.54 mmol) and 4-methylmorpholine (366.54 mmol) dissolved in anhydrous THF (200 mL) was added to an ice-cooled (isopropyl alcohol-dry ice bath) solution of trichlorophosphine (37.07 g, 16.0 mL, 183.27 mmol) in anhydrous THF (150 mL) placed in three neck round bottomed flask through cannula under Argon (start Temp: -10.0° C., Max: temp 0° C., 28 min addition) and the reaction mixture was warmed at 15° C. for 1 hr. After that the precipitated white solid was filtered by vacuum under argon using airfree filter tube (Chemglass: Filter Tube, 24/40 Inner Joints, 80 mm OD Medium Frit, Airfree, Schlenk). The solvent was removed with rota-evaporator under argon at low temperature (25° C.) and the crude semi-solid obtained was dried under vacuum overnight (~15 h) and was used for the next step directly.

General Procedure I for Chloroderivative: In some embodiments, in an example procedure, a chiral auxiliary (174.54 mmol) was dried by azeotropic evaporation with anhydrous toluene (80 mL×3) at 35° C. in a rota-evaporator and dried under high vacuum for overnight. A solution of this dried chiral auxiliary (174.54 mmol) and 4-methylmorpholine (366.54 mmol) dissolved in anhydrous THF (200 mL) was added to an ice-cooled (isopropyl alcohol-dry ice bath) solution of trichlorophosphine (37.07 g, 16.0 mL, 183.27 mmol) in anhydrous THF (150 mL) placed in three neck round bottomed flask through cannula under Argon (start Temp: -10.0° C., Max: temp 0° C., 28 min addition) and the reaction mixture was warmed at 15° C. for 1 hr. After that the precipitated white solid was filtered by vacuum under argon using airfree filter tube (Chemglass: Filter Tube, 24/40 Inner Joints, 80 mm OD Medium Frit, Airfree, Schlenk). The solvent was removed with rota-evaporator under argon at low temperature (25° C.) and the crude semi-solid obtained was dried under vacuum overnight (~15 h) and was used for the next step directly.

General Procedure III for Coupling: In some embodiments, in an example procedure, a nucleoside (9.11 mmol) was dried by co-evaporation with 60 mL of anhydrous toluene (60 mL×2) at 35° C. and dried under high vacuum for overnight. The dried nucleoside was dissolved in dry THF (78 mL), followed by the addition of triethylamine (63.80 mmol) and then cooled to -5° C. under Argon (for 2'F-dG/2'OMe-dG case 0.95 eq of TMS-Cl used). The THF solution of the crude (made from general procedure I (or) II, 14.57 mmol), was added through cannula over 3 min then gradually warmed to room temperature. After 1 hr at room temperature, TLC indicated conversion of SM to product (total reaction time 1 h), the reaction mixture was then quenched with H$_2$O (4.55 mmol) at 0° C., and anhydrous MgSO$_4$ (9.11 mmol) was added and stirred for 10 min. Then the reaction mixture was filtered under argon using airfree filter tube, washed with THF, and dried under rotary evaporation at 26° C. to afford white crude solid product, which was dried under high vacuum overnight. The crude product was purified by ISCO-Combiflash system (rediSep high performance silica column pre-equilibrated with Acetonitrile) using Ethyl acetate/Hexane with 1% TEA as a solvent (compound eluted at 100% EtOAc/Hexanes/1% Et$_3$N) (for 2'F-dG case Acetonitrile/Ethyl acetate with 1% TEA used). After evaporation of column fractions pooled together, the residue was dried under high vacuum to afford the product as a white solid.

Preparation of Amidites (1030-1039).

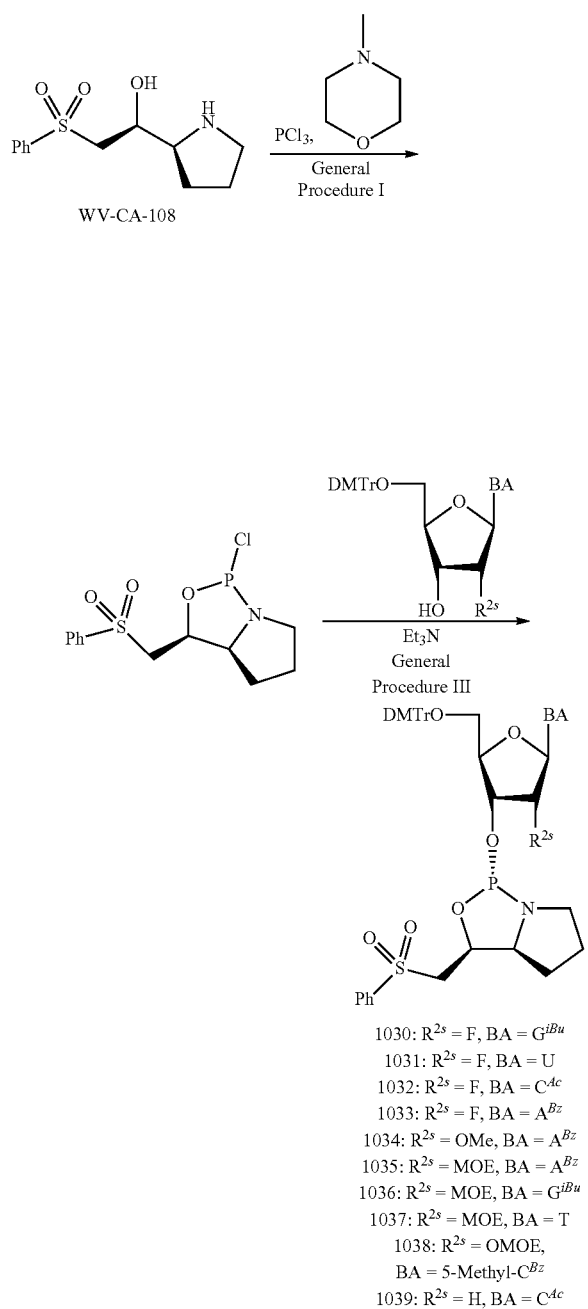

1030: R$^{2s}$ = F, BA = G$^{iBu}$
1031: R$^{2s}$ = F, BA = U
1032: R$^{2s}$ = F, BA = C$^{Ac}$
1033: R$^{2s}$ = F, BA = A$^{Bz}$
1034: R$^{2s}$ = OMe, BA = A$^{Bz}$
1035: R$^{2s}$ = MOE, BA = A$^{Bz}$
1036: R$^{2s}$ = MOE, BA = G$^{iBu}$
1037: R$^{2s}$ = MOE, BA = T
1038: R$^{2s}$ = OMOE, BA = 5-Methyl-C$^{Bz}$
1039: R$^{2s}$ = H, BA = C$^{Ac}$ Preparation of 1030: General Procedure I followed by General Procedure III used. Off-white foamy solid. Yield: (73%). $^{31}$P NMR (162 MHz, CDCl$_3$) δ 153.32. (ES) m z Calculated for C$_{47}$H$_{50}$FN$_6$O$_{10}$PS: 940.98 [M]$^+$, Observed: 941.78 [M+H]$^+$.

Preparation of 1031: General Procedure I followed by General Procedure III used. Off-white foamy solid. Yield: (78%). $^{31}$P NMR (162 MHz, CDCl$_3$) δ 153.62. (ES) m z Calculated for C$_{42}$H$_{43}$FN$_3$O$_{10}$PS: 831.85 [M]$^+$, Observed: 870.58 [M+K]$^+$.

Preparation of 1032: General Procedure I followed by General Procedure III used. Off-white foamy solid. Yield: (68%). $^{31}$P NMR (162 MHz, CDCl$_3$) δ 153.95. (ES) m z Calculated for C$_{44}$H$_{46}$FN$_4$O$_{10}$PS: 872.26 [M]$^+$, Observed: 873.62 [M+H]$^+$.

Preparation of 1033: General Procedure I followed by General Procedure III used. white foamy solid. Yield: (87%). $^{31}$P NMR (162 MHz, CDCl$_3$) δ 151.70. (ES) m z Calculated for C$_{50}$H$_{48}$FN$_6$O$_9$PS: 958.29 [M]$^+$, Observed: 959.79, 960.83 [M+H]$^+$.

Preparation of 1034: General Procedure I followed by General Procedure III used. Off-white foamy solid. Yield: (65%). $^{31}$P NMR (162 MHz, CDCl$_3$) δ 154.80. (ES) m z Calculated for C$_{51}$H$_{51}$N$_6$O$_{10}$PS: 971.31 [M]$^+$, Observed: 971.81 [M+H]$^+$.

Preparation of 1035: General Procedure I followed by General Procedure III used. Off-white foamy solid. Yield: (76%). $^{31}$P NMR (162 MHz, CDCl$_3$) δ 156.50. (ES) m z Calculated for C$_{53}$H$_{55}$N$_6$O$_{11}$PS: 1014.33 [M]$^+$, Observed: 1015.81 [M+H]$^+$.

Preparation of 1036: General Procedure I followed by General Procedure III used. Off-white foamy solid. Yield: (78%). $^{31}$P NMR (162 MHz, CDCl$_3$) δ 156.40. (ES) m z Calculated for C$_{50}$H$_{57}$N$_6$O$_{12}$PS: 996.34 [M]$^+$, Observed: 997.90 [M+H]$^+$.

Preparation of 1037: General Procedure I followed by General Procedure III used. Off-white foamy solid. Yield: (73%). $^{31}$P NMR (162 MHz, CDCl$_3$) δ 154.87. (ES) m z Calculated for C$_{46}$H$_{52}$N$_3$O$_{12}$PS: 901.30 [M]$^+$, Observed: 940.83 [M+K]$^+$.

Preparation of 1038: General Procedure I followed by General Procedure III used. Off-white foamy solid. Yield: (75%). $^{31}$P NMR (162 MHz, CDCl$_3$) δ 154.94. (ES) m z Calculated for C$_{53}$H$_{57}$N$_4$O$_{12}$PS: 1004.34 [M]$^+$, Observed: 1005.86 [M+H]$^+$.

Preparation of 1039: General Procedure I followed by General Procedure III used. Off-white foamy solid. Yield: (80%). $^{31}$P NMR (162 MHz, CDCl$_3$) δ 153.52. (ES) m z Calculated for C$_{44}$H$_{47}$N$_4$O$_{10}$PS: 854.28 [M]$^+$, Observed: 855.41 [M+H]$^+$.

Preparation of Amidites (1040-1049).

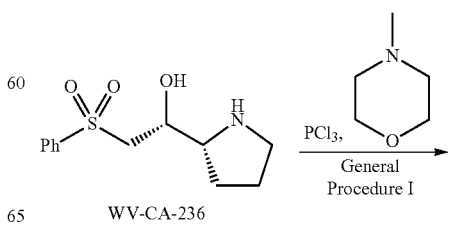

WV-CA-236

-continued

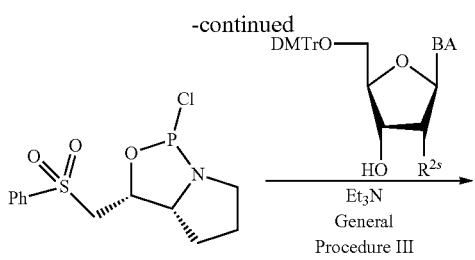

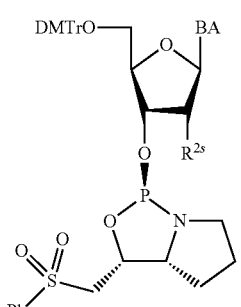

1040: $R^{2s}$ = F, BA = $G^{iBu}$
1041: $R^{2s}$ = F, BA = U
1042: $R^{2s}$ = F, BA = $C^{Ac}$
1043: $R^{2s}$ = F, BA = $A^{Bz}$
1044: $R^{2s}$ = OMe, BA = $A^{Bz}$
1045: $R^{2s}$ = OMOE, BA = $A^{Bz}$
1046: $R^{2s}$ = OMOE, BA = $G^{iBu}$
1047: $R^{2s}$ = OMOE, BA = T
1048: $R^{2s}$ = OMOE, BA = 5-Methyl-$C^{Bz}$
1049: $R^{2s}$ = H, BA = $C^{Ac}$ Preparation of 1040: General Procedure I followed by General Procedure III used. Off-white foamy solid. Yield: (78%). $^{31}$P NMR (162 MHz, CDCl$_3$) δ 157.80. (ES) m z Calculated for $C_{47}H_{50}FN_6O_{10}PS$: 940.98 [M]$^+$, Observed: 941.68 [M+H]$^+$.

Preparation of 1041: General Procedure I followed by General Procedure III used. Off-white foamy solid. Yield: (78%). $^{31}$P NMR (162 MHz, CDCl$_3$) δ 157.79. (ES) m z Calculated for $C_{42}H_{43}FN_3O_{10}PS$: 831.85 [M]$^+$, Observed: 870.68 [M+K]f.

Preparation of 1042: General Procedure I followed by General Procedure III used. Off-white foamy solid. Yield: (78%). $^{31}$P NMR (162 MHz, CDCl$_3$) δ 158.07. (ES) m z Calculated for $C_{44}H_{46}FN_4O_{10}PS$: 872.26 [M]$^+$, Observed: 873.62 [M+H]$^+$.

Preparation of 1043: General Procedure I followed by General Procedure III used. white foamy solid. Yield: (86%). $^{31}$P NMR (162 MHz, CDCl$_3$) δ 156.48. (ES) m z Calculated for $C_{50}H_{48}FN_6O_9PS$: 958.29 [M]$^+$, Observed: 959.79, 960.83 [M+H]$^+$.

Preparation of 1044: General Procedure I followed by General Procedure III used. Off-white foamy solid. Yield: (65%). $^{31}$P NMR (162 MHz, CDCl$_3$) δ 154.80. (ES) m z Calculated for $C_{51}H_{51}N_6O_{11}PS$: 971.31 [M]$^+$, Observed: 971.81 [M+H]$^+$.

Preparation of 1045: General Procedure I followed by General Procedure III used. Off-white foamy solid. Yield: (77%). $^{31}$P NMR (162 MHz, CDCl$_3$) δ 154.74. (ES) m z Calculated for $C_{53}H_{55}N_6O_{11}PS$: 1014.33 [M]$^+$, Observed: 1015.81 [M+H]$^+$.

Preparation of 1046: General Procedure I followed by General Procedure III used. Off-white foamy solid. Yield: (76%). $^{31}$P NMR (162 MHz, CDCl$_3$) δ 155.05. (ES) m z Calculated for $C_{50}H_{57}N_6O_{12}PS$: 996.34 [M]$^+$, Observed: 997.90 [M+H]$^+$.

Preparation of 1047: General Procedure I followed by General Procedure III used. Off-white foamy solid. Yield: (75%). $^{31}$P NMR (162 MHz, CDCl$_3$) δ 155.44. (ES) m z Calculated for $C_{46}H_{52}N_3O_{12}PS$: 901.30 [M]$^+$, Observed: 940.83 [M+K]$^+$.

Preparation of 1048: General Procedure I followed by General Procedure III used. Off-white foamy solid. Yield: (73%). $^{31}$P NMR (162 MHz, CDCl$_3$) δ 155.96. (ES) m z Calculated for $C_{53}H_{57}N_4O_{12}PS$: 1004.34 [M]$^+$, Observed: 1005.86 [M+H]$^+$.

Preparation of 1049: General Procedure I followed by General Procedure III used. Off-white foamy solid. Yield: (80%). $^{31}$P NMR (162 MHz, CDCl$_3$) δ 156.37. (ES) m z Calculated for $C_{44}H_{47}N_4O_{10}PS$: 854.28 [M]$^+$, Observed: 855.31 [M+H]$^+$.

Example 7. Example Technologies for Chirally Controlled Oligonucleotide Preparation—Example Cycles, Conditions and Reagents for Oligonucleotide Synthesis In some embodiments, the present disclosure provides technologies (e.g., reagents, solvents, conditions, cycle parameters, cleavage methods, deprotection methods, purification methods, etc.) that are particularly useful for preparing chirally controlled internucleotidic linkages. In some embodiments, such internucleotidic linkages, e.g., non-negatively charged internucleotidic linkages or neutral internucleotidic linkages, etc., comprise P—N=, wherein P is the linkage phosphorus. In some embodiments, the linkage phosphorus is trivalent. In some embodiments, the linkage phosphorus is pentavalent. As demonstrated herein, technologies of the present disclosure can provide mild reaction conditions, high functional group compatibility, alternative deprotection and/or cleavage conditions, high crude and/or purified yields, high crude purity, high product purity, and/or high stereoselectivity.

In some embodiments, a cycle for preparing natural phosphate linkages comprises or consists of deprotection (e.g., detritylation), coupling, oxidation (e.g., using I$_2$/Pyr/Water or other suitable methods available in the art) and capping (e.g., cap 2 described herein or other suitable methods available in the art). An example cycle is depicted below, wherein B1 and B2 are independently nucleobases. As appreciated by those skilled in the art, various modifications, e.g., sugar modifications, base modifications, etc. are compatible and may be included.

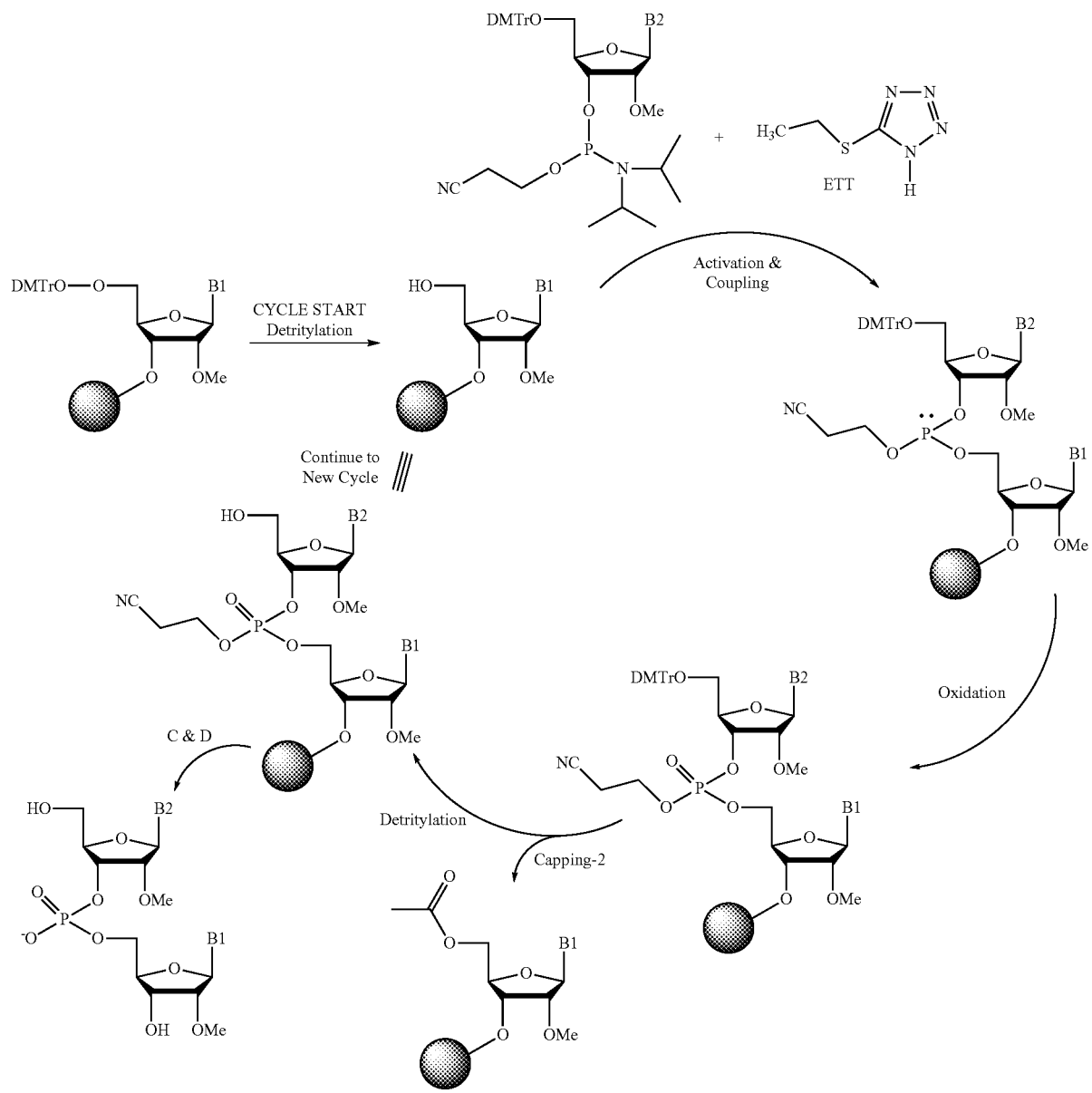

In some embodiments, a cycle for preparing non-natural phosphate linkages (e.g., phosphorothioate internucleotidic linkages) comprises or consists of deprotection (e.g., detritylation), coupling, a first capping (e.g., capping-1 as described herein), modification (e.g., thiolation using XH or other suitable methods available in the art), and a second capping (e.g., capping-2 as described herein or other suitable methods available in the art). An example cycle is depicted below, wherein B1 and B2 are independently nucleobases. As appreciated by those skilled in the art, various modifications, e.g., sugar modifications, base modifications, etc. are compatible and may be included. In some embodiments, a cycle using a DPSE chiral auxiliary is referred to as a DPSE cycle or DPSE amidite cycle.

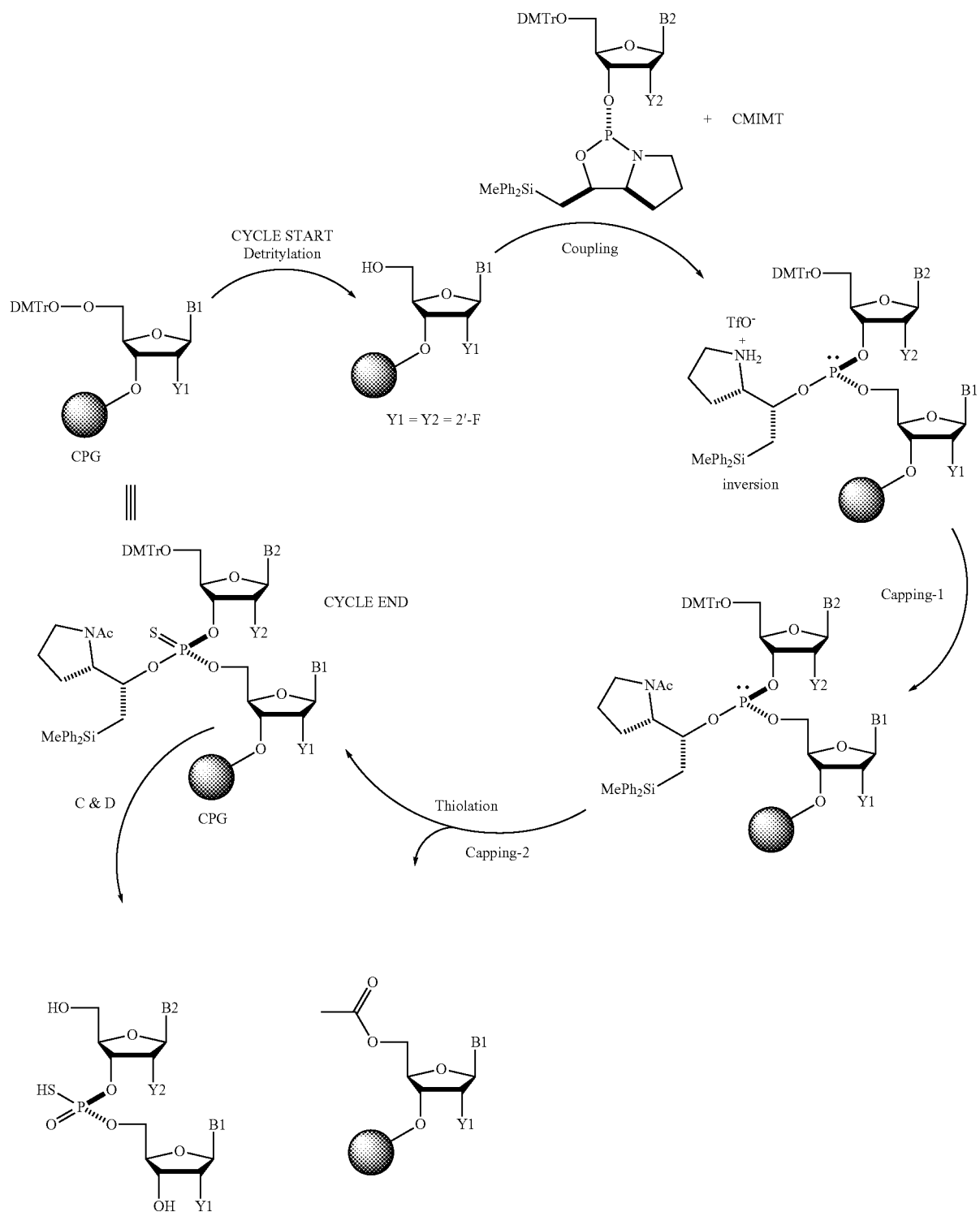

In some embodiments, a cycle for preparing non-natural phosphate linkages (e.g., certain non-negatively charged internucleotidic linkages, neutral internucleotidic linkages, etc.) or a salt form thereof, comprises or consists of deprotection (e.g., detritylation), coupling, a first capping (e.g., capping-1 as described herein), modification (e.g., using ADIH or other suitable methods available in the art), and a second capping (e.g., capping-2 as described herein or other suitable methods available in the art). An example cycle is depicted below, wherein B1 and B2 are independently nucleobases. As appreciated by those skilled in the art, various modifications, e.g., sugar modifications, base modifications, etc. are compatible and may be included. In some embodiments, a cycle using a PSM chiral auxiliary is referred to as a PSM cycle or PSM amidite cycle.

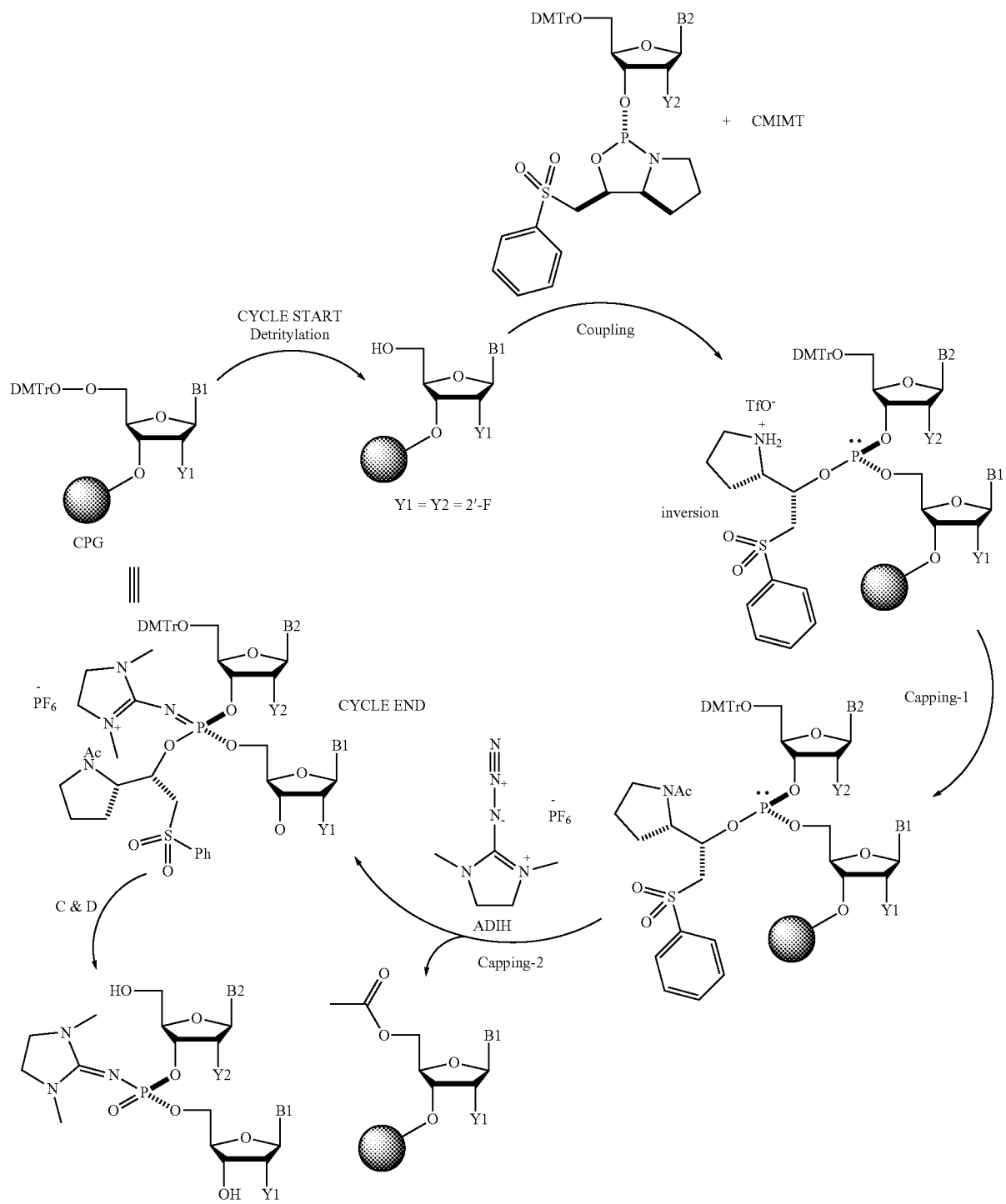

Various cleavage and deprotection methods may be utilized in accordance with the present disclosure. In some embodiments, as appreciated by those skilled in the art, parameters of cleavage and deprotection (e.g., bases, solvents, temperatures, equivalents, time, etc.) can be adjusted in view of, e.g., structures of DMD oligonucleotides to be prepared (e.g., nucleobases, sugars, internucleotidic linkages, and modifications/protections thereof), solid supports, reaction scales, etc. In some embodiments, cleavage and deprotection comprise one, or two or more, individual steps. For example, in some embodiments, a two-step cleavage and deprotection is utilized. In some embodiments, a cleavage and deprotection step comprises a fluoride-containing reagent (e.g., TEA-HF, optionally buffered with additional bases such as TEA) in a suitable solvent (e.g., DMSO/H$_2$O) at a suitable amount (e.g., about 100 or more (e.g., 100±5) mL/mmol) and is performed at a suitable temperature (e.g., about 0-100, 0-80, 0-50, 0-40, 0-30, 0, 10, 20, 30, 40, 50, 60, 70, 80, 90 or 100° C. (e.g., in one example, 27±2° C.)) for a suitable period of time (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or more hours (e.g., in one example, 6±0.5 h)). In some embodiments, a cleavage and deprotection step comprises a suitable base (e.g., $NR_3$) in a suitable solvent (e.g., water) (e.g., conc. $NH_4OH$) at a suitable amount (e.g., about 200 or more (e.g., 200±5) mL/mmol) and is performed at a suitable temperature (e.g., about 0-100, 0-80, 0-50, 0-40, 0-30, 0, 10, 20, 30, 40, 50, 60, 70, 80, 90 or 100° C. (e.g., in one example, 37±2° C.)) for a suitable period of time (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or more hours (e.g., in one example, 24±1 h)). In some embodiments, cleavage and deprotection comprises or consists of two steps, wherein one step (e.g., step 1) is 1×TEA-HF in $DMSO/H_2O$, 100±5 mL/mmol, 27±2° C. and 6±0.5 h, and the other step (e.g., step 2) is conc. $NH_4OH$, 200±5 mL/mmol, 37±2° C. and 24±1 h. Certain examples of cleavage and deprotection processes are described here.

As appreciated by those skilled in the art, DMD oligonucleotide synthesis is often performed on solid support. Many types of solid support are commercially available and/or can be otherwise prepared/obtained and can be utilized in accordance with the present disclosure. In some embodiments, a solid support is CPG. In some embodiments, a solid support is NittoPhase HL. Types and sizes of solid support can be selected based on desired applications, and in some cases, for a specific use one type of solid support may perform better than the other. In some embodiments, it was observed that for certain preparations CPG can deliver higher crude yields and/or purities compared to certain polymer solid supports such as NittoPhase HL.

Amidites are typically dissolved in solvents at suitable concentrations. In some embodiments, amidites are dissolved in ACN. In some embodiments, amidites are dissolved in a mixture of two or more solvents. In some embodiments, amidites are dissolved in a mixture of ACN and IBN (e.g., 20% ACN/80% IBN). Various concentrations of amidites may be utilized, and may be adjusted in view of specific conditions (e.g., solid support, DMD oligonucleotides to be prepared, reaction times, scales, etc.). In some embodiments, a concentration of about 0.01-0.5, 0.05-0.5, 0.1-0.5, 0.05, 0.1, 0.15, 0.2, 0.25, 0.3, 0.35, 0.4, 0.45 or 0.5 M is utilized. In some embodiments, a concentration of about 0.2 M is utilized. In many embodiments, amidite solutions are dried. In some embodiments, 3 A molecular sieves are utilized to dry amidite solutions (or keep amidite solutions dry). In some embodiments, molecular sieves are utilized at about 15-20% v/v.

Various equivalents of amidites may be useful for DMD oligonucleotide synthesis. As those skilled in the art will appreciate, equivalents of amidites can be adjusted in view of specific conditions (e.g., solid support, DMD oligonucleotides to be prepared, reaction times, scales, etc.), and the same or different equivalents may be utilized during synthesis. In some embodiments, equivalents of amidites are about 1, 1.5, 2, 2.5, 3, 3.5, 4, 4.5, 5 or more. In some embodiments, a suitable equivalent is about 2. In some embodiments, a suitable equivalent is about 2.5. In some embodiments, a suitable equivalent is about 3. In some embodiments, a suitable equivalent is about 3.5. In some embodiments, a suitable equivalent is about 4.

A number of activators are available in the art and may be utilized in accordance with the present disclosure. In some embodiments, an activator is ETT. In some embodiments, an activator is CMIMT. In some embodiments, CMIMT is utilized for chirally controlled synthesis. As appreciated by those skilled in the art, the same or different activators may be utilized for different amidites, and may be utilized at different amounts. In some embodiments, activators are utilized at about 40-100%, e.g., 40%, 50%, 60%, 70%, 80% or 90% delivery. In some embodiments, a delivery is about 60% (e.g., for ETT). In some embodiments, a delivery is about 70% (e.g., for CMIMT). In some embodiments, molar ratio of activator/amidite is about 1, 2, 3, 4, 5, 6, 7, 8, 9, 10 or more. In some embodiments, a molar ratio is about 3-6. In some embodiments, a molar ratio is about 1. In some embodiments, a molar ratio is about 2. In some embodiments, a molar ratio is about 3. In some embodiments, a molar ratio is about 4. In some embodiments, a molar ratio is about 5. In some embodiments, a molar ratio is about 6. In some embodiments, a molar ratio is about 7. In some embodiments, a molar ratio is about 8. In some embodiments, a molar ratio is about 9. In some embodiments, a molar ratio is about 10. In some embodiments, a molar ratio is about 2-5, 2-4 or 3-4 (e.g., for ETT). In some embodiments, a molar ratio is about 3.7 (e.g., for ETT). In some embodiments, a molar ratio is about 3-8, 4-8, 4-7, 4-6, 5-7, 5-8 or 5-6 (e.g., for CMIMT). In some embodiments, a molar ratio is about 5.8 (e.g., for CMIMT).

As appreciated by those skilled in the art, various suitable flowrates and reaction times may be utilized for DMD oligonucleotide synthesis, and may be adjusted according to DMD oligonucleotides to be prepared, scales, synthetic setups, etc. In some embodiments, a recycle flow rate utilized for synthesis is about 200 cm/h. In some embodiments, a recycle time is about 1-10 minutes. In some embodiments, a recycle time is about 8 minutes. In some embodiments, a recycle time is about 10 minutes.

Many technologies are available to modify P(III) linkages, e.g., after coupling. For example, various methods are available to convert a P(III) linkage to a P(V) P(═O)-type linkage, e.g., via oxidation. In some embodiments, $I_2$/Pyr/$H_2O$ is utilized. Similarly, many methods are available to convert a P(III) linkage to a P(V) P(═S)-type linkage, e.g., via sulfurization. In some embodiments, as illustrated herein, XH is utilized as a thiolation reagent. Technologies for converting P(III) linkages to P(V) P(═N—)-type linkages are also widely available and can be utilized in accordance with the present disclosure. In some embodiments, as illustrated herein ADIH is employed. Suitable reaction parameters are described herein. In some embodiments, ADIH is used at a concentration of about 0.01-0.5, 0.05-0.5, 0.1-0.5, 0.05, 0.1, 0.15, 0.2, 0.25, 0.3, 0.35, 0.4, 0.45 or 0.5 M. In some embodiments, concentration of ADIH is about 0.25 M. In some embodiments, concentration of ADIH is about 0.3 M. In some embodiments, ADIH is utilized at about 1-50, 1-40, 1-30, 1-25, 1-20, 1-10, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45 or 50 or more equivalent. In some embodiments, equivalent of ADIH is about 7.5. In some embodiments, equivalent of ADIH is about 10. In some embodiments, equivalent of ADIH is about 15. In some embodiments, equivalent of ADIH is about 20. In some embodiments, equivalent of ADIH is about 23. In some embodiments, equivalent of ADIH is about 25. In some embodiments, equivalent of ADIH is about 30. In some embodiments, equivalent of ADIH is about 35. In some embodiments, one experiment, ADIH was utilized at 15.2 equivalent, and 15 min contact time. In some embodiments, depending on amidites, concentrations, equivalents, contact times, etc. of reagents, e.g., ADIH, may be adjusted.

Technologies of the present disclosure are suitable for preparation at various scales. In some embodiments, synthesis are performed at hundreds of umol or more. In some embodiments, a scale is about 200 umol. In some embodiments, a scale is about 300 umol. In some embodiments, a scale is about 400 umol. In some embodiments, a scale is about 500 umol. In some embodiments, a scale is about 550 umol. In some embodiments, a scale is about 600 umol. In some embodiments, a scale is about 650 umol. In some embodiments, a scale is about 700 umol. In some embodiments, a scale is about 750 umol. In some embodiments, a scale is about 800 umol. In some embodiments, a scale is about 850 umol. In some embodiments, a scale is about 900 umol. In some embodiments, a scale is about 950 umol. In some embodiments, a scale is about 1, 2, 3, 4, 5, 6, 7, 8, 9, 10, 11, 12, 13, 14, 15, 16, 17, 18, 19, 20, 21, 22, 23, 24, or 25, or more mmol. In some embodiments, a scale is about 1 mmol or more. In some embodiments, a scale is about 2 mmol or more. In some embodiments, a scale is about 5 mmol or more. In some embodiments, a scale is about 10 mmol or more. In some embodiments, a scale is about 15 mmol or more. In some embodiments, a scale is about 20 mmol or more. In some embodiments, a scale is about 25 mmol or more.

In some embodiments, observed yields were 85-90 OD/umol (e.g., 85,000 OD/mmol for a 10.2 mmol synthesis, with 58.4% crude purity (% FLP)).

Technologies of the present disclosure, among other things, can provide various advantages when utilized for preparing DMD oligonucleotides comprising chirally controlled internucleotidic linkages, e.g., those comprising P—N= wherein P is a linkage phosphorus. For example, as demonstrated herein, technologies of the present disclosure can provide high crude purities and yields (e.g., in many embodiments, about 55-60% full-length product for a 20-mer DMD oligonucleotide) with minimal amount of shorter DMD oligonucleotides (e.g., from incomplete coupling, decomposition, etc.). Such high crude yields and/or purities, among other things, can significantly reduce downstream purification and can significantly reduce production cost and cost of goods, and in some embodiments, greatly facilitate or make possible large scale commercial production, clinical trials and/or commercial sales.

Example Procedure for Preparing Chirally Controlled DMD Oligonucleotide Compositions —WV-13864.

Described below are example procedures for preparing WV-13864 using controlled pore glass (CPG) low bulk density solid support(e.g., 2'-fC (acetyl) via CNA linker CPG (600A LBD)). Useful phosphoramidites include 5'-ODMTr-2'—F-dA(N$_6$-Bz)-(L)-DPSE phosphoramidite, 5'-ODMTr-2'—F-dC(N4-Ac)-(L)-DPSE phosphoramidite, 5'-ODMTr-2'—F-dG(N2-iBu)-(L)-DPSE phosphoramidite, 5'-ODMTr-2'—F-dU-(L)-DPSE phosphoramidite, 5'-ODMTr-2'-OMe-G(N$^2$-iBu)-(L)-DPSE phosphoramidite, 5'-ODMTr-2'—F-dC(N$_4$-Ac)-(L)-PSM phosphoramidite, 5'-ODMTr-2'—F-dG(N2-iBu)-(L)-PSM phosphoramidite, 5'-DMT-2'-OMe-A (Bz)-β-Cyanoethyl phosphoramidite, and 5'-DMT-2'-OMe-C(Ac)-β-Cyanoethyl phosphoramidite.

0.1 M Xanthane hydride solution (XH) was used for thiolation. Neutral PN linkages were formed utilizing 0.3 M of 2-azido-1,3-dimethyl-imidazolinium hexafluorophosphate (ADIH) in acetonitrile. Oxidation solution was 0.04-0.06 M iodine in pyridine/water, 90/10, v/v. Cap A was N-Methylimidazole in acetonitrile, 20/80, v/v. Cap B was acetic anhydride/2,6-Lutidine/Acetonitrile, 20/30/50, v/v/v. Deblocking was performed using 3% dichloroacetic acid in toluene. NH$_4$OH used was 28-30% concentrated ammonium hydroxide.

Detritylation.

To initiate the synthesis, the 5'-ODMTr-2'—F-dC(N4—Ac)-CPG solid support was subjected to acid catalyzed removal of the DMTr protecting group from the 5'-hydroxyl by treatment with 3% (DCA) in toluene. The DMTr removal step was usually visualized with strong red or orange color and can be monitored by UV watch command at the wavelength of 436 nm.

DMTr removal can be repeated at the beginning of a synthesis cycle. In every case, following detritylation, the support-bound material was washed with acetonitrile in preparation for the next step of the synthesis.

Coupling.

Amidites were dissolved either in acetonitrile (ACN) or in 20% isobutyronitrile (IBN)/80% ACN at a concentration of 0.2M without density correction. The solutions were dried over molecular sieves (3A) not less than 4 h before use (15-20%, v/v).

| Amidite | Solvent | Concentration | MS3Å |
|---|---|---|---|
| 5'-ODMTr-2'-OMe-A(N6-Bz)-CE | ACN | 0.2M | 15-20%, v/v |
| 5'-ODMTr-2'-OMe-C(N4-Ac)-CE | ACN | 0.2M | 15-20%, v/v |
| 5'-ODMTr-2'-F-dA(N6-Bz)-(L)-DPSE | ACN | 0.2M | 15-20%, v/v |
| 5'-ODMTr-2'-F-dC(N4-Ac)-(L)-DPSE | ACN | 0.2M | 15-20%, v/v |
| 5'-ODMTr-2'-F-dU-(L)-DPSE | 20% IBN/ 80% ACN | 0.2M | 15-20%, v/v |
| 5'-ODMTr-2'-F-dG(N2-iBu)-(L)-DPSE | ACN | 0.2M | 15-20%, v/v |
| 5'-ODMTr-2'-OMe-G(N2-iBu)-(L)-DPSE | 20% IBN/ 80% ACN | 0.2M | 15-20%, v/v |
| 5'-ODMTr-2'-F-dC(N4-Ac)-(L)-PSM | ACN | 0.2M | 15-20%, v/v |
| 5'-ODMTr-2'-F-dG(N2-iBu)-(L)-PSM | ACN | 0.2M | 15-20%, v/v |

Dual activators (CMIMT and ETT) coupling approach were utilized. Both activators were dissolved in ACN at a concentration of 0.5M. CMIMT has been used for chirally controlled coupling with CMIMT to amidite molar ratio of 5.833/1. ETT was used for the coupling of standard amidites (for natural phosphate linkages) with ETT to amidite molar ratio of 3.752/1. Recycle time for all DPSE and PSM amidites was 10 min except mG-L-DPSE which was 8 min. All standard amidites were coupled for 8 min.

Cap-1 (Capping-1, First Capping).

Cap B (Ac$_2$0/2,6-lutidine/MeCN (2:3:5, v/v/v)) was used. In some embodiments, Cap-1 capped secondary amine groups, e.g., on the chrial auxiliaries. In some embodiments, incomplete protection of secondary amines may lead side reaction resulting in a failed coupling or formation of one or more by-products. In some embodiments, Cap-1 may not be an efficient condition for esterification (e.g., a condition less efficient than Cap-2 (the second capping) for capping unreacted 5'-OH).

Thiolation for DPSE Cycles.

Following Cap-1, phosphite intermediates, P(III), were modified with sulfurizing reagent. In an example preparation, 1.2 CV (6-7 equivalent) of sulfurizing reagent (0.1 M XH/pyridine-ACN, 1:1, v/v) was delivered through the synthetic column via flow through mode over 6 min contact time to form P(V).

Azide Reaction for PSM Cycles.

After Cap-1, a suitable reagent (e.g., comprising —N$_3$ such as ADIH), in ACN was used to form neutral internucleotidic linkages (PN linkages). In an example preparation, 10.3 eq. of 0.25 M ADIH over 10 min contact time for fG-L-PSM and 25.8 eq. of 0.3 M ADIH over 15 min contact time for fC-L-PSM were utilized in the respective cycles.

Oxidation for Standard Nucleotide Cycles.

Cap-1 step was not necessary for standard amidite cycle. After coupling of a standard amidite onto the solid support, the phosphite intermediate, P(III), was oxidized with 0.05 M of iodine/water/pyridine solution to form P(V). In an example preparation, 3.5 eq. of oxidation solution delivered to the column by a flow through mode over 2 min contact time for efficient oxidation.

Cap-2 (Capping-2, a Second Capping).

Coupling efficiency on the solid phase DMD oligonucleotide synthesis for each cycle was approx. 97-100% and monitored by, e.g., release of DMTr cation. Residual uncoupled 5'-hydroxyl groups, typically 1-3% by detrit monitoring, on the solid support were blocked with Cap A (20% N-Methylimidazole in acetonitrile (NMI/ACN=20/80, v/v)) and Cap B (20%:30%:50%=Ac$_2$0:2,6-Lutidine: ACN (v/v/v)) reagents (e.g., 1:1). Both reagents (e.g., 0.4 CV) were delivered to the column by flow through mode over 0.8 min contact time to prevent formation of failure sequences. Uncapped amine groups may also be protected in this step.

As illustrated herein, in some embodiments, a DPSE amidite or DPSE cycle is Detritylation→Coupling→Cap-1 (Capping-1, first capping)→Thiolation→Cap-2 (Capping-1, Post-capping, second capping); in some embodiments, a PSM amidite or PSM cycle is Detritylation→Coupling→Cap-1 (Capping-1, first capping)→Azide reaction-→Cap-2 (Capping-1, Post-capping, second capping); in some embodiments, a standard amidite or standard cycle (traditional, non-chirally controlled) is Detritylation→Coupling→Oxidation→Cap-2 (Capping-1, Post-capping, second capping).

Synthetic cycles were selected and repeated until the desired length was achieved.

Amine Wash.

In some embodiments, provided technologies are particularly effective for preparing DMD oligonucleotides comprising internucleotidic linkages that comprise P—N=, wherein P is the linkage phosphorus. In some embodiments, provided technologies comprise contacting a DMD oligonucleotide intermediate with a base. In some embodiments, a contact is performed after desired DMD oligonucleotide lengths have been achieved. In some embodiments, such a contact provides a DMD oligonucleotide comprising internucleotidic linkages that comprise P—N=, wherein P is the linkage phosphorus. In some embodiments, a contact removes a chiral auxiliary (e.g., those with a $G^2$ that is connected to the rest of the molecule through a carbon atom, and the carbon atom is connected to at least one electron-withdrawing group (e.g., WV-CA-231, WV-CA-236, WV-CA-240, etc.)). In some embodiments, a contact is performed utilizing a base or a solution of a base which is substantially free of OH$^-$ or water (anhydrous). In some embodiments, a base is an amine (e.g., N(R)$_3$). In some embodiments, a base is N, N-diethylamine (DEA). In some embodiments, a base solution is 20% DEA/ACN. In some embodiments, such a contact with a base lowers levels of by-products which, at one or more locations of internucleotidic linkages that comprise P—N=, have instead natural phosphate linkages.

In an example preparation, an on-column amine wash was performed after completion of DMD oligonucleotide nucleotide synthesis cycles, by five column volume of 20% DEA in acetonitrile over 15 min contact time.

In some embodiments, contact with a base may also remove 2-cyanoethyl group used for construction of standard natural phosphate linkage. In some embodiments, contact with a base provide a natural phosphate linkage (e.g., in a salt form in which the cation is the corresponding ammonium salt of the amine base).

Cleavage and Deprotection.

After contact with a base, DMD oligonucleotides are exposed to further cleavage and deprotection. In an example preparation, auxiliary removal (e.g., DPSE), cleavage & deprotection was a two steps process. In step 1, CPG solid support with DMD oligonucleotides was treated with 1×TEA-HF solution (DMSO: Water: TEA.3HF: TEA=43: 8.6: 2.8: 1=v/v/v/v, 100±5 uL/umol) for 6±0.5 h at 27±2° C. The bulk slurry was then treated with concentrated ammonium hydroxide (28-30%, 200±10 mL/mmol) for 24±1 h at 37±2° C. (step 2) to release DMD oligonucleotide from the solid support. Crude product was collected by filtration. Filtrates were combined with washes (e.g., water) of the solid support. In some embodiments, observed yields were about 80-90 OD/umole.

Among other things, provided technologies provided high crude purities and/or yields. In many preparations (various scales, reagents concentrations, reaction times, etc.), about 55-60% crude purities (% FLP) were obtained, with minimal amount of shorter DMD oligonucleotides (e.g., from incomplete coupling, decomposition, side-reactions, etc.). In many embodiments, amounts of the most significant shorter DMD oligonucleotide is no more than about 2-10%, often no more than 2-4% (e.g., in some embodiments, as low as about 2% (the most significant shorter DMD oligonucleotide being N-3)).

Various technologies are available for DMD oligonucleotide purification and can be utilized in accordance with the present disclosure. In some embodiments, crude products were further purified (e.g., over 90% purity) using, e.g., AEX purification, and/or UF/DF.

Using technologies described herein, various DMD oligonucleotides comprising diverse base sequences, modifications (e.g., nucleobase, sugar, and internucleotidic linkage modifications) and/or patterns thereof, linkage phosphorus stereochemistry and/or patterns thereof, etc. were prepared at various scales from umol to mmol. Such DMD oligonucleotides have various targets and may function through various mechanisms. Certain such DMD oligonucleotides were presented in the Tables of the present disclosure.

As appreciated by those skilled in the art, examples described herein are for illustration only. Those skilled in the art will appreciate that various conditions, parameters, etc. may be adjusted according to, e.g., instrumentation, scales, reagents, reactants, desired outcomes, etc. Certain results may be further improved using various technologies in accordance with the present disclosure. Among other things, provided DMD oligonucleotides and compositions thereof can provide significantly improved properties and/or skipping of exon 51 or 53, e.g., in various assays and in vivo models, and may be particularly useful for preventing and/or treating various conditions, disorders or diseases. Certain data are provided in Examples herein.

Example 8. Timelines for 'Pre-Differentiation' of Patient Myoblasts for Gymnotic Dosing Various technologies, e.g., those described in U.S. Pat. Nos. 9,394,333, 9,744,183, 9,605,019, 9,598,458, US 2015/0211006, US 2017/0037399, WO 2017/015555, WO 2017/192664, WO 2017/015575, WO2017/062862, WO 2017/

160741, WO 2017/192679, and WO 2017/210647, etc., can be utilized in accordance with the present disclosure to assess properties and/or activities of technologies of the present disclosure. In some embodiments, technologies of the present disclosure, e.g., DMD oligonucleotides and compositions and methods of use thereof, demonstrate unexpectedly superior results compared to a suitable reference technology (e.g., a technology based on a stereorandom composition of DMD oligonucleotides having the same base sequence but no neutral and/or cationic internucleotidic linkages at physiological pH). Described below are example technologies that can be useful for assessing properties and/or activities of DMD oligonucleotides described in the present disclosure. Those skilled in the art understand that conditions illustrated below may be varied/modified, and additionally and/or alternatively, other suitable reagents, temperatures, conditions, time periods, amounts, etc., may be utilized in accordance with the present disclosure.

Unless otherwise noted, in various experiments, cells and animals used in experiments were used in conditions typical for those cells or animals. Unless otherwise noted, in in vitro experiments, various cells were grown under standard conditions (e.g., the most common conditions used for a particular cell type, cell line or a similar cell type or line), e.g., with ordinary growth medium, normal temp (37C), and gravity and atmospheric pressure typical of Cambridge, MA. Animals were kept under standard laboratory conditions, generally at room temperature, or a few degrees cooler, with normal conditions of feeding, cage size, etc. Neither cells nor animals, unless otherwise described, were subjected to extremes of temperature (e.g., cold shock or heat shock), pressure, gravity, ambient sound, food or nutrient deprivation, etc.

Maintenance of Patient Derived Myoblast Cell Lines:

DMD A52 and DMD A45-52 myoblast cells were maintained in complete Skeletal Muscle Growth Medium (Promocell, Heidelberg, Germany) supplemented with 5% FBS, 1X Penicillin-Streptomycin and 1X L-Glutamine. Flasks or plates were coated with Matrigel:DMEM solution (1:100) for a suitable period of time, e.g., 30 mins, after which Matrigel:DMEM solution was removed via aspiration before seeding of cells in complete Skeletal Muscle Growth Medium.

Standard Dosing Procedure (0 Days Pre-Differentiation)

On Day 1: Coat suitable cell growth containers, e.g., 6-well plates or 24-well plates, with Matrigel: DMEM Solution. Incubate at a condition, e.g., 37° C., 5% $CO_2$ for a suitable period of time, e.g., 30 mins. Aspirate, and seed a suitable number of cells to cell growth containers, e.g., 150K cells/well in a total of 1500 μl of complete growth medium in 6-well plate, and 30K cells/well in 500 ul of growth medium in a 24-well plate. Incubate at a suitable condition for a suitable period of time, .e.g., 37° C., 5% $CO_2$ overnight.

On Day 2: Prepare a suitable Differentiation medium, e.g., DMEM+5% Horse Serum+10 μg/ml Insulin. Prepare suitable DMD oligonucleotide dilutions in Differentiation Medium, e.g., serial dilutions of 30 uM, 10 uM, 3.33 uM, 1.11 uM, 0.37 uM. Aspirate growth medium off of adherent cells, and add DMD oligonucleotide:Differentiation Medium solution to cells. Oligonucleotides remain on cells (no media change) until cell harvesting.

On Day 6: Obtain RNA. In a typical procedure, a suitable number of cells, e.g., cells from wells of a 24-well plate, were washed, e.g., with cold PBS, followed by addition of a suitable amount of a reagent for RNA extraction and storage of sample/RNA extraction, e.g., 500 ul/well TRIZOL in 24-well plate and freezing plate at −80° C. or continuing with RNA extraction to obtain RNA.

On Day 8: Obtain protein. In a typical procedure, a suitable number of cells, e.g., cells in wells of 6-well plate, were washe, e.g., with cold PBS. A suitable amount of a suitable lysis buffer was then added—e.g., in a typical procedure, 200 ul/well of RIPA supplemented with protease inhibitors for a 6-well plate. After lysis the sample can be stored, e.g., freezing at −80° C., or continue with protein extraction.

Other suitable procedures may be employed, for example, those described below. As appreciated by those skilled in the art, many parameters, such as reagents, temperatures, conditions, time periods, amounts, etc., may be modified.

4 days Pre-Differentiation Dosing Procedure

On Day 1: Coat 6-well plates or 24-well plates with Matrigel: DMEM Solution. Incubate at 37° C., 5% $CO_2$ for 30 mins. Aspirate, seed 150K cells/well in a total of 1500 μl of complete growth medium in 6-well plate, and 30K cells/well in 500 ul of growth medium in a 24-well plate. Incubate at 37° C., 5% $CO_2$ overnight.

On Day 2: Prepare Differentiation medium as follows: DMEM+5% Horse Serum+10 μg/ml Insulin. Aspirate Growth Media and replace with Differentiation Media.

On Day 6: Cells have differentiated for 4 days. Prepare DMD oligonucleotide dilutions in Differentiation Medium, for example serial dilutions of 30 uM, 10 uM, 3.33 uM, 1.11 uM, 0.37 uM. Aspirate Differentiation medium off of adherent cells, and add DMD oligonucleotide:Differentiation Medium solution to cells. Oligonucleotides remain on cells (no media change) until cell harvesting.

On Day 10: Wash cells in 24-well plate with cold PBS, add 500 ul/well TRIZOL in 24-well plate and freeze plate at −80° C. or continue with RNA extraction.

On Day 12: Wash cells in 6-well plate with cold PBS. Add 200 ul/well of RIPA supplemented with protease inhibitors. Freeze plate at −80° C. or continue with protein extraction.

7 days Pre-Differentiation Dosing Procedure

On Day 1: Coat 6-well plates or 24-well plates with Matrigel: DMEM Solution. Incubate at 37° C., 5% $CO_2$ for 30 mins. Aspirate, seed 150K cells/well in a total of 1500 μl of complete growth medium in 6-well plate, and 30K cells/well in 500 ul of growth medium in a 24-well plate. Incubate at 37° C., 5% $CO_2$ overnight.

On Day 2: Prepare Differentiation medium as follows: DMEM+5% Horse Serum+10 μg/ml Insulin. Aspirate Growth Media and replace with Differentiation Media.

On Day 9: Cells have differentiated for 7 days. Prepare DMD oligonucleotide dilutions in Differentiation Medium, for example serial dilutions of 30 uM, 10 uM, 3.33 uM, 1.11 uM, 0.37 uM. Aspirate Differentiation medium off of adherent cells, and add DMD oligonucleotide:Differentiation Medium solution to cells. Oligonucleotides remain on cells (no media change) until cell harvesting.

On Day 13: Wash cells in 24-well plate with cold PBS, add 500 ul/well TRIZOL in 24-well plate and freeze plate at −80° C. or continue with RNA extraction.

On Day 15: Wash cells in 6-well plate with cold PBS. Add 200 ul/well of RIPA supplemented with protease inhibitors. Freeze plate at −80° C. or continue with protein extraction.

10 days Pre-Differentiation Dosing Procedure

On Day 1: Coat 6-well plates or 24-well plates with Matrigel: DMEM Solution. Incubate at 37° C., 5% $CO_2$ for 30 mins. Aspirate, seed 150K cells/well in a total of 1500 μl of complete growth medium in 6-well plate, and 30K cells/well in 500 ul of growth medium in a 24-well plate. Incubate at 37° C., 5% $CO_2$ overnight.

On Day 2: Prepare Differentiation medium as follows: DMEM+5% Horse Serum+10 μg/ml Insulin. Aspirate Growth Media and replace with Differentiation Media.

On Day 12: Cells have differentiated for 10 days. Prepare DMD oligonucleotide dilutions in Differentiation Medium, for example serial dilutions of 30 uM, 10 uM, 3.33 uM, 1.11 uM, 0.37 uM. Aspirate Differentiation medium off of adherent cells, and add DMD oligonucleotide:Differentiation Medium solution to cells. Oligonucleotides remain on cells (no media change) until cell harvesting.

On Day 16: Wash cells in 24-well plate with cold PBS, add 500 ul/well TRIZOL in 24-well plate and freeze plate at −80° C. or continue with RNA extraction.

On Day 18: Wash cells in 6-well plate with cold PBS. Add 200 ul/well of RIPA supplemented with protease inhibitors. Freeze plate at −80° C. or continue with protein extraction.

EQUIVALENTS

Having described some illustrative embodiments of the disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the disclosure. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations, if any, recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present disclosure is not to be limited in scope by examples provided. Examples are intended as illustration of one or more aspect of an invention and other functionally equivalent embodiments are within the scope of the invention. Various modifications in addition to those shown and described herein will become apparent to those skilled in the art from the foregoing description and fall within the scope of the appended claims. Advantages and objects of the invention are not necessarily encompassed by each embodiment of the invention.

The invention claimed is:

1. An oligonucleotide, wherein the oligonucleotide is: fC * SfU * SfCn001RfC * SfG * SfGn001RfU * SfU * SmCfU * SmG * SfA * SmAfG * SfG * SfU * SfGn001RfU * SfU * SfC (SEQ ID NO: 11) or a pharmaceutically acceptable salt thereof, wherein:
f represents a 2'—F modified nucleoside;
* S represents a Sp phosphorothioate;
m represents a 2'-OMe modified nucleoside; and
n001R is

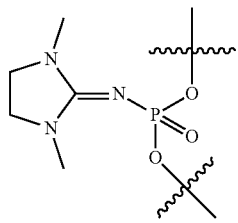 [SMILES: *OP(=O)(N=C1N(C)CCN1C)O*]

wherein the phosphorus is of the Rp configuration.

2. The oligonucleotide of claim 1, wherein the oligonucleotide is a sodium salt.

3. The oligonucleotide of claim 2, wherein the number of sodium ions in the sodium salt equals the total number of phosphorothioate and phosphate linkages in the oligonucleotide.

4. The oligonucleotide of claim 3, wherein each chiral internucleotidic linkage of the oligonucleotide independently has a diastereopurity of at least 95%.

5. The oligonucleotide of claim 2, wherein each chiral internucleotidic linkage of the oligonucleotide independently has a diastereopurity of at least 95%.

6. The oligonucleotide of claim 1, wherein each chiral internucleotidic linkage of the oligonucleotide independently has a diastereopurity of at least 90%.

7. The oligonucleotide of claim 1, wherein the oligonucleotide is a pharmaceutically acceptable salt.

8. The oligonucleotide of claim 7, wherein each chiral internucleotidic linkage of the oligonucleotide independently has a diastereopurity of at least 90%.

9. The composition of claim 7, wherein each chiral internucleotidic linkage of the oligonucleotide independently has a diastereopurity of at least 98%.

10. A chirally controlled oligonucleotide composition comprising an oligonucleotide, wherein the oligonucleotide is:
fC * SfU * SfCn001RfC * SfG * SfGn001RfU * SfU * SmCfU * SmG * SfA * SmAfG * SfG * SfU * SfGn001RfU * SfU * SfC (SEQ ID NO: 11) or a pharmaceutically acceptable salt thereof,
wherein:
f represents a 2'—F modified nucleoside;
* S represents a Sp phosphorothioate;
m represents a 2'-OMe modified nucleoside;

n001R is

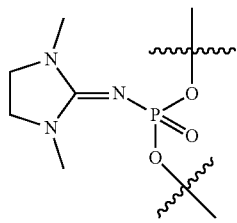 [SMILES: *OP(=O)(N=C1N(C)CCN1C)O*]

wherein the phosphorus is of the Rp configuration; and each chiral internucleotidic linkage of the oligonucleotide independently has a diastereopurity of at least 95%.

11. The composition of claim 10, wherein the oligonucleotide is a pharmaceutically acceptable salt.

12. The composition of claim 11, wherein the oligonucleotide is a sodium salt.

13. The composition of claim 12, wherein the number of sodium ions in the sodium salt equals the total number of phosphorothioate and phosphate linkages in the oligonucleotide.

14. A pharmaceutical composition, comprising an oligonucleotide and a pharmaceutically acceptable carrier, wherein the oligonucleotide is:

fC * SfU * SfCn001RfC * SfG * SfGn001RfU * SfU * SmCfU * SmG * SfA * SmAfG * SfG * SfU * SfGn001RfU * SfU * SfC (SEQ ID NO: 11) or a pharmaceutically acceptable salt thereof, wherein:
f represents a 2'—F modified nucleoside;
* S represents a Sp phosphorothioate;
m represents a 2'-OMe modified nucleoside; and
n001R is

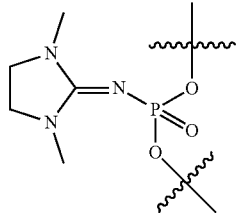 [SMILES: *OP(=O)(N=C1N(C)CCN1C)O*]

wherein the phosphorus is of the Rp configuration.

15. The composition of claim 14, wherein the pharmaceutical composition is a solution.

16. The composition of claim 14, wherein each chiral internucleotidic linkage of the oligonucleotide independently has a diastereopurity of at least 95%.

17. The composition of claim 16, wherein the oligonucleotide is a sodium salt.

18. The composition of claim 17, wherein the number of sodium ions in the sodium salt equals the total number of phosphorothioate and phosphate linkages in the oligonucleotide.

19. The composition of claim 18, wherein the pharmaceutically acceptable carrier is a pharmaceutically acceptable diluent or excipient.

20. The composition of claim 18, wherein the pharmaceutically acceptable carrier is a pH buffered solution.

21. The composition of claim 20, wherein each chiral internucleotidic linkage of the oligonucleotide independently has a diastereopurity of at least 98%.

22. The composition of claim 14, wherein the oligonucleotide is a pharmaceutically acceptable salt.

23. The composition of claim 22, wherein each chiral internucleotidic linkage of the oligonucleotide independently has a diastereopurity of at least 90%.

24. The composition of claim 22, wherein each chiral internucleotidic linkage of the oligonucleotide independently has a diastereopurity of at least 95%.

25. The composition of claim 24, wherein the pharmaceutically acceptable carrier is a pharmaceutically acceptable diluent or excipient.

26. The composition of claim 24, wherein the pharmaceutically acceptable carrier is a pH buffered solution.

27. The composition of claim 26, wherein each chiral internucleotidic linkage of the oligonucleotide independently has a diastereopurity of at least 98%.

28. The composition of claim 22, wherein each chiral internucleotidic linkage of the oligonucleotide independently has a diastereopurity of at least 98%.

29. The composition of claim 14, wherein the pharmaceutically acceptable carrier is a pharmaceutically acceptable diluent or excipient.

30. The composition of claim 14, wherein the pharmaceutically acceptable carrier is a pH buffered solution.

31. The composition of claim 30, wherein each chiral internucleotidic linkage of the oligonucleotide independently has a diastereopurity of at least 98%.

32. The composition of claim 14, wherein the composition comprises two or more pharmaceutically acceptable salts of fC * SfU * SfCn001RfC * SfG * SfGn001RfU * SfU * SmCfU * SmG * SfA * SmAfG * SfG * SfU * SfGn001RfU * SfU * SfC (SEQ ID NO: 11).

* * * * *

SEQUENCE LISTING

```
<160> NUMBER OF SEQ ID NOS: 132

<210> SEQ ID NO 1
<211> LENGTH: 20
<212> TYPE: RNA
<213> ORGANISM: Artificial Sequence
<220> FEATURE:
<223> OTHER INFORMATION: Synthetic

<400> SEQUENCE: 1
ucaaggaaga uggcauuucu                                               20

<210> SEQ ID NO 2
<211> LENGTH: 20
<212> TYPE: RNA
<213> ORGANISM: Artificial Sequence
<220> FEATURE:
<223> OTHER INFORMATION: Synthetic

<400> SEQUENCE: 2
ucaaggaaga uggcauuucu                                               20

<210> SEQ ID NO 3
<211> LENGTH: 20
<212> TYPE: RNA
<213> ORGANISM: Artificial Sequence
<220> FEATURE:
<223> OTHER INFORMATION: Synthetic

<400> SEQUENCE: 3
cuccgguucu gaagguguuc                                               20
```

```
<210> SEQ ID NO 4
<211> LENGTH: 20
<212> TYPE: RNA
<213> ORGANISM: Artificial Sequence
<220> FEATURE:
<223> OTHER INFORMATION: Synthetic

<400> SEQUENCE: 4
cuccgguucu gaagguguuc                                              20

<210> SEQ ID NO 5
<211> LENGTH: 25
<212> TYPE: DNA
<213> ORGANISM: Artificial Sequence
<220> FEATURE:
<223> OTHER INFORMATION: Synthetic

<400> SEQUENCE: 5
gttgcctccg gttctgaagg tgttc                                        25

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ctccggttct gaaggtgttc                                              20

<210> SEQ ID NO 7
<211> LENGTH: 28
<212> TYPE: DNA
<213> ORGANISM: Artificial Sequence
<220> FEATURE:
<223> OTHER INFORMATION: Synthetic

<400> SEQUENCE: 7
tgcctccggt tctgaaggtg ttcttgta                                     28

<210> SEQ ID NO 8
<211> LENGTH: 19
<212> TYPE: RNA
<213> ORGANISM: Artificial Sequence
<220> FEATURE:
<223> OTHER INFORMATION: Synthetic

<400> SEQUENCE: 8
uccgguucug aagguguuc                                               19

<210> SEQ ID NO 9
<211> LENGTH: 19
<212> TYPE: RNA
<213> ORGANISM: Artificial Sequence
<220> FEATURE:
<223> OTHER INFORMATION: Synthetic

<400> SEQUENCE: 9
cuccgguucu gaagguguu                                               19

<210> SEQ ID NO 10
<211> LENGTH: 20
<212> TYPE: RNA
<213> ORGANISM: Artificial Sequence
<220> FEATURE:
<223> OTHER INFORMATION: Synthetic
```

```
<400> SEQUENCE: 10
uccgguucug aagguguucu                                           20

<210> SEQ ID NO 11
<211> LENGTH: 20
<212> TYPE: RNA
<213> ORGANISM: Artificial Sequence
<220> FEATURE:
<223> OTHER INFORMATION: Synthetic

<400> SEQUENCE: 11
cuccgguucu gaagguguuc                                           20

<210> SEQ ID NO 12
<211> LENGTH: 20
<212> TYPE: RNA
<213> ORGANISM: Artificial Sequence
<220> FEATURE:
<223> OTHER INFORMATION: Synthetic

<400> SEQUENCE: 12
cuccgguucu gaagguguuc                                           20

<210> SEQ ID NO 13
<211> LENGTH: 20
<212> TYPE: RNA
<213> ORGANISM: Artificial Sequence
<220> FEATURE:
<223> OTHER INFORMATION: Synthetic

<400> SEQUENCE: 13
ucaaggaaga uggcauuucu                                           20

<210> SEQ ID NO 14
<211> LENGTH: 20
<212> TYPE: RNA
<213> ORGANISM: Artificial Sequence
<220> FEATURE:
<223> OTHER INFORMATION: Synthetic

<400> SEQUENCE: 14
ucaaggaaga uggcauuucu                                           20

<210> SEQ ID NO 15
<211> LENGTH: 20
<212> TYPE: RNA
<213> ORGANISM: Artificial Sequence
<220> FEATURE:
<223> OTHER INFORMATION: Synthetic

<400> SEQUENCE: 15
uccgguucug aagguguucu                                           20

<210> SEQ ID NO 16
<211> LENGTH: 20
<212> TYPE: RNA
<213> ORGANISM: Artificial Sequence
<220> FEATURE:
<223> OTHER INFORMATION: Synthetic

<400> SEQUENCE: 16
ucaaggaaga uggcauuucu                                           20

<210> SEQ ID NO 17
```

```
<211> LENGTH: 20
<212> TYPE: RNA
<213> ORGANISM: Artificial Sequence
<220> FEATURE:
<223> OTHER INFORMATION: Synthetic

<400> SEQUENCE: 17
ucaaggaaga uggcauuucu                                                   20

<210> SEQ ID NO 18
<211> LENGTH: 20
<212> TYPE: RNA
<213> ORGANISM: Artificial Sequence
<220> FEATURE:
<223> OTHER INFORMATION: Synthetic

<400> SEQUENCE: 18
ucaaggaaga uggcauuucu                                                   20

<210> SEQ ID NO 19
<211> LENGTH: 20
<212> TYPE: RNA
<213> ORGANISM: Artificial Sequence
<220> FEATURE:
<223> OTHER INFORMATION: Synthetic

<400> SEQUENCE: 19
ucaaggaaga uggcauuucu                                                   20

<210> SEQ ID NO 20
<211> LENGTH: 20
<212> TYPE: RNA
<213> ORGANISM: Artificial Sequence
<220> FEATURE:
<223> OTHER INFORMATION: Synthetic

<400> SEQUENCE: 20
ucaaggaaga uggcauuucu                                                   20

<210> SEQ ID NO 21
<211> LENGTH: 20
<212> TYPE: RNA
<213> ORGANISM: Artificial Sequence
<220> FEATURE:
<223> OTHER INFORMATION: Synthetic

<400> SEQUENCE: 21
ucaaggaaga uggcauuucu                                                   20

<210> SEQ ID NO 22
<211> LENGTH: 20
<212> TYPE: RNA
<213> ORGANISM: Artificial Sequence
<220> FEATURE:
<223> OTHER INFORMATION: Synthetic

<400> SEQUENCE: 22
ucaaggaaga uggcauuucu                                                   20

<210> SEQ ID NO 23
<211> LENGTH: 20
<212> TYPE: RNA
<213> ORGANISM: Artificial Sequence
<220> FEATURE:
<223> OTHER INFORMATION: Synthetic

<400> SEQUENCE: 23
```
ucaaggaaga uggcauuucu                                          20

<210> SEQ ID NO 24
<211> LENGTH: 20
<212> TYPE: RNA
<213> ORGANISM: Artificial Sequence
<220> FEATURE:
<223> OTHER INFORMATION: Synthetic

<400> SEQUENCE: 24
ucaaggaaga uggcauuucu                                          20

<210> SEQ ID NO 25
<211> LENGTH: 20
<212> TYPE: RNA
<213> ORGANISM: Artificial Sequence
<220> FEATURE:
<223> OTHER INFORMATION: Synthetic

<400> SEQUENCE: 25
ucaaggaaga uggcauuucu                                          20

<210> SEQ ID NO 26
<211> LENGTH: 20
<212> TYPE: RNA
<213> ORGANISM: Artificial Sequence
<220> FEATURE:
<223> OTHER INFORMATION: Synthetic

<400> SEQUENCE: 26
ucaaggaaga uggcauuucu                                          20

<210> SEQ ID NO 27
<211> LENGTH: 20
<212> TYPE: RNA
<213> ORGANISM: Artificial Sequence
<220> FEATURE:
<223> OTHER INFORMATION: Synthetic

<400> SEQUENCE: 27
ugaaaucugc cagagcaggu                                          20

<210> SEQ ID NO 28
<211> LENGTH: 20
<212> TYPE: RNA
<213> ORGANISM: Artificial Sequence
<220> FEATURE:
<223> OTHER INFORMATION: Synthetic

<400> SEQUENCE: 28
ugaaaucugc cagagcaggu                                          20

<210> SEQ ID NO 29
<211> LENGTH: 20
<212> TYPE: RNA
<213> ORGANISM: Artificial Sequence
<220> FEATURE:
<223> OTHER INFORMATION: Synthetic

<400> SEQUENCE: 29
aaucugccag agcagguacc                                          20

<210> SEQ ID NO 30
<211> LENGTH: 20
<212> TYPE: RNA

```
<213> ORGANISM: Artificial Sequence
<220> FEATURE:
<223> OTHER INFORMATION: Synthetic

<400> SEQUENCE: 30
cugccagagc agguaccucc                                               20

<210> SEQ ID NO 31
<211> LENGTH: 20
<212> TYPE: RNA
<213> ORGANISM: Artificial Sequence
<220> FEATURE:
<223> OTHER INFORMATION: Synthetic

<400> SEQUENCE: 31
ccagagcagg uaccuccaac                                               20

<210> SEQ ID NO 32
<211> LENGTH: 20
<212> TYPE: RNA
<213> ORGANISM: Artificial Sequence
<220> FEATURE:
<223> OTHER INFORMATION: Synthetic

<400> SEQUENCE: 32
gagcagguac cuccaacauc                                               20

<210> SEQ ID NO 33
<211> LENGTH: 20
<212> TYPE: RNA
<213> ORGANISM: Artificial Sequence
<220> FEATURE:
<223> OTHER INFORMATION: Synthetic

<400> SEQUENCE: 33
cagguaccuc caacaucaag                                               20

<210> SEQ ID NO 34
<211> LENGTH: 20
<212> TYPE: RNA
<213> ORGANISM: Artificial Sequence
<220> FEATURE:
<223> OTHER INFORMATION: Synthetic

<400> SEQUENCE: 34
agguaccucc aacaucaagg                                               20

<210> SEQ ID NO 35
<211> LENGTH: 20
<212> TYPE: RNA
<213> ORGANISM: Artificial Sequence
<220> FEATURE:
<223> OTHER INFORMATION: Synthetic

<400> SEQUENCE: 35
gguaccucca acaucaagga                                               20

<210> SEQ ID NO 36
<211> LENGTH: 20
<212> TYPE: RNA
<213> ORGANISM: Artificial Sequence
<220> FEATURE:
<223> OTHER INFORMATION: Synthetic

<400> SEQUENCE: 36
guaccuccaa caucaaggaa                                               20
```

```
<210> SEQ ID NO 37
<211> LENGTH: 20
<212> TYPE: RNA
<213> ORGANISM: Artificial Sequence
<220> FEATURE:
<223> OTHER INFORMATION: Synthetic

<400> SEQUENCE: 37
uaccuccaac aucaaggaag                                                     20

<210> SEQ ID NO 38
<211> LENGTH: 20
<212> TYPE: RNA
<213> ORGANISM: Artificial Sequence
<220> FEATURE:
<223> OTHER INFORMATION: Synthetic

<400> SEQUENCE: 38
accuccaaca ucaaggaaga                                                     20

<210> SEQ ID NO 39
<211> LENGTH: 20
<212> TYPE: RNA
<213> ORGANISM: Artificial Sequence
<220> FEATURE:
<223> OTHER INFORMATION: Synthetic

<400> SEQUENCE: 39
ccuccaacau caaggaagau                                                     20

<210> SEQ ID NO 40
<211> LENGTH: 20
<212> TYPE: RNA
<213> ORGANISM: Artificial Sequence
<220> FEATURE:
<223> OTHER INFORMATION: Synthetic

<400> SEQUENCE: 40
cuccaacauc aaggaagaug                                                     20

<210> SEQ ID NO 41
<211> LENGTH: 20
<212> TYPE: RNA
<213> ORGANISM: Artificial Sequence
<220> FEATURE:
<223> OTHER INFORMATION: Synthetic

<400> SEQUENCE: 41
uccaacauca aggaagaugg                                                     20

<210> SEQ ID NO 42
<211> LENGTH: 20
<212> TYPE: RNA
<213> ORGANISM: Artificial Sequence
<220> FEATURE:
<223> OTHER INFORMATION: Synthetic

<400> SEQUENCE: 42
ccaacaucaa ggaagauggc                                                     20

<210> SEQ ID NO 43
<211> LENGTH: 20
<212> TYPE: RNA
<213> ORGANISM: Artificial Sequence
<220> FEATURE:
```

<223> OTHER INFORMATION: Synthetic

<400> SEQUENCE: 43
caacaucaag gaagauggca                                                    20

<210> SEQ ID NO 44
<211> LENGTH: 20
<212> TYPE: RNA
<213> ORGANISM: Artificial Sequence
<220> FEATURE:
<223> OTHER INFORMATION: Synthetic

<400> SEQUENCE: 44
aacaucaagg aagauggcau                                                    20

<210> SEQ ID NO 45
<211> LENGTH: 20
<212> TYPE: RNA
<213> ORGANISM: Artificial Sequence
<220> FEATURE:
<223> OTHER INFORMATION: Synthetic

<400> SEQUENCE: 45
acaucaagga agauggcauu                                                    20

<210> SEQ ID NO 46
<211> LENGTH: 20
<212> TYPE: RNA
<213> ORGANISM: Artificial Sequence
<220> FEATURE:
<223> OTHER INFORMATION: Synthetic

<400> SEQUENCE: 46
caucaaggaa gauggcauuu                                                    20

<210> SEQ ID NO 47
<211> LENGTH: 20
<212> TYPE: RNA
<213> ORGANISM: Artificial Sequence
<220> FEATURE:
<223> OTHER INFORMATION: Synthetic

<400> SEQUENCE: 47
aucaaggaag auggcauuuc                                                    20

<210> SEQ ID NO 48
<211> LENGTH: 20
<212> TYPE: RNA
<213> ORGANISM: Artificial Sequence
<220> FEATURE:
<223> OTHER INFORMATION: Synthetic

<400> SEQUENCE: 48
ucaaggaaga uggcauuucu                                                    20

<210> SEQ ID NO 49
<211> LENGTH: 20
<212> TYPE: RNA
<213> ORGANISM: Artificial Sequence
<220> FEATURE:
<223> OTHER INFORMATION: Synthetic

<400> SEQUENCE: 49
ucaaggaaga uggcauuucu                                                    20

```
<210> SEQ ID NO 50
<211> LENGTH: 20
<212> TYPE: RNA
<213> ORGANISM: Artificial Sequence
<220> FEATURE:
<223> OTHER INFORMATION: Synthetic

<400> SEQUENCE: 50
caaggaagau ggcauuucua                                            20

<210> SEQ ID NO 51
<211> LENGTH: 20
<212> TYPE: RNA
<213> ORGANISM: Artificial Sequence
<220> FEATURE:
<223> OTHER INFORMATION: Synthetic

<400> SEQUENCE: 51
aaggaagaug gcauuucuag                                            20

<210> SEQ ID NO 52
<211> LENGTH: 20
<212> TYPE: RNA
<213> ORGANISM: Artificial Sequence
<220> FEATURE:
<223> OTHER INFORMATION: Synthetic

<400> SEQUENCE: 52
aggaagaugg cauuucuagu                                            20

<210> SEQ ID NO 53
<211> LENGTH: 20
<212> TYPE: RNA
<213> ORGANISM: Artificial Sequence
<220> FEATURE:
<223> OTHER INFORMATION: Synthetic

<400> SEQUENCE: 53
ggaagauggc auuucuaguu                                            20

<210> SEQ ID NO 54
<211> LENGTH: 20
<212> TYPE: RNA
<213> ORGANISM: Artificial Sequence
<220> FEATURE:
<223> OTHER INFORMATION: Synthetic

<400> SEQUENCE: 54
gaagauggca uuucuaguuu                                            20

<210> SEQ ID NO 55
<211> LENGTH: 20
<212> TYPE: RNA
<213> ORGANISM: Artificial Sequence
<220> FEATURE:
<223> OTHER INFORMATION: Synthetic

<400> SEQUENCE: 55
aagauggcau uucuaguuug                                            20

<210> SEQ ID NO 56
<211> LENGTH: 20
<212> TYPE: RNA
<213> ORGANISM: Artificial Sequence
<220> FEATURE:
<223> OTHER INFORMATION: Synthetic
```

```
<400> SEQUENCE: 56
aagauggcau uucuaguuug                                           20

<210> SEQ ID NO 57
<211> LENGTH: 20
<212> TYPE: RNA
<213> ORGANISM: Artificial Sequence
<220> FEATURE:
<223> OTHER INFORMATION: Synthetic

<400> SEQUENCE: 57
agauggcauu ucuaguuugg                                           20

<210> SEQ ID NO 58
<211> LENGTH: 20
<212> TYPE: RNA
<213> ORGANISM: Artificial Sequence
<220> FEATURE:
<223> OTHER INFORMATION: Synthetic

<400> SEQUENCE: 58
gauggcauuu cuaguuugga                                           20

<210> SEQ ID NO 59
<211> LENGTH: 20
<212> TYPE: RNA
<213> ORGANISM: Artificial Sequence
<220> FEATURE:
<223> OTHER INFORMATION: Synthetic

<400> SEQUENCE: 59
auggcauuuc uaguuuggag                                           20

<210> SEQ ID NO 60
<211> LENGTH: 20
<212> TYPE: RNA
<213> ORGANISM: Artificial Sequence
<220> FEATURE:
<223> OTHER INFORMATION: Synthetic

<400> SEQUENCE: 60
auggcauuuc uaguuuggag                                           20

<210> SEQ ID NO 61
<211> LENGTH: 20
<212> TYPE: RNA
<213> ORGANISM: Artificial Sequence
<220> FEATURE:
<223> OTHER INFORMATION: Synthetic

<400> SEQUENCE: 61
uggcauuucu aguuuggaga                                           20

<210> SEQ ID NO 62
<211> LENGTH: 20
<212> TYPE: RNA
<213> ORGANISM: Artificial Sequence
<220> FEATURE:
<223> OTHER INFORMATION: Synthetic

<400> SEQUENCE: 62
ggcauuucua guuuggagau                                           20

<210> SEQ ID NO 63
<211> LENGTH: 20
```

```
<212> TYPE: RNA
<213> ORGANISM: Artificial Sequence
<220> FEATURE:
<223> OTHER INFORMATION: Synthetic

<400> SEQUENCE: 63
gcauuucuag uuuggagaug                                                    20

<210> SEQ ID NO 64
<211> LENGTH: 20
<212> TYPE: RNA
<213> ORGANISM: Artificial Sequence
<220> FEATURE:
<223> OTHER INFORMATION: Synthetic

<400> SEQUENCE: 64
gcauuucuag uuuggagaug                                                    20

<210> SEQ ID NO 65
<211> LENGTH: 20
<212> TYPE: RNA
<213> ORGANISM: Artificial Sequence
<220> FEATURE:
<223> OTHER INFORMATION: Synthetic

<400> SEQUENCE: 65
cauuucuagu uuggagaugg                                                    20

<210> SEQ ID NO 66
<211> LENGTH: 20
<212> TYPE: RNA
<213> ORGANISM: Artificial Sequence
<220> FEATURE:
<223> OTHER INFORMATION: Synthetic

<400> SEQUENCE: 66
auuucuaguu uggagauggc                                                    20

<210> SEQ ID NO 67
<211> LENGTH: 20
<212> TYPE: RNA
<213> ORGANISM: Artificial Sequence
<220> FEATURE:
<223> OTHER INFORMATION: Synthetic

<400> SEQUENCE: 67
uuucuaguuu ggagauggca                                                    20

<210> SEQ ID NO 68
<211> LENGTH: 20
<212> TYPE: RNA
<213> ORGANISM: Artificial Sequence
<220> FEATURE:
<223> OTHER INFORMATION: Synthetic

<400> SEQUENCE: 68
uucuaguuug gagauggcag                                                    20

<210> SEQ ID NO 69
<211> LENGTH: 20
<212> TYPE: RNA
<213> ORGANISM: Artificial Sequence
<220> FEATURE:
<223> OTHER INFORMATION: Synthetic

<400> SEQUENCE: 69
```
ucuaguuugg agauggcagu                                             20

<210> SEQ ID NO 70
<211> LENGTH: 20
<212> TYPE: RNA
<213> ORGANISM: Artificial Sequence
<220> FEATURE:
<223> OTHER INFORMATION: Synthetic

<400> SEQUENCE: 70
cuaguuugga gauggcaguu                                             20

<210> SEQ ID NO 71
<211> LENGTH: 20
<212> TYPE: RNA
<213> ORGANISM: Artificial Sequence
<220> FEATURE:
<223> OTHER INFORMATION: Synthetic

<400> SEQUENCE: 71
uaguuuggag auggcaguuu                                             20

<210> SEQ ID NO 72
<211> LENGTH: 20
<212> TYPE: RNA
<213> ORGANISM: Artificial Sequence
<220> FEATURE:
<223> OTHER INFORMATION: Synthetic

<400> SEQUENCE: 72
aguuuggaga uggcaguuuc                                             20

<210> SEQ ID NO 73
<211> LENGTH: 20
<212> TYPE: RNA
<213> ORGANISM: Artificial Sequence
<220> FEATURE:
<223> OTHER INFORMATION: Synthetic

<400> SEQUENCE: 73
guuuggagau ggcaguuucc                                             20

<210> SEQ ID NO 74
<211> LENGTH: 20
<212> TYPE: RNA
<213> ORGANISM: Artificial Sequence
<220> FEATURE:
<223> OTHER INFORMATION: Synthetic

<400> SEQUENCE: 74
uuuggagaug gcaguuuccu                                             20

<210> SEQ ID NO 75
<211> LENGTH: 20
<212> TYPE: RNA
<213> ORGANISM: Artificial Sequence
<220> FEATURE:
<223> OTHER INFORMATION: Synthetic

<400> SEQUENCE: 75
uuggagaugg caguuuccuu                                             20

<210> SEQ ID NO 76
<211> LENGTH: 20
<212> TYPE: RNA
<213> ORGANISM: Artificial Sequence

```
<220> FEATURE:
<223> OTHER INFORMATION: Synthetic

<400> SEQUENCE: 76
uggagauggc aguuccuua                                                    20

<210> SEQ ID NO 77
<211> LENGTH: 20
<212> TYPE: RNA
<213> ORGANISM: Artificial Sequence
<220> FEATURE:
<223> OTHER INFORMATION: Synthetic

<400> SEQUENCE: 77
ggagauggca guuccuuag                                                    20

<210> SEQ ID NO 78
<211> LENGTH: 20
<212> TYPE: RNA
<213> ORGANISM: Artificial Sequence
<220> FEATURE:
<223> OTHER INFORMATION: Synthetic

<400> SEQUENCE: 78
gagauggcag uuccuuagu                                                    20

<210> SEQ ID NO 79
<211> LENGTH: 20
<212> TYPE: RNA
<213> ORGANISM: Artificial Sequence
<220> FEATURE:
<223> OTHER INFORMATION: Synthetic

<400> SEQUENCE: 79
agauggcagu uccuuagua                                                    20

<210> SEQ ID NO 80
<211> LENGTH: 20
<212> TYPE: RNA
<213> ORGANISM: Artificial Sequence
<220> FEATURE:
<223> OTHER INFORMATION: Synthetic

<400> SEQUENCE: 80
gauggcaguu uccuuaguaa                                                   20

<210> SEQ ID NO 81
<211> LENGTH: 20
<212> TYPE: RNA
<213> ORGANISM: Artificial Sequence
<220> FEATURE:
<223> OTHER INFORMATION: Synthetic

<400> SEQUENCE: 81
auggcaguuu ccuuaguaac                                                   20

<210> SEQ ID NO 82
<211> LENGTH: 20
<212> TYPE: RNA
<213> ORGANISM: Artificial Sequence
<220> FEATURE:
<223> OTHER INFORMATION: Synthetic

<400> SEQUENCE: 82
uggcaguuuc cuuaguaacc                                                   20
```

```
<210> SEQ ID NO 83
<211> LENGTH: 20
<212> TYPE: RNA
<213> ORGANISM: Artificial Sequence
<220> FEATURE:
<223> OTHER INFORMATION: Synthetic

<400> SEQUENCE: 83
ggcaguuucc uuaguaacca                                               20

<210> SEQ ID NO 84
<211> LENGTH: 20
<212> TYPE: RNA
<213> ORGANISM: Artificial Sequence
<220> FEATURE:
<223> OTHER INFORMATION: Synthetic

<400> SEQUENCE: 84
gcaguuuccu uaguaaccac                                               20

<210> SEQ ID NO 85
<211> LENGTH: 20
<212> TYPE: RNA
<213> ORGANISM: Artificial Sequence
<220> FEATURE:
<223> OTHER INFORMATION: Synthetic

<400> SEQUENCE: 85
caguuuccuu aguaaccaca                                               20

<210> SEQ ID NO 86
<211> LENGTH: 20
<212> TYPE: RNA
<213> ORGANISM: Artificial Sequence
<220> FEATURE:
<223> OTHER INFORMATION: Synthetic

<400> SEQUENCE: 86
aguuuccuua guaaccacag                                               20

<210> SEQ ID NO 87
<211> LENGTH: 20
<212> TYPE: RNA
<213> ORGANISM: Artificial Sequence
<220> FEATURE:
<223> OTHER INFORMATION: Synthetic

<400> SEQUENCE: 87
guuuccuuag uaaccacagg                                               20

<210> SEQ ID NO 88
<211> LENGTH: 20
<212> TYPE: RNA
<213> ORGANISM: Artificial Sequence
<220> FEATURE:
<223> OTHER INFORMATION: Synthetic

<400> SEQUENCE: 88
uuuccuuagu aaccacaggu                                               20

<210> SEQ ID NO 89
<211> LENGTH: 20
<212> TYPE: RNA
<213> ORGANISM: Artificial Sequence
<220> FEATURE:
<223> OTHER INFORMATION: Synthetic
```

<400> SEQUENCE: 89
uuccuuagua accacagguu                                                    20

<210> SEQ ID NO 90
<211> LENGTH: 20
<212> TYPE: RNA
<213> ORGANISM: Artificial Sequence
<220> FEATURE:
<223> OTHER INFORMATION: Synthetic

<400> SEQUENCE: 90
uccuuaguaa ccacagguug                                                    20

<210> SEQ ID NO 91
<211> LENGTH: 20
<212> TYPE: RNA
<213> ORGANISM: Artificial Sequence
<220> FEATURE:
<223> OTHER INFORMATION: Synthetic

<400> SEQUENCE: 91
ccuuaguaac cacagguugu                                                    20

<210> SEQ ID NO 92
<211> LENGTH: 20
<212> TYPE: RNA
<213> ORGANISM: Artificial Sequence
<220> FEATURE:
<223> OTHER INFORMATION: Synthetic

<400> SEQUENCE: 92
cuuaguaacc acagguugug                                                    20

<210> SEQ ID NO 93
<211> LENGTH: 20
<212> TYPE: RNA
<213> ORGANISM: Artificial Sequence
<220> FEATURE:
<223> OTHER INFORMATION: Synthetic

<400> SEQUENCE: 93
uuaguaacca cagguugugu                                                    20

<210> SEQ ID NO 94
<211> LENGTH: 20
<212> TYPE: RNA
<213> ORGANISM: Artificial Sequence
<220> FEATURE:
<223> OTHER INFORMATION: Synthetic

<400> SEQUENCE: 94
uaguaaccac agguuguguc                                                    20

<210> SEQ ID NO 95
<211> LENGTH: 20
<212> TYPE: RNA
<213> ORGANISM: Artificial Sequence
<220> FEATURE:
<223> OTHER INFORMATION: Synthetic

<400> SEQUENCE: 95
aguaaccaca gguuguguca                                                    20

<210> SEQ ID NO 96

```
<211> LENGTH: 20
<212> TYPE: RNA
<213> ORGANISM: Artificial Sequence
<220> FEATURE:
<223> OTHER INFORMATION: Synthetic

<400> SEQUENCE: 96
guaaccacag guugugucac                                           20

<210> SEQ ID NO 97
<211> LENGTH: 20
<212> TYPE: RNA
<213> ORGANISM: Artificial Sequence
<220> FEATURE:
<223> OTHER INFORMATION: Synthetic

<400> SEQUENCE: 97
uaaccacagg uugugucacc                                           20

<210> SEQ ID NO 98
<211> LENGTH: 20
<212> TYPE: RNA
<213> ORGANISM: Artificial Sequence
<220> FEATURE:
<223> OTHER INFORMATION: Synthetic

<400> SEQUENCE: 98
aaccacaggu ugugucacca                                           20

<210> SEQ ID NO 99
<211> LENGTH: 20
<212> TYPE: RNA
<213> ORGANISM: Artificial Sequence
<220> FEATURE:
<223> OTHER INFORMATION: Synthetic

<400> SEQUENCE: 99
accacagguu gugucaccag                                           20

<210> SEQ ID NO 100
<211> LENGTH: 20
<212> TYPE: RNA
<213> ORGANISM: Artificial Sequence
<220> FEATURE:
<223> OTHER INFORMATION: Synthetic

<400> SEQUENCE: 100
ccacagguug ugucaccaga                                           20

<210> SEQ ID NO 101
<211> LENGTH: 20
<212> TYPE: RNA
<213> ORGANISM: Artificial Sequence
<220> FEATURE:
<223> OTHER INFORMATION: Synthetic

<400> SEQUENCE: 101
cacagguugu gucaccagag                                           20

<210> SEQ ID NO 102
<211> LENGTH: 20
<212> TYPE: RNA
<213> ORGANISM: Artificial Sequence
<220> FEATURE:
<223> OTHER INFORMATION: Synthetic

<400> SEQUENCE: 102
```
acagguugug ucaccagagu          20

<210> SEQ ID NO 103
<211> LENGTH: 20
<212> TYPE: RNA
<213> ORGANISM: Artificial Sequence
<220> FEATURE:
<223> OTHER INFORMATION: Synthetic

<400> SEQUENCE: 103
cagguugugu caccagagua          20

<210> SEQ ID NO 104
<211> LENGTH: 20
<212> TYPE: RNA
<213> ORGANISM: Artificial Sequence
<220> FEATURE:
<223> OTHER INFORMATION: Synthetic

<400> SEQUENCE: 104
agguuguguc accagaguaa          20

<210> SEQ ID NO 105
<211> LENGTH: 20
<212> TYPE: RNA
<213> ORGANISM: Artificial Sequence
<220> FEATURE:
<223> OTHER INFORMATION: Synthetic

<400> SEQUENCE: 105
gguuguguca ccagaguaac          20

<210> SEQ ID NO 106
<211> LENGTH: 20
<212> TYPE: RNA
<213> ORGANISM: Artificial Sequence
<220> FEATURE:
<223> OTHER INFORMATION: Synthetic

<400> SEQUENCE: 106
guugugucac cagaguaaca          20

<210> SEQ ID NO 107
<211> LENGTH: 20
<212> TYPE: RNA
<213> ORGANISM: Artificial Sequence
<220> FEATURE:
<223> OTHER INFORMATION: Synthetic

<400> SEQUENCE: 107
uugugucacc agaguaacag          20

<210> SEQ ID NO 108
<211> LENGTH: 20
<212> TYPE: RNA
<213> ORGANISM: Artificial Sequence
<220> FEATURE:
<223> OTHER INFORMATION: Synthetic

<400> SEQUENCE: 108
ugugucacca gaguaacagu          20

<210> SEQ ID NO 109
<211> LENGTH: 20
<212> TYPE: RNA

```
<213> ORGANISM: Artificial Sequence
<220> FEATURE:
<223> OTHER INFORMATION: Synthetic

<400> SEQUENCE: 109
gugucaccag aguaacaguc                                              20

<210> SEQ ID NO 110
<211> LENGTH: 20
<212> TYPE: RNA
<213> ORGANISM: Artificial Sequence
<220> FEATURE:
<223> OTHER INFORMATION: Synthetic

<400> SEQUENCE: 110
ugucaccaga guaacagucu                                              20

<210> SEQ ID NO 111
<211> LENGTH: 20
<212> TYPE: RNA
<213> ORGANISM: Artificial Sequence
<220> FEATURE:
<223> OTHER INFORMATION: Synthetic

<400> SEQUENCE: 111
gucaccagag uaacagucug                                              20

<210> SEQ ID NO 112
<211> LENGTH: 20
<212> TYPE: RNA
<213> ORGANISM: Artificial Sequence
<220> FEATURE:
<223> OTHER INFORMATION: Synthetic

<400> SEQUENCE: 112
ucaccagagu aacagucuga                                              20

<210> SEQ ID NO 113
<211> LENGTH: 20
<212> TYPE: RNA
<213> ORGANISM: Artificial Sequence
<220> FEATURE:
<223> OTHER INFORMATION: Synthetic

<400> SEQUENCE: 113
caccagagua acagucugag                                              20

<210> SEQ ID NO 114
<211> LENGTH: 20
<212> TYPE: RNA
<213> ORGANISM: Artificial Sequence
<220> FEATURE:
<223> OTHER INFORMATION: Synthetic

<400> SEQUENCE: 114
accagaguaa cagucugagu                                              20

<210> SEQ ID NO 115
<211> LENGTH: 20
<212> TYPE: RNA
<213> ORGANISM: Artificial Sequence
<220> FEATURE:
<223> OTHER INFORMATION: Synthetic

<400> SEQUENCE: 115
ccagaguaac agucugagua                                              20
```

```
<210> SEQ ID NO 116
<211> LENGTH: 20
<212> TYPE: RNA
<213> ORGANISM: Artificial Sequence
<220> FEATURE:
<223> OTHER INFORMATION: Synthetic

<400> SEQUENCE: 116
cagaguaaca gucugaguag                                              20

<210> SEQ ID NO 117
<211> LENGTH: 20
<212> TYPE: RNA
<213> ORGANISM: Artificial Sequence
<220> FEATURE:
<223> OTHER INFORMATION: Synthetic

<400> SEQUENCE: 117
agaguaacag ucugaguagg                                              20

<210> SEQ ID NO 118
<211> LENGTH: 20
<212> TYPE: RNA
<213> ORGANISM: Artificial Sequence
<220> FEATURE:
<223> OTHER INFORMATION: Synthetic

<400> SEQUENCE: 118
gaguaacagu cugaguagga                                              20

<210> SEQ ID NO 119
<211> LENGTH: 20
<212> TYPE: RNA
<213> ORGANISM: Artificial Sequence
<220> FEATURE:
<223> OTHER INFORMATION: Synthetic

<400> SEQUENCE: 119
aguaacaguc ugaguaggag                                              20

<210> SEQ ID NO 120
<211> LENGTH: 20
<212> TYPE: RNA
<213> ORGANISM: Artificial Sequence
<220> FEATURE:
<223> OTHER INFORMATION: Synthetic

<400> SEQUENCE: 120
guaacagucu gaguaggagc                                              20

<210> SEQ ID NO 121
<211> LENGTH: 20
<212> TYPE: RNA
<213> ORGANISM: Artificial Sequence
<220> FEATURE:
<223> OTHER INFORMATION: Synthetic

<400> SEQUENCE: 121
uaacagucug aguaggagcu                                              20

<210> SEQ ID NO 122
<211> LENGTH: 20
<212> TYPE: RNA
<213> ORGANISM: Artificial Sequence
<220> FEATURE:
```

<223> OTHER INFORMATION: Synthetic

<400> SEQUENCE: 122
aacagucuga guaggagcua                                             20

<210> SEQ ID NO 123
<211> LENGTH: 20
<212> TYPE: RNA
<213> ORGANISM: Artificial Sequence
<220> FEATURE:
<223> OTHER INFORMATION: Synthetic

<400> SEQUENCE: 123
acagucugag uaggagcuaa                                             20

<210> SEQ ID NO 124
<211> LENGTH: 20
<212> TYPE: RNA
<213> ORGANISM: Artificial Sequence
<220> FEATURE:
<223> OTHER INFORMATION: Synthetic

<400> SEQUENCE: 124
cagucugagu aggagcuaaa                                             20

<210> SEQ ID NO 125
<211> LENGTH: 20
<212> TYPE: RNA
<213> ORGANISM: Artificial Sequence
<220> FEATURE:
<223> OTHER INFORMATION: Synthetic

<400> SEQUENCE: 125
agucugagua ggagcuaaaa                                             20

<210> SEQ ID NO 126
<211> LENGTH: 20
<212> TYPE: RNA
<213> ORGANISM: Artificial Sequence
<220> FEATURE:
<223> OTHER INFORMATION: Synthetic

<400> SEQUENCE: 126
gucugaguag gagcuaaaau                                             20

<210> SEQ ID NO 127
<211> LENGTH: 20
<212> TYPE: RNA
<213> ORGANISM: Artificial Sequence
<220> FEATURE:
<223> OTHER INFORMATION: Synthetic

<400> SEQUENCE: 127
ucugaguagg agcuaaaaua                                             20

<210> SEQ ID NO 128
<211> LENGTH: 20
<212> TYPE: RNA
<213> ORGANISM: Artificial Sequence
<220> FEATURE:
<223> OTHER INFORMATION: Synthetic

<400> SEQUENCE: 128
cugaguagga gcuaaaauau                                             20

```
<210> SEQ ID NO 129
<211> LENGTH: 60
<212> TYPE: DNA
<213> ORGANISM: Mus musculus

<400> SEQUENCE: 129
gtggttacta aggaaactgt catctccaaa ctagaaatgc catcttcttt gctgttggag      60

<210> SEQ ID NO 130
<211> LENGTH: 60
<212> TYPE: DNA
<213> ORGANISM: Homo sapiens

<400> SEQUENCE: 130
gtggttacta aggaaactgc catctccaaa ctagaaatgc catcttcctt gatgttggag      60

<210> SEQ ID NO 131
<211> LENGTH: 20
<212> TYPE: RNA
<213> ORGANISM: Artificial Sequence
<220> FEATURE:
<223> OTHER INFORMATION: Synthetic

<400> SEQUENCE: 131
ucaaggaaga uggcauuucu                                                  20

<210> SEQ ID NO 132
<211> LENGTH: 20
<212> TYPE: RNA
<213> ORGANISM: Artificial Sequence
<220> FEATURE:
<223> OTHER INFORMATION: Synthetic

<400> SEQUENCE: 132
gcaaagaaga uggcauuucu                                                  20
```